United States Patent
Bailey et al.

(10) Patent No.: US 7,060,717 B2
(45) Date of Patent: Jun. 13, 2006

(54) NICOTINAMIDE DERIVATIVES USEFUL AS PDE4 INHIBITORS

(75) Inventors: Simon Bailey, La Jolla, CA (US); Elisabeth C. L. Gautier, Sandwich (GB); Alan J. Henderson, Sandwich (GB); Thomas V. Magee, Groton, CT (US); Anthony Marfat, Groton, CT (US); John P. Mathias, Sandwich (GB); Dale G. McLeod, Groton, CT (US); Sandra M. Monaghan, Sandwich (GB); Blanda L. C. Stammen, Sandwich (GB)

(73) Assignee: Pfizer Inc, New York, NY (US)

( * ) Notice: Subject to any disclaimer, the term of this patent is extended or adjusted under 35 U.S.C. 154(b) by 65 days.

(21) Appl. No.: 10/865,263

(22) Filed: Jun. 9, 2004

(65) Prior Publication Data

US 2004/0224975 A1 Nov. 11, 2004

Related U.S. Application Data

(62) Division of application No. 10/361,062, filed on Feb. 6, 2003.

(60) Provisional application No. 60/433,330, filed on Dec. 13, 2002, provisional application No. 60/425,474, filed on Nov. 12, 2002, provisional application No. 60/414,304, filed on Sep. 26, 2002, provisional application No. 60/361,991, filed on Mar. 5, 2002.

(30) Foreign Application Priority Data

| Feb. 11, 2002 | (GB) | ................... 0203196.1 |
| Sep. 10, 2002 | (GB) | ................... 0220999.7 |
| Oct. 21, 2002 | (GB) | ................... 0224453.1 |
| Nov. 20, 2002 | (GB) | ................... 0227139.3 |

(51) Int. Cl.
*A61K 31/445* (2006.01)
*C07D 211/72* (2006.01)

(52) U.S. Cl. ..................... 514/350; 546/298
(58) Field of Classification Search ............... 546/298; 514/350
See application file for complete search history.

(56) References Cited

FOREIGN PATENT DOCUMENTS

| WO | WO 9111172 | 8/1991 |
| WO | WO 9402518 | 2/1994 |
| WO | WO 9845268 | 10/1998 |
| WO | WO 9855148 | 12/1998 |
| WO | WO 0157036 | 8/2001 |
| WO | 0157036 | * 9/2001 |
| WO | WO 0368232 | 8/2003 |
| WO | WO 0368233 | 8/2003 |
| WO | WO 0368234 | 8/2003 |

OTHER PUBLICATIONS

Torphy et al., Environ. Health Eprspect., 1994, 102, Suppl. 10. p. 79-84.
Duplantier et al., J. Med. Chem., 1996, 39, p. 120-125.
Schneider et al., Pharmacol. Biochem. Behav., 1995, 50, p. 211-217.
Banner and Page, Br. J. Pharmacol., 1995, 114, p. 93-98.
Barnette et al., J. Pharmacol. Exp. Ther., 1995, 273, p. 674-679.
Wright et al., Can. J. Physiol. Pharmacol., 1997, 75, p. 1001-1008.
Manabe et al., Eur. J. Pharmacol., 1997, 332, p. 97-107.
Ukita et al.., J. Med. Chem., 1999, 42, p. 1088-1099.
Berge et al., J. Pharm. Sci, 66, 1-19, 1977.

* cited by examiner

*Primary Examiner*—James O. Wilson
*Assistant Examiner*—Binta Robinson
(74) *Attorney, Agent, or Firm*—Gregg C. Benson; Robert T. Ronau

(57) ABSTRACT

The invention relates to nicotinamide derivatives and to processes for the preparation of, intermediates used in the preparation of, compositions containing and the uses of, such derivatives. The nicotinamide derivatives according to the present invention are useful in numerous diseases, disorders and conditions, in particular inflammatory, allergic, respiratory diseases, disorders and conditions, as well as wounds.

10 Claims, No Drawings

NICOTINAMIDE DERIVATIVES USEFUL AS PDE4 INHIBITORS

This invention relates to nicotinamide derivatives of general formula:

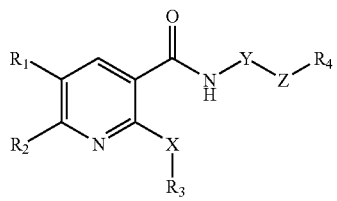

in which $R_1$, $R_2$, $R_3$, $R_4$, X, Y, and Z have the meanings indicated below,
and to processes for the preparation of, intermediates used in the preparation of, compositions containing and the uses of, such derivatives.

The 3',5'-cyclic nucleotide phosphodiesterases (PDEs) comprise a large class of enzymes divided into at least eleven different families which are structurally, biochemically and pharmacologically distinct from one another. The enzymes within each family are commonly referred to as isoenzymes, or isozymes. A total of more than fifteen gene products is included within this class, and further diversity results from differential splicing and post-translational processing of those gene products. The present invention is primarily concerned with the four gene products of the fourth family of PDEs, i.e., PDE4A, PDE4B, PDE4C, and PDE4D. These enzymes are collectively referred to as being isoforms or subtypes of the PDE4 isozyme family.

The PDE4s are characterized by selective, high affinity hydrolytic degradation of the second messenger cyclic nucleotide, adenosine 3',5'-cyclic monophosphate (cAMP), and by sensitivity to inhibition by rolipram. A number of selective inhibitors of the PDE4s have been discovered in recent years, and beneficial pharmacological effects resulting from that inhibition have been shown in a variety of disease models (see, e.g., Torphy et al., *Environ. Health Perspect.*, 1994, 102 Suppl. 10, p. 79–84; Duplantier et al., *J. Med. Chem.*, 1996, 39, p. 120–125; Schneider et al., *Pharmacol. Biochem. Behav.*, 1995, 50, p. 211–217; Banner and Page, *Br. J. Pharmacol.*, 1995, 114, p. 93–98; Barnette et al., *J. Pharmacol. Exp. Ther.*, 1995, 273, p. 674–679; Wright et al., *Can. J. Physiol. Pharmacol.*, 1997, 75, p. 1001–1008; Manabe et al., *Eur. J. Pharmacol.*, 1997, 332, p. 97–107 and Ukita et al., *J. Med. Chem.*, 1999, 42, p. 1088–1099). Accordingly, there continues to be considerable interest in the art with regard to the discovery of further selective inhibitors of PDE4s.

Successful results have already been obtained in the art with the discovery and development of selective PDE4 inhibitors. In vivo, PDE4 inhibitors reduce the influx of eosinophils to the lungs of allergen-challenged animals while also reducing the bronchoconstriction and elevated bronchial responsiveness occurring after allergen challenge. PDE4 inhibitors also suppress the activity of immune cells (including CD4+ T-lymphocytes, monocytes, mast cells, and basophils), reduce pulmonary edema, inhibit excitatory nonadrenergic noncholinergic neurotransmission (eNANC), potentiate inhibitory nonadrenergic noncholinergic neurotransmission (iNANC), reduce airway smooth muscle mitogenesis, and induce bronchodilation. PDE4 inhibitors also suppress the activity of a number of inflammatory cells associated with the pathophysiology of COPD, including monocytes/macrophages, CD4+ T-lymphocytes, eosinophils and neutrophils. PDE4 inhibitors also reduce vascular smooth muscle mitogenesis and potentially interfere with the ability of airway epithelial cells to generate pro-inflammatory mediators. Through the release of neutral proteases and acid hydrolases from their granules, and the generation of reactive oxygen species, neutrophils contribute to the tissue destruction associated with chronic inflammation, and are further implicated in the pathology of conditions such as emphysema. Therefore, PDE4 inhibitors are particularly useful for the treatment of a great number of inflammatory, respiratory and allergic diseases, disorders or conditions and for wounds and some of them are in clinical development mainly for tretament of asthma, COPD, bronchitis and emphysema.

The effects of PDE4 inhibitors on various inflammatory cell responses can be used as a basis for profiling and selecting inhibitors for further study. These effects include elevation of cAMP and inhibition of superoxide production, degranulation, chemotaxis, and tumor necrosis factor alpha (TNF☐) release in eosinophils, neutrophils and monocytes.

Some nicotinamide derivatives having a PDE4 inhibitory activity have already been synthetized. For example, the patent application N° WO 98/45268 discloses nicotinamide derivatives having activity as selective inhibitors of PDE4D isozyme. These selective PDE4D inhibitors are represented by the following formula:

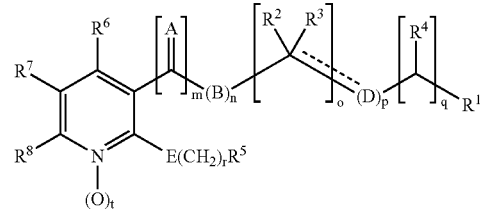

wherein r may be equal to 0, $(A)_m$ may be oxygen and $(B)_n$ may be NH, o may be equal to 0 or 1, $R^2$ and $R^3$ may be taken together with the carbon to which they are attached to form a $(C_3–C_7)$cycloalkyl ring, $(D)_p$ may be absent or may be —NH— or —N$(C_1–C_6)$alkyl-, q may be equal to 0 or 1, $R^4$ may be absent or may represent a carboxy, $R^1$ may be choosen from numerous substituents among which a $(C_1–C_6)$alkyl, a $(C_3–C_7)$cycloalkyl, a $(C_6–C_{10})$aryl or an (un)saturated $(C_3–C_7)$heterocyclic group, wherein each of said cycloalkyl, aryl or heterocycle may be optionally substituted by one to three substitutents.

The patent application N° WO 01/57036 also discloses nicotinamide derivatives which are PDE4 inhibitors useful in the treatment of various inflammatory allergic and respiratory diseases and conditions, of formula:

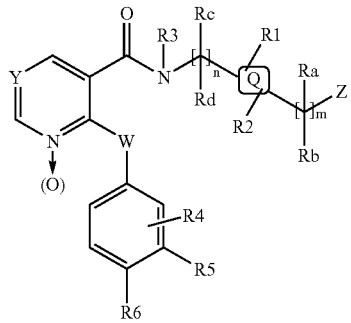

wherein in particular: n is 1 or 2, m is 0 to 2, Y is $=C(R^E)-$ or $-[N\rightarrow(O)]-$, W is $-O-$, $-S(=O)_t-$ or $-N(R_3)-$, Q represents various rings among which the monocyclic $(C_5-C_7)$cycloalkyl moieties, Z is $-OR_{12}$, $-C(=O)R_{12}$ or CN and $R_{12}$ is choosen from alkyl, alkenyl, cycloalkyl, phenyl, benzyl and monocyclic heterocyclic moieties.

However, there is still a huge need for additional PDE4 inhibitors showing improved therapeutic index with possibly less adverse effects such as for example emesis.

Thus, the present invention concerns new nicotinamide derivatives of general formula (1):

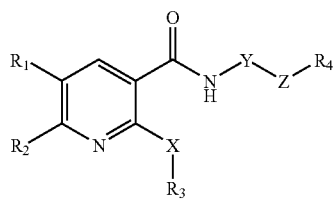

(1)

in which:

$R_1$ and $R_2$ are each a member independently selected from the group consisting of hydrogen atom, halo, cyano, $(C_1-C_4)$alkyl and $(C_1-C_4)$alkoxy, X is $-O-$, $-S-$ or $-NH-$, $R_3$ is a member selected from the groups consisting of:

(a) phenyl, naphthyl, heteroaryl and $(C_3-C_8)$cycloalkyl, each optionally substituted with 1 to 3 substituents each independently selected from the group consisting of halo, cyano, trifluoromethyl, trifluoroethyl, trifluoromethoxy, trifluoroethyloxy, $(C_1-C_4)$alkyl, $(C_1-C_4)$alkoxy, $(C_1-C_4)$ thioalkyl, $-C(=O)NH_2$, $-C(=O)NH((C_1-C_4)$alkyl), hydroxy, $-O-C(=O)(C_1-C_4)$alkyl, $-C(=O)-O-(C_1-C_4)$alkyl, hydroxy$(C_1-C_4)$alkyl, $(C_3-C_8)$cycloalkyl and $(C_3-C_8)$cycloalkyloxy, or (b) the bicyclic groups conforming to one of the following structures (1.1) to (1.4):

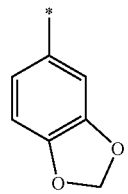
(1.1)

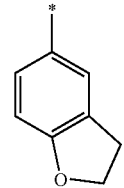
(1.2)

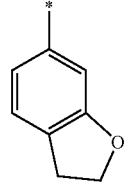
(1.3)

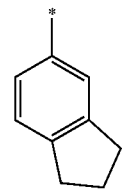
(1.4)

where the symbol "*" indicates the point of attachment of each partial formula (1.1) through (1.4) to the remaining portion of formula (1), Y is a member selected from the group consisting of partial formulas (1.5) through (1.8):

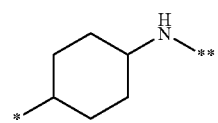
(1.5)

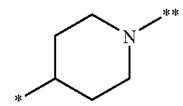
(1.6)

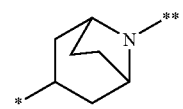
(1.7)

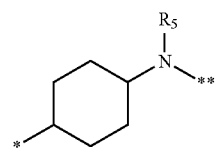
(1.8)

where the symbol "*" indicates the point of attachment of each partial formula (1.5) through (1.8) to the remaining portions —NH— of formula (1) and "**" indicates the point of attachment of each partial formula (1.5) through (1.8) to the remaining portions Z of formula (1), and wherein $R_5$ is a member selected from the groups consisting of $(C_1-C_4)$alkyl and $(C_1-C_4)$alkyl-phenyl, where said phenyl group is optionally substituted with 1 to 3 substituents each independently selected from the group consisting of halo, cyano, $(C_1-C_4)$alkyl, $(C_1-C_4)$alkoxy, hydroxy, hydroxy$(C_1-C_4)$alkyl, carboxylic acid (—COOH), —C(=O)—O—$(C_1-C_4)$alkyl, $(C_1-C_4)$haloalkyl and C(=O)NH$_2$, Z is a member selected from the group consisting of partial formulas (1.9) through (1.15):

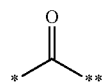
(1.9)

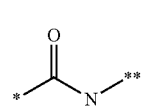
(1.10)

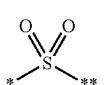
(1.11)

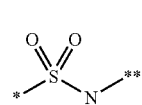
(1.12)

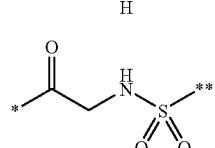
(1.13)

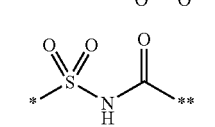
(1.14)

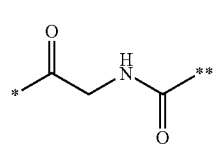
(1.15)

where the symbol "*" indicates the point of attachment of each partial formula (1.9) through (1.15) to the remaining portions Y of formula (1) and "**" indicates the point of attachment of each partial formula (1.9) through (1.15) to the remaining portions $R_4$ of formula (1), or alternatively Y-Z together represents a group of formula (1.16):

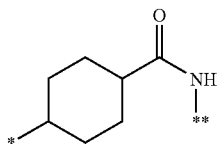
(1.16)

where the symbol "*" indicates the point of attachment of the partial formula (1.16) to the remaining portions —NH— of formula (1) and "**" indicates the point of attachment of the partial formula (1.16) to the remaining portions —$R_4$ of formula (1), and $R_4$ is a member selected from the groups consisting of:

(a) phenyl, naphthyl heteroaryl and $(C_3-C_8)$cycloalkyl, each optionally substituted with 1 to 3 substituents each independently selected from the group consisting of carboxylic acid (—COOH), —C(=O)—O—$(C_1-C_4)$alkyl, —$(C_1-C_4)$alkyl-COOH, —$(C_1-C_4)$alkyl-C(=O)—O—$(C_1-C_4)$alkyl, halo, cyano, —C(=O)NH$_2$, —$(C_1-C_4)$alkyl, —$(C_1-C_4)$alkoxy, —$(C_1-C_4)$haloalkyl, hydroxy and hydroxy$(C_1-C_4)$alkyl, or (b) $(C_1-C_6)$alkyl optionally substituted by 1 or 2 substituents independently selected from the group consisting of hydroxy, carboxylic acid, —C(=O)—O—$(C_1-C_4)$alkyl, phenyl, naphthyl, heteroaryl or $(C_3-C_8)$cycloalkyl group, where said phenyl, naphthyl, heteroaryl and $(C_3-C_8)$ cycloalkyl groups are each optionally substituted with 1 to 3 substituents each independently selected from the group consisting of carboxylic acid (—COOH), C(=O)O$(C_1-C_4)$alkyl, halo, cyano, —C(=O)NH$_2$, $(C_1-C_4)$alkyl, $(C_1-C_4)$alkoxy, $(C_1-C_4)$haloalkyl, hydroxy and hydroxy $(C_1-C_4)$alkyl, or, if appropriate, their pharmaceutically acceptable salts and/or isomers, tautomers, solvates, polymorphs, isotopic variations and metabolites thereof, with the proviso that:

1) when:

$R_1$ is selected from the group consisting of hydrogen atom, halo and methyl, $R_2$ is a hydrogen atom, X is —O—, $R_3$ is a phenyl substituted by a $(C_1-C_4)$thioalkyl in the −3 or −4 position of said phenyl and is also optionally substituted by 1 substituent selected from the group consisting of halo, $(C_1-C_3)$alkyl and $(C_1-C_3)$alkoxy, Y is a partial formula (1.5) or (1.8):

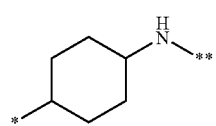
(1.5)

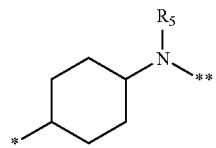
(1.8)

where the symbol "*" indicates the point of attachment of each partial formula to the remaining portions —NH— of formula (1) and "**" indicates the point of attachment of each partial formula to the remaining portions Z of formula (1), and wherein $R_5$ is a member selected from the groups consisting of $(C_1-C_4)$alkyl and $(C_1-C_4)$alkyl-phenyl, where said phenyl group is optionally substituted by halo, $(C_1-C_3)$alkyl, $(C_1-C_3)$alkoxy or hydroxy, and Z is a radical —C(=O)— then $R_4$ cannot be:

a) a $(C_3-C_8)$cycloalkyl optionally substituted by $(C_1-C_3)$alkyl, b) a phenyl or a 5- or 6-membered heterocyclic ring incorporating 1 to 3 heteroatom(s) independently selected from N, O and S, which phenyl and heterocyclic ring are each optionally substituted by hydroxy, halo, $(C_1-C_3)$alkyl or $(C_1-C_3)$alkoxy, or c) a $(C_1-C_6)$alkyl optionally substituted with a hydroxy, or with a phenyl or a 5- or 6-membered heterocyclic ring incorporating 1 to 3 heteroatom(s) independently selected from N, O and S, which phenyl and heterocyclic ring are each optionally substituted by hydroxy, halo, $(C_1-C_3)$alkyl or $(C_1-C_3)$alkoxy, 2) and when:

$R_1$ is selected from the group consisting of hydrogen atom, halo and methyl, $R_2$ is a hydrogen atom, X is —O—, $R_3$ is a phenyl substituted by a $(C_1-C_4)$thioalkyl in the -3 or -4 position of said phenyl and is also optionally substituted by 1 substituent selected from the group consisting of halo, $(C_1-C_3)$alkyl and $(C_1-C_3)$alkoxy, and Y-Z represents a partial formula (1.16):

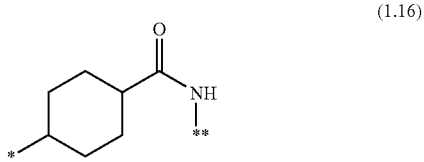

(1.16)

where the symbol "*" indicates the point of attachment of the partial formula (1.16) to the remaining portions —NH— of formula (1) and "**" indicates the point of attachment of the partial formula (1.16) to the remaining portions —$R_4$ of formula (1), then $R_4$ cannot be:

a) a $(C_3-C_8)$cycloalkyl or b) a $(C_1-C_6)$alkyl optionally substituted by a phenyl or a 5- or 6-membered heterocyclic ring incorporating 1 to 3 heteroatom(s) independently selected from N, O and S, which phenyl and heterocyclic ring are each optionally substituted by hydroxy, halo, $(C_1-C_3)$alkyl or $(C_1-C_3)$alkoxy, 3) and when:

$R_1$ is selected from the group consisting of hydrogen atom, halo and methyl, $R_2$ is a hydrogen atom, X is —O—, $R_3$ is a phenyl substituted by a $(C_1-C_4)$thioalkyl in the -3 or -4 position of said phenyl and is also optionally substituted by 1 or 2 substituent(s) each independently selected from the group consisting of halo, $(C_1-C_3)$alkyl and $(C_1-C_3)$alkoxy, and Y is a partial formula (1.6):

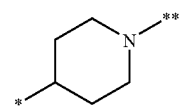

(1.6)

where the symbol "*" indicates the point of attachment of each partial formula to the remaining portions —NH— of formula (1) and "**" indicates the point of attachment of each partial formula to the remaining portions Z of formula (1), and Z is a radical —C(=O)—, then $R_4$ cannot be a $(C_1-C_6)$alkyl optionally substituted by a hydroxy, or by a 5- or 6-membered heterocyclic ring incorporating 1 to 3 heteroatom(s) independently selected from N, O and S.

It has been found that these nicotinamide derivatives are inhibitors of PDE4 isoenzymes, particularly useful for the treatment of inflammatory, respiratory and allergic diseases and conditions or for wounds by showing excellent therapeutic utility and therapeutic index.

In the here above general formula (1), halo denotes a halogen atom selected from the group consisting of fluoro, chloro, bromo and iodo in particular fluoro or chloro.

$(C_1-C_4)$alkyl or $(C_1-C_6)$alkyl radicals denote a straight-chain or branched group containing respectively 1 to 4 and 1 to 6 carbon atoms. This also applies if they carry substituents or occur as substituents of other radicals, for example in $(C_1-C_4)$alkoxy radicals, $(C_1-C_4)$thioalkyl radicals, $(C_1-C_4)$haloalkyl radicals, hydroxy$(C_1-C_4)$alkyl radicals, C(=O)O$(C_1-C_4)$alkyl radicals etc. . . . Examples of suitable $(C_1-C_4)$alkyl and $(C_1-C_6)$alkyl radicals are methyl, ethyl, n-propyl, isopropyl, n-butyl, iso-butyl, sec-butyl, tert-butyl, pentyl and hexyl. Examples of suitable $(C_1-C_4)$alkoxy radicals are methoxy, ethoxy, n-propyloxy, iso-propyloxy, n-butyloxy, iso-butyloxy, sec-butyloxy and tert-butyloxy. Examples of suitable $(C_1-C_4)$thioalkyl radicals are thiomethyl, thioethyl, thio-n-propyl, thio-iso-propyl, thio-n-butyl, thio-iso-butyl, thio-sec-butyl and thio-tert-butyl. $(C_1-C_4)$haloalkyl radicals are alkyl radicals substituted by halo. They can contain 1, 2, 3, 4, 5, 6 or 7 halogen atoms, if not stated otherwise. Said halo is preferably a fluoro, a chloro, a bromo or a iodo, in particular fluoro or chloro. For example in a fluoro-substituted alkyl radical, a methyl group can be present as a trifluoromethyl group. The same applies to hydroxy(C1–C4)alkyl radicals except that they are alkyl radicals substituted by a hydroxy group (—OH). According to a preferred embodiment of said invention, such radicals contain one hydroxy substituent. Examples of suitable hydroxy$(C_1-C_4)$alkyl radicals are hydroxymethyl, 1-hydroxyethyl or 2-hydroxyethyl.

$(C_3-C_8)$cycloalkyl radicals represent 3-membered to 8-membered saturated monocyclic rings. Examples of suitable $(C_3-C_8)$cycloalkyl radicals are in particular cyclopropyl, cyclobutyl, cyclopentyl, cyclohexyl, cycloheptyl and cyclooctyl. These radical can be optionally substituted as indicated in the definition of $R_3$. Examples of substituted $(C_3-C_8)$cycloalkyl radicals are for example 2-methylcyclohexyl, 3-methylcyclohexyl, 4-methylcyclohexyl, 5-methylcyclohexyl, 6-methylcyclohexyl, 2-hydroxycyclohexyl, 3-hydroxycyclohexyl, 4-hydroxycyclohexyl, 5-hydroxycyclohexyl, 6-hydroxycyclohexyl, 2-fluorocyclohexyl, 3-fluorocyclohexyl, 4-fluorocyclohexyl, 5-fluorocyclohexyl, 6-fluorocyclohexyl 2-methyl-3-hydroxycyclohexyl, 2-methyl-4-hydroxycyclohexyl, 2-hydroxy-4-methylcyclohexyl, etc . . . .

In the hereabove general formula (1), heteroaryl is a radical of a monocyclic or polycyclic aromatic system having 5 to 14 ring members, which contains 1, 2, 3, 4 or 5 heteroatom(s) depending in number and quality of the total number of ring members. Examples of heteroatoms are nitrogen (N), oxygen (O) and sulphur (S). If several heteroatoms are contained, these can be identical or different. Heteroaryl radicals can also be unsubstituted, monosubstituted or polysubstituted, as indicated in the definition of $R_3$ and $R_4$ hereabove for general formula (1) according to the present invention. Preferably heteroaryl is a monocyclic or bicyclic aromatic radical which contains 1, 2, 3 or 4, in particular 1, 2 or 3, identical or different heteroatoms selected from the group consisting of N, O and S. Particularly preferably, heteroaryl is a monocyclic or bicyclic aromatic radical having 5 to 10 ring members, in particular a 5-membered to 6-membered monocyclic aromatic radical which contains (i) from 1 to 4 nitrogen heteroatom(s) or (ii) 1 or 2 nitrogen heteroatom(s) and 1 oxygen heteroatom or 1 sulphur heteroatom or (iii) 1 or 2 oxygen or sulphur heteroatom(s). Examples of suitable heteroaryl radicals are the radicals derived from pyrrole, furan, furazan, thiophene, imidazole, pyrazole, oxazole, isoxazole, thiazole, isothiazole, tetrazole, triazine, pyridine, pyrazine, pyrimidine, pyridazine, indolizine, indole, isoindole, indazole, purine, naphthyridine, phthalazine, quinoline, isoquinoline, quinoxaline, quinazoline, cinnoline, and benzo-fused derivatives of these heteroaryls, such as for example benzofuran, benzothiophene, benzoxazole, and benzothiazole. Particularly preferred are the heteroaryl radicals selected from pyrrolyl, pyrazolyl, 1,2,3-triazolyl, 1,2,4-triazolyl, tetrazolyl, oxazolyl, isoxazolyl, thiazolyl, isothiazolyl, 1,2,4-oxadiazolyl, 1,3,4-oxadiazolyl, furanyl, thienyl, pyridinyl, pyridazinyl, pyrimidinyl, and pyrazinyl. Nitrogen heteroaryl radicals can also be present as N-oxides or as quaternary salts.

In the general formula (1) according to the present invention, when a radical is mono- or poly-substituted, said substituent(s) can be located at any desired position(s). Also, when a radical is polysubstituted, said substituents can be identical or different, unless otherwise stated.

The nicotinamide derivatives of the formula (1) can be prepared using conventional procedures such as by the following illustrative methods in which $R_1$, $R_2$, $R_3$, $R_4$, X, Y, and Z are as previously defined for the nicotinamide derivatives of the formula (1) unless otherwise stated.

Where Z in the general formula (1) represents a group of partial formula (1.9) through (1.15), the nicotinamide derivatives of the formula (1) may be prepared starting from a compound of formula (2.1):

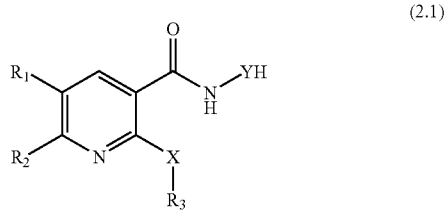

(2.1)

where $R_1$, $R_2$, X, $R_3$ and Y are as previously described for the nicotinamide derivatives of formula (1).

Where Z represents a group of partial formula (1.11), (1.12) or (1.14), the compounds of formula (2.1) may be reacted with the corresponding $R_4$-sulfonyl chloride derivative ($R_4SO_2Cl$ or $R_4NHSO_2Cl$ or $R_4C(=O)NHSO_2Cl$) in a suitable solvent (e.g. dichloromethane) and in the presence of an organic base (e.g. triethylamine) at a temperature ranging from 0° C. to room temperature (about 20° C.).

Where Z represents a group of partial formula (1.9), (1.13) or (1.15), the compounds of formula (2.1) may be reacted with the corresponding $R_4$-carboxylic acid derivative ($R_4COOH$ or $R_4SO_2NH$—$CH_2$—COOH or $R_4C(=O)$ NH—$CH_2$—COOH) using an activating agent in the presence of a suitable solvent (e.g. dimethylformamide) and organic base (e.g. N-methylmorpholine) at room temperature. Activation of the acid may be achieved by using for example:

a) 1-hydroxybenzotriazole and 1-(3-dimethylaminopropyl)-3-ethylcarbodiimide hydrochloride, or
b) carbonyldiimidazole, or
c) oxalyl chloride and dimethylformamide (with dichloromethane as the solvent), or
d) o-(7-azabenzotriazol-1-yl)-N,N,N',N'-tetramethyluronium hexafluorophos-phate (HATU reagent).

Where Z represents a group of partial formula (1.10), the compounds of formula (2.1) may be reacted with carbonyldiimidazole in a suitable solvent (such as dichloromethane) or with a phosgene equivalent (such as triphosgene) and the obtained intermediate is reacted with an amine bearing the substituent $R_4$.

It must be emphasized that when $R_3$ and $R_4$ in the nicotinamide derivatives of formula (1) represent alkoxy substituted phenyl rings, these structures can be converted to the hydroxy analogue using certain deprotection conditions well-known by the one skilled in the art. Similarly when $R_4$ contains an ester functionality, these structures can be easily converted to the carboxylic acid by simple saponification using alkali metal hydroxides well-known by the one skilled in the art.

The compounds of general formula (2.1) may be prepared by removal of the protecting group "Prot" from the compounds of general formula (3.1):

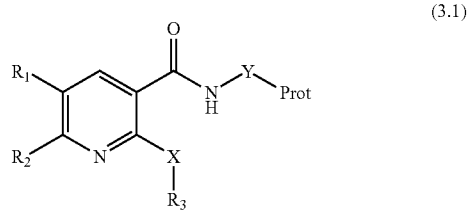

(3.1)

wherein $R_1$, $R_2$, X, $R_3$ and Y are as previously described for the nicotinamide derivatives of formula (1) and Prot is a suitable protecting group, which includes but is not limited to benzyl or a carbamate (e.g. butoxycarbonyl), by methods well known to those skilled in the art.

The compounds of formula (3.1) may be prepared according to two synthetic routes. The first synthetic route is shown in scheme 1:

Scheme 1

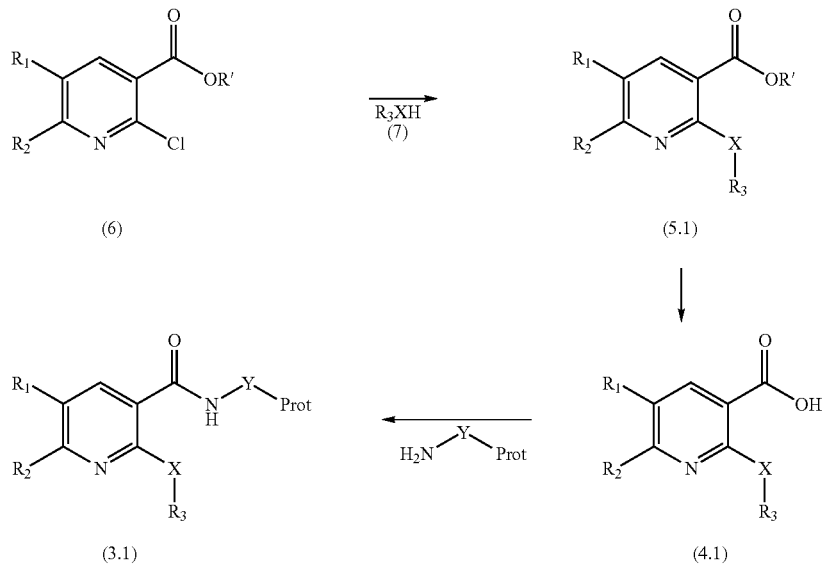

wherein $R_1$, $R_2$, X, $R_3$, Y and Prot are as previously described and R' represents a $(C_1–C_4)$alkyl radical.

In a typical procedure the nicotinate ester of the formula (6) may be reacted with the appropriate alcohol, thiol or amine of formula $R_3XH$ (7) in the appropriate solvent (for example dimethylformamide or dioxan) containing a base, such as cesium carbonate, at temperatures ranging from room temperature to 100° C. to give a compound of the formula (5.1). This can be saponified with an alkali-hydroxide to give an acid of the formula (4.1) which is then converted to a compound of the formula (3) by reaction with a monoprotected diamine of the formula $NH_2$—Y-Prot, using an activating agent such as those described in one of the activation methods outlined before (i.e. a) 1-hydroxy-benzotriazole and 1-(3-dimethylaminopropyl)-3-ethylcarbodiimide hydrochloride or b) carbonyldiimidazole or c) oxalyl chloride and dimethylformamide or d) HATU reagent with dichloromethane as the solvent).

According to another alternative, the compounds of formula (3.1) may be prepared as shown in scheme 2:

Scheme 2

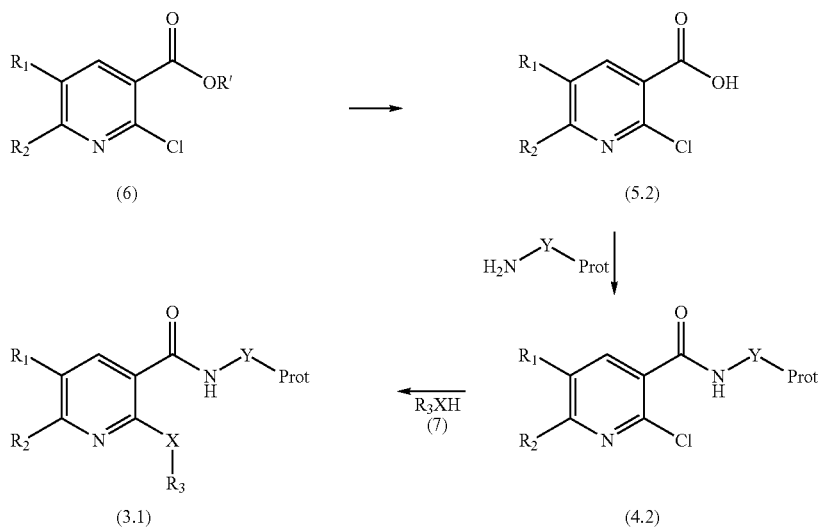

wherein $R_1$, $R_2$, X, $R_3$, Y, R' and Prot are as previously described.

In a typical procedure the nicotinate ester of the formula (6) may be hydrolysed using an alkaline metal hydroxide to a nicotinic acid of the formula (5.2), which is reacted with a monoprotected diamine of the formula $NH_2$—Y-Prot, using one of the activation methods outlined before. The chloropyridine of the formula (4.2) obtained at the preceding step may then be reacted with the appropriate alcohol, thiol or amine of formula $R_3XH$ (7) in the appropriate solvent (for example dimethylformamide or dioxan) containing a base, such as cesium carbonate, at temperatures ranging from room temperature (about 20° C.) to 100° C.

The compounds of formula (6) and (7), as well as the monoprotected diamine of the formula $NH_2$—Y-Prot, are either commercial or they can be prepared by conventional procedures well known to the one skilled in the art.

Where Y-Z in the general formula (1) represents together a group of partial formula (1.16), the nicotinamide derivatives of the formula (1) may be prepared starting from a compound of formula (2.2):

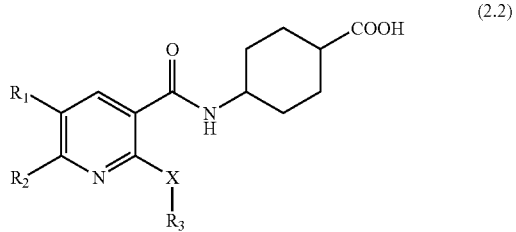

(2.2)

where $R_1$, $R_2$, X, and $R_3$ are as previously described for the nicotinamide derivatives of formula (1), by reaction of an amine bearing a $R_4$ substituent and using one of the activation methods outlined before.

The compounds of formula (2.2) may be prepared starting from the corresponding ester of formula (3.2):

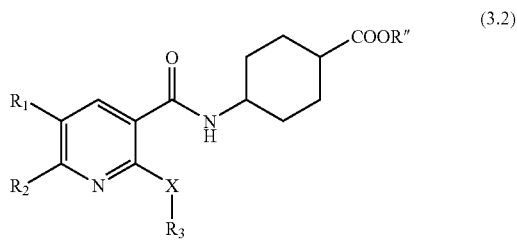

(3.2)

wherein $R_1$, $R_2$, X and $R_3$ are as previously described for the nicotinamide derivatives of formula (1) and R" represents a $(C_1-C_4)$ alkyl radical or a benzyl radical. If R" represents a $(C_1-C_4)$ alkyl radical, the compounds of formula (2.2) are obtained via saponification according to the standard procedures, else the compounds of formula (2.2) are obtained via hydrogenation according to the standard procedures well known by the one skilled in the art.

The compounds of formula (3.2) may be prepared according to two synthetic routes. The first synthetic route is shown in scheme 3:

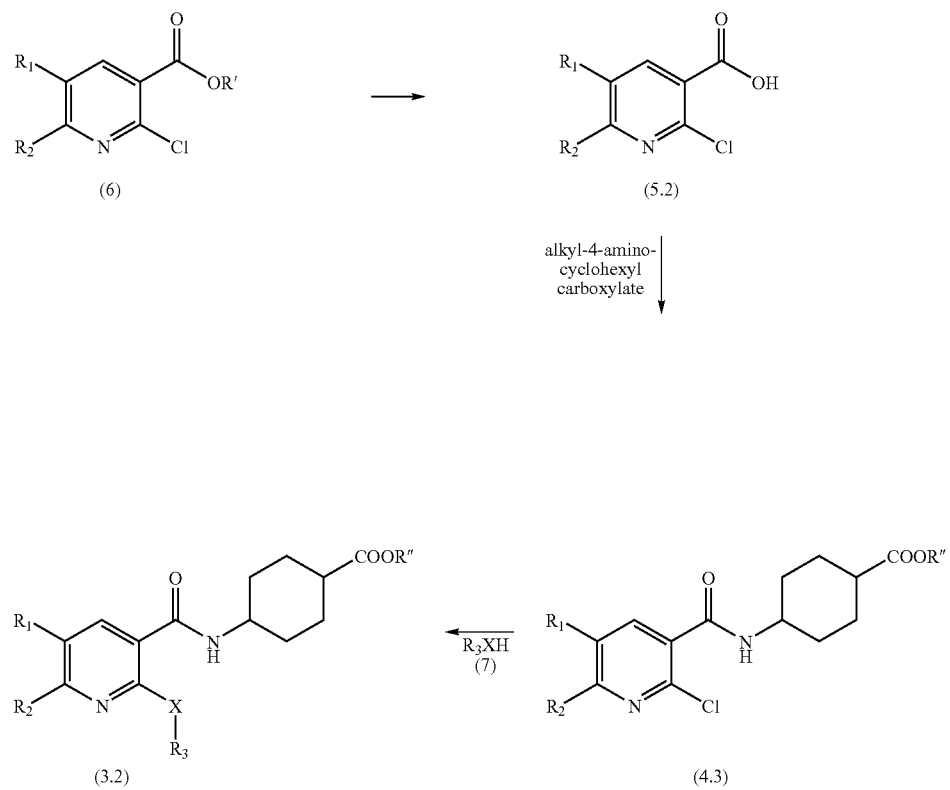

where $R_1$, $R_2$, X, $R_3$, R' and R" are as previously described.

In a typical procedure, the nicotinic acid of formula (5.2), which is obtained from a compound of formula (6) as previously described, may be reacted with an alkyl-4-aminocyclohexylcarboxylate using one of the activation method outlined before. The chloropyridine of formula (4.3) is then reacted with the appropriate alcohol, thiol or amine of formula $R_3XH$ (7) in the appropriate solvent (for example dimethylformamide or dioxan) containing a base, such as cesium carbonate, at temperatures ranging from room temperature (about 20° C.) to 100° C.

According to another alternative, the compounds of formula (3.2) may also be prepared directly from compounds of formula (4.1) as previously described:

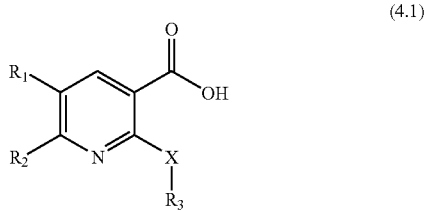

(4.1)

by reaction with an alkyl-4-aminocyclohexylcarboxylate using one of the activation method outlined before. Said compound of formula (4.1) may be prepared as already described here above.

According to a final alternative, the nicotinamide derivatives of formula (1) may also be prepared by reaction of the acid of formula (4.1) as previously described:

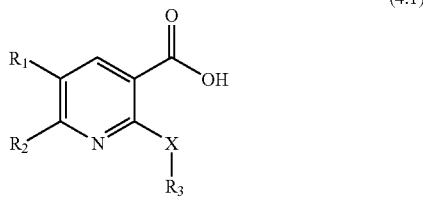

(4.1)

with an amine derivative of formula (8): $NH_2$—Y-Z-$R_4$, using one one of the activation method outlined before. Said compound of formula (4.1) may be prepared as already described here above.

The amine derivative of formula (8) may be prepared according to the following scheme 4:

Scheme 4

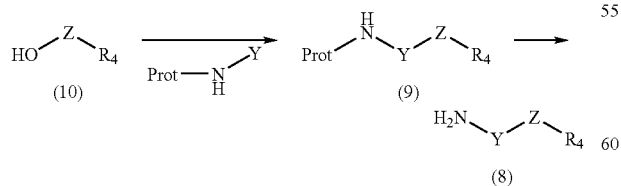

wherein $R_4$, Z and Y are as previously described for the nicotinamide derivatives of formula (1) and Prot is a suitable protecting group, which includes but is not limited to benzyl or a carbamate (e.g. butoxycarbonyl).

In a typical procedure, the protected amine Prot-NH—Y may be reacted with the acid of formula (10), using one of the activation methods outlined previously. Deprotection of the resulting compound of formula (9) by methods well known to those skilled in the art, affords the amine of formula (8).

The compounds of formula (10) as well as the monoprotected amine of the formula Y-Prot-NH—Y, are either commercial or they can be prepared by conventional procedures well known to the one skilled in the art.

All of the above reactions and the preparations of novel starting materials using in the preceding methods are conventional and appropriate reagents and reaction conditions for their performance or preparation as well as procedures for isolating the desired products will be well-known to those skilled in the art with reference to literature precedents and the examples and preparations hereto.

For some of the steps of the here above described process of preparation of the nicotinamide derivatives of formula (1), it can be necessary to protect the potential reactive functions that are not wished to react. In such a case, any compatible protecting radical can be used. In particular methods such as those described by T. W. GREENE (*Protective Groups in Organic Synthesis*, A. Wiley-Interscience Publication, 1981) or by McOMIE (*Protective Groups in Organic Chemistry*, Plenum Press, 1973), can be used.

Also, the nicotinamide derivatives of formula (1) as well as intermediate for the preparation thereof can be purified according to various well-known methods, such as for example crystallization or chromatography.

According to a first aspect, particularly preferred are nicotinamide derivatives of the formula (1) in which:

$R_1$ and $R_2$ are each a member independently selected from the group consisting of hydrogen atom, halo, cyano, $(C_1-C_4)$alkyl and $(C_1-C_4)$alkoxy, X is —O—, $R_3$ is a member selected from the groups consisting of:

(a) phenyl optionally substituted with 1 to 3 substituents each independently selected from the group consisting of halo, cyano, trifluoromethyl, trifluoromethoxy, $(C_1-C_4)$alkyl or $(C_1-C_4)$alkoxy, $(C_1-C_4)$thioalkyl, —C(=O)$NH_2$, —C(=O)NH (($C_1-C_4$)alkyl), hydroxy, —O—C(=O)($C_1-C_4$)alkyl, —C(=O)—O—($C_1-C_4$)alkyl, hydroxy $(C_1-C_4)$alkyl, $(C_3-C_8)$cycloalkyl and $(C_3-C_8)$cycloalkyloxy, or (b) the bicyclic groups conforming to one of the following structures (1.1) to (1.4):

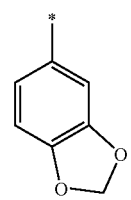

(1.1)

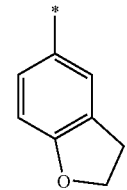

(1.2)

-continued (1.3)
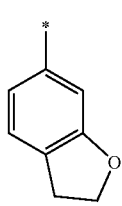

(1.4)
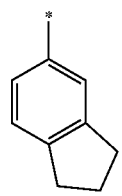

where the symbol "*" indicates the point of attachment of each partial formula (1.1) through (1.4) to the remaining portion of formula (1), Y is a member selected from the group consisting of partial formulas (1.5) through (1.8):

(1.5)
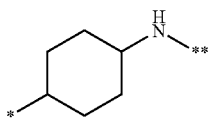

(1.6)
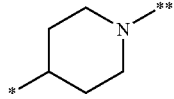

(1.7)
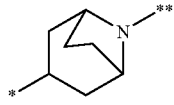

(1.8)
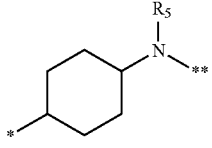

where the symbol "*" indicates the point of attachment of each partial formula (1.5) through (1.8) to the remaining portions —NH— of formula (1) and "**" indicates the point of attachment of each partial formula (1.5) through (1.8) to the remaining portions Z of formula (1), and wherein $R_5$ is a member selected from the groups consisting of $(C_1-C_4)$alkyl and $(C_1-C_4)$alkyl-phenyl, where said phenyl group is optionally substituted with 1 to 3 substituents each independently selected from the group consisting of halo, cyano, $(C_1-C_4)$alkyl, $(C_1-C_4)$alkoxy, hydroxy, hydroxy$(C_1-C_4)$alkyl, carboxylic acid, —C(=O)—O—$(C_1-C_4)$alkyl, $(C_1-C_4)$haloalkyl and —C(=O)NH$_2$, Z is a member selected from the group consisting of partial formulas (1.9) through (1.11) and (1.15):

(1.9)
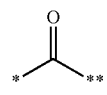

(1.10)
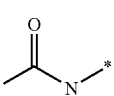

(1.11)
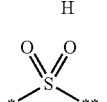

(1.15)
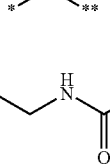

where the symbol "*" indicates the points of attachment of each partial formula (1.9) through (1.11) and (1.15) to the remaining portions Y of formula (1) and "**" indicates the point of attachment of each partial formula (1.9) through (1.11) and (1.15) to the remaining portions $R_4$ of formula (1), or alternatively Y-Z together represents a group of formula (1.16):

(1.16)
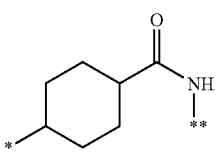

where the symbol "*" indicates the point of attachment of the partial formula (1.16) to the remaining portions —NH— of formula (1) and "**" indicates the point of attachment of the partial formula (1.16) to the remaining portions —$R_4$ of formula (1), and $R_4$ is a member selected from the groups consisting of:
(a) phenyl, naphthyl, heteroaryl and $(C_3-C_8)$cycloalkyl, each optionally substituted with 1 to 3 substituents each independently selected from the group consisting of carboxylic acid (—COOH), —C(=O)—O—$(C_1-C_4)$alkyl, $(C_1-C_4)$alkyl-COOH, $(C_1-C_4)$alkyl-C(=O)—O—$(C_1-C_4)$alkyl, halo, cyano, —C(=O)NH$_2$, $(C_1-C_4)$alkyl, $(C_1-C_4)$alkoxy, $(C_1-C_4)$haloalkyl, hydroxy and hydroxy$(C_1-C_4)$alkyl, or
(b) $(C_1-C_6)$alkyl optionally substituted by 1 or 2 substituents independently selected from the group consisting of hydroxy, carboxylic acid, —C(=O)—O—$(C_1-C_4)$alkyl, phenyl, naphthyl, heteroaryl or $(C_3-C_8)$cycloalkyl group, where said phenyl, naphthyl, heteroaryl and $(C_3-C_8)$ cycloalkyl groups are each optionally substituted with 1 to 3 substituents each independently selected from the group consisting of carboxylic acid, C(=O)O$(C_1-C_4)$alkyl, halo, cyano, —C(=O)NH$_2$, $(C_1-C_4)$alkyl or $(C_1-C_4)$ alkoxy, $(C_1-C_4)$haloalkyl, hydroxy and hydroxy$(C_1-C_4)$ alkyl, or, if appropriate, their pharmaceutically acceptable salts and/or isomers, tautomers, solvates, polymorphs, isotopic variations and metabolites thereof, with the proviso that:

1) when:

R$_1$ is selected from the group consisting of hydrogen atom, halo and methyl,

R$_2$ is a hydrogen atom,

X is —O—,

R$_3$ is a phenyl substituted by a (C$_1$–C$_4$)thioalkyl in the -3 or -4 position of said phenyl and is also optionally substituted by 1 substituent selected from the group consisting of halo, (C$_1$–C$_3$)alkyl and (C$_1$–C$_3$)alkoxy, Y is a partial formula (1.5) or (1.8):

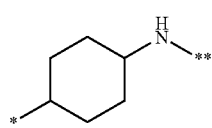

(1.5)

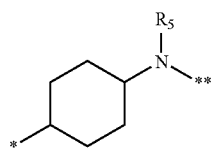

(1.8)

where the symbol "*" indicates the point of attachment of each partial formula to the remaining portions —NH— of formula (1) and "**" indicates the point of attachment of each partial formula to the remaining portions Z of formula (1), and wherein R$_5$ is a member selected from the groups consisting of (C$_1$–C$_4$)alkyl and (C$_1$–C$_4$)alkyl-phenyl, where said phenyl group is optionally substituted by halo, (C$_1$–C$_3$)alkyl, (C$_1$–C$_3$)alkoxy or hydroxy, and Z is a radical —C(=O)— then R$_4$ cannot be:

a) a (C$_3$–C$_8$)cycloalkyl optionally substituted by (C$_1$–C$_3$)alkyl, b) a phenyl or a 5- or 6-membered heterocyclic ring incorporating 1 to 3 heteroatom(s) independently selected from N, O and S, which phenyl and heterocyclic ring are each optionally substituted by hydroxy, halo, (C$_1$–C$_3$)alkyl or (C$_1$–C$_3$)alkoxy, or c) a (C$_1$–C$_6$)alkyl optionally substituted with a hydroxy, or with a phenyl or a 5- or 6-membered heterocyclic ring incorporating 1 to 3 heteroatom(s) independently selected from N, O and S, which phenyl and heterocyclic ring are each optionally substituted by hydroxy, halo, (C$_1$–C$_3$) alkyl or (C$_1$–C$_3$)alkoxy, 2) and when:

R$_1$ is selected from the group consisting of hydrogen atom, halo and methyl,

R$_2$ is a hydrogen atom,

X is —O—,

R$_3$ is a phenyl substituted by a (C$_1$–C$_4$)thioalkyl in the -3 or -4 position of said phenyl and is also optionally substituted by 1 substituent selected from the group consisting of halo, (C$_1$–C$_3$)alkyl and (C$_1$–C$_3$)alkoxy, and Y-Z represents a partial formula (1.16):

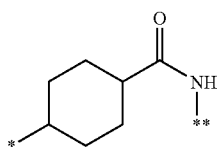

(1.16)

where the symbol "*" indicates the point of attachment of the partial formula (1.16) to the remaining portions —NH— of formula (1) and "**" indicates the point of attachment of the partial formula (1.16) to the remaining portions —R$_4$ of formula (1), then R$_4$ cannot be:

a) a (C$_3$–C$_8$)cycloalkyl or b) a (C$_1$–C$_6$)alkyl optionally substituted by a phenyl or a 5- or 6-membered heterocyclic ring incorporating 1 to 3 heteroatom(s) independently selected from N, O and S, which phenyl and heterocyclic ring are each optionally substituted by hydroxy, halo, (C$_1$–C$_3$)alkyl or (C$_1$–C$_3$) alkoxy, 3) and when:

R$_1$ is selected from the group consisting of hydrogen atom, halo and methyl,

R$_2$ is a hydrogen atom,

X is —O—,

R$_3$ is a phenyl substituted by a (C$_1$–C$_4$)thioalkyl in the -3 or -4 position of said phenyl and is also optionally substituted by 1 or 2 substituent(s) each independently selected from the group consisting of halo, (C$_1$–C$_3$)alkyl and (C$_1$–C$_3$)alkoxy, and Y is a partial formula (1.6):

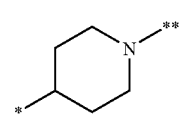

(1.6)

where the symbol "*" indicates the point of attachment of each partial formula to the remaining portions —NH— of formula (1) and "**" indicates the point of attachment of each partial formula to the remaining portions Z of formula (1), and Z is a radical —C(=O)—, then R$_4$ cannot be a (C$_1$–C$_6$)alkyl optionally substituted by a hydroxy, or by a 5- or 6-membered heterocyclic ring incorporating 1 to 3 heteroatom(s) independently selected from N, O and S.

More particularly preferred are the nicotinamide derivatives of the formula (1) in which:

R$_1$ and R$_2$ are each a member independently selected from the group consisting of hydrogen atom and halo, X is —O—, R$_3$ is a member selected from the groups consisting of:

(a) phenyl optionally substituted with 1 or 2 substituents each independently selected from the group consisting of halo, (C$_1$–C$_4$)alkyl, (C$_1$–C$_4$)alkoxy, trifluoromethyl, trifluoromethoxy, (C$_3$–C$_8$)cycloalkyl, (C$_3$–C$_8$)cycloalkyloxy and (C$_1$–C$_4$)thioalkyl, or (b) the bicyclic groups conforming to one of the following structures (1.1), (1.3) or (1.4)

Z is a member selected from the group consisting of partial formulas (1.9) through (1.11) and (1.15):

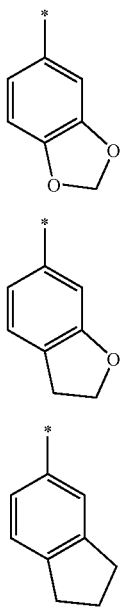

(1.1)

(1.3)

(1.4)

where the symbol "*" indicates the point of attachment of each partial formula (1.1), (1.3) or (1.4) to the remaining portion of formula (1), Y is a member selected from the group consisting of partial formulas (1.5) through (1.8):

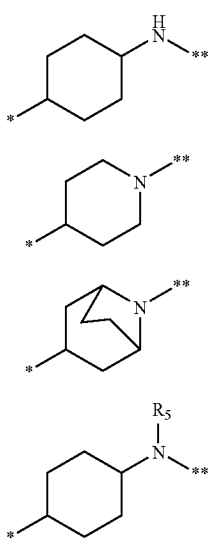

(1.5)

(1.6)

(1.7)

(1.8)

where the symbol "*" indicates the point of attachment of each partial formula (1.5) through (1.8) to the remaining portions —NH— of formula (1) and "**" indicates the point of attachment of each partial formula (1.5) through (1.8) to the remaining portions Z of formula (1), and wherein $R_5$ is a group $(C_1-C_4)$alkyl-phenyl where said phenyl is optionally substituted with 1 to 3 substituents each independently selected from the group consisting of hydroxy, carboxylic acid, C(=O)O(C1–C4)alkyl and hydroxy(C1–C4)alkyl,

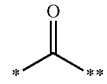

(1.9)

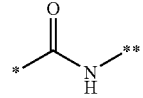

(1.10)

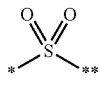

(1.11)

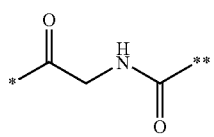

(1.15)

where the symbol "*" indicates the points of attachment of each partial formula (1.9) through (1.11) and (1.15) to the remaining portions Y of formula (1) and "**" indicates the point of attachment of each partial formula (1.9) through (1.11) and (1.15) to the remaining portions $R_4$ of formula (1), or alternatively Y-Z together represents a group of formula (1.16):

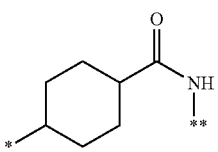

(1.16)

where the symbol "*" indicates the point of attachment of the partial formula (1.16) to the remaining portions —NH— of formula (1) and "**" indicates the point of attachment of the partial formula (1.16) to the remaining portions —$R_4$ of formula (1), and $R_4$ is a member selected from the groups consisting of:
(a) phenyl, naphthyl, heteroaryl and $(C_3-C_8)$cycloalkyl, each optionally substituted with 1 to 3 substituents each independently selected from the group consisting of carboxylic acid (—COOH), —C(=O)—O—$(C_1-C_4)$alkyl, $(C_1-C_4)$alkyl-COOH, $(C_1-C_4)$alkyl-C(=O)—O—$(C_1-C_4)$alkyl, halo, $(C_1-C_4)$alkyl, $(C_1-C_4)$alkoxy, hydroxy$(C_1-C_4)$alkyl and hydroxy, or
(b) $(C_1-C_6)$alkyl optionally substituted by 1 or 2 substituents independently selected from the group consisting of hydroxy, carboxylic acid, —C(=O)—O—$(C_1-C_4)$alkyl, phenyl, naphthyl, heteroaryl or $(C_3-C_8)$cycloalkyl group, where said phenyl, naphthyl, heteroaryl and $(C_3-C_8)$ cycloalkyl groups are each optionally substituted with 1 to 3 substituents each independently selected from the group consisting of carboxylic acid (—COOH), C(=O)O $(C_1-C_4)$alkyl, halo, $(C_1-C_4)$alkyl, $(C_1-C_4)$alkoxy, hydroxy$(C_1-C_4)$alkyl and hydroxy, or, if appropriate, their pharmaceutically acceptable salts and/or isomers, tautomers, solvates, polymorphs, isotopic variations and metabolites thereof, with the proviso that:

1) when:

$R_1$ is selected from the group consisting of hydrogen atom and halo, $R_2$ is a hydrogen atom, X is —O—, $R_3$ is a phenyl substituted by a $(C_1-C_4)$thioalkyl in the -3 or -4 position of said phenyl and is also optionally substituted by 1 substituent selected from the group consisting of halo and $(C_1-C_3)$alkyl, Y is a partial formula (1.5) or (1.8):

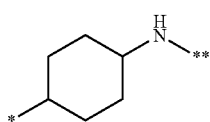
(1.5)

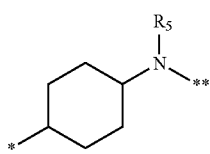
(1.8)

where the symbol "*" indicates the point of attachment of each partial formula to the remaining portions —NH— of formula (1) and "**" indicates the point of attachment of each partial formula to the remaining portions Z of formula (1), and wherein $R_5$ is a $(C_1-C_4)$alkyl-phenyl, where said phenyl group is optionally substituted by hydroxy, and Z is a radical —C(=O)— then $R_4$ cannot be:

a) a $(C_3-C_8)$cycloalkyl optionally substituted by $(C_1-C_3)$alkyl, b) a phenyl or a 5- or 6-membered heterocyclic ring incorporating 1 to 3 heteroatom(s) independently selected from N, O and S, which phenyl and heterocyclic ring are each optionally substituted by hydroxy, halo, $(C_1-C_3)$alkyl or $(C_1-C_3)$alkoxy, or c) a $(C_1-C_6)$alkyl optionally substituted with a hydroxy, or with a phenyl or a 5- or 6-membered heterocyclic ring incorporating 1 to 3 heteroatom(s) independently selected from N, O and S, which phenyl and heterocyclic ring are each optionally substituted by hydroxy, halo, $(C_1-C_3)$alkyl or $(C_1-C_3)$alkoxy, 2) and when:

$R_1$ is selected from the group consisting of hydrogen atom and halo, $R_2$ is a hydrogen atom, X is —O—, $R_3$ is a phenyl substituted by a $(C_1-C_4)$thioalkyl in the -3 or -4 position of said phenyl and is also optionally substituted by 1 substituent selected from the group consisting of halo and $(C_1-C_3)$alkyl, and Y-Z represents a partial formula (1.16):

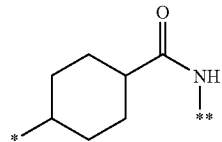
(1.16)

where the symbol "*" indicates the point of attachment of the partial formula (1.16) to the remaining portions —NH— of formula (1) and "**" indicates the point of attachment of the partial formula (1.16) to the remaining portions —$R_4$ of formula (1), then $R_4$ cannot be:

a) a $(C_3-C_8)$cycloalkyl or b) a $(C_1-C_6)$alkyl optionally substituted by a phenyl or a 5- or 6-membered heterocyclic ring incorporating 1 to 3 heteroatom(s) independently selected from N, O and S, which phenyl and heterocyclic ring are each optionally substituted by hydroxy, halo, $(C_1-C_3)$alkyl or $(C_1-C_3)$alkoxy, 3) and when:

$R_1$ is selected from the group consisting of hydrogen atom and halo, $R_2$ is a hydrogen atom, X is —O—, $R_3$ is a phenyl substituted by a $(C_1-C_4)$thioalkyl in the -3 or -4 position of said phenyl and is also optionally substituted by 1 substituent(s) selected from the group consisting of halo and $(C_1-C_3)$alkyl, Y is a partial formula (1.6):

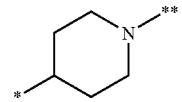
(1.6)

where the symbol "*" indicates the point of attachment of each partial formula to the remaining portions —NH— of formula (1) and "**" indicates the point of attachment of each partial formula to the remaining portions Z of formula (1), and Z is a radical —C(=O)—, then $R_4$ cannot be a $(C_1-C_6)$alkyl optionally substituted by a hydroxy, or by a 5- or 6-membered heterocyclic ring incorporating 1 to 3 heteroatom(s) independently selected from N, O and S.

Still more particularly preferred are the nicotinamide derivatives of the formula (1) in which:

$R_1$ is a hydrogen atom or fluoro and $R_2$ is a hydrogen atom,

X is —O—, $R_3$ is a member selected from the groups consisting of:

(a) phenyl optionally substituted with 1 or 2 substituents independently selected from the group consisting of fluoro, chloro, bromo, methyl, ethyl, methoxy, trifluoromethyl, trifluoromethoxy, cyclopropyl, cyclobutyloxy, and methylthio, or (b) the bicyclic groups conforming to one of the following structures (1.1), (1.3) or (1.4)

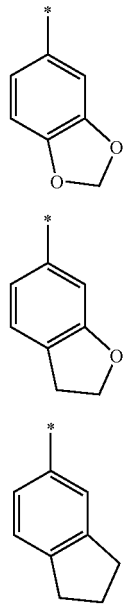

(1.1)

(1.3)

(1.4)

where the symbol "*" indicates the point of attachment of each partial formula (1.1), (1.3) or (1.4) to the remaining portion of formula (1), Y is a member selected from the group consisting of partial formulas (1.5) through (1.8):

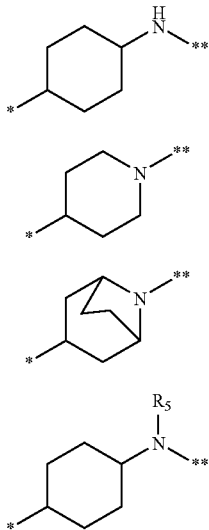

(1.5)

(1.6)

(1.7)

(1.8)

where the symbol "*" indicates the point of attachment of each partial formula (1.5) through (1.8) to the remaining portions —NH— of formula (1) and "**" indicates the point of attachment of each partial formula (1.5) through (1.8) to the remaining portions Z of formula (1), and wherein $R_5$ is a group benzyl group substituted by a hydroxy substitutent on the ring, Z is a member selected from the group consisting of partial formulas (1.9) through (1.11) and (1.15):

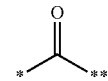

(1.9)

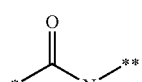

(1.10)

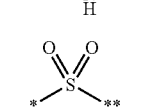

(1.11)

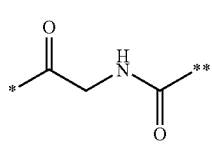

(1.15)

where the symbol "*" indicates the points of attachment of each partial formula (1.9) through (1.11) and (1.15) to the remaining portions Y of formula (1) and "**" indicates the point of attachment of each partial formula (1.9) through (1.11) and (1.15) to the remaining portions $R_4$ of formula (1), or alternatively Y-Z together represents a group of formula (1.16):

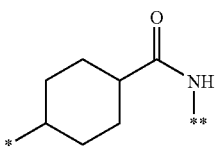

(1.16)

where the symbol "*" indicates the point of attachment of the partial formula (1.16) to the remaining portions —NH— of formula (1) and "**" indicates the point of attachment of the partial formula (1.16) to the remaining portions —$R_4$ of formula (1), and $R_4$ is a member selected from the groups consisting of:

(a) phenyl optionally substituted with 1 to 3 substituents each independently selected from the group consisting of carboxylic acid, —C(=O)—O-methyl, fluoro, chloro, methyl, iso-propyl, methoxy and hydroxy, or (b) naphthyl optionally substituted by a hydroxy, (c) pyridyl optionally substituted by a hydroxy or a —C(=O)Omethyl group, (d) a ($C_3$–$C_8$)cycloalkyl optionally substituted with a substituent selected from the group consisting of hydroxy, —C(=O)—O—($C_1$–$C_4$)alkyl and ($C_1$–$C_4$)alkyl-C(=O)—O—($C_1$–$C_4$)alkyl, (e) ($C_1$–$C_6$)alkyl optionally substituted by 1 or 2 substituents independently selected from the group consisting of hydroxy, carboxylic acid, —C(=O)Omethyl, —C(=O)Oethyl, ($C_3$–$C_8$)cycloalkyl and phenyl, where said phenyl is optionally substituted with 1 or 2 substituents each independently selected from the group consisting of fluoro, chloro, methyl, methoxy and hydroxy, or, if appropriate, their pharmaceutically acceptable salts and/or isomers, tautomers, solvates, polymorphs, isotopic variations and metabolites thereof,
with the proviso that:
1) when:
$R_1$ is selected from the group consisting of hydrogen atom and fluoro,
$R_2$ is a hydrogen atom,
X is —O—,
$R_3$ is a phenyl substituted by a —S-methyl in the -3 or -4 position of said phenyl and is also optionally substituted by 1 substituent selected from the group consisting of fluoro, chloro, methyl and ethyl,
Y is a partial formula (1.5) or (1.8):

(1.5)

(1.8)

where the symbol "*" indicates the point of attachment of each partial formula to the remaining portions —NH— of formula (1) and "**" indicates the point of attachment of each partial formula to the remaining portions Z of formula (1),
and wherein $R_5$ is a benzyl optionally substituted by hydroxy, and
Z is a radical —C(=O)—
then $R_4$ cannot be:
a) an unsubstituted $(C_3-C_8)$cycloalkyl,
b) a phenyl optionally substituted by hydroxy, fluoro, chloro, methyl, iso-propyl or methoxy or $(C_1-C_3)$alkoxy,
c) a pyridyl optionally substituted by a hydroxy, or
d) a $(C_1-C_6)$alkyl optionally substituted with a hydroxy, or with a phenyl optionally substituted by hydroxy, fluoro, chloro, methyl or methoxy,
2) and when:
$R_1$ is selected from the group consisting of hydrogen atom and fluoro,
$R_2$ is a hydrogen atom,
X is —O—,
$R_3$ is a phenyl substituted by —S-methyl in the -3 or -4 position of said phenyl and is also optionally substituted by 1 substituent selected from the group consisting of fluoro, chloro, methyl and ethyl, and
Y-Z represents a partial formula (1.16):

(1.16)

where the symbol "*" indicates the point of attachment of the partial formula (1.16) to the remaining portions —NH— of formula (1) and "**" indicates the point of attachment of the partial formula (1.16) to the remaining portions —$R_4$ of formula (1),
then $R_4$ cannot be:
a) a $(C_3-C_8)$cycloalkyl or
b) a $(C_1-C_6)$alkyl optionally substituted by a phenyl optionally substituted by hydroxy, fluoro, chloro, methyl and methoxy,
3) and when:
$R_1$ is selected from the group consisting of hydrogen atom and fluoro,
$R_2$ is a hydrogen atom,
X is —O—,
$R_3$ is a phenyl substituted by —S-methyl in the -3 or -4 position of said phenyl and is also optionally substituted by 1 substituent(s) selected from the group consisting of fluoro, chloro, methyl and ethyl,
Y is a partial formula (1.6):

(1.6)

where the symbol "*" indicates the point of attachment of each partial formula to the remaining portions —NH— of formula (1) and "**" indicates the point of attachment of each partial formula to the remaining portions Z of formula (1), and
Z is a radical —C(=O)—,
then $R_4$ cannot be a $(C_1-C_6)$alkyl optionally substituted by a hydroxy.

Particularly preferred examples of the nicotinamide derivatives compounds of the formula (1) are as described in the Examples section hereafter.

The nicotinamide derivatives of formula (1) may also be optionally transformed in pharmaceutically acceptable salts. In particular, these pharmaceutically acceptable salts of the nicotinamide derivatives of the formula (1) include the acid addition and the base salts thereof.

Suitable acid addition salts are formed from mineral or organic non-toxic acids which form non-toxic salts. Suitable examples of these acid addition salts are the hydrochloride, hydrobromide, hydroiodide, sulphate, bisulphate, nitrate, phosphate, hydrogen phosphate, acetate, maleate, fumarate, lactate, tartrate, citrate, gluconate, succinate, saccharate, benzoate, methanesulphonate, ethanesulphonate, benzenesulphonate, p-toluenesulphonate and pamoate salts.

Suitable base salts are formed from bases, which form non-toxic salts, such as alkali metal salts, earth metal salts or addition salts with ammonia and physiologically tolerable organic amines. Suitable examples of these base salts are the sodium, potassium, aluminium, calcium, magnesium, zinc or ammonium salts as well as addition salts with triethylamine, ethanolamine, diethanolamine, trimethylamine, methylamine, propylamine, diisopropylamine, N,N-dimethylethanolamine, benzylamine, dicylohexylamine, N-benzyl-β-phenethylamine, N,N'-dibenzylethylenediamine, diphénylènediamine, quinine, choline, arginine, lysine, leucine, dibenzylamine, tris(2-hydroxyethyl)amine, or α,α,α-tris (hydroxymethyl)methylamine.

Compounds, which contain both acidic groups and basic groups can also be present in the form of internal salts or betaines, which are also included by the present invention. For a review on suitable salts see Berge et al, J. Pharm. Sci., 66, 1–19, 1977.

Salts can generally be obtained from the nicotinamide derivatives of the formula (1) according to customary procedures known to the person skilled in the art, for example by combining with an organic or inorganic acid or base solvent or dispersant, or alternatively from other salts by anion exchange or cation exchange. The salt may precipitate from solution and be collected by filtration or may be recovered by evaporation of the solvent.

The nicotinamide derivatives of the formula (1) can also be present in stereoisomeric forms. If the nicotinamide derivatives of the formula (1) contain one or more centers of asymmetry, these can independently of one another have the (S) configuration or the (R) configuration. The invention includes all possible stereoisomers of the nicotinamide derivatives of the formula (1), for example enantiomers and diastereomers, and mixtures of two or more stereoisomeric forms, for example mixtures of enantiomers and/or diastereomers, in all ratios. The invention thus relates to enantiomers in enantiomerically pure form, both as levorotatory and dextrorotatory antipodes, in the form of racemates and in the form of mixtures of the two enantiomers in all ratios. The invention likewise relates to diastereomers in diastereomerically pure form and in the form of mixtures in all ratios. In the presence of cis/trans isomerism, the invention relates to both the cis form and the trans form and mixtures of these forms in all ratios. Individual stereoisomers can be prepared, if desired, by use of stereochemically homogeneous starting substances in the synthesis, by stereoselective synthesis or by separation of a mixture according to customary methods, for example by chromatography, crystallization or by chromatography on chiral phases. If appropriate, derivatization can be carried out before separation of stereoisomers. A stereoisomer mixture can be separated at the stage of the nicotinamide derivatives of the formula (1) or at the stage of a starting substance or of an intermediate in the course of the synthesis.

The compounds of the formula (1) according to the invention can moreover contain mobile hydrogen atoms, i.e. be present in various tautomeric forms. The present invention also relates to all tautomers of the compounds of the formula (1).

The present invention furthermore includes other types of derivatives of nicotinamide derivatives of the formula (1), for example, solvates such as hydrates and polymorphs, i.e. the various different crystalline structures of the nicotinamide derivatives according to the present invention.

The present invention also includes all suitable isotopic variations of the nicotinamide derivatives of the formula (1) or a pharmaceutically acceptable salt thereof. An isotopic variation of the nicotinamide derivatives of the formula (1) or a pharmaceutically acceptable salt thereof is defined as one in which at least one atom is replaced by an atom having the same atomic number but an atomic mass different from the atomic mass usually found in nature. Examples of isotopes that can be incorporated into the nicotinamide derivatives of the formula (1) and pharmaceutically acceptable salts thereof include isotopes of hydrogen, carbon, nitrogen, oxygen, sulphur, fluorine and chlorine such as $^2$H, $^3$H, $^{13}$C, $^{14}$C, $^{15}$N, $^{17}$O, $^{18}$O, $^{35}$S, $^{18}$F and $^{36}$Cl, respectively. Certain isotopic variations of the nicotinamide derivatives of the formula (1) and pharmaceutically acceptable salts thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of the nicotinamide derivatives of the formula (1) and pharmaceutically acceptable salts thereof of this invention can generally be prepared by conventional procedures such as by the illustrative methods or by the preparations described in the Examples and Preparations sections hereafter using appropriate isotopic variations of suitable reagents.

If appropriate, the present invention also concerns the active metabolites of the nicotinamide derivatives of the formula (1), i.e. the derivatives which are formed during the cellular metabolism and that are active on organism. For example, such metabolites can be glucuronide derivatives, N-oxide derivatives or sulfonate derivatives of the compounds of the formula (1).

According to a further aspect, the present invention concerns mixtures of nicotinamide derivatives of the formula (1), as well as mixtures with or of their pharmaceutically acceptable salts, solvates, polymorphs, isomeric forms, metabolites and/or isotope forms.

According to the present invention, all the here above mentioned forms of the nicotinamide derivatives of formula (1) except the pharmaceutically acceptable salts (i.e. said solvates, polymorphs, isomeric forms, metabolites and isotope forms), are defined as "derived forms" of the nicotinamide derivatives of formula (1) in what follows.

The nicotinamide derivatives of formula (1), their pharmaceutically acceptable salts and/or derived forms, are valuable pharmaceutical active compounds, which are suitable for the therapy and prophylaxis of numerous disorders in which the PDE4 enzymes are involved, in particular the inflammatory disorders, allergic disorders, respiratory diseases and wounds. The nicotinamide derivatives of formula (1) and their pharmaceutically acceptable salts and derived forms as mentioned above can be administered according to the invention to animals, preferably to mammals, and in particular to humans, as pharmaceuticals for therapy or prophylaxis. They can be administered per se, in mixtures with one another or in the form of pharmaceutical preparations which permit enteral (gastric) or parenteral (non-gastric) administration and which as active constituent contain an efficacious dose of at least one nicotinamide derivative of the formula (1), its pharmaceutically acceptable salts and/or derived forms, in addition to customary pharmaceutically innocuous excipients and/or additives.

Thus, the present invention also relates to pharmaceutical compositions containing an efficacious dose of at least one nicotinamide derivative of formula (1) and/or their pharmaceutically acceptable salts and/or derived forms, in addition to customary pharmaceutically innocuous excipients and/or additives. Such compositions are prepared according to well-known methods compatible with the standard pharmaceutical practice. Said composition generally contain from 0.5% to 60% in weight of the active compound and from 40% to 99.5% in weight of excipients and/or additives. According to the present invention, said excipients and/or additives are agents well known to the artisan for providing favourable properties in the final pharmaceutical composition. Typical excipients and/or additives include, but are by no mean limited to, acidifying and alkalizing agents, aerosol propellants, anti-microbial agents (including anti-bacterial, anti-fungal and anti-protozoal agents), antioxidants, buffering agents, chelating agents, dermatologically active agents, dispersing agents, suspending agents, emollients, emulsifying agents, penetration enhancers, preservatives, sequestering agents, solvents, stabilizers, stiffening agents, sugars, surfactants and flavouring agents. Furthermore, said compositions are prepared in a form compatible for the intended route of administration, which is used for any given patient, as well as appropriate to the disease, disorder or condition for which any given patient is being treated. Suitable routes of administration that can be envisaged are enteral and parenteral routes of adiministration, such as for example the topical, oral, intranasal, pulmonary, rectal, intra-veinous, intra-arterial, intra-peritoneal, intra-thecal, intra-ventricular, intra-urethral, intra-sternal, intra-cranial, intra-muscular, subcutaneous or ocular routes.

When an administration by the oral route is intended, the nicotinamide derivatives of formula (1), their pharmaceutically acceptable salts and/or their derived forms, can be administered in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The nicotinamide derivatives of formula (1), their pharmaceutically acceptable salts and/or their derived forms, may also be administered as fast-dispersing or fast-dissolving dosage forms or in the form of a high energy dispersion or as coated particles. Suitable formulations of the nicotinamide derivatives of formula (1), their pharmaceutically acceptable salts and/or their derived forms, may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

As a general example, a formulation of the tablet could typically contain between about 0.01 mg and 500 mg of active compound whilst tablet fill weights may range from 50 mg to 1000 mg. The tablets may be manufactured by a standard process, for example direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the nicotinamide derivatives of the formula (1), their pharmaceutically acceptable salts and/or their derived forms, may be combined with various sweetening or flavouring agents, colouring matter or dyes, with emulsifying and/or suspending agents and with diluents such as water, ethanol, propylene glycol and glycerin, and combinations thereof.

The nicotinamide derivatives of the formula (1), their pharmaceutically acceptable salts and/or their derived forms, can also be administered by injection, for example, intravenously, intra-arterially, intraperitoneally, intrathecally, intraventricularly, intraurethrally, intrasternally, intracranially, intramuscularly or subcutaneously, or they may be administered by infusion or needleless injection techniques. For such administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of such formulations under sterile conditions is readily accomplished by standard pharmaceutical techniques well-known to those skilled in the art.

For both oral administration and injection to human patients, the daily dosage level of the nicotinamide derivatives of the formula (1), their pharmaceutically acceptable salts and/or their derived forms, will usually be from 0.001 mg/kg to 100 mg/kg (in single or divided doses).

The nicotinamide derivatives of the formula (1), their pharmaceutically acceptable salts and/or their derived forms, can also be administered intra-nasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a nicotinamide derivative of the formula (1) and a suitable powder base such as lactose or starch.

Aerosol or dry powder formulations are preferably arranged so that each metered dose or "puff" contains from 1 µg to 4000 µg of a nicotinamide derivative of the formula (1) for delivery to the patient. The overall daily dose with an aerosol will be in the range of from 1 µg to 20 mg, which may be administered in a single dose or, more usually, in divided doses throughout the day.

The nicotinamide derivatives of the formula (1), their pharmaceutically acceptable salts and/or their derived forms, can also be administered topically, or transdermally, in the form of creams, gels, suspensions, lotions, ointments, dusting powders, sprays, foams, mousses, drug-incorporated dressings, solutions, sponges, fibres, microemulsions, films, skin patches, ointments such as petrolatum or white soft paraffin based ointments or via a skin patch or other device. Penetration enhancers may be used, and the compound may be used in combination with cyclodextrins. In addition, the compound may be delivered using iontophoresis, electropration, phonophoresis or sonophoresis. They could be administered directly onto a wound site. They could be incorporated into a coated suture. For example they can be incorporated into a lotion or cream consisting of an aqueous or oily emulsion of mineral oils, sorbitan monostearate, polysorbate 60, cetyl esters wax, cetearyl alcohol, 2-octyldodecanol, benzyl alcohol, water, polyethylene glycols and/or liquid paraffin, or they can be incorporated into a suitable ointment consisting of one or more of the following: mineral oil, liquid petrolatum, white petrolatum, propylene glycol, polyoxyethylene polyoxypropylene compound, emulsifying wax and water, or as hydrogel with cellulose or polyacrylate derivatives or other viscosity modifiers, or as a dry powder or liquid spray or aerosol with butane/propane, HFA, CFC, CO2 or other suitable propellant, optionally also including a lubricant such as sorbitan trioleate, or as a drug-incorporated dressing either as a tulle dressing, with white soft paraffin or polyethylene glycols impregnated gauze dressings or with hydrogel, hydrocolloid, alginate or film dressings.

For topical administration to human patients with acute/surgical wounds or scars, the daily dosage level of the compounds, in suspension or other formulation, could be from 0.01 to 50 mg/ml, preferably from 0.3 to 30 mg/ml. The dosage will vary with the size of the wound, whether or not the wound is open or closed or partially closed, and whether or not the skin is intact.

Alternatively, the nicotinamide derivatives of the formula (1), their pharmaceutically acceptable salts and/or their derived forms, can be rectally administered, for example in the form of a suppository of a gel, although other forms can be considered.

They may also be administered via the ocular route, in particular for ocular scarring. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

The various pharmaceutical formulations as decribed here above are also detailed in "Pharmacie galénique" from A. Lehir (Ed. Mason, 1992, $2^{nd}$ edition).

The physician in any event will determine the actual dosage which will be most suitable for any individual patient and it will vary with the age, weight, health state and sex of the patient as well as the severity of the disease, disorder or condition to treat, the optional combination with other treatment(s), the response of the particular patient and in general any factor peculiar to the concerned disease, disorder or condition and to the patient. Thus, the daily dose among men may usually contain from 50 mg to 5 g of active compound for administration singly or two or more at a time, as appropriate. There can, of course, be individual instances where higher or lower dosage ranges are merited and such are within the scope of this invention.

According to the present invention, the nicotinamide derivatives of the formula (1), their pharmaceutically acceptable salts and/or their derived forms, may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. α-, β- and γ-cyclodextrins are most commonly used and suitable examples are described in WO-A-91/11172, WO-A-94/02518 and WO-A-98/55148.

According to another embodiment of the present invention, the nicotinamide derivatives of the formula (1), their pharmaceutically acceptable salts and/or their derived forms, can also be used as a combination with one or more additional therapeutic agents to be co-administered to a patient to obtain some particularly desired therapeutic end result. The second and more additional therapeutic agents may also be a nicotinamide derivatives of the formula (1), their pharmaceutically acceptable salts and/or their derived forms, or one or more PDE4 inhibitors known in the art. More typically, the second and more therapeutic agents will be selected from a different class of therapeutic agents.

As used herein, the terms "co-administration", "co-administered" and "in combination with", referring to the nicotinamide derivatives of formula (1) and one or more other therapeutic agents, is intended to mean, and does refer to and include the following:

simultaneous administration of such combination of nicotinamide derivative(s) and therapeutic agent(s) to a patient in need of treatment, when such components are formulated together into a single dosage form which releases said components at substantially the same time to said patient, substantially simultaneous administration of such combination of nicotinamide derivative(s) and therapeutic agent(s) to a patient in need of treatment, when such components are formulated apart from each other into separate dosage forms which are taken at substantially the same time by said patient, whereupon said components are released at substantially the same time to said patient, sequential administration of such combination of nicotinamide derivative(s) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of nicotinamide derivative(s) and therapeutic agent(s) to a patient in need of treatment, when such components are formulated together into a single dosage form which releases said components in a controlled manner whereupon they are concurrently, consecutively, and/or overlappingly administered at the same and/or different times by said patient.

Suitable examples of other therapeutic agents which may be used in combination with the nicotinamide derivatives of the formula (1), their pharmaceutically acceptable salts and/or their derived forms include, but are by no mean limited to:
(a) 5-Lipoxygenase (5-LO) inhibitors or 5-lipoxygenase activating protein (FLAP) antagonists,
(b) Leukotriene antagonists (LTRAs) including antagonists of $LTB_4$, $LTC_4$, $LTD_4$, and $LTE_4$,
(c) Histaminic receptor antagonists including H1 and H3 antagonists,
(d) $\alpha_1$- and $\alpha_2$-adrenoceptor agonist vasoconstrictor sympathomimetic agents for decongestant use,
(e) Muscarinic M3 receptor antagonists or anticholinergic agents,
(f) $\beta_2$-adrenoceptor agonists,
(g) Theophylline,
(h) Sodium cromoglycate,
(i) COX-1 inhibitors (NSAIDs) and COX-2 selective inhibitors,
(j) Oral or inhaled Glucocorticosteroids,
(k) Monoclonal antibodies active against endogenous inflammatory entities,
(l) Anti-tumor necrosis factor (anti-TNF-α) agents,
(m) Adhesion molecule inhibitors including VLA-4 antagonists,
(n) Kinin-$B_1$- and $B_2$-receptor antagonists,
(o) Immunosuppressive agents,
(p) Inhibitors of matrix metalloproteases (MMPs), (q) Tachykinin $NK_1$, $NK_2$ and $NK_3$ receptor antagonists,
(r) Elastase inhibitors,
(s) Adenosine A2a receptor agonists,
(t) Inhibitors of urokinase,
(u) Compounds that act on dopamine receptors, e.g. D2 agonists and
(v) Modulators of the NFκ☐ pathway, e.g. IKK inhibitors.

According to the present invention, combination of the nicotinamide derivatives of formula (1) with:

muscarinic M3 receptor agonists or anticholinergic agents including in particular ipratropium salts, namely bromide, tiotropium salts, namely bromide, oxitropium salts, namely bromide, perenzepine, and telenzepine, $β_2$-adrenoceptor agonists including albutarol, salbutamol, formoterol and salmeterol, glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, and mometasone furoate, or adenosine A2a receptor agonists, are preferred.

It is to be appreciated that all references herein to treatment include curative, palliative and prophylactic treatment. The description which follows concerns the therapeutic applications to which the nicotinamide derivatives of formula (1) may be put.

The nicotinamide derivatives of formula (1) inhibit the PDE4 isozyme and thereby have a wide range of therapeutic applications, as described further below, because of the essential role, which the PDE4 family of isozymes plays in the physiology of all mammals. The enzymatic role performed by the PDE4 isozymes is the intracellular hydrolysis of adenosine 3',5'-monophosphate (cAMP) within pro-inflammatory leukocytes. cAMP, in turn, is responsible for mediating the effects of numerous hormones in the body, and as a consequence, PDE4 inhibition plays a significant role in a variety of physiological processes. There is extensive literature in the art describing the effects of PDE inhibitors on various inflammatory cell responses, which in addition to cAMP increase, include inhibition of superoxide production, degranulation, chemotaxis and tumor necrosis factor (TNF) release in eosinophils, neutrophils and monocytes.

Therefore, a further aspect of the present invention relates to the use of the nicotinamide derivatives of formula (1), their pharmaceutically acceptable salts and/or derived forms, in the treatment of diseases, disorders, and conditions in which the PDE4 isozymes are involved. More specifically, the present invention also concerns the use of the nicotinamide derivatives of formula (1), their pharmaceutically acceptable salts and/or derived forms, in the treatment of diseases, disorders, and conditions selected from the group consisting of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma and wheezy infant syndrome, chronic or acute bronchoconstriction, chronic bronchitis, small airways obstruction, and emphysema, obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated therewith, COPD that is characterized by irreversible, progressive airways obstruction, adult respiratory distress syndrome (ARDS) and exacerbation of airways hyperreactivity consequent to other drug therapy, pneumoconiosis of whatever type, etiology, or pathogenesis, in particular pneumoconiosis that is a member selected from the group consisting of aluminosis or bauxite workers' disease, anthracosis or miners' asthma, asbestosis or steam-fitters' asthma, chalicosis or flint disease, ptilosis caused by inhaling the dust from ostrich feathers, siderosis caused by the inhalation of iron particles, silicosis or grinders' disease, byssinosis or cotton-dust asthma and talc pneumoconiosis;

bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, *staphylococcus* or streptococcal bronchitis and vesicular bronchitis, bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis, seasonal allergic rhinitis or perennial allergic rhinitis or sinusitis of whatever type, etiology, or pathogenesis, in particular sinusitis that is a member selected from the group consisting of purulent or nonpurulent sinusitis, acute or chronic sinusitis and ethmoid, frontal, maxillary, or sphenoid sinusitis, rheumatoid arthritis of whatever type, etiology, or pathogenesis, in particular rheumatoid arthritis that is a member selected from the group consisting of acute arthritis, acute gouty arthritis, chronic inflammatory arthritis, degenerative arthritis, infectious arthritis, Lyme arthritis, proliferative arthritis, psoriatic arthritis and vertebral arthritis, gout, and fever and pain associated with inflammation, an eosinophil-related disorder of whatever type, etiology, or pathogenesis, in particular an eosinophil-related disorder that is a member selected from the group consisting of eosinophilia, pulmonary infiltration eosinophilia, Loffler's syndrome, chronic eosinophilic pneumonia, tropical pulmonary eosinophilia, bronchopneumonic aspergillosis, aspergilloma, granulomas containing eosinophils, allergic granulomatous angiitis or Churg-Strauss syndrome, polyarteritis nodosa (PAN) and systemic necrotizing vasculitis, atopic dermatitis, allergic dermatitis, contact dermatitis, or allergic or atopic eczema, urticaria of whatever type, etiology, or pathogenesis, in particular urticaria that is a member selected from the group consisting of immune-mediated urticaria, complement-mediated urticaria, urticariogenic material-induced urticaria, physical agent-induced urticaria, stress-induced urticaria, idiopathic urticaria; acute urticaria, chronic urticaria, angioedema, cholinergic urticaria, cold urticaria in the autosomal dominant form or in the acquired form, contact urticaria, giant urticaria and papular urticaria, conjunctivitis of whatever type, etiology, or pathogenesis, in particular conjunctivitis that is a member selected from the group consisting of actinic conjunctivitis, acute catarrhal conjunctivitis, acute contagious conjunctivitis, allergic conjunctivitis, atopic conjunctivitis, chronic catarrhal conjunctivitis, purulent conjunctivitis and vernal conjunctivitis, uveitis of whatever type, etiology, or pathogenesis, in particular uveitis that is a member selected from the group consisting of inflammation of all or part of the uvea, anterior uveitis, iritis, cyclitis, iridocyclitis, granulomatous uveitis, nongranulomatous uveitis, phacoantigenic uveitis, posterior uveitis, choroiditis; and chorioretinitis, psoriasis;

multiple sclerosis of whatever type, etiology, or pathogenesis, in particular multiple sclerosis that is a member selected from the group consisting of primary progressive multiple sclerosis and relapsing remitting multiple sclerosis, autoimmune/inflammatory diseases of whatever type, etiology, or pathogenesis, in particular an autoimmune/inflammatory disease that is a member selected from the group consisting of autoimmune hematological disorders, hemolytic anemia, aplastic anemia, pure red cell anemia, idiopathic thrombocytopenic purpura, systemic lupus erythematosus, polychondritis, scleroderma, Wegner's granulomatosis, dermatomyositis, chronic active hepatitis, myasthenia gravis, Stevens-Johnson syndrome, idiopathic sprue, autoimmune inflammatory bowel diseases, ulcerative colitis, endocrin opthamopathy, Grave's disease, sarcoidosis, alveolitis, chronic hypersensitivity pneumonitis, primary biliary cirrhosis, juvenile diabetes or diabetes mellitus type I, keratoconjunctivitis sicca, epidemic keratoconjunctivitis, diffuse interstitial pulmonary fibrosis or interstitial lung fibrosis, idiopathic pulmonary fibrosis, cystic fibrosis, glomerulonephritis with and without nephrotic syndrome, acute glomerulonephritis, idiopathic nephrotic syndrome, minimal change nephropathy, inflammatory/hyperproliferative skin diseases, benign familial pemphigus, pemphigus erythematosus, pemphigus foliaceus, and pemphigus vulgaris, prevention of allogeneic graft rejection following organ transplantation, inflammatory bowel disease (IBD) of whatever type, etiology, or pathogenesis, in particular inflammatory bowel disease that is a member selected from the group consisting of collagenous colitis, colitis polyposa, transmural colitis, ulcerative colitis and Crohn's disease (CD), septic shock of whatever type, etiology, or pathogenesis, in particular septic shock that is a member selected from the group consisting of renal failure, acute renal failure, cachexia, malarial cachexia, hypophysial cachexia, uremic cachexia, cardiac cachexia, cachexia suprarenalis or Addison's disease, cancerous cachexia and cachexia as a consequence of infection by the human immunodeficiency virus (HIV), liver injury, pulmonary hypertension of whatever type, etiology or pathogenesis including primary pulmonary hypertension/essential hypertension, pulmonary hypertension secondary to congestive heart failure, pulmonary hypertension secondary to chronic obstructive pulmonary disease, pulmonary venous hypertension, pulmonary arterial hypertension and hypoxia-induced pulmonary hypertension, bone loss diseases, primary osteoporosis and secondary osteoporosis, central nervous system disorders of whatever type, etiology, or pathogenesis, in particular a central nervous system disorder that is a member selected from the group consisting of depression, Alzheimers disease, Parkinson's disease, learning and memory impairment, tardive dyskinesia, drug dependence, arteriosclerotic dementia and dementias that accompany Huntington's chorea, Wilson's disease, paralysis agitans, and thalamic atrophies, infection, especially infection by viruses wherein such viruses increase the production of TNF-α in their host, or wherein such viruses are sensitive to upregulation of TNF-α in their host so that their replication or other vital activities are adversely impacted, including a virus which is a member selected from the group consisting of HIV-1, HIV-2, and HIV-3, cytomegalovirus (CMV), influenza, adenoviruses and Herpes viruses including Herpes zoster and Herpes simplex, yeast and fungus infections wherein said yeast and fungi are sensitive to upregulation by TNF-α or elicit TNF-α production in their host, e.g., fungal meningitis, particularly when administered in conjunction with other drugs of choice for the treatment of systemic yeast and fungus infections, including but are not limited to, polymixins, e.g. Polymycin B, imidazoles, e.g. clotrimazole, econazole, miconazole, and ketoconazole, triazoles, e.g. fluconazole and itranazole as well as amphotericins, e.g. Amphotericin B and liposomal Amphotericin B, ischemia-reperfusion injury, ischemic heart disease, autoimmune diabetes, retinal autoimmunity, chronic lymphocytic leukemia, HIV infections, lupus erythematosus, kidney and ureter disease, urogenital and gastrointestinal disorders and prostate diseases, reduction of scar formation in the human or animal body, such as scar formation in the healing of acute wounds, and psoriasis, other dermatological and cosmetic uses, including antiphlogistic, skin-softening, skin elasticity and moisture-increasing activities.

A still further aspect of the present invention also relates to the use of the nicotinamide derivatives of formula (1), their pharmaceutically acceptable salts and/or derived forms, for the manufacture of a drug having a PDE4 inhibitory activity. In particular, the present inventions concerns the use of the nicotinamide derivatives of formula (1), their pharmaceutically acceptable salts and/or derived forms, for the manufacture of a drug for the treatment of inflammatory, respiratory, allergic and scar-forming diseases, disorders, and conditions, and more precisely for the treatment of diseases, disorders, and conditions that are listed above.

As a consequence, the present invention provides a particularly interesting method of treatment of a mammal, including a human being, with a PDE4 inhibitor including treating said mammal with an effective amount of a nicotinamide derivative of formula (1), its pharmaceutically acceptable salts and/or derived forms. More precisely, the present invention provides a particularly interesting method of treatment of a mammal, including a human being, to treat an inflammatory, respiratory, allergic and scar-forming disease, disorder or condition, including treating said mammal with an effective amount of a nicotinamide derivative of formula (1), its pharmaceutically acceptable salts and/or derived forms.

The following examples illustrate the preparation of the nicotinamide derivatives of the formula (1):

EXAMPLES

Example 1 anti-2-(Benzo[1,3]dioxol-5-yloxy)-N-[4-(2-hydroxy-benzoyl amino)-cyclohexyl]-nicotinamide

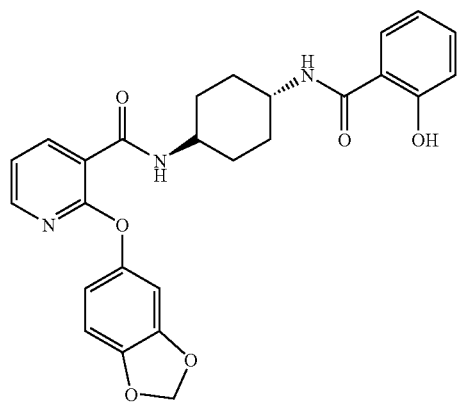

2-Hydroxybenzoic acid (101 mg, 0.767 mmol), 1-hydroxybenzotriazole hydrate (155 mg, 1.15 mmol) and 1-(3-dimethylaminopropyl)-3-ethylcarbodiimide hydrochloride (220 mg, 1.15 mmol) were stirred in N,N-dimethylformamide (5 ml) under an atmosphere of nitrogen at room temperature for 1.5 hours. Anti-N-(4-Amino-cyclohexyl)-2-(benzo[1,3]dioxol-5-yloxy)-nicotinamide hydrochloride (0.3 g, 0.767 mmol) (see Preparation 2) and N-methyl morpholine (0.167 ml, 0.767 mmol) were then added, and the reaction mixture stirred at room temperature for a further 18 hours. The mixture was then partitioned between dichloromethane (10 ml) and 10% citric acid (10 ml). The organic layer was separated and passed through a hydrophobic frit. The solvent was removed in vacuo, and the residue was triturated with methanol (5 ml) to give anti-2-(benzo[1,3]dioxol-5-yloxy)-N-[4-(2-hydroxy-benzoylamino)-cyclohexyl]-nicotinamide (160.7 mg) as a white solid.

$^1$H NMR (400 MHz, CDCl$_3$): $\square$=12.30 (1H, s), 8.57–8.61 (1H, d), 8.01–8.05 (1H, d), 7.74–7.79 (1H, d), 7.33–7.40 (1H, d), 7.12–7.17 (1H, m), 6.93–6.99 (1H, d), 6.78–6.84 (2H, m), 6.69–6.70 (1H, d), 6.59–6.63 (1H, d), 6.19–6.23 (1H, d), 6.02 (2H, s), 3.96–4.09 (2H, m), 2.14–2.26 (4H, m), 1.39–1.50 (4H, m) ppm. LRMS (thermospray): m/z [M+H]$^+$ 476.

Examples 2–10

The compounds of the following tabulated examples (Table 1) of the general formula:

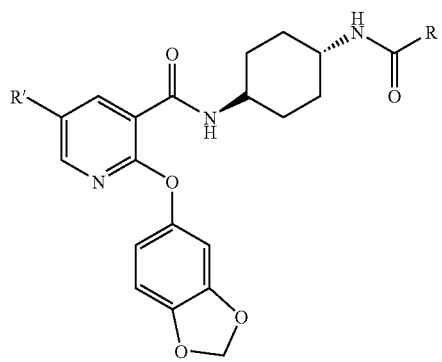

were prepared by a similar method to that of Example 1 using the appropriate carboxylic acid and amine as the starting materials.

TABLE 1

| Example No. | Starting Amine Prep No. | R' | R |
|---|---|---|---|
| 2 | 2 | H | ![4-methyl-2-hydroxyphenyl] Me, OH |
| 3 | 2 | H | ![3-methyl-2-hydroxyphenyl] Me, OH |
| 4 | 2 | H | ![3-hydroxynaphthyl] OH |
| 5[1] | 39 | F | ![2-fluoro-6-hydroxyphenyl] F, OH |
| 6[1] | 39 | F | ![4-hydroxyphenyl] OH |

TABLE 1-continued

| Example No. | Starting Amine Prep No. | R' | R |
|---|---|---|---|
| 7[1] | 39 | F | 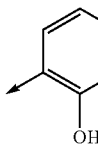 |
| 8[1] | 39 | F | 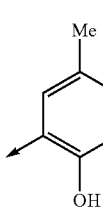 |
| 9[1] | 39 | F | 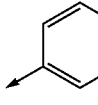 |
| 10[1] | 39 | F | 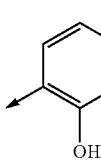 |

[1]These examples were purified by flash column chromatography on silica gel eluting with a solvent mixture of dichloromethane:pentane (1:1, by volume) changing to dichloromethane:methanol (50:1, by volume) prior to trituration with diethylether.

Example 2

$^1$H NMR (400 MHz, CDCl$_3$): δ=12.08 (1H, s), 8.57–8.61 (1H, d), 8.20–8.24 (1H, d), 7.74–7.79 (1H, d), 7.10–7.20 (3H, m), 6.81–6.89 (2H, m), 6.69 (1H, s), 6.59–6.63 (1H, d), 6.13–6.18 (1H, d), 6.02 (2H, s), 3.96–4.09 (2H, m), 2.31 (3H, s); 2.09–2.29 (4H, m), 1.39–1.53 (4H, m) ppm. LRMS (electrospray): m/z [M+H]$^+$ 490

Example 3

$^1$H NMR (400 MHz, CDCl$_3$): δ=12.23 (1H, s), 8.73–8.78 (1H, d), 8.18–8.22 (1H, d), 7.67–7.76 (1H, d), 7.14–7.20 (1H, d), 7.05–7.12 (1H, m), 6.79–6.82 (1H, d), 6.77 (1H, s), 6.64 (1H, s), 6.56–6.62 (2H, m), 6.00–6.04 (1H, d), 5.99 (2H, s), 3.90–4.05 (2H, m), 2.30 (3H, s); 2.05–2.22 (4H, m), 1.36–1.49 (4H, m) ppm. LRMS (electrospray): m/z [M+H]$^+$ 490

Example 4

$^1$H NMR (400 MHz, CDCl$_3$): δ=11.68 (1H, s), 8.53–8.58 (1H, d), 8.17–8.19 (1H, d), 7.93 (1H, s), 7.70–7.78 (2H, m), 7.62–7.66 (1H, d), 7.38–7.44 (1H, t), 7.23–7.28 (2H, m), 7.03–7.08 (1H, m), 6.79–6.83 (1H, d), 6.64 (1H, s), 6.52–6.60 (2H, m), 6.00 (2H, s), 3.97–4.05 (2H, m), 2.17–2.23 (4H, brt), 1.39–1.58 (4H, m) ppm. LRMS (thermospray): m/z [M+H]$^+$ 526

Example 5

$^1$H NMR (400 MHz, CDCl$_3$): δ=13.24 (1H, s), 8.34–8.38 (1H, m), 8.05–8.07 (1H, d), 7.73–7.99 (1H, d), 7.25–7.32 (1H, m, partially masked by solvent), 6.88–6.96 (1H, m), 6.83–6.87 (1H, d), 6.76–6.81 (1H, d), 6.66 (1H, s), 6.53–6.63 (2H, m), 6.03 (2H, s), 3.95–4.15 (2H, m), 2.12–2.26 (4H, m), 1.39–1.54 (4H, m) ppm. LCMS (electrospray): m/z [M−H]$^+$ 510

Example 6

$^1$H NMR (400 MHz, CDCl$_3$): δ=8.28–8.35 (1H, m), 8.03–8.08 (1H, d), 7.73–7.84 (1H, d), 7.57–7.71 (2H, d), 6.76–6.91 (3H, m), 6.67 (1H, s), 6.57–6.62 (1H, d), 6.16 (1H, s), 6.02 (2H, s), 5.83–5.92 (1H, d), 3.90–4.08 (2H, m), 2.08–2.23 (4H, m), 1.35–1.50 (4H, m) ppm. LCMS (electrospray): m/z [M−H]$^+$ 492

Example 7

$^1$H NMR (400 MHz, CDCl$_3$): δ=8.30–8.36 (1H, m), 8.04–8.08 (1H, d), 7.73–7.82 (1H, d), 7.29–7.41 (2H, m), 6.93–6.98 (1H, d), 6.79–6.87 (2H, m), 6.66 (1H, s), 6.57–6.63 (1H, d), 6.11–6.20 (1H, d), 6.03 (2H, s), 3.93–4.10 (2H, m), 2.10–2.29 (4H, m), 1.39–1.57 (4H, m) ppm. LRMS (electrospray): m/z [M−H]$^+$ 492

Example 8

$^1$H NMR (400 MHz, CDCl$_3$): δ=8.27–8.36 (1H, m), 8.01–8.07 (1H, m), 7.73–7.82 (1H, m), 7.15–7.22 (1H, m), 6.78–6.90 (2H, m), 6.63–6.67 (1H, m), 6.54–6.62 (1H, m), 6.05–6.15 (1H, m), 6.02 (2H, s), 3.88–4.09 (2H, m), 2.29 (3H, s), 2.09–2.26 (4H, m), 1.37–1.49 (4H, m) ppm. LRMS (electrospray): m/z [M−H]$^+$ 506

Example 9

$^1$H NMR (400 MHz, CDCl$_3$): δ=8.03–8.09 (1H, d), 7.93–7.99 (1H, m), 7.17–7.27 (3H, m), 6.87–6.93 (1H, m), 6.77–6.84 (1H, d), 6.70–6.73 (1H, d), 6.57–6.62 (1H, d), 5.97 (2H, s), 3.80–3.98 (2H, m), 1.96–2.18 (4H, m), 1.41–1.63 (4H, m) ppm. LRMS (electrospray): m/z [M−H]$^+$ 492

Example 10

$^1$H NMR (400 MHz, CDCl$_3$): δ=12.26 (1H, s), 8.30–8.36 (1H, m), 8.04–8.07 (1H, d), 7.74–7.82 (1H, d), 7.17–7.22 (1H, d), 6.83–6.86 (1H, d), 6.77 (1H, s), 6.55–6.67 (3H, m), 6.03–6.12 (1H, d), 6.02 (2H, s), 3.92–4.08 (2H, m), 2.33 (3H, s), 2.12–2.25 (4H, m), 1.36–1.51 (4H, m) ppm. LRMS (electrospray): m/z [M−H]$^+$ 506

Example 11 anti-N-[4-(2-fluoro-6-hydroxy-benzoylamino)-cyclohexyl]-2-(4-fluoro-phenoxy)-nicotinamide

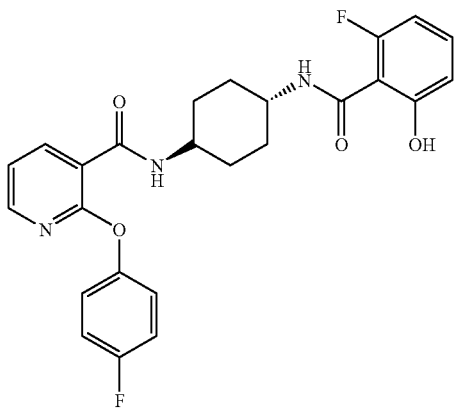

2-Fluoro-6-hydroxybenzoic acid (128 mg, 0.82 mmol), 1-hydroxybenzotriazole (166 mg, 1.23 mmol), 1-(3-dimethylaminopropyl)-3-ethylcarbodiimide hydrochloride (204 mg, 1.07 mmol), anti-N-(4-amino-cyclohexyl)-2-(4-fluoro-phenoxy)-nicotinamide hydrochloride (300 mg, 0.82 mmol) (see Preparation 4) and N-methyl morpholine (0.18 ml, 1.64 mmol) were stirred in N,N-dimethylformamide (5 ml) under at atmosphere of nitrogen at room temperature for 18 hours. The mixture was then partitioned between dichloromethane (6 ml) and 10% acetic acid (6 ml) and the organic layer separated. The organic layer was dried over anhydrous magnesium sulphate and concentrated in vacuo. The residue was triturated with diethylether (5 ml) to give anti-N-[4-(2-fluoro-6-hydroxy-benzoylamino)-cyclohexyl]-2-(4-fluoro-phenoxy)-nicotinamide (110 mg) as a white solid.

$^1$H NMR (400 MHz, DMSO-d$^6$): ☐=10.95 (1H, brs), 8.23–8.28 (1H, d), 8.19–8.22 (1H, d), 8.04–8.18 (1H, m), 7.98–8.03 (1H, d), 7.15–7.28 (5H, m), 6.60–6.75 (2H, m), 3.70–3.80 (2H, m), 1.80–2.00 (4H, m), 1.31–1.49 (4H, m) ppm. LRMS (thermospray): m/z [M+H]$^+$ 468

Examples 12–40

The compounds of the following tabulated examples (Table 2) of the general formula:

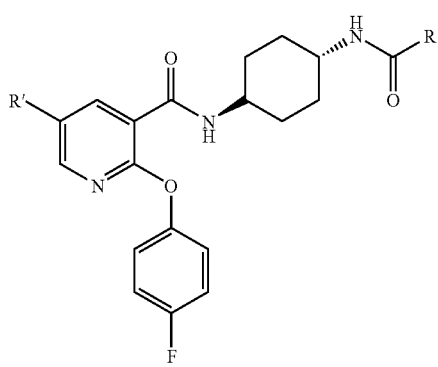

were prepared by a similar method to that of Example 11 using the appropriate carboxylic acid and amine as the starting materials.

TABLE 2

| Example No. | Starting Amine Prep No. | R' | R |
|---|---|---|---|
| 12 | 4 | H | 2-hydroxyphenyl |
| 13 | 4 | H | 4-methyl-2-hydroxyphenyl |
| 14 | 4 | H | 4-methyl-2-hydroxyphenyl (alt) |
| 15[1] | 7 | F | 2-hydroxyphenyl |
| 16[1] | 7 | F | 4-methyl-2-hydroxyphenyl |
| 17[1] | 7 | F | 2-fluoro-6-hydroxyphenyl |
| 18[1] | 7 | F | 4-fluoro-2-hydroxyphenyl |
| 19[1,2] | 7 | F | 2-hydroxybenzyl |

TABLE 2-continued
| Example No. | Starting Amine Prep No. | R' | R |
|---|---|---|---|
| 20[1] | 7 | F | 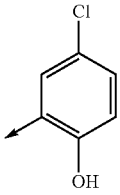 |
| 21[1] | 7 | F | 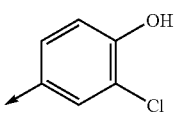 |
| 22[1] | 7 | F | 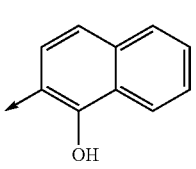 |
| 23[1] | 7 | F | 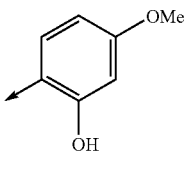 |
| 24[1] | 7 | F | 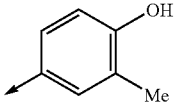 |
| 25[1] | 7 | F | 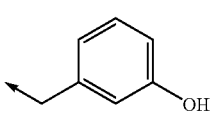 |
| 26[1] | 7 | F | 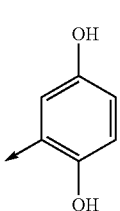 |
| 27[1] | 7 | F | 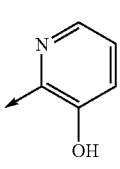 |
| 28[1] | 7 | F | 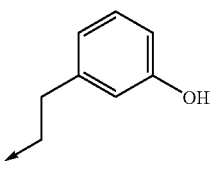 |
| 29[1] | 7 | F | 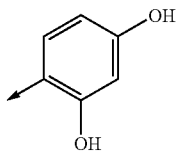 |
| 30[1] | 7 | F | 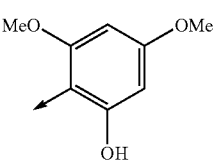 |
| 31[1] | 7 | F | 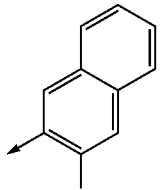 |
| 32[1] | 7 | F | 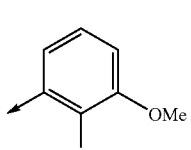 |
| 33[1] | 7 | F | 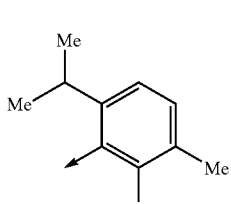 |
| 34[1] | 7 | F | 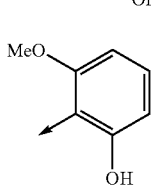 |
| 35[1] | 7 | F | 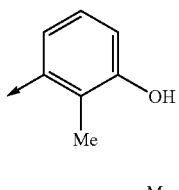 |
| 36[1] | 7 | F | 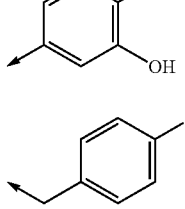 |
| 37[1] | 7 | F |  |

TABLE 2-continued

| Example No. | Starting Amine Prep No. | R' | R |
|---|---|---|---|
| 38[1] | 7 | F | 4-OMe, 3-OH phenyl (methylene linker) |
| 39[1] | 9 | F | 4-hydroxyphenyl-CH2-C(O)-NH-CH2- |
| 40[1] | 9 | F | 2-hydroxyphenyl-CH2-C(O)-NH-CH2- |

[1]These examples were partitioned between ethyl acetate and water, and the organic phase was washed with a saturated aqueous solution of sodium chloride.
[2]These examples were purified by flash column chromatography on silica gel eluting with a solvent gradient of dichloromethane methanol (100:0 changing to 95:5, by volume) to give the final compound.

Example 12

$^1$H NMR (400 MHz, CDCl$_3$): □=12.29 (1H, s), 8.56–8.60 (1H, d), 8.18–8.21 (1H, d), 7.66–7.72 (1H, d), 7.36–7.40 (2H, m), 7.12–7.18 (4H, d), 6.96–6.99 (1H, d), 6.78–6.83 (1H, d), 6.17–6.22 (1H, d), 3.96–4.12 (2H, m), 2.12–2.29 (4H, m), 1.40–1.53 (4H, m) ppm. LRMS (thermospray): m/z [M+H]$^+$ 450

Example 13

$^1$H NMR (400 MHz, CDCl$_3$): □=12.05 (1H, s), 8.58–8.62 (1H, d), 8.18–8.22 (1H, d), 7.68–7.75 (1H, d), 7.09–7.20 (6H, m), 6.83–6.88 (1H, d), 6.15–6.19 (1H, d), 3.94–4.11 (2H, m), 2.29 (3H, s), 2.13–2.24 (4H, m), 1.40–1.55 (4H, m) ppm. LRMS (thermospray): m/z [M+H]$^+$ 464

Example 14

$^1$H NMR (400 MHz, DMSO-d$^6$): □=12.26 (1H, s), 8.58–8.62 (1H, d), 8.18–8.22 (1H, m), 7.68–7.73 (1H, d), 7.20–7.24 (1H, d), 7.10–7.19 (4H, m), 6.78 (1H, s), 6.61–6.67 (2H, d), 6.04–6.10 (2H, d), 3.92–4.10 (2H, m), 2.32 (3H, s), 2.15–2.23 (4H, m), 1.40–1.55 (4H, m) ppm. LRMS (thermospray): m/z [M+H]$^+$ 464 Found C, 67.14; H, 5.62; N, 8.82. C$_{26}$H$_{26}$FN$_3$O$_4$ requires C, 67.37; H, 5.65; N, 9.07%.

Example 15

$^1$H NMR (300 MHz, DMSO-d$^6$): □=12.55 (1H, s), 8.43–8.49 (1H, d), 8.24–8.30 (1H, d), 8.08–8.14 (1H, d), 7.84–7.90 (1H, d), 7.22–7.35 (1H, t), 7.08–7.20 (4H, m), 6.74–6.83 (2H, d), 3.60–3.80 (2H, m), 1.76–1.90 (4H, m), 1.20–1.50 (4H, m) ppm. LRMS (electrospray): m/z [M−H]$^+$ 466

Example 16

$^1$H NMR (300 MHz, DMSO-d$^6$): □=12.28 (1H, s), 8.50–8.57 (1H, m), 8.02–8.06 (1H, d), 7.70–7.78 (1H, d), 7.10–7.20 (4H, m), 6.68 (1H, s), 6.62–6.67 (1H, d), 6.12–6.21 (1H, d), 3.85–3.95 (2H, m), 2.33 (3H, s), 2.00–2.28 (4H, m), 1.40–1.50 (4H, m) ppm. LRMS (thermospray): m/z [M+H]$^+$ 482

Example 17

$^1$H NMR (300 MHz, CDCl$_3$): □=13.25 (1H, s), 8.33–8.40 (1H, m), 8.03–8.07 (1H, d), 7.70–7.79 (1H, d) 7.25–7.35 (1H, m, partially masked by solvent), 7.12–7.20 (4H, m), 6.85–7.00 (1H, dd), 6.75–6.83 (1H, d), 6.50–6.63 (1H, dd), 3.87–4.12 (2H, m), 2.13–2.26 (4H, m), 1.41–1.52 (4H, m) ppm. LRMS (thermospray): m/z [M+NH$_4$]$^+$ 503

Example 18

$^1$H NMR (300 MHz, DMSO-d$^6$): □=8.55–8.63 (1H, d), 8.32–8.38 (1H, d), 8.19–8.23 (1H, d), 7.92–7.99 (1H, m), 7.70–7.80 (1H, d), 7.17–7.28 (5H, m), 6.88–6.96 (1H, m), 3.69–3.85 (2H, m), 1.83–2.00 (4H, m), 1.33–1.53 (4H, m) ppm. LRMS (thermospray): m/z [M+NH$_4$]$^+$ 503

Example 19

$^1$H NMR (300 MHz, DMSO-d$^6$): □=9.69 (1H, s), 8.23–8.34 (1H, d), 8.18 (1H, s), 7.90–7.98 (2H, m), 7.15–7.28 (5H, m), 6.98–7.07 (1H, t), 6.66–6.80 (2H, m), 3.61–3.78 (1H, m), 3.40–3.60 (1H, m), 3.35 (2H, s, masked by solvent), 1.75–1.95 (4H, m), 1.22–1.46 (4H, m) ppm. LRMS (thermospray): m/z [M+H]$^+$ 482

Example 20

$^1$H NMR (300 MHz, DMSO-d$^6$): □=8.63–8.69 (1H, d), 8.32–8.37 (1H, d), 8.17–8.21 (1H, d), 7.92–7.99 (2H, m), 7.37–7.42 (1H, m), 7.16–7.27 (4H, m), 6.86–6.93 (1H, d), 3.70–3.86 (2H, m), 1.85–2.01 (4H, m), 1.30–1.52 (4H, m) ppm. LRMS (thermospray): m/z [M+H]$^+$ 502, 504

Example 21

$^1$H NMR (300 MHz, DMSO-d$^6$): □=10.72 (1H, s) 8.29–8.36 (1H, m), 8.17–8.22 (1H, m), 8.05–8.15 (1H, m), 7.92–7.98 (1H, m), 7.85 (1H, s), 7.63–7.68 (1H, d), 7.15–7.26 (4H, m), 6.92–6.99 (1H, d), 3.63–3.82 (2H, m), 1.76–1.98 (4H, m), 1.28–1.48 (4H, m) ppm. LRMS (thermospray): m/z [M+H]$^+$ 502, 504

Example 22

$^1$H NMR (300 MHz, DMSO-d$^6$): □=14.67 (1H, s), 8.63–8.76 (1H, m), 8.34–8.43 (1H, m), 8.16–8.32 (2H, m), 7.83–8.03 (3H, m), 7.59–7.69 (1H, t), 7.32–7.40 (1H, d), 7.17–7.31 (4H, m), 6.88–6.96 (1H, m), 3.69–3.85 (2H, m), 1.83–2.00 (4H, m), 1.33–1.53 (4H, m) ppm. LRMS (thermospray): m/z [M+H]$^+$ 518

Example 23

$^1$H NMR (300 MHz, DMSO-d$^6$): δ=13.08 (1H, s) 8.28–8.36 (2H, t), 8.18–8.22 (1H, d), 7.91–7.97 (1H, m), 7.77–7.82 (1H, d), 7.15–7.31 (4H, m), 6.40–6.44 (1H, d), 6.38 (1H, s), 3.65–3.88 (2H, m), 1.78–2.04 (4H, m), 1.30–1.60 (4H, m) ppm. LRMS (thermospray): m/z [M+H]$^+$ 498

Example 24

$^1$H NMR (300 MHz, DMSO-d$^6$): δ=9.76 (1H, s) 8.29–8.35 (1H, d), 8.18–8.21 (1H, d), 7.90–7.96 (1H, m), 7.83–7.89 (1H, d), 7.58 (1H, s), 7.45–7.52 (1H, m), 7.16–7.23 (4H, m), 6.72–6.78 (1H, d), 3.63–3.83 (2H, m), 2.11 (3H, s), 1.80–1.98 (4H, m), 1.30–1.52 (4H, m) ppm. LRMS (thermospray): m/z [M+H]$^+$ 482

Example 25

$^1$H NMR (300 MHz, DMSO-d$^6$): δ=9.24 (1H, s), 8.25–8.32 (1H, d), 8.20 (1H, s), 7.84–7.99 (2H, t), 7.17–7.27 (4H, m), 6.99–7.10 (1H, t), 6.54–6.68 (3H, m), 3.60–3.77 (2H, m), 3.35 (2H, s, masked by solvent), 1.74–1.95 (4H, m), 1.12–1.42 (4H, m) ppm. LRMS (thermospray): m/z [M+H]$^+$ 482

Example 26

$^1$H NMR (300 MHz, DMSO-d$^6$): δ=11.68 (1H, s), 8.96 (1H, s), 8.45–8.50 (1H, d), 8.32–8.37 (1H, d), 8.18–8.22 (1H, d), 7.92–7.99 (1H, m), 7.16–7.32 (5H, m), 6.81–6.87 (1H, m), 6.68–6.74 (1H, d), 3.67–4.06 (2H, m), 1.78–1.98 (4H, m), 1.35–1.56 (4H, m) ppm. LRMS (thermospray) : m/z [M+H]$^+$ 484

Example 27

$^1$H NMR (300 MHz, DMSO-d$^6$): δ=12.59 (1H, s), 8.89–8.97 (1H, d), 8.32–8.38 (1H, d), 8.19–8.22 (1H, d), 8.13–8.17 (1H, m), 7.93–8.01 (1H, m), 7.93–8.01 (1H, m), 7.48–7.53 (1H, m), 7.38–7.42 (1H, m), 7.16–7.36 (4H, m), 3.67–3.90 (2H, m), 1.79–2.02 (4H, m), 1.48–1.77 (2H, m), 1.32–1.47 (2H, m) ppm. LRMS (thermospray): m/z [M+H]$^+$ 469 Found C, 60.94; H, 4.79; N, 11.83. $C_{24}H_{22}F_2N_4O_4$. 0.1 mol $CH_2Cl_2$ requires C, 60.69; H, 4.69; N, 11.75%.

Example 28

$^1$H NMR (300 MHz, DMSO-d$^6$): δ=9.19 (1H, s), 8.23–8.31 (1H, d), 8.18–8.21 (1H, m), 7.91–7.96 (1H, d), 7.65–70 (1H, d), 7.16–7.25 (4H, m), 6.98–7.09 (1H, m), 6.51–6.62 (3H, m), 3.56–3.77 (2H, m), 2.61–2.47 (2H, m), 2.23–2.33 (2H, m), 1.72–1.93 (4H, m), 1.18–1.40 (4H, m) ppm. LRMS (thermospray): m/z [M+H]$^+$ 496

Example 29

$^1$H NMR (300 MHz, DMSO-d$^6$): δ=12.96 (1H, s), 10.04 (1H, s), 8.18–8.42 (3H, m), 7.90–8.10 (1H, m), 7.63–7.76 (1H, m), 7.07–7.45 (4H, m), 6.13–6.40 (2H, m), 3.60–3.90 (2H, m), 1.72–2.15 (4H, m), 1.28–1.60 (4H, m) ppm. LRMS (thermospray): m/z [M+H]$^+$ 484 Found C, 60.11; H, 4.99; N, 7.95. $C_{25}H_{23}F_2N_3O_5$. 0.25 mol $CH_2Cl_2$ requires C, 60.09; H, 4.64; N, 8.33%.

Example 30

$^1$H NMR (300 MHz, DMSO-d$^6$): δ=14.27 (1H, s), 8.33–8.38 (1H, d), 8.19–8.23 (1H, d), 7.92–8.01 (1H, m), 7.17–7.37 (5H, m), 6.12 (1H, s), 6.08 (1H, s), 3.60–4.00 (8H, partially masked by solvent), 1.82–2.03 (4H, d), 1.24–1.60 (4H, m) ppm. LRMS (thermospray): m/z [M+H]$^+$ 528

Example 31

$^1$H NMR (300 MHz, DMSO-d$^6$): δ=12.08 (1H, brs), 8.80–8.86 (1H, d), 8.51 (1H, s), 8.35–8.42 (1H, d), 8.20–8.24 (1H, d), 7.92–7.99 (1H, m), 7.84–7.89 (1H, d), 7.72–7.78 (1H, d), 7.44–7.52 (1H, t), 7.28–7.36 (1H, t), 7.19–7.24 (5H, m), 3.72–3.93 (2H, m), 1.93–2.06 (4H, d), 1.36–1.62 (4H, m) ppm. LRMS (thermospray): m/z [M+H]$^+$ 518

Example 32

$^1$H NMR (300 MHz, DMSO-d$^6$): δ=12.77 (1H, s), 8.50–8.58 (1H, d), 8.33–8.38 (1H, d), 8.18–8.23 (1H, d), 7.92–8.02 (1H, m), 7.42–7.48 (1H, d), 7.16–7.38 (4H, m), 7.07–7.14 (1H, d), 6.73–6.83 (1H, t), 3.70–3.92 (5H, m), 1.80–2.08 (4H, m), 1.23–1.58 (4H, m) ppm. LRMS (thermospray): m/z [M+H]$^+$ 498

Example 33

$^1$H NMR (300 MHz, DMSO-d$^6$): δ=8.26–8.38 (1H, d), 8.19–8.22 (1H, m), 7.92–8.08 (2H, m), 7.16–7.36 (4H, m), 6.96–7.05 (1H, d), 6.68–6.75 (1H, m), 3.62–3.83 (2H, m), 2.80–2.95 (1H, m), 2.16 (3H, s), 1.78–2.02 (4H, m), 1.23–1.48 (4H, m), 1.08–1.16 (6H, d) ppm. LRMS (electrospray): m/z [M–H]$^+$ 522

Example 34

$^1$H NMR (300 MHz, DMSO-d$^6$): δ=13.43 (1H, s), 8.32–8.39 (2H, m), 8.22–8.25 (1H, d), 7.92–8.02 (1H, m), 7.18–7.37 (5H, m), 6.54–6.60 (1H, d), 6.47–6.53 (1H, d), 3.89 (3H, s), 3.73–3.88 (2H, m), 1.89–2.04 (4H, d), 1.37–1.43 (4H, m) ppm. LCMS (electrospray): m/z [M–H]$^+$ 496

Example 35

$^1$H NMR (300 MHz, DMSO-d$^6$): δ=9.41 (1H, s), 8.32–8.38 (1H, d), 8.08–8.10 (1H, d), 7.96–8.04 (2H, m), 7.20–7.30 (4H, m), 6.96–7.02 (1H, t), 6.78–6.83 (1H, d), 6.64–6.70 (1H, d), 3.61–3.78 (2H, brs), 2.08 (3H, s), 1.80–1.98 (4H, m), 1.30–1.44 (4H, m) ppm. LCMS (thermospray): m/z [M+H]$^+$ 482, [M+NH$_4$]$^+$ 499.

Example 36

$^1$H NMR (300 MHz, DMSO-d$^6$): δ=9.42 (1H, s), 8.32–8.38 (1H, d), 8.18–8.20 (1H, d), 8.00–8.05 (1H, d), 7.93–8.00 (1H, m), 7.15–7.26 (6H, m), 7.08–7.13 (1H, m), 3.66–3.80 (2H, brs), 2.14 (3H, s), 1.80–1.97 (4H, m), 1.27–1.50 (4H, m) ppm. LCMS (thermospray): m/z [M+H]$^+$ 482, [M+NH$_4$]$^+$ 499.

Example 37

$^1$H NMR (300 MHz, DMSO-d$^6$): □=9.18 (1H, s), 8.28–8.33 (1H, d), 8.18–8.20 (1H, d), 7.93–7.99 (1H, m), 7.83–7.89 (1H, d), 7.17–7.28 (4H, m), 6.98–7.05 (2H, d), 6.63–6.67 (2H, d), 3.60–3.80 (2H, brs), 3.30 (2H, s, masked by solvent), 1.73–1.92 (4H, m), 1.19–1.40 (4H, m) ppm. LCMS (thermospray): m/z [M+H]$^+$ 482, [M+NH$_4$]$^+$ 499.

Example 38

$^1$H NMR (300 MHz, DMSO-d$^6$): □=9.08–9.13 (1H, brs), 8.32–8.37 (1H, d), 8.09–8.11 (1H, m), 7.94–8.00 (2H, m), 7.19–7.32 (6H, m), 6.91–6.96 (1H, d), 3.64–3.84 (5H, s+brs), 1.80–1.98 (4H, m), 1.30–1.50 (4H, m) ppm. LCMS (thermospray): m/z [M+H]$^+$ 498.

Example 39

$^1$H NMR (300 MHz, DMSO-d$^6$): □=9.18–9.28 (1H, brs), 8.28–8.34 (1H, d), 8.19–8.21 (1H, d), 8.02–8.08 (1H, t), 7.95–7.99 (1H, m), 7.67–7.71 (1H, d), 7.18–7.29 (4H, m), 7.00–7.08 (2H, d), 6.65–6.70 (2H, d), 3.60–3.79 (3H, brs+d), 3.35–3.59 (3H, m, masked by solvent), 1.74–1.96 (4H, m), 1.19–1.42 (4H, m) ppm. LCMS (thermospray): m/z [M+H]$^+$ 539.

Example 40

$^1$H NMR (300 MHz, DMSO-d$^6$): □=9.63 (1H, s), 8.25–8.35 (1H, d), 8.19–8.21 (1H, d), 8.00–8.07 (1H, t), 7.93–7.98 (1H, m), 7.58–7.63 (1H, d), 7.15–7.30 (4H, m), 7.00–7.14 (2H, m), 6.77–6.82 (1H, d), 6.70–6.76 (1H, t), 3.60–3.80 (3H, m+d), 3.41–3.58 (3H, m+s), 1.69–1.99 (4H, m), 1.20–1.44 (4H, m) ppm. LCMS (thermospray): m/z [M+H]$^+$ 539.

Example 41 anti-5-Fluoro-2-(3,4-difluoro-phenoxy)-N-[4-(2-fluoro-6-hydroxy-benzoyl mino)-cyclohexyl]-nicotinamide

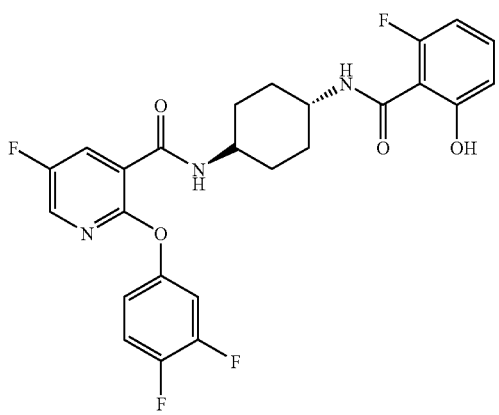

2-Fluoro-6-hydroxybenzoic acid (115 mg, 0.736 mmol), 1-hydroxybenzotriazole hydrate (149 mg, 1.11 mmol), 1-(3-dimethylaminopropyl)-3-ethylcarbodiimide hydrochloride (184 mg, 0.957 mmol), anti-N-(4-amino-cyclohexyl)-5-fluoro-2-(3,4-difluoro-phenoxy)-nicotinamide hydrochloride (296 g, 0.736 mmol) (see Preparation 11) and N-methyl morpholine (0.16 ml, 1.46 mmol) were stirred in N,N-dimethylformamide (6 ml) under an atmosphere of nitrogen at room temperature for 18 hours. The mixture was then partitioned between ethyl acetate (6 ml) and water (6 ml). The organic layer was separated, washed with a saturated aqueous solution of sodium chloride (6 ml) and dried over anhydrous magnesium sulphate. It was then concentrated in vacuo, and the residue triturated with diethylether (3-fold 5 ml) to give anti-5-fluoro-2-(3,4-difluoro-phenoxy)-N-[4-(2-fluoro-6-hydroxy-benzoylamino)-cyclohexyl]-nicotinamide (240 mg) as an off-white solid.

$^1$H NMR (300 MHz, DMSO-d$^6$): □=10.92 (1H, brs) 8.29–8.33 (1H, d), 8.23–8.27 (1H, d), 8.08–8.17 (1H, m), 7.90–8.03 (1H, m), 7.31–7.52 (2H, m), 7.18–7.30 (1H, m), 7.02–7.12 (1H, m), 6.60–6.71 (2H, m), 3.65–3.82 (2H, m), 1.82–2.00 (4H, m), 1.28–1.50 (4H, m) ppm. LRMS (thermospray): m/z [M+H]$^+$ 504

Example 42 anti-5-Fluoro-2-(3-chloro-4-fluoro-phenoxy)-N-[4-(2-fluoro-6-hydroxy-benzoylamino)-cyclohexyl]-nicotinamide

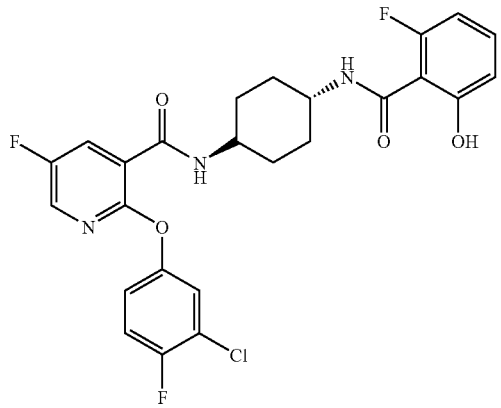

2-Fluoro-6-hydroxybenzoic acid (117 mg, 0.753 mmol), 1-hydroxybenzotriazole hydrate (153 mg, 1.13 mmol), 1-(3-dimethylaminopropyl)-3-ethylcarbodiimide hydrochloride (188 mg, 0.979 mmol), anti-N-(4-amino-cyclohexyl)-5-fluoro-2-(3-chloro-4-fluoro-phenoxy)-nicotinamide hydrochloride (315 mg, 0.736 mmol) (see Preparation 13) and N-methyl morpholine (0.17 ml, 1.51 mmol) were stirred in N,N-dimethylformamide (6 ml) under an atmosphere of nitrogen at room temperature for 18 hours. The mixture was then partitioned between ethyl acetate (6 ml) and water (6 ml). The organic layer was separated, washed with a saturated aqueous solution of sodium chloride (6 ml) and dried over anhydrous magnesium sulphate. It was then concentrated in vacuo, and the residue was triturated with diethylether (3-fold 5 ml) to give anti-5-fluoro-2-(3-chloro-4-fluoro-phenoxy)-N-[4-(2-fluoro-6-hydroxy-benzoylamino)-cyclohexyl]-nicotinamide (250 mg) as an off-white solid.

$^1$H NMR (300 MHz, DMSO-d$^6$): □=10.94 (1H, brs) 8.28–8.35 (1H, d), 8.23–8.26 (1H, d), 8.07–8.17 (1H, m), 7.92–8.03 (1H, m), 7.42–7.54 (2H, m), 7.17–7.28 (2H, m), 6.58–6.73 (2H, m), 3.64–3.83 (2H, m), 1.83–2.00 (4H, m), 1.31–1.50 (4H, m) ppm. LRMS (thermospray): m/z [M+H]$^+$ 520, 522

Example 43 syn-N-(4-{[5-Fluoro-2-(4-fluoro-phenoxy)-pyridine-3-carbonyl]-amino}-cyclohexyl)-phthalamic acid methyl ester

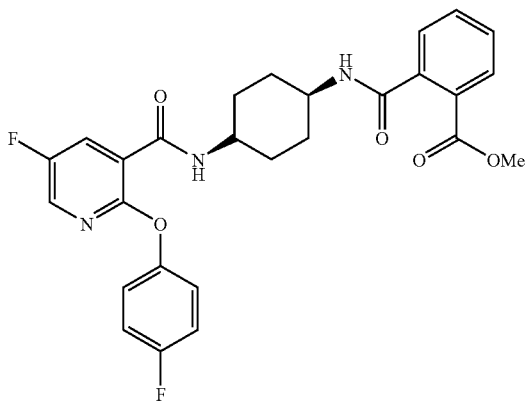

Phthalic acid monomethyl ester (141 mg, 0.781 mmol), 1-hydroxybenzotriazole hydrate (158 mg, 1.17 mmol) and 1-(3-dimethylaminopropyl)-3-ethylcarbodiimide hydrochloride (195 mg, 1.02 mmol) were stirred in N,N-dimethylformamide (6 ml) at room temperature and syn-N-(4-amino-cyclohexyl)-5-fluoro-2-(4-fluoro-phenoxy)-nicotinamide hydrochloride (300 mg, 0.781 mmol) (see Preparation 22) added followed by addition of N-methyl morpholine (0.17 ml, 1.56 mmol). The reaction mixture was stirred under an atmosphere of nitrogen at room temperature for 18 hours, the reaction mixture then partitioned between ethyl acetate (20 ml) and water (20 ml), and the organic layer separated. The organic layer was then washed with a saturated aqueous solution of sodium chloride (20 ml) dried over anhydrous magnesium sulphate and the solvent removed in vacuo. The residue was triturated with diethylether (5 ml) giving syn-N-(4-{[5-fluoro-2-(4-fluoro-phenoxy)-pyridine-3-carbonyl]-amino}-cyclohexyl)-phthalamic acid methyl ester (385 mg) as an off-white solid.

$^1$H NMR (300 MHz, DMSO-d$^6$): □=8.28–8.35 (1H, d), 8.20–8.24 (1H, d), 8.01–8.08 (2H, m), 7.75–7.80 (1H, d), 7.48–7.64 (2H, m), 7.38–7.43 (1H, d), 7.20–7.38 (4H, m), 4.04–4.16 (1H, m), 3.84–3.99 (1H, m), 3.74 (3H, s), 1.56–1.88 (8H, m) ppm. LRMS (thermospray): m/z [M+H]$^+$ 510

Example 44 anti-N-{4-[Acetyl-(2-hydroxybenzyl)-amino]-cyclohexyl}-5-fluoro-2-(4-fluoro-phenoxy)-nicotinamide

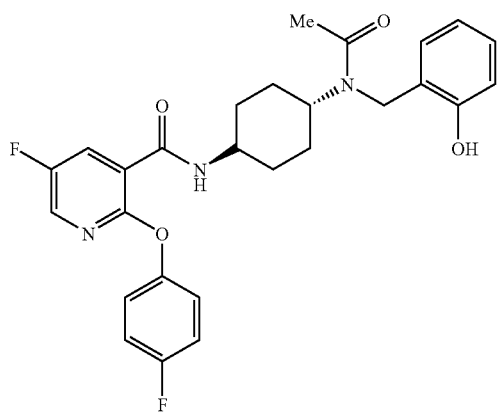

Anti-Acetic acid 1-{[acetyl-(4-{[5-fluoro-2-(4-fluoro-phenoxy)-pyridine-3-carbonyl]-amino}-cyclohexyl)-amino]-methyl}-phenyl ester (275 mg, 0.512 mmol) (see Preparation 19) and lithium hydroxide (monohydrate, 32 mg, 0.767 mmol) were dissolved in tetrahydrofuran (10 ml) and water (10 ml) and the reaction mixture stirred at room temperature for 2 hours. 2M Hydrochloric acid (0.4 ml) was added and the resultant precipitate filtered off and washed with water (30 ml). The solid was then dissolved in dichloromethane/diethylether and dried over anhydrous sodium sulphate. The solvent was removed in vacuo giving anti-N-{4-[acetyl-(2-hydroxybenzyl)-amino]-cyclohexyl}-5-fluoro-2-(4-fluoro-phenoxy)-nicotinamide (100 mg) as a white solid.

$^1$H NMR (400 MHz, CDCl$_3$): □=9.77 (1H, s), 8.32–8.39 (1H, m), 8.01–8.05 (1H, d), 7.68–7.78 (1H, d), 7.07–7.23 (6H, m), 6.85–6.90 (1H, d), 6.77–6.84 (1H, t), 4.52 (2H, s), 3.92–4.10 (1H, m), 3.59–3.70 (1H, m), 2.22–2.31 (2H, d), 2.18 (3H, s), 1.75–1.98 (4H, m), 1.26–1.43 (2H, m) ppm. LRMS (electrospray): m/z [M−H]$^+$ 494

Example 45 anti-N-{4-[Acetyl-(3-hydroxybenzyl)-amino]-cyclohexyl}-5-fluoro-2-(4-fluoro-phenoxy)-nicotinamide

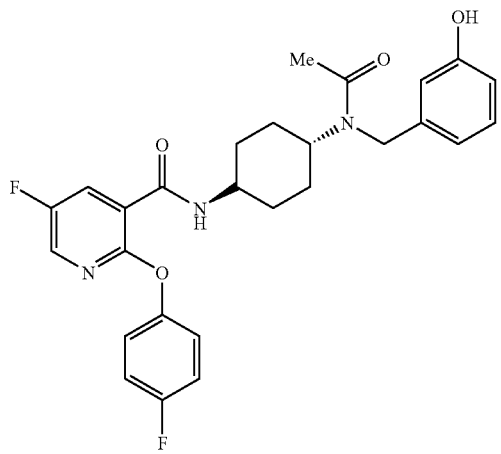

Anti-N-{4-[3-(tert-Butyl-dimethyl-silanyloxy)-benzylamino]-cyclohexyl}-5-fluoro-2-(4-fluoro-phenoxy)-nicotinamide (337 mg, 0.512 mmol) (see Preparation 18) was dissolved in dichloromethane (10 ml) and diisopropylethylamine (0.15 ml, 0.831 mmol) added followed by addition of acetyl chloride (0.051 ml, 0.712 mmol). The reaction mixture was held at room temperature under an atmosphere of nitrogen for 2 hours, and the solvent then removed in vacuo. The residue was dissolved in methanol (15 ml) and amberlyst 15 resin (1 g) was added. The reaction was held at room temperature for a further 18 hours. The mixture was then filtered through a short column of celite (5 g) and the celite washed with methanol (2-fold 10 ml). The filtrates were then combined, concentrated in vacuo and the residue azeotroped with diethylether. The resulting white solid was slurried with pentane and filtered off giving anti-N-{4-[acetyl-(3-hydroxybenzyl)-amino]-cyclohexyl}-5-fluoro-2-(4-fluoro-phenoxy)-nicotinamide (290 mg) as a white solid.

$^1$H NMR (400 MHz, DMSO-d$^6$): □=9.32 (0.5H, s), 9.18 (0.5H, s), 8.20–8.25 (1H, m), 8.15–8.19 (1H, d), 7.90–7.98 (1H, m), 7.17–7.22 (4H, m), 6.98–7.16 (1H, 2×t), 6.52–6.65 (3H, m), 4.36–4.48 (2H, 2×s), 4.20–4.33 (0.5H, m), 3.57–3.76 (1.5H, m), 2.13 (1.3H, s), 1.78–1.90 (2.7H, m), 1.25–1.64 (7H, m) ppm. LRMS (electrospray): m/z [M–H]$^+$ 494

Example 46 anti-N-{4-[Acetyl-(4-hydroxybenzyl)-amino]-cyclohexyl}-5-fluoro-2-(4-fluoro-phenoxy)-nicotinamide

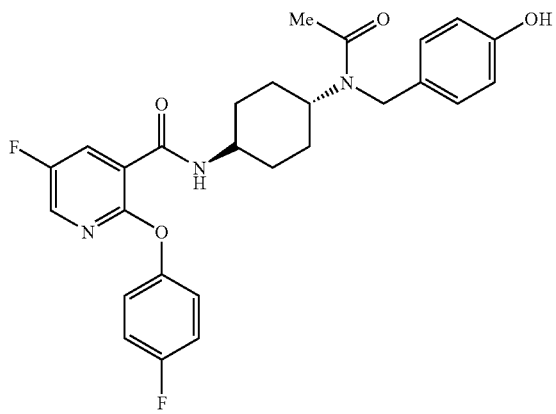

Anti-N-{4-[4-(tert-Butyl-dimethyl-silanyloxy)-benzylamino]-cyclohexyl}-5-fluoro-2-(4-fluoro-phenoxy)-nicotinamide (97 mg, 0.171 mmol) (see Preparation 17) was dissolved in dichloromethane (5 ml) and diisopropylethylamine (0.042 ml, 0.239 mmol) added followed by addition of acetyl chloride (0.015 ml, 0.205 mmol). The reaction mixture was held at room temperature under and atmosphere of nitrogen for 2 hours, before removing the solvent in vacuo. The residue was dissolved in methanol (10 ml) and amberlyst 15 resin (1 g) and trifluoroacetic acid (0.1 ml) added. The reaction mixture was held at room temperature for a further 18 hours. The mixture was then filtered through a short column of celite (5 g) and the celite washed with methanol (2-fold 10 ml). The filtrates were combined, concentrated in vacuo and the residue azeotroped with diethylether. The resulting white solid was slurried with pentane and filtered off giving anti-N-{4-[acetyl-(4-hydroxybenzyl)-amino]-cyclohexyl}-5-fluoro-2-(4-fluoro-phenoxy)-nicotinamide (46 mg) as a white solid.

$^1$H NMR (400 MHz, DMSO-d$^6$): □=8.17–8.21 (1H, m), 8.13–8.16 (1H, d), 7.88–7.95 (1H, m), 7.11–7.21 (4H, m), 6.92–6.99 (2H, d), 6.67–6.73 (1H, d), 6.57–6.63 (1H, d), 4.30–4.41 (2H, 2×s), 4.12–4.22 (1H, m), 3.57–3.72 (1H, m), 2.10 (1H, s), 1.86 (2H, s), 1.76–1.83 (2H, d), 1.43–1.60 (4H, m), 1.20–1.40 (2H, m) ppm. LRMS (electrospray): m/z [M+H]$^+$ 496

Example 47 syn-5-Fluoro-2-(4-fluoro-phenoxy)-N-[4-(2-hydroxy-4-methyl-benzoylamino)-cyclohexyl]-nicotinamide

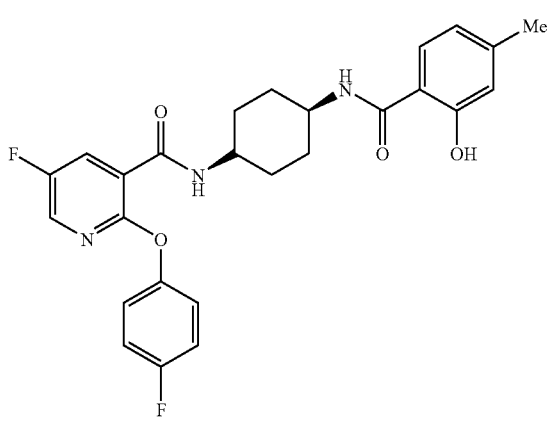

2-Hydroxy-4-methylbenzoic acid (91 mg, 0.595 mmol), 1-hydroxybenzotriazole hydrate (80 mg, 0.595 mmol), 1-(3-dimethylaminopropyl)-3-ethylcarbodiimide hydrochloride (134 mg, 0.703 mmol), syn-N-(4-amino-cyclohexyl)-5-fluoro-2-(4-fluoro-phenoxy)-nicotinamide hydrochloride (200 mg, 0.541 mmol) (see Preparation 22) and N-methyl morpholine (0.18 ml, 1.62 mmol) were stirred in N,N-dimethylformamide (5 ml) under an atmospherer of nitrogen at room temperature for 18 hours. The N,N-dimethylformamide was removed in vacuo, and the residue partitioned between dichloromethane (15 ml) and water (15 ml). The organic phase was separated and washed sequentially with a 10% solution of citric acid in water (15 ml) followed by a saturated aqueous solution of sodium hydrogen carbonate (15 ml). The organic phase was then dried over anhydrous magnesium sulphate and the solvent removed in vacuo. The residue was triturated with ethyl acetate/pentane (1:1, by volume, 5 ml) giving syn-5-fluoro-2-(4-fluoro-phenoxy)-N-[4-(2-hydroxy-4-methyl-benzoyl amino)-cyclohexyl]-nicotinamide (130 mg) as a white solid.

$^1$H NMR (400 MHz, CDCl$_3$): □=12.17 (1H, s), 8.32–8.38 (1H, m), 8.00–8.08 (2H, m), 7.15–7.22 (4H, d), 6.97–7.01 (1H, d), 6.78 (1H, s), 6.60–6.65 (1H, d), 5.84–5.92 (1H, d), 4.23–4.31 (1H, m), 4.02–4.15 (1H, m), 2.34 (3H, s), 1.80–2.00 (6H, m), 1.49–1.67 (2H, m, partially masked by solvent) ppm. LRMS (electrospray): m/z [M–H]$^+$ 480

Examples 48–71

The compounds of the following tabulated examples (Table 3) of the general formula:

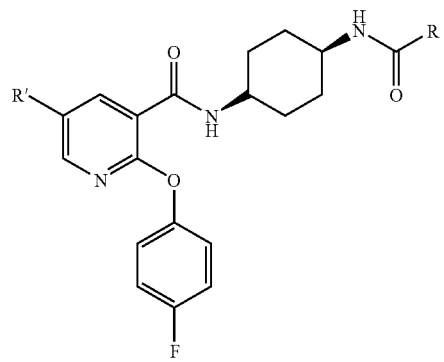

were prepared by a similar method to that of Example 47 using the appropriate carboxylic acid and amine as the starting materials.

TABLE 3

| Example No. | Starting Amine Prep No. | R' | R |
|---|---|---|---|
| 48 | 22 | F | 3-hydroxyphenyl |
| 49 | 22 | F | 4-hydroxyphenyl |
| 50 | 22 | F | 2-hydroxyphenyl |
| 51 | 22 | F | 2-hydroxybenzyl |
| 52 | 22 | F | 3-hydroxybenzyl |
| 53 | 22 | F | 4-hydroxybenzyl |
| 54[1] | 22 | F | 3-hydroxy-4-methoxybenzyl |
| 55[1] | 22 | F | 4-hydroxy-3-methylbenzyl |
| 56[1] | 22 | F | 3-fluoro-4-hydroxybenzyl |
| 57[1] | 22 | F | 4-hydroxy-3-methoxybenzyl |
| 58[1] | 22 | F | 3-chloro-4-hydroxybenzyl |
| 59[1] | 22 | F | 3-hydroxy-5-methoxybenzyl |
| 60[1] | 22 | F | 3-hydroxy-4-methoxybenzyl |
| 61[2] | 22 | H | 2-hydroxybenzyl |
| 62[1] | 22 | F | 2,4-dihydroxybenzyl |
| 63[1] | 22 | F | 2-hydroxy-4-methoxybenzyl |
| 64[1] | 22 | F | 4-hydroxy-3-methylbenzyl |

TABLE 3-continued

| Example No. | Starting Amine Prep No. | R' | R |
|---|---|---|---|
| 65[1] | 22 | F | 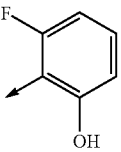 |
| 66[1,3] | 24 | F | 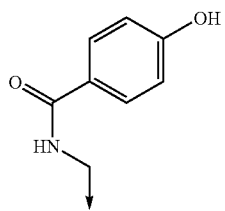 |
| 67[1,3] | 24 | F | 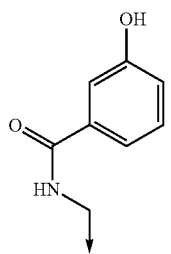 |
| 68[1,3] | 24 | F | 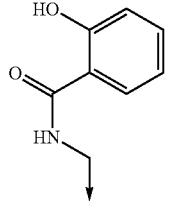 |
| 69[1,3] | 24 | F | 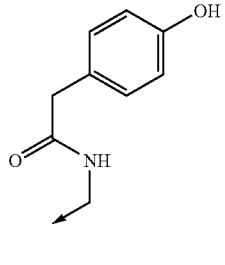 |
| 70[1,3] | 24 | F | 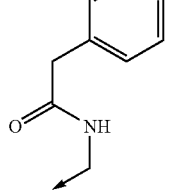 |
| 71[1,3] | 24 | F | 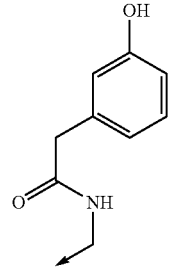 |

[1]These examples were worked up by partitioning the reaction mixture between ethyl acetate and water, and the organic phase was washed with a saturated aqeous solution of sodium chloride.
[2]These examples were purified by flash column chromatography on silica gel eluting with a solvent gradient of dichloromethane:methanol (100:0 changing to 95:5 then 70:30, by volume). The product was then dissolved in ethyl acetate, washed sequentially with water and a saturated aqeous solution of sodium chloride, dried over anhydrous magnesium sulphate and concentrated under reduced pressure to give the desired compound.
[3]These compounds were diluted with methanol and ethyl acetate until completely soluble before drying over anhydrous magnesium sulphate.

Example 48

$^1$H NMR (400 MHz, DMSO-d$^6$): □=9.50 (1H, s), 8.22–8.26 (1H, d), 8.17–8.21 (1H, d), 7.95–7.99 (1H, m), 7.84–7.92 (1H, d), 7.12–7.23 (7H, m), 6.80–6.85 (1H, d), 3.86–3.95 (1H, m), 3.72–3.82 (1H, m), 1.56–1.82 (8H, m) ppm. LRMS (electrospray): m/z [M–H]$^+$ 466

Example 49

$^1$H NMR (400 MHz, DMSO-d$^6$): □=9.83 (1H, s), 8.21–8.24 (1H, m), 8.17–8.20 (1H, d), 7.93–7.97 (1H, m), 7.63–7.67 (1H, d), 7.57–7.62 (1H, d), 7.17–7.24 (4H, m), 6.70–6.77 (1H, d), 3.87–3.92 (1H, m), 3.72–3.80 (1H, m), 1.76–1.83 (2H, m), 1.55–1.72 (6H, m) ppm. LRMS (electrospray): m/z [M–H]$^+$ 466

Example 50

$^1$H NMR (400 MHz, DMSO-d$^6$): □=12.18 (1H, brs), 8.34–8.41 (1H, m), 8.16–8.19 (1H, d), 7.93–7.97 (1H, m), 7.80–7.86 (1H, d), 7.28–7.35 (1H, t), 7.15–7.23 (4H, m), 6.78–6.86 (2H, m), 3.89–3.94 (1H, m), 3.80–3.88 (1H, m), 1.58–1.80 (8H, m) ppm. LRMS (electrospray): m/z [M–H]$^+$ 466

Example 51

$^1$H NMR (400 MHz, CD$_3$OD): □=8.03–8.07 (2H, m), 7.10–7.21 (4H, m), 6.96–7.08 (2H, m), 6.68–6.78 (2H, m), 3.97–4.07 (1H, m), 3.75–3.80 (1H, m), 3.43 (2H, s), 1.63–1.80 (6H, m), 1.52–1.62 (6H, m) ppm. LRMS (electrospray): m/z [M–H]$^+$ 480

Example 52

$^1$H NMR (400 MHz, CD$_3$OD): □=8.00–8.08 (2H, m), 7.09–7.19 (4H, m), 7.00–7.08 (1H, t), 6.57–6.72 (3H, m), 4.00–4.09 (1H, m), 3.72–3.81 (1H, m), 3.37 (2H, s), 1.66–1.80 (6H, m), 1.51–1.62 (6H, m) ppm. LRMS (electrospray): m/z [M–H]+ 480

Example 53

$^1$H NMR (400 MHz, DMSO-d$^6$): δ=9.08 (1H, s), 8.22–8.26 (1H, d), 8.14–8.17 (1H, d), 7.92–7.96 (1H, d), 7.63–7.67 (1H, d), 7.16–7.23 (4H, d), 6.94–6.99 (2H, d), 6.57–6.62 (2H, d), 3.78–3.86 (1H, m), 3.52–3.61 (1H, m), 3.23 (2H, s), 1.46–1.86 (8H, m) ppm. LRMS (electrospray): m/z [M–H]+ 480

Example 54

$^1$H NMR (300 MHz, DMSO-d$^6$): δ=9.08 (1H, s), 8.26–8.32 (1H, d), 8.21–8.25 (1H, d), 8.01–8.07 (1H, m), 7.75–7.82 (1H, m), 7.19–7.38 (6H, m), 6.92–6.97 (1H, d), 3.76–4.01 (5H, m), 1.54–1.80 (8H, m) ppm. LRMS (thermospray): m/z [M+H]+ 498

Example 55

$^1$H NMR (300 MHz, DMSO-d$^6$): δ=9.48 (1H, brs), 8.26–8.33 (1H, d), 8.20–8.25 (1H, d), 7.98–8.06 (1H, m), 7.74–7.80 (1H, d), 7.18–7.41 (6H, m), 6.77–6.82 (1H, d), 3.76–4.03 (5H, m), 1.50–1.92 (8H, m) ppm. LRMS (thermospray): m/z [M+H]+ 498

Example 56

$^1$H NMR (300 MHz, DMSO-d$^6$): δ=9.58 (1H, s), 8.25–8.30 (1H, d), 8.20–8.24 (1H, d), 8.00–8.07 (1H, m), 7.77–7.83 (1H, d), 7.20–7.30 (4H, d), 6.96–7.03 (1H, d), 6.77–6.83 (2H, m), 3.82–3.93 (1H, m), 3.55–3.64 (1H, m), 3.26 (2H, s, partially masked by solvent), 1.52–1.80 (8H, m) ppm. LRMS (thermospray): m/z [M+H]+ 500

Example 57

$^1$H NMR (300 MHz, DMSO-d$^6$): δ=8.73 (1H, s), 8.27–8.32 (1H, d), 8.21–8.25 (1H, d), 7.96–8.05 (1H, m), 7.70–7.78 (1H, d), 7.20–7.30 (4H, d), 6.57–6.80 (3H, m), 3.82–3.94 (1H, m), 3.58–3.78 (4H, m), 3.24 (2H, s, partially masked by solvent), 1.52–1.78 (8H, m) ppm. LRMS (thermospray): m/z [M+H]+ 512

Example 58

$^1$H NMR (300 MHz, DMSO-d$^6$): δ=9.92 (1H, s), 8.26–8.32 (1H, d), 8.19–8.24 (1H, d), 7.91–8.05 (1H, m), 7.78–7.84 (1H, d), 7.16–7.30 (5H, m), 6.95–7.02 (1H, m), 6.83–6.88 (1H, d), 3.82–3.96 (1H, m), 3.57–3.69 (1H, m), 3.26 (2H, s, partially masked by solvent), 1.53–1.78 (8H, m) ppm. LRMS (thermospray): m/z [M+H]+ 516

Example 59

$^1$H NMR (300 MHz, DMSO-d$^6$): δ=8.70 (1H, s), 8.28–8.33 (1H, d), 8.20–8.24 (1H, d), 7.96–8.02 (1H, m), 7.70–7.77 (1H, d), 7.20–7.28 (4H, d), 6.57–6.82 (3H, m), 3.81–3.94 (1H, m), 3.60–3.80 (4H, m), 3.24 (2H, s, partially masked by solvent), 1.52–1.78 (8H, m) ppm. LRMS (thermospray): m/z [M+H]+ 512

Example 60

$^1$H NMR (300 MHz, DMSO-d$^6$): δ=8.80 (1H, brs), 8.25–8.33 (1H, d), 8.18–8.23 (1H, d), 7.95–8.05 (1H, d), 7.73–7.78 (1H, d), 7.17–7.34 (4H, d), 6.56–6.82 (3H, m), 3.81–3.91 (1H, m), 3.67 (2H, s), 3.50–3.65 (1H, m), 3.22 (3H, s), 1.51–1.78 (8H, m) ppm. LRMS (thermospray): m/z [M+H]+ 512

Example 61

$^1$H NMR (400 MHz, CDCl$_3$): δ=9.63 (1H, s), 8.68–8.75 (1H, d), 7.79–7.83 (2H, m), 7.16–7.20 (1H, t), 7.11–7.14 (4H, 2×d), 7.00–7.10 (2H, m), 6.92–6.98 (1H, m), 6.78–6.84 (1H, t), 6.23–6.31 (1H, d), 4.00–4.08 (1H, m), 3.58 (2H, s), 2.43–2.54 (1H, m), 1.78–1.90 (6H, m), 1.60–1.75 (2H, m, partially masked by solvent) ppm. LRMS (electrospray): m/z [M–H]+ 462

Example 62

$^1$H NMR (300 MHz, DMSO-d$^6$): δ=12.58 (1H, s), 10.00 (1H, s), 8.30–8.36 (1H, d), 8.01–8.03 (1H, d), 8.06–8.13 (1H, m), 7.99–8.06 (1H, m), 7.70–7.76 (1H, d), 7.20–7.29 (4H, d), 6.20–6.30 (2H, d+s), 3.88–3.99 (1H, brs), 3.60–3.88 (1H, brs), 1.53–1.88 (8H, m) ppm. LRMS (thermospray): m/z [M+H]+ 484

Example 63

$^1$H NMR (300 MHz, DMSO-d$^6$): δ=12.74–12.80 (1H, brs), 8.30–8.36 (1H, d), 8.18–8.23 (2H, m), 7.98–8.04 (1H, m), 7.80–7.85 (1H, d), 7.20–7.25 (4H, d), 6.39–6.48 (2H, d+s), 3.93–4.01 (1H, brs), 3.80–3.91 (1H, brs), 3.77 (3H, s), 1.62–1.90 (8H, m) ppm. LRMS (thermospray): m/z [M+H]+ 498.

Example 64

$^1$H NMR (300 MHz, DMSO-d$^6$): δ=8.26–8.32 (1H, d), 8.01–8.03 (1H, d), 7.98–8.04 (1H, dd), 7.58–7.64 (1H, d), 7.19–7.28 (4H, d), 7.12–7.18 (1H, t), 6.68–6.79 (3H, m), 4.42 (2H, s), 3.85–3.97 (1H, brs), 3.70–3.80 (1H, brs), 2.24 (3H, s), 1.53–1.79 (8H, m) ppm. LRMS (thermospray): m/z [M+H]+ 496.

Example 65

$^1$H NMR (300MHz, DMSO-d$^6$): δ=11.00 (1H, s), 8.26–8.31 (1H, d), 8.20–8.21 (1H, d), 7.93–8.03 (2H, m), 7.18–7.34 (5H, m), 6.60–6.73 (2H, m), 3.83–3.99 (2H, brs), 1.52–1.80 (8H, m) ppm. LRMS (thermospray): m/z [M+H]+ 486.

Example 66

$^1$H NMR (400 MHz, CD$_3$OD): δ=8.02–8.10 (2H, m), 7.71–7.76 (2H, m), 7.11–7.22 (4H, m), 6.78–6.84 (2H, d), 4.04–4.11 (1H, brs), 3.95 (2H, s), 3.80–3.90 (1H, brs), 1.73–1.87 (6H, m), 1.60–1.72 (2H, m) ppm. LRMS (electrospray): m/z [M+Na]+ 547, [M–H]+ 523.

Example 67

$^1$H NMR (400 MHz, CD$_3$OD): δ=8.05–8.09 (2H, m), 7.22–7.30 (3H, m), 7.13–7.21 (4H, m), 6.91–6.96 (1H, m), 4.05–4.10 (1H, m), 3.96 (2H, s), 3.82–3.90 (1H, m), 1.73–1.85 (6H, m), 1.60–1.72 (2H, m) ppm. LRMS (electrospray): m/z [M+Na]⁺ 547, [M–H]⁺ 523.

Example 68

¹H NMR (400 MHz, DMSO-d⁶): □=8.93–9.00 (1H, brs), 8.26–8.32 (1H, d), 8.20 (1H, s), 7.95–8.00 (1H, m), 7.81–7.87 (2H, m), 7.34–7.40 (1H, t), 7.18–7.27 (4H, d), 6.83–6.91 (2H, m), 3.83–3.93 (3H, m), 3.64–3.72 (1H, m), 1.56–1.75 (8H, 2×m) ppm. LRMS (electrospray): m/z [M+Na]⁺ 547, [M–H]⁺ 523. Found C, 59.29; H, 4.85; N, 10.38. $C_{27}H_{26}F_2N_4O_5$. 0.1 mol N,N-dimethyl formamide, 1 mol $H_2O$ requires C, 59.63; H, 5.26; N, 10.44%.

Example 69

¹H NMR (400 MHz, CD₃OD): □=8.25–8.35 (1H, brs), 8.07–8.12 (2H, m), 7.53–7.63 (1H, m), 7.06–7.22 (6H, 2×m), 6.68–6.73 (2H, d), 3.99–4.08 (1H, brs), 3.75–3.85 (3H, m), 3.43 (2H, s), 1.65–1.80 (6H, m), 1.53–1.63 (2H, m) ppm. LRMS (electrospray): m/z [M+Na]⁺ 561, [M–H]⁺ 537.

Example 70

¹H NMR (400 MHz, CD₃OD): □=8.05–8.12 (2H, m), 7.52–7.57 (1H, m), 7.09–7.21 (5H, m), 7.00–7.08 (1H, t), 6.73–6.79 (2H, m), 4.00–4.08 (1H, brs), 3.74–3.85 (3H, m), 3.52 (2H, s), 1.67–1.82 (6H, m), 1.57–1.66 (2H, m) ppm. LRMS (electrospray): m/z [M+Na]⁺ 561, [M–H]⁺ 537.

Example 71

¹H NMR (400 MHz, CD₃OD): □=8.25–8.33 (1H, d), 8.04–8.10 (2H, m), 7.53–7.60 (1H, m), 7.11–7.22 (4H, m), 7.06–7.11 (1H, t), 6.72–6.76 (2H, m), 6.59–6.64 (1H, d), 4.00–4.08 (1H, brs), 3.74–3.85 (3H, m), 3.47 (2H, s), 1.66–1.83 (6H, m), 1.56–1.65 (2H, m) ppm. LRMS (electrospray): m/z [M+Na]⁺ 561, [M–H]⁺ 537.

Example 72 syn-5-Fluoro-2-(4-fluoro-phenoxy)-N-{4-[3-(2-hydroxy-benzyl)-ureido]-cyclohexyl}-nicotinamide

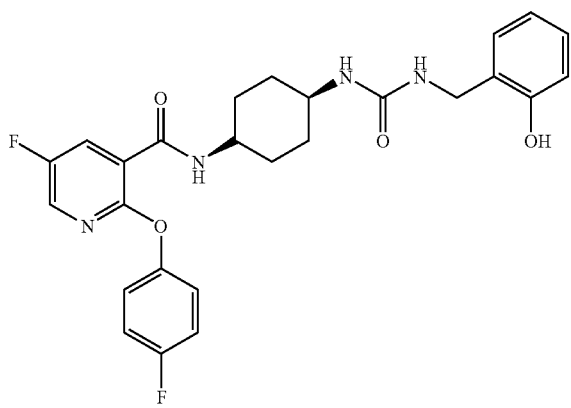

2-Aminomethyl phenol (62 mg, 0.386 mmol), syn-5-fluoro-2(4-fluoro-phenoxy)-N-{4-[(imidazole-1-carbonyl)-amino]-cyclohexyl}-nicotinamide (142 mg, 0.322 mmol) (see Preparation 25) and triethylamine (0.06 ml, 0.386 mmol) were stirred in dichloromethane (10 ml) under an atmosphere of nitrogen at room temperature for 18 hours. The reaction mixture was then washed sequentially with water (6 ml) and a 10% solution of citric acid in water (6 ml). The organic phase was separated and dried over anhydrous magnesium sulphate. The solvent was then removed in vacuo and the residue triturated with diethylether (3-fold 5 ml) to give syn-5-fluoro-2-(4-fluoro-phenoxy)-N-{4-[3-(2-hydroxy-benzyl)-ureido]-cyclohexyl}-nicotinamide (102 mg) as a pale yellow solid.

¹H NMR (400 MHz, CDCl₃): □=9.75 (1H, s), 8.29–8.35 (1H, m), 8.00–8.04 (1H, d), 7.88–7.95 (1H, d), 7.05–7.21 (5H, m), 6.97–7.03 (1H, d), 6.85–6.92 (1H, d), 6.74–6.79 (1H, t), 4.76–4.85 (1H, t), 4.27–4.35 (1H, m), 4.21–4.26 (2H, d), 4.07–4.17 (1H, m), 3.56–3.68 (1H, m), 1.62–1.86 (6H, m), 1.35–1.51 (2H, m) ppm. LRMS (electrospray): m/z [M–H]⁺ 495

Examples 73–75

The compounds of the following tabulated examples (Table 4) of the general formula:

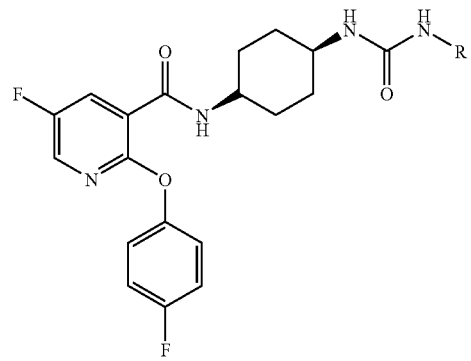

were prepared by a similar method to that of Example 72 using the appropriate amine starting material.

TABLE 4

| Example No. | Starting Intermediate Prep No. | R |
|---|---|---|
| 73 | 25 | ![m-hydroxybenzyl] |
| 74¹ | 25 | ![p-hydroxybenzyl] |
| 75 | 25 | ![4-hydroxy-2-fluorobenzyl] |

¹This compound was isolated by filtering the aqueous phase after work-up. The solid was dissolved in methanol, dried over anhydrous magnesium sulphate and concentrated under reduced pressure. The residue was triturated with diethylether to give the desired compound.

Example 73

$^1$H NMR (400 MHz, CD$_3$OD): □=8.00–8.06 (2H, m), 7.01–7.20 (5H, m), 6.64–6.70 (2H, m), 6.58–6.63 (1H, d), 4.19 (2H, s), 3.98–4.06 (1H, brs), 3.62–3.71 (1H, brs), 1.64–1.82 (6H, m), 1.50–1.61 (2H, m) ppm. LRMS (electrospray): m/z [M+Na]$^+$ 519, [M–H]$^+$ 495.

Example 74

$^1$H NMR (400 MHz, DMSO-d$^6$): □=9.17 (1H, s), 8.21–8.25 (1H, d), 8.16–8.18 (1H, d), 7.93–7.97 (1H, dd), 7.15–7.21 (4H, d), 6.95–7.00 (2H, d), 6.40–6.44 (2H, d), 5.99–6.04 (1H, t), 5.68–5.75 (1H, d), 3.97–4.01 (2H, d), 3.78–3.87 (1H, brs), 3.44–3.55 (1H, brs), 1.40–1.64 (8H, m) ppm. LRMS (electrospray): m/z [M+H]$^+$ 497, [M+Na]$^+$ 519, [M–H]$^+$ 495.

Example 75

$^1$H NMR (400 MHz, CD$_3$OD): □=8.00–8.06 (2H, m), 7.02–7.18 (4H, m), 6.93–6.99 (1H, t), 6.48–6.52 (1H, d), 6.39–6.46 (1H, m), 4.34 (1H, s), 4.18 (1H, s), 3.97–4.06 (1H, brs), 3.60–3.72 (1H, m), 1.61–1.82 (6H, m), 1.48–1.60 (2H, m) ppm. LRMS (electrospray): m/z [M+Na]$^+$ 537, [M–H]$^+$ 513.

Example 76 syn-N-(4-{[5-Fluoro-2-(4-fluoro-phenoxy)-pyridine-3-carbonyl]-amino}-cyclohexyl)-phthalamic acid

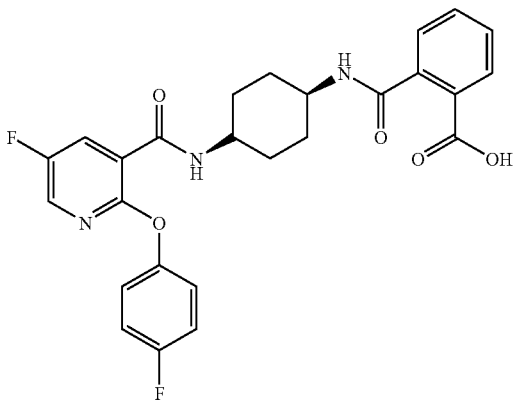

syn-N-(4-{[5-Fluoro-2-(4-fluoro-phenoxy)-pyridine-3-carbonyl]-amino}-cyclohexyl)-phthalamic acid methyl ester (378 mg, 0.742 mmol) (see Example 43) and a 1 M solution of lithium hydroxide in water (1.5 ml, 1.484 mmol) were dissolved in tetrahydrofuran (5 ml) and the reaction was stirred at room temperature for 18 hours. 2 M Hydrochloric acid (0.8 ml) was added, and the reaction mixture extracted with dichloromethane (3-fold 10 ml). The combined organic extracts were dried over anhydrous magnesium sulphate and the solvent removed in vacuo. The residue was triturated with diethylether (5 ml) giving syn-N-(4-{[5-fluoro-2-(4-fluoro-phenoxy)-pyridine-3-carbonyl]-amino}-cyclohexyl)-phthalamic acid (235 mg) as an off-white solid.

$^1$H NMR (300 MHz, DMSO-d$^6$): □=12.63 (1H, brs), 8.20–8.30 (2H, m), 8.12–8.17 (1H, d), 7.98–8.06 (1H, m), 7.73–7.81 (1H, d), 7.48–7.58 (2H, m), 7.30–7.35 (1H, d), 7.18–7.28 (4H, d), 3.78–3.96 (2H, m), 1.60–1.83 (8H, m) ppm. LRMS (electrospray): m/z [M–H]$^+$ 494

Example 76a syn-N-(4-{[5-Fluoro-2-(4-fluoro-phenoxy)-pyridine-3-carbonyl]-amino}-cyclohexyl)-isophthalamic acid methyl ester

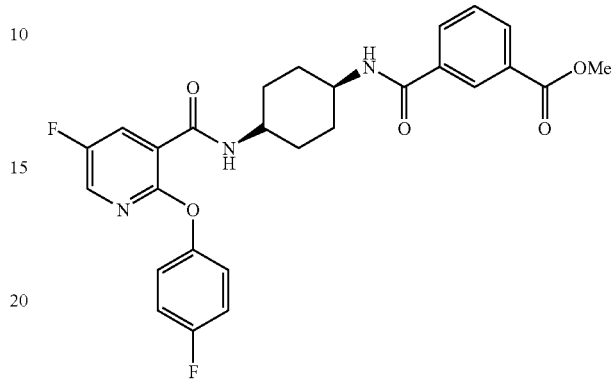

Isophthalic acid monomethyl ester (141 mg, 0.781 mmol), 1-hydroxybenzotriazole hydrate (158 mg, 1.17 mmol) and 1-(3-dimethylaminopropyl)-3-ethylcarbodiimide hydrochloride (195 mg, 1.02 mmol) were dissolved in N,N-dimethylformamide (6 ml) at room temperature and syn-N-(4-amino-cyclohexyl)-5-fluoro-2-(4-fluoro-phenoxy)-nicotinamide hydrochloride (300 mg, 0.781 mmol) (see Preparation 22) added followed by addition of N-methyl morpholine (0.17 ml, 1.56 mmol). The reaction mixture was stirred under an atmosphere of nitrogen at room temperature for 18 hours and then partitioned between ethyl acetate (20 ml) and water (20 ml) and the organic layer separated. The organic phase was then washed with a saturated aqueous solution of sodium chloride (20 ml), dried over anhydrous magnesium sulphate and the solvent removed in vacuo. The residue was triturated with diethylether (5 ml) giving syn-N-(4-{[5-fluoro-2-(4-fluoro-phenoxy)-pyridine-3-carbonyl]-amino}-cyclohexyl)-isophthalamic acid methyl ester (398 mg) as an off-white solid.

$^1$H NMR (300 MHz, DMSO-d$^6$): □=8.32–8.45 (2H, m), 8.28 (1H, s), 7.92–8.18 (4H, m), 7.60–7.68 (1H, t), 7.20–7.40 (4H, m), 3.80–4.20 (5H, m), 1.56–1.97 (8H, m) ppm. LRMS (thermospray): m/z [M+H]$^+$ 510

Example 76b syn-N-(4-{[5-Fluoro-2-(4-fluoro-phenoxy)-pyridine-3-carbonyl]-amino}-cyclohexyl)-terephthalamic acid methyl ester

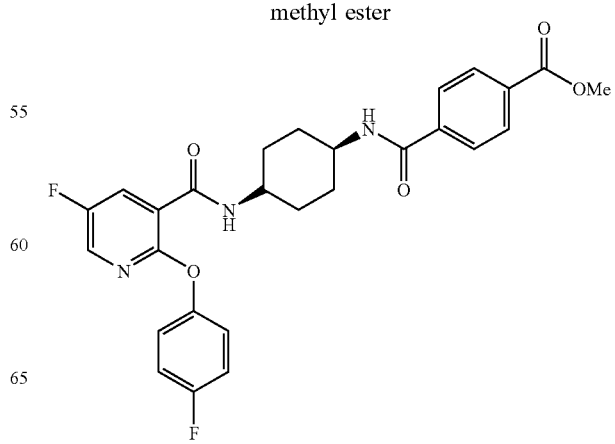

Terephthalic acid monomethyl ester (141 mg, 0.781 mmol), 1-hydroxybenzotriazole hydrate (158 mg, 1.17 mmol) and 1-(3-dimethylaminopropyl)-3-ethylcarbodiimide hydrochloride (195 mg, 1.02 mmol) were dissolved in N,N-dimethylformamide (6 ml) at room temperature and syn-N-(4-amino-cyclohexyl)-5-fluoro-2-(4-fluoro-phenoxy)-nicotinamide hydrochloride (300 mg, 0.781 mmol) (see Preparation 22) added followed by addition of N-methyl morpholine (0.17 ml, 1.56 mmol). The reaction mixture was stirred under an atmosphere of nitrogen at room temperature for 18 hours, and then partitioned between ethyl acetate (20 ml) and water (20 ml) and the organic layer separated. The organic layer was then washed with a saturated aqueous solution of sodium chloride (20 ml), dried over anhydrous magnesium sulphate and the solvent removed in vacuo. The residue was triturated with diethylether (5 ml) giving syn-N-(4-{[5-fluoro-2-(4-fluoro-phenoxy)-pyridine-3-carbonyl]-amino}-cyclohexyl)-terephthalamic acid methyl ester (395 mg) as an off-white solid.

$^1$H NMR (300 MHz, DMSO-d$^6$): □=8.21–8.37 (3H, m), 8.00–8.16 (3H, d), 7.89–7.94 (2H, d), 7.40–7.34 (4H, d), 3.80–4.08 (5H, m), 1.56–1.95 (8H, m) ppm. LRMS (thermospray): m/z [M+H]$^+$ 510

Examples 77–78

The compounds of the following tabulated examples (Table 5) of the general formula:

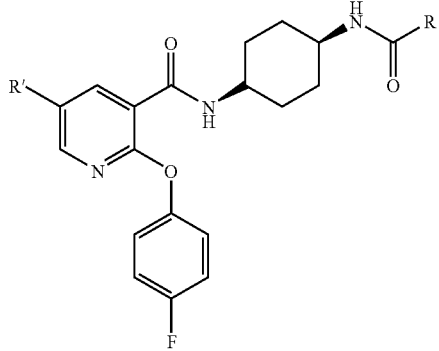

were prepared by a similar method to that of Example 76 using the appropriate ester as the starting materials.

TABLE 5

| Example No. | Starting Material Prep No. | R' | R |
|---|---|---|---|
| 77 | Example 76a | F | ![3-carboxyphenyl] |
| 78 | Example 76b | F | ![4-carboxyphenyl] |

Example 77

$^1$H NMR (300 MHz, DMSO-d$^6$): □=13.14 (1H, brs), 8.39 (1H, s), 8.29–8.35 (2H, d), 8.20–8.28 (1H, d), 7.96–8.16 (3H, m), 7.52–7.62 (1H, t), 7.18–7.40 (4H, m), 3.91–4.00 (1H, m), 3.78–3.90 (1H, m), 1.56–1.89 (8H, m) ppm. LRMS (electrospray): m/z [M–H]$^+$ 494

Example 78

$^1$H NMR (300 MHz, DMSO-d$^6$): □=13.16 (1H, brs), 8.30–8.35 (1H, d), 8.20–8.28 (2H, m), 7.97–8.09 (3H, m), 7.85–7.91 (2H, d), 7.20–7.35 (4H, d), 3.91–4.02 (1H, m), 3.80–3.90 (1H, m), 1.60–1.92 (8H, m) ppm. LRMS (electrospray): m/z [M–H]$^+$ 494

Example 79

5-Fluoro-2-(4-fluoro-phenoxy)-N-[1-(2-hydroxy-4-methyl-benzoyl)-piperidin-4-yl]-nicotinamide

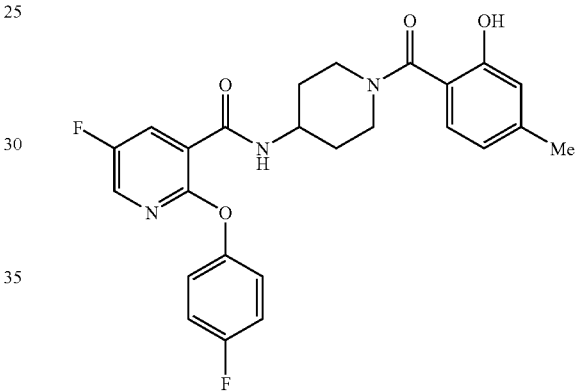

4-Methylsalicylic acid (91 mg, 0.595 mmol), 1-hydroxybenzotriazole hydrate (110 mg, 0.811 mmol), 1-(3-dimethylaminopropyl)-3-ethylcarbodiimide hydrochloride (135 mg, 0.703 mmol), 5-fluoro-2-(4-fluoro-phenoxy)-N-piperidin-4-yl-nicotinamide hydrochloride (200 mg, 0.541 mmol) (see Preparation 29) and N-methyl morpholine (0.12 ml, 1.08 mmol) were stirred in N,N-dimethylformamide (4 ml) under an atmosphere of nitrogen at room temperature for 18 hours. The reaction mixture was then partitioned between ethyl acetate (10 ml) and water (10 ml), the organic layer separated, washed with a saturated aqueous solution of sodium chloride (10 ml) and dried over anhydrous magnesium sulphate. The solvent was then removed in vacuo and the residue purified via flash column chromatography on silica gel eluting with a solvent gradient of 100% dichloromethane changing to 99:1, by volume, dichloromethane:methanol. The resulting white foam was triturated with pentane (5 ml) giving 5-fluoro-2-(4-fluoro-phenoxy)-N-[1-(2-hydroxy-4-methyl-benzoyl)-piperidin-4-yl]-nicotinamide (169 mg) as a white solid.

$^1$H NMR (400 MHz, CDCl$_3$): □=8.34–8.38 (1H, m), 8.01–8.03 (1H, d), 7.80–7.84 (1H, d) 7.08–7.18 (5H, m), 7.81 (1H, s). 6.60–6.65 (1H, d), 4.24–4.36 (3H, m), 3.17–3.25 (2H, t), 2.30 (3h, s), 2.10–2.18 (2H, d), 1.50–1.62 (2H, m) ppm. LRMS (electrospray): m/z [M+H]$^+$ 468, [M+Na]$^+$ 490

Examples 80–91

The compounds of the following tabulated examples (Table 6) of the general formula:

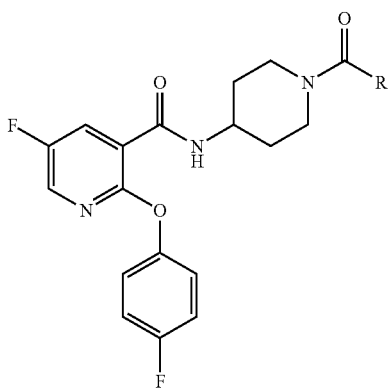

were prepared by a similar method to that of Example 79 using the appropriate carboxylic acid as the starting material.

TABLE 6

| Example No. | Starting Material Prep No. | R |
|---|---|---|
| 80 | 29 | 3-hydroxyphenyl |
| 81 | 29 | 1-hydroxy-2-naphthyl |
| 82 | 29 | 4-hydroxyphenyl |
| 83 | 29 | 2-hydroxyphenyl |
| 84 | 29 | 4-methyl-3-hydroxyphenyl |
| 85 | 29 | 4-fluoro-3-hydroxyphenyl |
| 86 | 29 | 2-fluoro-6-hydroxyphenyl |
| 87 | 29 | 2-methyl-3-hydroxyphenyl |
| 88 | 29 | 4-hydroxybenzyl |
| 89 | 29 | 2-hydroxybenzyl |
| 90 | 29 | 3-hydroxybenzyl |
| 91 | 29 | 2-(2-hydroxyphenyl)ethyl |

Example 80

$^1$H NMR (400 MHz, DMSO-d$^6$): δ=9.55 (1H, brs), 8.36–8.41 (1H, d), 8.17 (1H, s), 7.90–7.96 (1H, m) 7.12–7.23 (5H, m), 6.74–6.79 (1H, d), 6.65–6.72 (1H, d), 6.64 (1H, s), 4.08–4.30 (1H, m), 3.98–4.06 (1H, m), 3.41–3.60 (1H, m), 2.91–3.20 (2H, m), 1.72–1.91 (2H, d), 1.30–1.54 (2H, m) ppm. LRMS (thermospray): m/z [M+H]$^+$ 454, [M+Na]$^+$ 476

Example 81

$^1$H NMR (400 MHz, CDCl$_3$): δ=11.16 (1H, s), 8.31–8.37 (2H, m), 7.98–8.02 (1H, d), 7.80–7.85 (1H, d), 7.72–7.77 (1H, d), 7.44–7.56 (2H, m), 7.19–7.23 (2H, d), 7.04–7.16 (4H, m), 4.23–4.39 (3H, m), 3.22–3.30 (2H, t), 2.12–2.19 (2H, d), 1.50–1.63 (2H, m) ppm. LRMS (electrospray): m/z [M−H]$^+$ 502

Example 82

$^1$H NMR (400 MHz, CDCl$_3$): δ=8.32–8.37 (1H, m), 8.02–8.05 (1H, d), 7.80–7.86 (1H, d), 7.20–7.26 (1H, m, partially masked by solvent), 7.08–7.20 (4H, m), 6.71–6.81 (3H, m), 4.00–4.35 (3H, m), 3.08–3.23 (2H, m), 2.05–2.18 (2H, d), 1.40–1.60 (2H, m) ppm. LRMS (electrospray): m/z [M−H]$^+$ 452

Example 83

¹H NMR (400 MHz, CDCl₃): □=9.55 (1H, s), 8.34–8.39 (1H, m), 8.04–8.07 (1H, d), 7.79–7.88 (1H, d), 7.28–7.36 (1H, m), 7.21–7.24 (1H, d), 7.08–7.16 (4H, m), 6.96–7.02 (1H, d), 6.78–6.85 (1H, t), 4.24–4.37 (3H, m), 3.18–3.28 (2H, t), 2.12–2.21 (2H, d), 1.69–1.83 (2H, m, partially masked by solvent) ppm. LRMS (electrospray): m/z [M–H]⁺ 452 Found C, 61.85; H, 4.68; N, 9.19. $C_{24}H_{21}F_2N_3O_4$. 0.7 mol $H_2O$ requires C, 61.85; H, 4.84; N, 9.02%.

Example 84

¹H NMR (400 MHz, CDCl₃): □=8.33–8.37 (1H, m), 8.04 (1H, s), 7.79–7.85 (1H, d), 7.08–7.18 (4H, m), 7.02–7.07 (1H, d), 6.85–6.92 (1H, brs), 6.74–6.78 (1H, d), 4.38–4.65 (1H, m), 4.21–4.36 (1H, m), 3.78–3.94 (1H, m), 3.01–3.24 (2H, m), 2.21 (3H, s), 1.98–2.19 (2H, d), 1.38–1.60 (2H, m) ppm. LRMS (electrospray): m/z [M–H]⁺ 466

Example 85

¹H NMR (400 MHz, CDCl₃): □=9.18 (1H, s), 8.32–8.37 (1H, m), 8.02–8.04 (1H, d), 7.80–7.86 (1H, d), 7.02–7.18 (2H, m), 7.08–7.20 (5H, m), 6.86–6.97 (2H, m), 4.22–4.37 (3H, m), 3.18–3.22 (2H, t), 2.13–2.22 (2H, d), 1.50–1.63 (2H, m, partially masked by solvent) ppm. LRMS (electrospray): m/z [M–H]⁺ 470

Example 86

¹H NMR (400 MHz, CDCl₃): □=8.28–8.36 (1H, m), 8.01–8.04 (1H, d), 7.75–7.84 (1H, d), 7.18–7.27 (1H, m, partially masked by solvent), 7.04–7.17 (4H, m), 6.75–6.80 (1H, d), 6.52–6.60 (1H, t), 4.35–4.63 (1H, m), 4.18–4.33 (1H, m), 3.60–3.90 (1H, m), 3.03–3.30 (2H, m), 2.02–2.19 (2H, d), 1.40–1.70 (2H, m, partially masked by solvent) ppm. LRMS (electrospray): m/z [M–H]⁺ 470

Example 87

¹H NMR (400 MHz, CDCl₃): □=8.26–8.32 (1H, m), 7.99–8.02 (1H, d), 7.77–7.84 (1H, d), 7.04–7.16 (4H, m), 6.93–7.02 (1H, m), 6.62–6.73 (2H, m), 5.88–6.00 (1H, d), 4.52–4.68 (1H, dd), 4.16–4.27 (1H, m), 3.41–3.48 (1H, d), 2.96–3.16 (1H, m), 2.10–2.19 (1H, m), 2.09 (3H, s), 1.88–2.02 (1H, m), 1.68–1.80 (1H, m, partially masked by solvent), 1.24–1.39 (1H, m) ppm. LRMS (electrospray): m/z [M–H]⁺ 466

Example 88

¹H NMR (400 MHz, CDCl₃): □=8.25–8.31 (1H, m), 7.98–8.02 (1H, d), 7.71–7.78 (1H, d), 6.96–7.18 (6H, m), 6.67–6.75 (2H, m), 5.84 (1H, s), 4.37–4.47 (1H, m), 4.10–4.22 (1H, m), 3.72–3.83 (1H, m), 3.62 (2H, s), 3.08–3.21 (1H, t), 2.82–2.95 (1H, t), 1.90–2.05 (2H, d), 1.35–1.46 (1H, m), 1.13–1.23 (1H, m) ppm. LRMS (electrospray): m/z [M–H]⁺ 466

Example 89

¹H NMR (400 MHz, CDCl₃): □=9.57 (1H, s), 8.30–8.36 (1H, m), 8.01–8.04 (1H, d), 7.72–7.80 (1H, d), 7.05–7.20 (5H, m), 6.90–7.02 (2H, m), 6.76–6.84 (1H, t), 4.43–4.55 (1H, d), 4.20–4.32 (1H, m), 4.08–4.18 (1H, d), 3.71 (2H, s), 3.32–3.44 (1H, t), 2.86–2.95 (1H, t), 2.15–2.24 (1H, d), 2.02–2.14 (1H, d), 1.37–1.50 (2H, m) ppm. LRMS (electrospray): m/z [M–H]⁺ 466

Example 90

¹H NMR (400 MHz, CDCl₃): □=8.28–8.31 (1H, m), 8.01–8.04 (1H, d), 7.72–7.79 (1H, d), 7.22 (1H, s), 7.05–7.17 (5H, m), 6.84 (1H, s), 6.65–6.70 (2H, d), 4.37–4.47 (1H, d), 4.12–4.22 (1H, m), 3.77–3.84 (1H, d), 3.64 (2H, s), 3.12–3.21 (1H, t), 2.81–2.88 (1H, t), 1.90–2.03 (2H, 2×d), 1.38–1.51 (1H, m), 1.10–1.20 (1H, m) ppm. LRMS (electrospray): m/z [M–H]⁺ 466

Example 91

¹H NMR (400 MHz, CDCl₃): □=9.36 (1H, s), 8.30–8.35 (1H, m), 8.02–8.04 (1H, d), 7.75–7.81 (1H, d), 7.00–7.16 (6H, m), 6.65–6.89 (1H, d), 6.76–6.82 (1H, t), 4.44–4.53 (1H, d), 4.17–4.27 (1H, m), 3.72–3.81 (1H, d), 3.13–3.24 (1H, t), 2.82–2.96 (3H, m), 2.68–2.75 (2H, m), 1.97–2.16 (2H, 2×d), 1.28–1.46 (2H, m) ppm. LRMS (electrospray): m/z [M–H]⁺ 480

Example 92 endo-5-Fluoro-2-(4-fluoro-phenoxy)-N-{8-[2-(4-hydroxy-phenyl)-acetyl]-8-aza-bicyclo[3.2.1]oct-3-yl}-nicotinamide

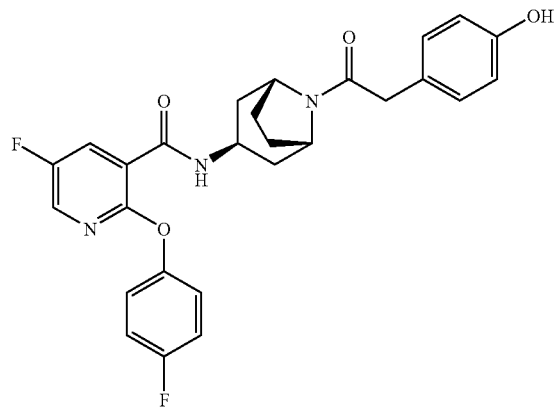

4-Hydroxy-phenyl-acetic acid (88 mg, 0.57 mmol), 1-hydroxybenzotriazole (84 mg, 0.62 mmol), 1-(3-dimethylaminopropyl)-3-ethylcarbodiimide hydrochloride (122 mg, 0.62 mmol), endo-N-(8-aza-bicyclo[3.2.1]oct-3-yl)-5-fluoro-2-(4-fluoro-phenoxy)-nicotinamide (204 mg, 0.57 mmol) (see Preparation 32) and N-methyl morpholine (0.07 ml, 0.62 mmol) were stirred in dichloromethane (5 ml) under an atmosphere of nitrogen at room temperature for 18 hours. The reaction mixture was then washed with a saturated aqueous solution of sodium chloride (6 ml), the organic layer separated and dried over anhydrous magnesium sulphate and the solvent removed in vacuo. The residue was then purified by flash column chromatography on silica gel eluting with a solvent gradient of dichloromethane:pentane (50:50, by volume) changing to dichloromethane:methanol (100:0 then 97:3, by volume) to give endo-5-fluoro-2-(4-fluoro-phenoxy)-N-{8-[2-(4-hydroxy-phenyl)-acetyl]-8-aza-bicyclo[3.2.1]oct-3-yl}-nicotinamide (50 mg) as a white foam.

$^1$H NMR (400 MHz, CDCl$_3$): □=8.48–8.57 (1H, d), 8.29–8.33 (1H, dd), 7.98–8.00 (1H, d), 7.00–7.14 (6H, m), 6.70–6.75 (2H, d), 5.88 (1H, s), 4.68–4.74 (1H, m), 4.28–4.35 (1H, m), 4.18–4.23 (1H, brs), 3.48–3.62 (2H, quartet), 2.24–2.29 (1H, m), 1.72–1.92 (7H, m) ppm. LRMS (electrospray): m/z [M+H]$^+$ 494, [M+Na]$^+$ 516, [M−H]$^+$ 492.

Examples 93–98

The compounds of the following tabulated examples (Table 7) of the general formula:

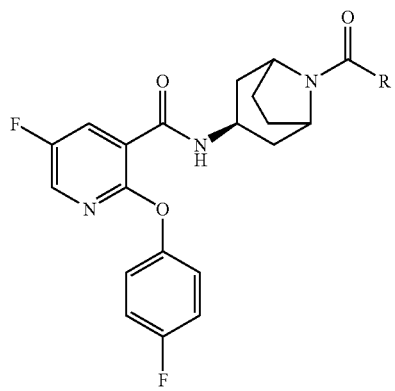

were prepared by a similar method to that of Example 92 using the appropriate amine and carboxylic acid as the starting material.

TABLE 7

| Example No. | Starting Amine Prep No. | Stereochem. of Ring | R |
|---|---|---|---|
| 93[1,2] | 35 | exo | 2-hydroxyphenyl |
| 94[1,3] | 35 | exo | 4-hydroxyphenyl |
| 95[1] | 37 | exo | 2-hydroxybenzamido-methyl |
| 96[1] | 37 | exo | 4-hydroxybenzamido-methyl |
| 97 | 37 | exo | 2-(4-hydroxyphenyl)acetamido-methyl |
| 98 | 37 | exo | 2-(2-hydroxyphenyl)acetamido-methyl |

[1]The eluent for flash column chromatography was dichloromethane:methanol (100:0 changing to 98:2, by volume).
[2]The compound was slurried in 20% ethyl acetate in pentane after chromatography, and was filtered, washed with pentane and dried in vacuo to give the desired product.
[3]The compound was triturated with diethylether after chromatography to give the desired product.

Example 93

¹H NMR (400 MHz, CDCl₃): □=10.42 (1H, s), 8.30–8.35 (1H, dd), 8.00–8.02 (1H, d), 7.64–7.73 (1H, d), 7.29–7.38 (2H, m), 7.05–7.19 (4H, m), 6.97–7.01 (1H, d), 6.80–6.85 (1H, t), 4.73–4.83 (2H, brs), 4.60–4.72 (1H, m), 2.15–2.24 (2H, d), 2.00–2.14 (2H, m), 1.92–2.00 (2H, d), 1.69–1.80 (2H, t) ppm. LRMS (electrospray): m/z [M+Na]⁺ 502, [M–H]⁺ 478.

Example 94

¹H NMR (400 MHz, DMSO-d⁶): □=9.91 (1H, s), 8.30–8.37 (1H, dd), 8.08–8.10 (1H, d), 7.90–7.97 (1H, dd), 7.27–7.33 (2H, d), 7.16–7.25 (4H, m), 6.74–6.80 (2H, d), 4.02–4.64 (3H, 2×brs+m), 1.48–2.01 (8H, m) ppm. LRMS (electrospray): m/z [M+Na]⁺ 502, [M–H]⁺ 478.

Example 95

¹H NMR (400 MHz, CDCl₃): □=12.08 (1H, s), 8.28–8.36 (1H, d), 8.02 (1H, s), 7.60–7.70 (1H, d), 7.16–7.30 (3H, m), 7.03–7.16 (4H, m), 6.94–6.99 (1H, d), 6.81–6.88 (1H, t), 4.77–4.84 (1H, brs), 4.60–4.75 (1H, m), 4.10–4.30 (3H, m), 2.22–2.30 (1H, d), 1.99–2.20 (3H, m), 1.87–1.98 (1H, d), 1.60–1.72 (1H, t), 1.46–1.60 (2H, m, partially masked by solvent) ppm. LRMS (electrospray): m/z [M+Na]⁺ 559, [M–H]⁺ 535.

Example 96

¹H NMR (400 MHz, CDCl₃): □=8.30–8.36 (1H, dd), 8.00–8.02 (1H, d), 7.62–7.73 (3H, d), 7.06–7.16 (4H, m), 7.01 (1H, s), 6.86–7.00 (1H, brs), 6.80–6.86 (2H, d), 4.77–4.81 (1H, brs), 4.60–4.76 (1H, m), 4.16–4.33 (3H, m), 3.67–3.77 (1H, m), 2.20–2.37 (1H, d), 1.98–2.20 (4H, m), 1.88–1.98 (1H, d), 1.51–1.70 (1H, m, partially masked by solvent) ppm. LRMS (electrospray): m/z [M+Na]⁺ 559, [M–H]⁺ 535.

Example 97

¹H NMR (400 MHz, CDCl₃): □=8.27–8.32 (1H, d), 8.01 (1H, s), 7.58–7.65 (1H, d), 7.07–7.18 (6H, m), 6.71–6.79 (2H, d), 6.43–6.49 (1H, brs), 6.04–6.13 (1H, brs), 4.66–4.74 (1H, brs), 4.56–4.66 (1H, m), 4.16–4.23 (1H, m), 3.92–4.07 (2H, m), 3.53 (2H, s), 2.14–2.23 (1H, d), 1.81–2.13 (5H, m), 1.50–1.64 (1H, m, partially masked by solvent), 1.40–1.50 (1H, t) ppm. LRMS (electrospray): m/z [M+Na]⁺ 573, [M–H]⁺ 549.

Example 98

¹H NMR (400 MHz, CDCl₃): □=9.40 (1H, s), 8.27–8.35 (1H, d), 8.02 (1H, s), 7.57–7.64 (1H, d), 6.92–7.20 (8H, m), 6.79–6.87 (1H, t), 4.72–4.79 (1H, brs), 4.58–4.70 (1H, m), 4.14–4.21 (1H, m), 3.95–4.05 (2H, m), 3.61 (2H, s), 2.17–2.24 (1H, d), 1.83–2.17 (5H, m), 1.57–1.64 (1H, t, partially masked by solvent), 1.40–1.51 (1H, t) ppm. LRMS (electrospray): m/z [M+Na]⁺ 573, [M–H]⁺ 549.

Example 99 exo-2-(3-{[5-Fluoro-2-(4-fluoro-phenoxy)-pyridine-3-carbonyl]-amino}-8-azo-bicyclo[3.2.1]-octane-8-carbonyl)-benzoic acid methyl ester

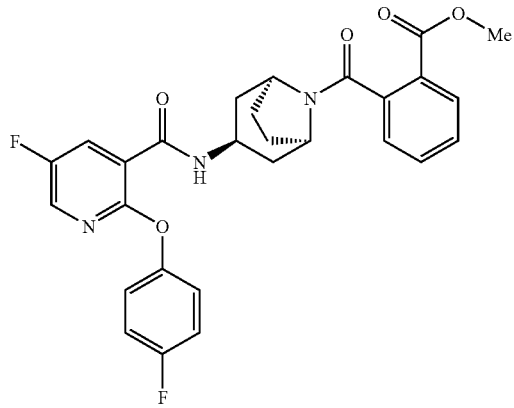

Phthalic acid monomethyl ester (155 mg, 0.83 mmol), 1-hydroxybenzotriazole (135 mg, 1 mmol) and 1-(3-dimethylaminopropyl)-3-ethylcarbodiimide hydrochloride (196 mg, 1 mmol) were stirred in dichloromethane (5 ml) at room temperature and exo-N-(8-aza-bicyclo[3.2.1]oct-3-yl)-5-fluoro-2-(4-fluooro-phenoxy)-nicotinamide (299 mg, 0.83 mmol) (see Preparation 35) added followed by addition of N-methyl morpholine (0.11 ml, 1 mmol). The reaction mixture was stirred under an atmosphere of nitrogen at room temperature for 18 hours, then washed with a saturated aqueous solution of sodium chloride (5 ml and the organic phase separated. The organic phase was concentrated in vacuo and the residue purified by flash column chromatography on silica gel eluting with 100:0 changing to 97:3, by volume, dichloromethane:methanol giving exo-2-(3-{[5-fluoro-2-(4-fluoro-phenoxy)-pyridine-3-carbonyl]-amino}-8-azo-bicyclo[3.2.1]-octane-8-carbonyl)-benzoic acid methyl ester (298 mg) as a white foam.

¹H NMR (400 MHz, CDCl₃): δ=8.30–8.36 (1H, dd), 8.00–8.01 (1H, d), 7.93–7.98 (1H, d), 7.75–7.82 (1H, d), 7.49–7.56 (1H, t), 7.40–7.47 (1H, t), 7.28–7.33 (1H, d), 7.12–7.19 (4H, d), 4.93–4.98 (1H, m), 4.59–4.71 (1H, m), 3.76–3.81 (1H, m), 3.63 (3H, s), 1.83–2.21 (6H, m), 1.39–1.49 (2H, t) ppm. LRMS (electrospray): m/z [M+Na]⁺ 544, [M–H]⁺ 520.

Example 100 exo-2-(3-{[5-Fluoro-2-(4-fluoro-phenoxy)-pyridine-3-carbonyl]-amino}8-aza-bicyclo[3.2.1]octane-8-carbonyl}-benzoic acid

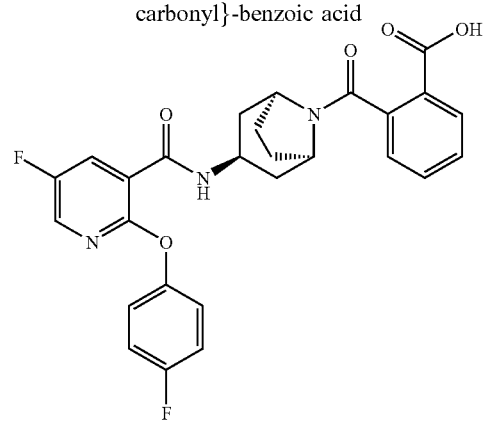

Exo-2-(3-{[5-Fluoro-2-(4-fluoro-phenoxy)-pyridine-3-carbonyl]-amino}8-aza-bicyclo[3.2.1]octane-8-carbonyl}-benzoic acid methyl ester (see Example 99) (225 mg, 0.43 mmol) and 1N aqueous lithium hydroxide (0.5 ml, 0.5 mmol) were stirred in methanol (5 ml) at room temperature for 18 hours. Starting material remained, so the reaction was heated at reflux and stirred for a further 5 hours. The reaction mixture was then cooled and glacial acetic acid added until the pH reached 5. The methanol was removed under reduced pressure, and the residue extracted with ethyl acetate (10 ml). The organic phase was separated, washed with a saturated aqueous solution of sodium chloride (10 ml), concentrated in vacuo and the residue triturated with diethylether (5 ml) to give exo-2-(3-{[5-fluoro-2-(4-fluoro-phenoxy)-pyridine-3-carbonyl]-amino}8-aza-bicyclo[3.2.1]octane-8-carbonyl}-benzoic acid (103 mg) as a white solid.

$^1$H NMR (400 MHz, DMSO-d$^6$): δ=8.26–8.38 (1H, brs), 8.18–8.20 (1H, d), 7.91–7.97 (1H, dd), 7.70–7.88 (1H, brs), 7.55–7.63 (1H, m), 7.43–7.53 (1H, m), 7.16–7.31 (5H, m), 4.63–4.72 (1H, brs), 4.27–4.40 (1H, m), 3.52–3.62 (1H, brs), 1.84–2.00 (4H, m), 1.63–1.82 (4H, m) ppm. LRMS (electrospray): m/z [M–H]$^+$ 506.

Example 101

Syn-5-Fluoro-2-(4-fluoro-phenoxy)-N-[4-(2-hydroxy-acetylamino)cyclohexyl]-nicotinamide

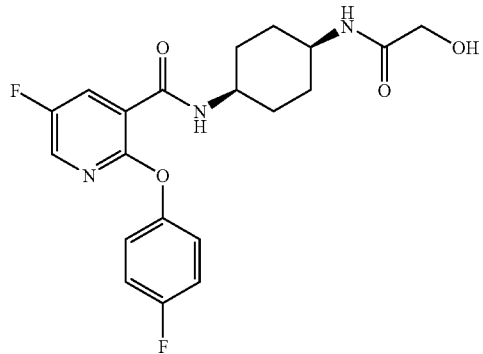

Glycolic acid (40 mg, 0.52 mmol), 1-hydroxybenzotriazole hydrate (80 mg, 0.52 mmol), 1-(3-dimethylaminopropyl)-3-ethylcarbodiimide hydrochloride (100 mg, 0.52 mmol), triethylamine (181 μl, 1.3 mmol) and syn-N-(4-Amino-cyclohexyl)-5-fluoro-2-(4-fluoro-phenoxy)-nicotinamide hydrochloride (150 mg, 0.39 mmol)(see Preparation 22) were dissolved in N,N-dimethylformamide and were stirred for 18 hours at room temperature. The mixture was partitioned between ethyl acetate and water, the organic phase was dried over magnesium sulphate and evaporated in-vacuo. The residue was purified by chromatography on silica gel using methanol in dichloromethane (5:95) and then further purified by chromatography on silica gel using methanol in ethyl acetate (gradient from 0:100 to 5:95) to give syn-5-fluoro-2-(4-fluoro-phenoxy)-N-[4-(2-hydroxy-acetylamino)cyclohexyl]-nicotinamide as a white powder (100 mg).

$^1$H NMR (400 MHz, CDCl$_3$): δ 8.33 (1H, d), 8.03 (1H, s), 7.99 (1H, d), 7.12 (4H, m), 6.22 (1H, d), 4.22 (1H, m), 4.09 (2H, s), 4.00 (1H, m), 2.20 (1H, s), 1.86 (5H, m), 1.79 (3H, m). LCMS (electrospray): m/z [M–H]$^-$ 404

Examples 102–125

The compounds of the following tabulated examples (Table 8) of the general formula:

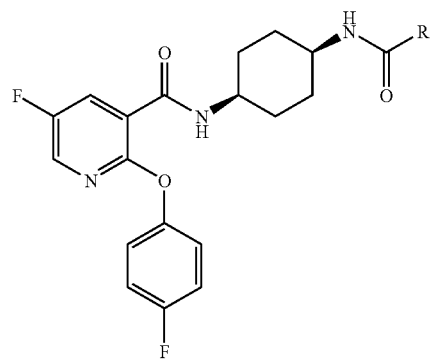

were prepared by a similar method to that of example 101 using the amine of Preparation 22 and the appropriate carboxylic acid.

TABLE 8

| Example N° | R group |
|---|---|
| 102[1] | ⌒⌒OH |
| 103[2] | OH, CH₃, CH₃ (branched) |
| 104[2] | OH, CH₂-phenyl |
| 105[2] | OH, C(CH₃)₂ |
| 106[2] | OH, cyclohexyl |
| 107[2] | OH, cyclohexyl |
| 108[2,4] | OH, phenyl |

TABLE 8-continued

| Example N° | R group |
|---|---|
| 109[2] | (1-hydroxycyclopropyl)methyl |
| 110 | methyl 3-(methyl)butanoate-like: -CH2CH2CH2C(=O)OCH3 |
| 111 | ethyl 2,2-dimethylpropanoate: -CH2C(CH3)2C(=O)OCH2CH3 |
| 112 | methyl (R)-3-methylbutanoate: -CH2CH(CH3)CH2C(=O)OCH3 |
| 113 | ethyl 2,2-dimethylbutanoate: -CH2C(CH3)2C(=O)OCH2CH3 (geminal dimethyl) |
| 114 | methyl pentanoate: -CH2CH2CH2C(=O)OCH3 |
| 115 | methyl (S)-3-methylbutanoate |
| 116 | methyl 2,2-dimethylpentanoate |
| 117 | tert-butyl 2-(cyclopentyl)acetate derivative |
| 118 | ethyl hexanoate: -CH2CH2CH2CH2C(=O)OCH2CH3 |
| 119 | methyl 2-(cyclopentyl)carboxylate (trans) |
| 120 | methyl 3-methoxy-4-substituted benzoate |
| 121[3] | methyl 2-chloro-4-substituted benzoate |
| 122 | methyl 6-substituted-nicotinate |
| 123 | methyl 6-substituted-picolinate |
| 124 | methyl 2-substituted-isonicotinate |
| 125 | 2-hydroxy-4-methylbenzyl |

[1] Purification by chromatography using a gradient from 95:5:0.5 to 90:10:0.5 ethyl acetate:methanol:ammonium hydroxide solution, then 95:5:0.5 dichloromethane:methanol:ammonium hydroxide solution.
[2] Triethylamine was replaced with N-methylmorpholine.
Aqueous solutions were further extracted four times with dichloromethane (5 ml)
Purification by chromatography on silica gel used 99:1:01 dichloromethane:methanol:ammonium hydroxide solution, then 97:3:0.1 dichloromethane:methanol:ammonium hydroxide solution
[3] The compound was pre-adsorbed onto silica gel prior to purification by chromatography on silica gel using 1% methanol in dichloromethane.
[4] After stirring 18 hours L-mandelic acid (10 mg, 0.065 mmol) was added and the mixture left to stir 24 hours

Example 102

$^1$H NMR (400 MHz, DMSO-$d_6$): δ 8.20 (1H, m), 7.99 (1H, m), 7.70 (1H, d), 7.21 (4H, m), 4.18 (1H, m), 3.84 (1H, m), 3.63 (1H, m), 3.52 (2H, m), 2.40 (1H, m), 2.28 (2H, m), 1.63–1.56 (8H, m). LCMS (electrospray): m/z [M−H]⁻ 418

Example 103

¹H NMR (400 MHz, CDCl₃) δ 8.35 (1H, d), 8.04 (1H, d), 7.93 (1H, d), 7.13 (4H, m), 6.40 (1H, s), 4.20 (1H, s), 4.08 (1H, m), 3.91 (1H, m), 2.05 (1H, m), 1.82 (8H, m), 1.60 (1H, m), 1.45 (2H, m) 0.90 (6H, m). LCMS (electrospray): m/z [M+Na]⁺ 484

Example 104

¹H NMR (400 MHz, CDCl₃): δ 8.38 (1H, m), 8.04 (1H, s), 7.97 (1H, d), 7.20 (9H, m), 6.25 (1H, d), 4.29 (1H, m), 4.18 (1H, m), 3.91 (1H, m), 3.91 (1H, m), 3.18 (1H, m), 2.92 (1H, m), 1.79 (4H, m), 1.61 (2H, m), 1.42 (2H, m). LCMS (electrospray): m/z [M−H]⁻ 494

Example 105

¹H NMR (400 MHz, CDCl₃): δ 8.33 (1H, m), 8.04 (1H, d), 7.93 (1H, d), 7.18 (4H, m), 6.59 (1H, s), 4.21 (1H, s), 3.96 (2H, m), 1.84 (4H, m), 1.77 (2H, m), 1.60 (6H, s), 1.48 (2H, m). LCMS (electrospray): m/z [M+H]⁺ 434

Example 106

¹H NMR (400 MHz, CDCl₃): δ 8.33 (1H, m), 8.02 (2H, m), 7.16 (4H, m), 6.40 (1H, d), 4.20 (1H, s), 3.90 (2H, m), 1.74 (12H, m), 1.43 (3H, m), 1.14 (5H, m). LCMS (electrospray): m/z [M−H]⁻ 486

Example 107

¹H NMR (400 MHz, CDCl₃): δ 8.37 (1H, m), 8.02 (2H, m), 7.16 (4H, m), 6.40 (1H, d), 4.20 (1H, s), 3.90 (2H, m), 1.75 (12H, m), 1.43 (3H, m), 1.18 (5H, m). LCMS (electrospray): m/z [M−H]⁻ 486

Example 108

¹H NMR (400 MHz, CDCl₃): δ 8.31 (1H, m), 8.04 (1H, s), 7.94 (1H, s), 7.25 (6H, m), 7.14 (4H, m), 6.21 (1H, d), 4.98 (1H, s), 4.14 (1H, m), 3.96 (1H, m), 1.79 (4H, m), 1.63 (2H, s), 1.24 (2H, m). LCMS (electrospray): m/z [M+Na]⁺ 504

Example 109

¹H NMR (400 MHz, CD₃OD): δ 8.32 (1H, m), 8.01 (2H, m), 7.14 (4H, m), 6.81 (1H, d), 4.18 (1H, s), 3.90 (1H, m), 1.81 (6H, m), 1.51 (2H, m), 1.25 (2H, m), 1.19 (2H, m). LCMS (electrospray): m/z [M+Na]⁺ 454

Example 110

¹H NMR (400 MHz, CDCl₃): δ 8.38 (1H, m), 8.04 (1H, s), 7.97 (1H, d), 7.14 (4H, m), 5.56 (1H, d), 4.20 (1H, s), 3.92 (1H, m), 3.89 (3H, s), 2.66 (2H, m), 2.41 (2H, m), 1.82 (4H, m), 1.73 (2H, m), 1.48 (2H, m). LCMS (electrospray): m/z [M−H]⁻ 486

Example 111

¹H NMR (400 MHz, CDCl₃): δ 8.38 (1H, d), 8.06 (1H, s), 7.98 (1H, d), 7.16 (4H, m), 6.50 (1H, d), 4.20 (1H, s), 4.11 (2H, q), 3.89 (1H, m), 1.93 (4H, m), 1.71 (2H, m), 1.48 (2H, m), 1.40 (6H, s), 1.22 (3H, t). LCMS (electrospray): m/z [M−H]⁻ 488

Example 112

¹H NMR (400 MHz, CDCl₃): δ 8.37 (1H, d), 8.04 (1H, s), 7.98 (1H, d), 7.17 (4H, m), 5.79 (1H, d), 4.20 (1H, m), 3.90 (1H, m), 3.60 (3H, s), 2.71 (1H, m), 2.60 (1H, m), 2.36 (1H, m), 1.83 (4H, m), 1.74 (2H, m), 1.49 (2H, m), 1.14 (3H, d). LCMS (electrospray): m/z [M+Na]⁺ 498

Example 113

¹H NMR (400 MHz, CDCl₃): δ 8.37 (1H, d), 8.04 (1H, s), 7.96 (1H, d), 7.17 (4H, m), 5.85 (1H, d), 4.19 (1H, s), 4.04 (2H, q), 3.90 (1H, s), 2.40 (2H, s), 1.82 (4H, m), 1.70 (2H, m), 1.43 (2H, m), 1.24 (6H, s) 1.21 (3H, t). LCMS (electrospray): m/z [M+Na]⁺ 526

Example 114

¹H NMR (400 MHz, CDCl₃): δ 8.37 (1H, d), 8.04 (1H, s), 7.96 (1H, d), 7.14 (4H, m), 5.38 (1H, s), 4.20 (1H, s), 3.91 (1H, s), 3.66 (3H, s), 2.18 (2H, t), 2.19 (2H, t), 1.91 (2H, m), 1.81 (4H, m), 1.76 (2H, m), 1.23 (2H, m). LCMS (electrospray): m/z [M−H]⁻ 474

Example 115

¹H NMR (400 MHz, CD₃OD): δ 8.18 (2H, s), 7.20 (4H, m), 4.10 (1H, s), 3.80 (1H, s), 3.66 (3H, s), 2.39 (2H, m), 2.20 (2H, m), 2.19 (1H, m), 1.80 (6H, m), 1.60 (2H, m) (0.95 (3H, d). LCMS (thermospray): m/z [M−H]⁻ 488

Example 116

¹H NMR (400 MHz, CDCl₃): δ 8.37 (1H, d), 8.04 (1H, s), 7.97 (1H, d), 7.16 (4H, m), 5.25 (1H, d), 4.20 (1H, s), 3.91 (1H, s), 3.68 (3H, s), 2.07 (2H, m), 1.84 (6H, m), 1.77 (2H, m), 1.44 (2H, m), 1.20 (6H, s). LCMS (electrospray): m/z [M−H]⁻ 502

Example 117

¹H NMR (400 MHz, CDCl₃): δ 8.37 (1H, d), 8.05 (1H, s), 7.99 (1H, d), 7.17 (4H, m), 5.38 (1H, d), 4.22 (1H, s), 3.88 (1H, s), 2.15 (2H, t), 1.92 (2H, m), 1.81 (6H, m), 1.60 (4H, m), 1.18 (15H, m). LCMS (electrospray): m/z [M−H]⁻ 570

Example 118

¹H NMR (400 MHz, CDCl₃): δ 8.37 (1H, d), 8.04 (1H, s), 7.96 (1H, d), 7.18 (4H, m), 5.30 (1H, d), 4.20 (1H, s), 4.10 (2H, q), 3.93 (1H, s), 2.31 (2H, m), 2.13 (2H, m), 1.91 (6H, m), 1.76 (2H, m), 1.64 (2H, m), 1.43 (2H, m) 1.24 (3H, t). LCMS (electrospray): m/z [M−H]⁻ 502

Example 119

¹H NMR (400 MHz, CD₃OD): δ 8.17 (2H, s), 7.20 (4H, m), 4.09 (1H, s), 3.80 (1H, s), 3.60 (3H, s), 3.03 (1H, m), 2.86 (1H, m), 2.04 (1H, m), 1.98 (1H, m), 1.70 (14H, m). LCMS (electrospray): m/z [M−H]⁻ 500

Example 120

¹H NMR (400 MHZ, CD₃OD): δ 8.08 (2H, M), 7.88 (1H, D), 7.70 (2H, M), 7.21 (2H, M), 7.16 (2H, M), 4.10 (2H, S), 3.93 (3H, S), 3.90 (3H, S), 1.83 (8H, M), LCMS (electrospray): m/z [M−H]⁻ 538

Example 121

¹H NMR (400 MHz, CDCl₃): δ 8.38 (1H, d), 8.04 (1H, s), 8.00 (1H, d), 7.85 (1H, d), 7.74 (1H, s), 7.57 (1H, d), 7.18 (4H, m), 5.80 (1H, d), 4.28 (1H, s), 4.10 (1H, m), 3.98 (3H, s), 1.93 (6H, m), 1.58 (2H, m). LCMS (electrospray): m/z [M−H]⁻ 542, 544 Found; C, 59.57; H, 4.50; N, 7.51; C₂₇H₂₄ClF₂N₃O₅ requires; C, 59.62; H, 4.45; N, 7.72%.

Example 122

¹H NMR (400 MHz, CD₃OD): δ 9.13 (1H, s) 8.50 (1H, d), 8.19 (1H, d), 8.10 (1H, m), 8.06 (1H, m), 7.22 (2H, m), 7.16 (2H, m), 4.18 (1H, m), 4.06 (1H, s) 3.93 (3H, s), 3.90 (6H, s), 1.79 (2H, m). LCMS (electrospray): m/z [M−H]⁻ 509

Example 123

¹H NMR (400 MHz, CDCl₃): δ 8.37 (2H, m), 8.20 (1H, d), 8.02 (4H, m), 7.08 (4H, m), 4.29 (1H, s), 4.10 (1H, m), 3.99 (3H, s), 1.90 (6H, m), 2.69 (2H, m). LCMS (electrospray): m/z [M−H]⁻ 509

Example 124

¹H NMR (400 MHz, CD₃OD): δ 8.79 (1H, d) 8.57 (1H, s), 8.07 (3H, m), 7.20 (4H, m), 4.19 (1H, m), 4.05 (1H, m) 3.99 (3H, s), 1.90 (6H, s), 1.78 (2H, m). LCMS (electrospray): m/z [M−H]⁻ 509

Example 125

¹H NMR (300 MHz, CD₃OD): δ 8.10 (2H, m), 7.19 (7H, m), 4.07 (2H, m), 3.50 (2H, m), 2.22 (3H, s), 1.75 (8H, m). LCMS (electrospray): m/z [M+H]⁺ 496

Example 126

Syn-5-(4-{[5-Fluoro-2-(4-fluoro-phenoxy)-pyridine-3-carbonyl]-amino}-cyclohexylsulphamoyl)-2-hydroxy-benzoic acid

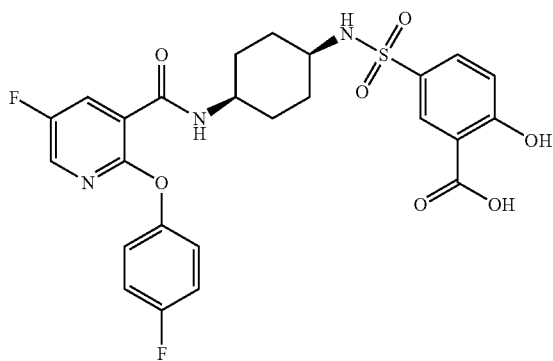

5-Chlorosulfonyl-2-hydroxy-benzoic acid (123 mg, 0.52 mmol) was added to a stirred suspension of syn-N-(4-aminocyclohexyl)-5-fluoro-2-(4-fluoro-phenoxy)-nicotinamide hydrochloride (200 mg, 0.521 mmol, see Preparation 22) in dichloromethane (5 ml) containing triethylamine (220 μl, 1.58 mmol) and was stirred under a nitrogen atmosphere for 18 hours at room temperature. The mixture was partitioned between dichloromethane and water. The dichloromethane layer was washed with a saturated aqueous solution of sodium chloride, dried over anhydrous magnesium sulphate and evaporated in-vacuo. The residue was triturated with diethylether to give syn-5-(4-{[5-fluoro-2-(4-fluoro-phenoxy)-pyridine-3-carbonyl]-amino}-cyclohexylsulphamoyl)-2-hydroxy-benzoic acid (170 mg).

¹H NMR (400 MHz, CDCl₃): δ 8.12 (3H, m), 7.92 (3H, m), 7.59 (1H, m), 7.07 (4H, m), 6.79 (1H, m), 5.53 (1H, s), 4.08 (1H, s), 3.97 (1H, m), 1.78 (8H, m). LCMS (electrospray): m/z [M−H]⁻ 546

Example 127

Syn-N-(4-{[5-Fluoro-2-(4-fluoro-phenoxy)-pyridine-3-carbonyl]-amino}-cyclohexyl)-2,2-dimethyl-malonamic acid

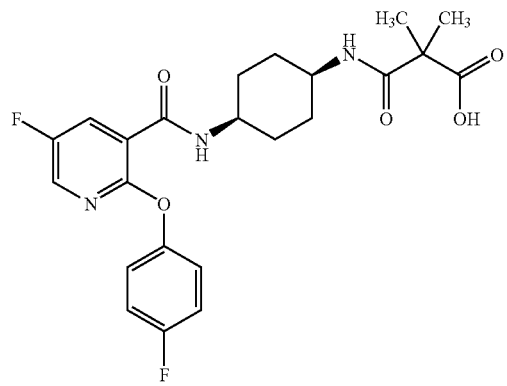

Syn-N-(4-{[5-fluoro-2-(4-fluoro-phenoxy)-pyridine-3-carbonyl]-amino}-cyclo-hexyl)-2,2-dimethyl-malonamic acid ethyl ester (125 mg, 0.26 mmol, see Example 111) was dissolved in tetrahydrofuran (4 ml) and 1M lithium hydroxide solution (600 μl, 0.6 mmol) was added. The mixture was stirred at room temperature for 18 hours and then was diluted with dichloromethane (5 ml). The dichloromethane layer was separated by pipette and the aqueous layer was partitioned between 1N hydrochloric acid and dichloromethane (5 ml). The aqueous phase was extracted with dichloromethane (5×5 ml) and the combined dichloromethane layers were evaporated in-vacuo. The residue was purified by chromatography on silica gel using methanol in dichloromethane containing ammonium hydroxide solution (stepwise from 10:90:1 to 20:80:3) to give syn-N-(4-{[5-fluoro-2-(4-fluoro-phenoxy)-pyridine-3-carbonyl]-amino}-cyclohexyl)-2,2-dimethyl-malonamic acid (90 mg).

¹H NMR (400 MHz, CD₃OD): δ 8.07 (1H, s), 8.01 (1H, d), 7.19 (4H, m), 4.06 (1H, s), 3.83 (1H, s), 1.78 (8H, m), 1.34 (6H, s), LCMS (electrospray): m/z [M−H]⁻ 460

Examples 128–133

The compounds of the following tabulated examples (Table 9) of the general formula:

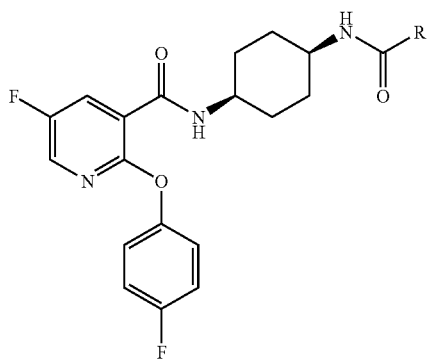

were prepared by a similar method to that of example 127 using the appropriate ester from the compounds of table 8.

TABLE 9

| Example N° | R group |
|---|---|
| 128 | ![structure](CH3 group with CH-CH2-COOH, stereo) |
| 129 | 2-COOH) |
| 130 | 2-COOH) |
| 131 | |
| 132 | ![structure](pyridine-2-carboxylic acid) |
| 133 | -CH2-COOH, stereo) |
| 134 | ![structure](trans-2-methylcyclopentane carboxylic acid) |

TABLE 9-continued

| Example N° | R group |
|---|---|
| 135 | ![structure](pyridine-4-carboxylic acid, 2-substituted) |
| 136 | ![structure](pyridine-3-carboxylic acid, 6-substituted) |
| 137 | ![structure](3-methoxy-4-substituted benzoic acid) |

Example 128

¹H NMR (400 MHZ, CD₃OD): δ 8.04 (1H, S), 8.03 (1H, D), 7.19 (4H, M), 4.14 (1H, T), 3.79 (1H, S), 2.72 (1H, M), 2.50 (1H, M), 2.21(1H, M), 1.70 (8H, M), 1.11 (3H, M) LCMS (electrospray): m/z [M+Na]⁺ 484

Example 129

¹H NMR (400 MHz, CD₃OD): δ 8.07 (1H, m), 8.02 (1H, m), 7.20 (4H, m), 4.08 (1H, s), 3.79 (1H, s), 2.26 (2H, d), 1.79 (8H, m), 1.17 (6H, m). LCMS (electrospray): m/z [M+Na]⁺ 498

Example 130

¹H NMR (400 MHz, CD₃OD): δ 8.07 (2H, m), 7.20 (4H, m), 4.07 (1H, s), 3.78 (1H, m), 2.18 (2H, m), 1.77 (8H, m), 1.59 (2H, m), 1.18 (6H, s). LCMS (electrospray): m/z [M+Na]⁺ 512

Example 131

1H NMR (400 MHz, CD3OD): δ 8.07 (2H, m), 7.18 (4H, m), 4.08 (1H, m), 3.80 (1H, m), 2.25 (2H, m), 2.18 (2H, m), 1.78 (6H, m), 1.60 (6H, m). LCMS (electrospray) m/z [M+Na]⁺ 498

Example 132

¹H NMR (400 MHz, CD₃OD): δ 8.19 (2H, m), 8.10 (3H, m), 7.19 (4H, m), 4.16 (1H, m), 4.02 (1H, m), 1.85 (8H, m). LCMS (electrospray): m/z [M−H]⁻ 495

Example 133

¹H NMR (400 MHz, CD₃OD): δ 8.07 (2H, m), 7.19 (4H, m), 4.08 (1H, s), 3.82 (1H, s), 2.29 (2H, m), 2.15 (2H, m), 2.00 (1H, m), 1.79 (6H, m), 1.63 (2H, m), 0.97 (3H, d). LCMS (electrospray): m/z [M−H]⁻ 474

Example 134

$^1$H NMR (400 MHz, CD$_3$OD): δ 8.08 (1H, d), 8.02 (1H, m), 7.19 (4H, m), 4.04 (1H, s), 3.86 (1H, s), 2.86 (2H, m), 2.03 (1H, m), 1.98 (1H, m), 1.74 (12H, m). LCMS (electrospray): m/z [M–H]$^-$ 486

Example 135

$^1$H NMR (400 MHz, CD$_3$OD): δ 8.64 (1H, d) 8.53 (1H, s), 8.09 (1H, m), 8.06 (1H, m), 7.95 (1H, m) 7.22 (2H, m), 7.16 (2H, m), 4.14 (1H, s) 4.06 (1H, s), 1.89 (6H, s), 1.78 (2H, m). LCMS (electrospray): m/z [M–H]$^-$ 495

Example 136

$^1$H NMR (400 MHz, CD$_3$OD): δ 9.07 (1H, s) 8.39 (1H, d), 8.05 (3H, m), 7.21 (2H, m), 7.15 (2H, s), 4.06 (1H, s), 1.88 (6H, s), 1.79 (2H, m). LCMS (electrospray): m/z [M–H]$^-$ 495

Example 137

$^1$H NMR (400 MHz, CD$_3$OD): δ 8.30 (1H, d), 8.06 (2H, m), 7.86 (1H, d), 7.68 (1H, s), 7.61 (1H, d), 7.19 (4H, m), 4.08 (2H, s), 3.89 (3H, s), 1.84 (8H, m). LCMS (electrospray): m/z [M–H]$^-$ 524

Example 138

Syn-2-Chloro-N-(4-{[5-fluoro-2-(4-fluoro-phenoxy)-pyridine-3-carbonyl]-amino}-cyclohexyl)-terephthalamic acid

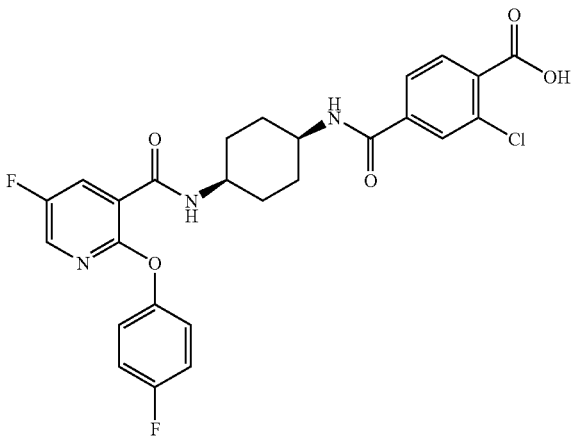

Syn-2-chloro-N-(4-{[5-fluoro-2-(4-fluoro-phenoxy)-pyridine-3-carbonyl]-amino}-cyclohexyl)-terephthalamic acid methyl ester (95 mg, 0.18 mmol, see Example 121) was suspended in 1,4-dioxane (3 ml) and 1M lithium hydroxide solution (350 μl, 0.35 mmol) was added. The mixture was stirred at room temperature for 18 hours, after which 1,4-dioxane (3 ml) and 1M lithium hydroxide solution (500 μl, 0.5 mmol) were added and the mixture stirred a further 24 hours. The reaction mixture was diluted with 1M hydrochloric acid (20 ml) and was extracted with dichloromethane (4×200 ml) and the combined dichloromethane layers were dried over magnesium sulphate and evaporated in-vacuo to give syn-2-chloro-N-(4-{[5-fluoro-2-(4-fluoro-phenoxy)-pyridine-3-carbonyl]-amino}-cyclohexyl)-terephthalamic acid as a white solid (66 mg).

$^1$H NMR (400 MHz, DMSO-d$_6$): δ 8.32 (2H, m), 8.20 (1H, s), 7.99 (1H, d), 7.90 (1H, s), 7.79 (1H, s), 7.22 (4H, m), 3.95 (1H, s), 3.91 (1H, s), 1.78 (8H, m). LCMS (electrospray): m/z [M–H]$^-$ 528, 530

Example 139

Syn-N-(4-{[5-Fluoro-2-(4-fluoro-phenoxy)-pyridine-3-carbonyl]-amino}-cyclohexyl)-succinamic acid

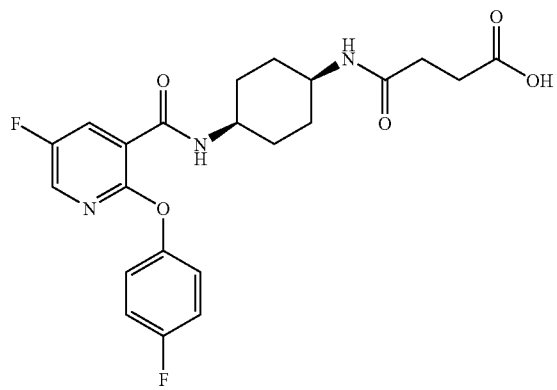

Syn-N-(4-{[5-fluoro-2-(4-fluoro-phenoxy)-pyridine-3-carbonyl]-amino}-cyclo-hexyl)-succinamic acid methyl ester (65 mg, 0.14 mmol, see Example 110) was dissolved in tetrahydrofuran (3 ml) and 1M lithium hydroxide solution (750 μl, 0.75 mmol) was added. The mixture was stirred at room temperature for 18 hours after which the solvent was evaporated in-vacuo. The residue was diluted with 1M hydrochloric acid (20 ml) and was extracted with dichloromethane (3×150 ml), the combined dichloromethane layers were dried over magnesium sulphate and evaporated in-vacuo to give syn-N-(4-{[5-fluoro-2-(4-fluoro-phenoxy)-pyridine-3-carbonyl]-amino}-cyclohexyl)-succinamic acid as a white solid (60 mg).

$^1$H NMR (400 MHz, DMSO-d$_6$): δ 8.26 (1H, d), 8.20 (1H, s), 7.98 (1H, d), 7.63 (1H, d), 7.22 (4H, m), 3.86 (1H, s), 3.63 (1H, d), 2.39 (2H, t), 2.30 (3H, t), 1.60 (8H, m). LCMS (electrospray): m/z [M–H]$^-$ 446

Example 140

Syn-3-[1-(4-{[5-Fluoro-2-(4-fluoro-phenoxy)-pyridine-3-carbonyl]-amino}-cyclohexylcarbamoyl)-cyclopentyl]-propionic acid

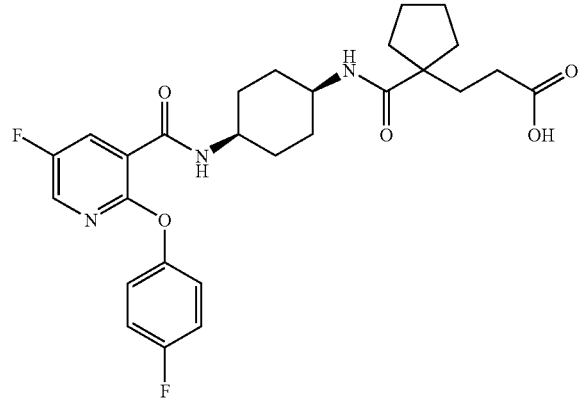

Syn-3-[1-(4-{[5-fluoro-2-(4-fluoro-phenoxy)-pyridine-3-carbonyl]-amino}-cyclohexylcarbamoyl)-cyclopentyl]-propionic acid tert-butyl ester (170 mg, 0.3 mmol, see Example 117) was dissolved in 1,4-dioxane and hydrogen chloride (4M solution in 1,4-dioxane) was added. The mixture was stirred at room temperature for 18 hours after which the solvent was evaporated in-vacuo. The residue was purified by chromatography on silica gel using methanol in dichloromethane containing ammonium hydroxide solution (from 10:90:1 to 15:85:2 to 20:80:3) to give syn-3-[1-(4-{[5-fluoro-2-(4-fluoro-phenoxy)-pyridine-3-carbonyl]-amino}-cyclohexylcarbamoyl)-cyclopentyl]-propionic acid (60 mg).

¹H NMR (400 MHz, CD₃OD): δ 8.06 (2H, m), 7.19 (4H, m), 7.04 (1H, d), 4.13 (1H, s), 3.78 (1H, s), 2.10 (2H, m), 2.01 (2H, m), 1.88 (4H, m), 1.77 (4H, m), 1.61(6H, m) 1.31 (2H, m). LCMS (electrospray): m/z [M−H]⁻ 514

Example 141

Syn-5-Fluoro-2-(4-fluoro-phenoxy)-N-{4-[3-(2-hydroxy-ethyl)-ureido]-cyclohexyl}-nicotinamide

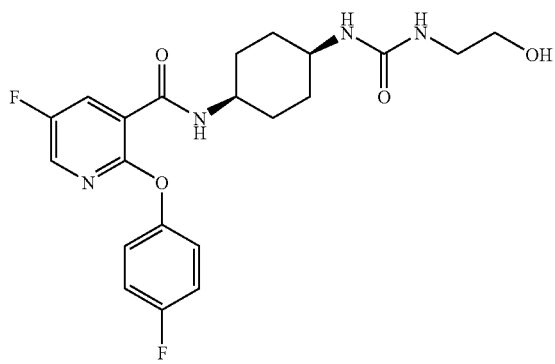

Syn-5-fluoro-2-(4-fluoro-phenoxy)-N-{4-[(imidazole-1-carbonyl)-amino]-cyclo-hexyl}-nicotinamide (110 mg, 0.25 mmol, see Preparation 25) was dissolved in dichloromethane (7 ml) containing triethylamine (42 µl, 0.3 mmol) and 2-aminoethanol (46 µl, 0.75 mmol) and was stirred at room temperature for 18 hours. The reaction mixture was diluted with water (200 ml) and the aqueous solution was extracted with dichloromethane (5×200 ml). The combined dichloromethane layers were dried over magnesium sulphate and evaporated in-vacuo. The residue was purified by chromatography on silica gel using methanol in dichloromethane (gradient from 4:96 to 10:90) to give syn-5-fluoro-2-(4-fluoro-phenoxy)-N-{4-[3-(2-hydroxy-ethyl)-ureido]-cyclohexyl}-nicotinamide as a white solid (40 mg).

¹H NMR (400 MHz, CD₃OD): δ 8.07 (2H, m), 7.17 (4H, m), 4.04 (1H, s), 3.68 (1H, s), 3.57 (2H, t), 3.21 (2H, t), 1.79 (6H, m), 1.59 (2H, m). LCMS (electrospray): m/z [M−H]⁻ 434

Example 142

Syn-5-Fluoro-2-(4-fluoro-phenoxy)-N-{4-[3-(3-hydroxy-propyl)-ureido]-cyclohexyl}-nicotinamide

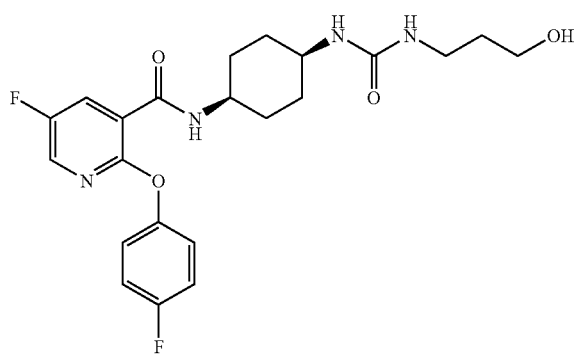

Syn-5-fluoro-2-(4-fluoro-phenoxy)-N-{4-[(imidazole-1-carbonyl)-amino]-cyclohexyl}-nicotinamide (150 mg, 0.34 mmol, see Preparation 25) was dissolved in dichloromethane (10 ml) containing triethylamine (57 µl, 0.41 mmol) and 3-amino-1-propanol (78 µl, 1.02 mmol) and was stirred at room temperature under a nitrogen atmosphere for 66 hours. The reaction mixture was washed with water (2×50 ml) and the dichloromethane layer was dried over magnesium sulphate and evaporated in-vacuo. The residue was purified by chromatography on silica gel using methanol in dichloromethane and ammonium hydroxide solution (gradient from 4:96:0 to 10:90:1) to give syn-5-fluoro-2-(4-fluoro-phenoxy)-N-{4-[3-(3-hydroxy-propyl)-ureido]-cyclohexyl}-nicotinamide as a white solid (90 mg).

¹H NMR (400 MHz, CD₃OD): δ 8.07 (2H, m), 7.20 (4H, m), 4.04 (1H, s), 3.66 (1H, s), 3.59 (2H, t), 3.19 (2H, t), 1.79 (6H, m), 1.60 (4H, m). LCMS (electrospray): m/z [M−H]⁻ 447

Example 143

Syn-3-[3-(4-{[5-Fluoro-2-(4-fluoro-phenoxy)-pyridine-3-carbonyl]-amino}-cyclohexyl)-ureido]-propionic acid methyl ester

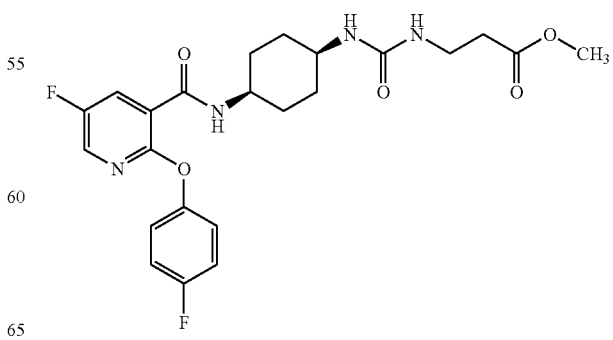

Syn-5-fluoro-2-(4-fluoro-phenoxy)-N-{4-[(imidazole-1-carbonyl)-amino]-cyclo-hexyl}-nicotinamide (150 mg, 0.34 mmol, see Preparation 25) was dissolved in dichloromethane (10 ml) containing triethylamine (57 μl, 0.41 mmol) and 3-aminopropionic acid methyl ester (48 mg, 0.41 mmol) and was stirred at room temperature under a nitrogen atmosphere for 66 hours. The reaction mixture was washed with 1M hydrochloric acid (50 ml), the dichloromethane layer was dried over magnesium sulphate and evaporated in-vacuo to give syn-3-[3-(4-{[5-fluoro-2-(4-fluoro-phenoxy)-pyridine-3-carbonyl]-amino}-cyclohexyl)-ureido]-propionic acid methyl ester as a white solid (130 mg).

$^1$H NMR (400 MHz, CDCl$_3$): δ 8.37 (1H, d), 8.04 (1H, s), 7.96 (1H, d), 7.18 (4H, m), 4.19 (1H, s), 3.70 (4H, m), 3.47 (2H, t), 2.55 (2H, t), 1.79 (8H, m), 1.50 (2H, m). LCMS (electrospray): m/z [M−H]$^−$ 475

Example 144

Syn-7-[3-(4-{[5-Fluoro-2-(4-fluoro-phenoxy)-pyridine-3-carbonyl]-amino}-cyclohexyl)-ureido]-heptanoic acid methyl ester

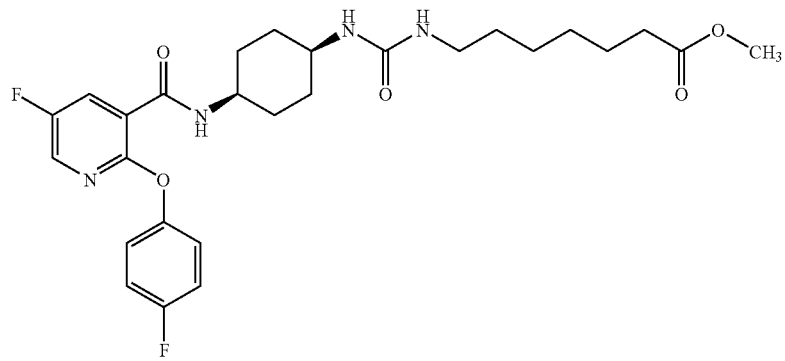

Example 145

Syn-3-[3-(4-{[5-Fluoro-2-(4-fluoro-phenoxy)-pyridine-3-carbonyl]-amino}-cyclohexyl)-ureido]-propionic acid

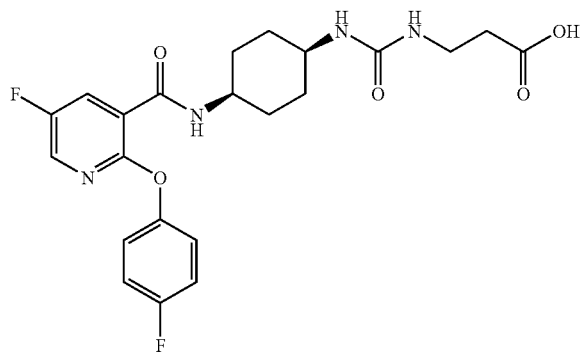

Syn-5-fluoro-2-(4-fluoro-phenoxy)-N-{4-[(imidazole-1-carbonyl)-amino]-cyclo-hexyl}-nicotinamide (150 mg, 0.34 mmol, see Preparation 25) was dissolved in dichloromethane (10 ml) containing triethylamine (57 μl, 0.41 mmol) and 7-aminoheptanoic acid methyl ester (68 mg, 0.43 mmol) and was stirred at room temperature for 18 hours. The reaction mixture was washed with water (2×50 ml) and then with 1M hydrochloric acid (2×50 ml). The dichloromethane layer was dried over magnesium sulphate and evaporated in-vacuo to give syn-7-[3-(4-{[5-fluoro-2-(4-fluoro-phenoxy)-pyridine-3-carbonyl]-amino}-cyclohexyl)-ureido]-heptanoic acid methyl ester as a white solid (168 mg).

$^1$H NMR (400 MHz, CDCl$_3$): δ 8.36 (1H, d), 8.02 (1H, s), 7.96 (1H, d), 7.16 (4H, m), 4.19 (1H, s), 3.67(4H, m), 3.13 (2H, t), 2.30 (2H, t), 1.82 (4H, m), 1.76 (3H, m), 1.61 (4H, m), 1.44 (4H, m), 1.36 (3H, m). LCMS (electrospray): m/z [M+Na]$^+$ 555

Syn-3-[3-(4-{[5-fluoro-2-(4-fluoro-phenoxy)-pyridine-3-carbonyl]-amino}-cyclo-hexyl)-ureido]-propionic acid methyl ester (110 mg, 0.23 mmol, see Example 143) was dissolved in tetrahydrofuran (1.5 ml). 1M Lithium hydroxide solution (460 μl, 0.46 mmol) was added and the mixture stirred at room temperature for 18 hours. The reaction mixture was dissolved in water and was washed with dichloromethane (2×50 ml). The aqueous layer was diluted with 1M hydrochloric acid (20 ml) and extracted with dichloromethane (4×150 ml). The combined dichloromethane layers were evaporated in-vacuo. The residue was re-dissolved in dichloromethane and was washed with 10% potassium carbonate solution (300 ml). The aqueous solution was acidified with 1M hydrochloric acid and extracted with dichloromethane (2×200 ml). These combined dichloromethane layers were dried over magnesium sulphate and evaporated in-vacuo to give syn-3-[3-(4-{[5-fluoro-2-(4-fluoro-phenoxy)-pyridine-3-carbonyl]-amino}-cyclohexyl)-ureido]-propionic acid as a white solid (30 mg).

$^1$H NMR (400 MHz, CD$_3$OD): δ 8.09 (2H, m), 7.04 (4H, m), 4.19 (1H, s), 3.66 (1H, s), 2.42 (2H, t), 1.79 (8H, m), 1.59 (2H, m). LCMS: (electrospray) m/z [M−H]$^−$ 461

Example 146

Syn-7-[3-(4-{[5-Fluoro-2-(4-fluoro-phenoxy)-pyridine-3-carbonyl-amino}-cyclohexyl)-ureido]-heptanoic acid

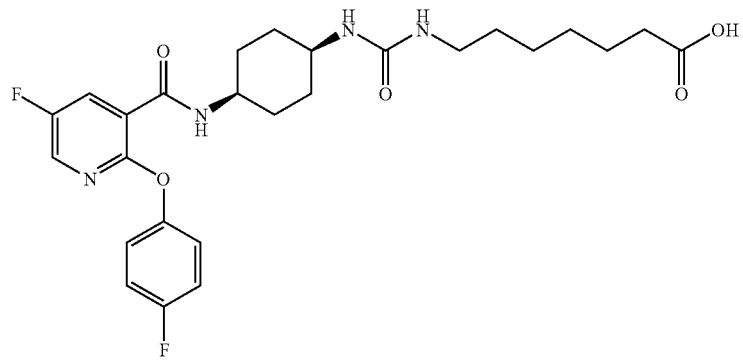

Syn-7-[3-(4-{[5-fluoro-2-(4-fluoro-phenoxy)-pyridine-3-carbonyl]-amino}-cyclo-hexyl)-ureido]-heptanoic acid methyl ester (130 mg, 0.24 mmol, see Example 144) was dissolved in tetrahydrofuran (1.5 ml) containing 1M lithium hydroxide solution (500 μl, 0.5 mmol) and the mixture was stirred at room temperature for 66 hours. The reaction mixture was dissolved in water (200 ml) and was washed with dichloromethane (2×200 ml). The aqueous layer was acidified with 1M hydrochloric acid (50 ml) and extracted with dichloromethane (3×150 ml). The combined dichloromethane layers were evaporated in-vacuo, to give syn-7-[3-(4-{[5-fluoro-2-(4-fluoro-phenoxy)-pyridine-3-carbonyl]-amino}-cyclohexyl)-ureido]-heptanoic acid (60 mg).

$^1$H NMR (400 MHz, CDCl$_3$): δ 8.36 (1H, d), 8.01 (2H, m), 7.04 (4H, m), 4.99 (1H, s), 4.50 (1H, s), 4.13 (1H, m), 3.74 (1H, m), 3.06 (2H, t) 2.33 (2H, t), 1.79 (6H, s), 1.63 (2H, m) 1.44 (4H, m), 1.37 (5H, s). LCMS (electrospray): m/z [M–H]$^-$ 517

Example 147

Anti-5-Fluoro-2-(4-fluoro-phenoxy)-N-[4-(2-hydroxy-4-methyl-benzoylamino)-cyclohexyl]-nicotinamide 2-Hydroxy-4-methyl-benzoic acid (119 mg, 0.78 mmol), 1-hydroxybenzotriazole hydrate (158 mg, 1.17 mmol) and 1-(3-dimethylaminopropyl)-3-ethylcarbodiimide hydrochloride (100 mg, 0.52 mmol), were dissolved in N,N-dimethylformamide (6 ml) under a nitrogen atmosphere and were stirred 30min. Anti-N-(4-amino-cyclohexyl)-5-fluoro-2-(4-fluoro-phenoxy)-nicotinamide hydro-chloride (300 mg, 0.782 mmol, see Preparation 7) and 4-methyl morpholine (170 μl, 1.56 mmol) were added and the mixture was stirred for 18 hours at room temperature. The mixture was partitioned between ethyl acetate and water and the organic phase was washed with a saturated solution of sodium chloride, dried over magnesium sulphate and evaporated in-vacuo. The residue was triturated with diethylether to give anti-5-fluoro-2-(4-fluoro-phenoxy)-N-[4-(2-hydroxy-4-methyl-benzoylamino)-cyclohexyl]-nicotinamide (210 mg).

$^1$H NMR (300 MHz, CDCl$_3$): δ 8.34 (1H, m), 8.03 (1H, m), 7.77 (1H, m), 7.22 (1H, m) 7.12 (5H, m), 6.79 (1H, s) 6.63 (1H, d), 6.19 (1H, d), 4.00 (2H, s), 2.34 (3H, s), 2.19 (4H, m), 1.42 (4H, m). LCMS (thermospray): [M+H]$^+$m/z 482

Example 148

Syn-2-(4-Fluoro-phenoxy)-N-[4-(2-hydroxy-benzoylamino)-cyclohexyl]-nicotinamide

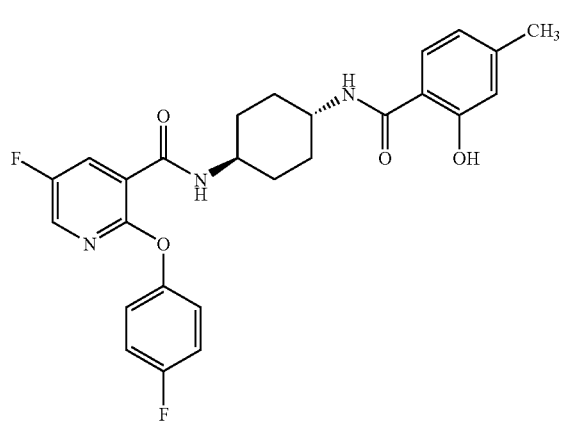

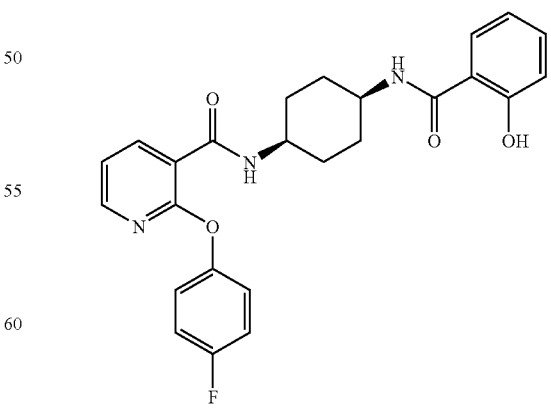

1-(3-Dimethylaminopropyl)-3-ethylcarbodiimide hydrochloride (225 mg, 1.17 mmol) was added to a suspension of 2-hydroxybenzoic acid (108 mg, 0.78 mmol), syn-N-(4-amino-cyclohexyl)-2-(4-fluoro-phenoxy)-nicotinamide hydrochloride (300 mg, 0.78 mmol, see Preparation 47), and 1-hydroxybenzotriazole hydrate (115 mg, 0.85 mmol) in N,N-dimethylformamide (5 ml) containing triethylamine (545 μl, 3.9 mmol) and the mixture was stirred for 18 hours. The solvent was removed in-vacuo and the residue was partitioned between ethyl acetate and 2N hydrochloric acid. The ethyl acetate layer was washed with water then concentrated sodium chloride solution then dried over magnesium sulphate and the solvent was removed in-vacuo. The residue was purified by chromatography on silica gel using ethyl acetate in cyclohexane as eluant (gradient from 10:90 to 60:40) to give syn-2-(4-fluoro-phenoxy)-N-[4-(2-hydroxy-benzoylamino)-cyclohexyl]-nicotinamide (150 mg).

$^1$H NMR (400 MHz, CD$_3$OD): δ 8.26 (1H, m), 8.18 (1H, m) 7.76 (1H, d), 7.36 (1H, t), 7.23 (3H, m), 7.15 (2H, m), 6.88 (2H, m), 4.17, (1H, m), 4.03 (1H, m), 1.88 (6H, m), 1.77 (2H, m). LCMS (electrospray): m/z [M–H]$^-$ 449

Example 149

Syn-2-(4-fluoro-phenoxy)-N-[4-(2-hydroxy-4-methyl-benzoyl-amino)-cyclohexyl]-nicotinamide

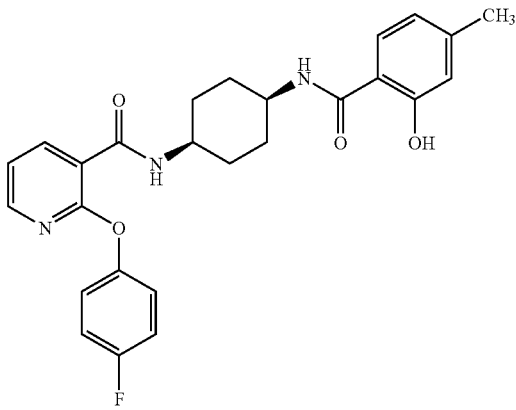

The title compound was obtained from syn-N-(4-amino-cyclohexyl)-2-(4-fluoro-phenoxy)-nicotinamide hydrochloride and 2-hydroxy-4-methylbenzoic acid in 35% yield following the procedure described in example 148.

$^1$H NMR (400 MHz, CD$_3$OD): δ 8.27 (1H, m), 8.19 (1H, m) 7.63 (1H, d), 7.23 (3H, m), 7.16 (2H, m), 6.73 (2H, m), 4.16, (1H, m), 4.01 (1H, m), 2.31 (3H, s), 1.88 (6H, m), 1.75 (2H, m). LCMS (electrospray): m/z [M+Na]$^+$ 486

Example 150

Syn-2-(4-Fluoro-phenoxy)-N-{4-[2-(2-hydroxy-phenyl)-acetylamino]-cyclohexyl}-nicotinamide

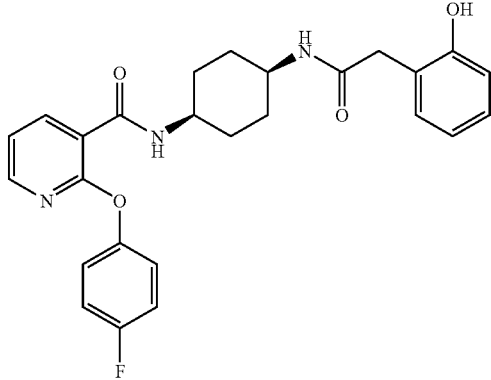

O-(7-Azabenzotriazol-1-yl)-N,N,N',N',-tetramethyluronium hexafluorophosphate (234 mg, 0.49 mmol) was added to a suspension of (2-hydroxyphenyl)acetic acid (74.9 mg, 0.49 mmol) and syn-N-(4-amino-cyclohexyl)-2-(4-fluoro-phenoxy)-nicotinamide hydrochloride (150 mg, 0.41 mmol, see Preparation 47), in N,N-dimethylformamide (2.7 ml) containing Hünigs base (820 μl, 0.82 mmol) and the mixture was stirred for 18 hours. The reaction mixture was diluted with water (10 ml) and was extracted with diethylether (2×12.5 ml). The combined organic layers were washed with concentrated sodium chloride solution then dried over magnesium sulphate and the solvent was removed in-vacuo. The residue was purified by chromatography on silica gel using methanol and ammonium hydroxide solution in dichloromethane as eluant (5:0.5:95) followed by a further purification by chromatography on silica gel using cyclohexane in ethyl acetate (33:67) as eluant to give syn-2-(4-fluoro-phenoxy)-N-{4-[2-(2-hydroxy-phenyl)-acetylamino]-cyclohexyl}-nicotinamide as an off white foam (25.1 mg).

$^1$H NMR (400 MHz, CDCl$_3$): δ 9.68 (1H, s), 8.62 (1H, d), 8.21 (1H, d) 7.97 (1H, m), 7.19 (6H, m), 6.98 (2H, m), 6.82 (1H, m), 5.78 (1H, m), 4.16, (1H, m), 3.89 (1H, m), 3.48 (2H, s), 1.80 (6H, m), 1.51 (2H, m). LCMS (electrospray): m/z [M+Na]$^+$ 486

Example 151

Syn-2-(4-fluoro-phenoxy)-N-{4-[3-(2-hydroxy-benzyl)-ureido]-cyclohexyl}-nicotinamide

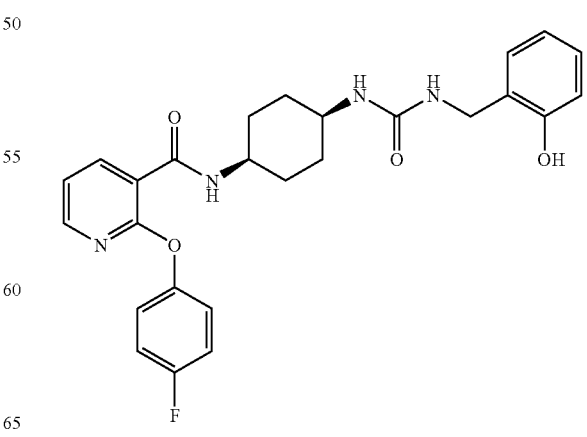

2-Aminomethylphenol (65 mg, 0.53 mmol) was added to a solution of 2-(4-fluoro-phenoxy)-N-{4-[(imidazole-1-carbonyl)-amino]-cyclohexyl}-nicotinamide (150 mg, 0.35 mmol, see Preparation 47) and 4-dimethylaminopyridine (43.3 mg, 0.35 mmol) in dichloromethane (3 ml) at room temperature under a nitrogen atmosphere. The mixture was stirred for 18 hours and then was washed with water (20 ml) and then diluted with 10% citric acid solution (20 ml). The mixture was extracted with dichloromethane (2×10 ml) and the combined organic layers were washed with a saturated solution of sodium chloride (20 ml) and dried over magnesium sulphate. The solvent was removed in-vacuo and the residue purified by chromatography on silica gel using cyclohexane in ethyl acetate (33.3:66.6) to give syn-2-(4-fluoro-phenoxy)-N-{4-[3-(2-hydroxy-benzyl)-ureido]-cyclohexyl}-nicotinamide as an off white foam (96 mg).

$^1$H NMR (400 MHz, CDCl$_3$): δ 9.75 (1H, s), 8.60 (1H, d), 8.20 (1H, d) 7.91 (1H, d), 7.18 (6H, m), 7.02 (1H, d), 6.98 (2H, m), 6.79 (1H, m), 4.84 (1H, m), 4.29, (2H, d), 3.71 (1H, m), 1.82 (6H, m), 1.49 (2H, m). LCMS (electrospray): m/z [M+Na]$^+$ 501

Example 152

Syn-2-(3-fluoro-phenoxy)-N-[4-(2-hydroxy-4-methoxy-benzoylamino)-cyclohexyl]-nicotinamide

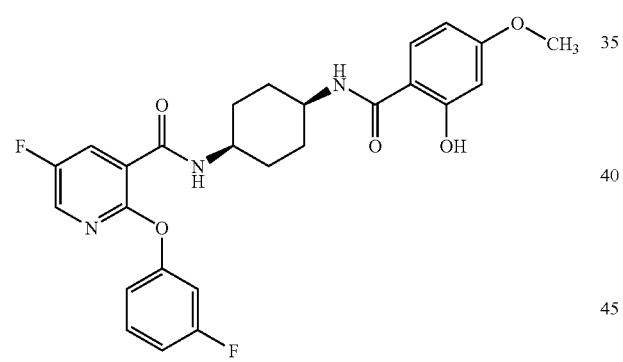

Caesium carbonate (170 mg, 0.52 mmol) was added to a solution of syn-2-chloro-N-[4-(2-hydroxy-4-methoxy-benzoylamino)-cyclohexyl]-nicotinamide (110 mg, 0.26 mmol, see Preparation 45) and 3-fluorophenol (35 mg, 0.31 mmol) in N,N-dimethylformamide (2 ml) and was stirred at 65° C. for 18 hours. The mixture was partitioned between ethyl acetate and water and the organic solution was dried using a Chem Elut® cartridge and evaporated in-vacuo. The residue was purified by chromatography on a Biotage™ cartridge to give syn-2-(3-fluoro-phenoxy)-N-[4-(2-hydroxy-4-methoxy-benzoylamino)-cyclohexyl]-nicotinamide (19 mg).

$^1$H NMR (400 MHz, CDCl$_3$): δ 12.56 (1H, s), 8.38 (1H, d), 8.09 (1H, s), 7.94 (1H, d), 7.44 (1H, m), 7.00 (4H, m), 6.46 (1H, s), 6.39 (1H, d), 5.78 (1H, d), 4.26 (1H, m), 4.07 (1H, m), 3.82 (3H, s), 1.90 (8H, m). LCMS (electrospray): m/z [M+Na]$^+$ 520

Examples 153–159

The compounds of the following tabulated examples (Table 10) of the general formula

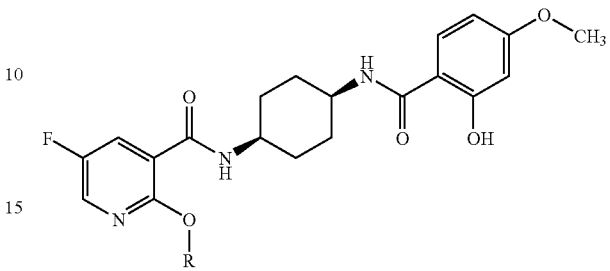

were prepared by a similar method to that of example 152 using 2-chloro-N-[4-(2-hydroxy-4-methoxy-benzoylamino)-cyclohexyl]-nicotinamide (see Preparation 45) and the appropriate phenol.

TABLE 10

| Example N° | R group |
|---|---|
| 153 | 4-Cl-C$_6$H$_4$ |
| 154 | 3-Cl-C$_6$H$_4$ |
| 155 | 3,4-diF-C$_6$H$_3$ |
| 156 | 3-Cl-4-F-C$_6$H$_3$ |
| 157 | 3-CH$_3$-C$_6$H$_4$ |

TABLE 10-continued

| Example N° | R group |
|---|---|
| 158 | 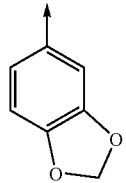 |
| 159 | 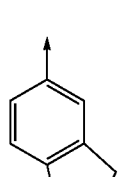 |

Example 153

$^1$H NMR (400 MHz, CDCl$_3$): δ 12.54 (1H, s), 8.37 (1H, d), 8.06 (1H, s), 7.97 (1H, d), 7.44 (2H, d), 7.14 (2H, d), 7.00 (1H, d), 6.43 (2H, m), 5.74 (1H, d), 4.28 (1H, m), 4.07 (1H, m), 3.82 (3H, s), 1.91 (8H, m). LCMS (electrospray): m/z [M+Na]$^+$ 536, 538

Example 154

$^1$H NMR (400 MHz, CDCl$_3$): δ 12.54 (1H, s), 8.38 (1H, d), 8.09 (1H, s), 7.93 (1H, d), 7.40 (1H, m), 7.30 (1H, m), 7.21 (1H, m), 7.07 (2H, m), 6.44 (1H, s), 6.39 (1H, d), 5.79 (1H, d), 4.26 (1H, s), 4.08 (1H, m), 3.81 (3H, s), 1.90 (8H, m). LCMS (electrospray): m/z [M+Na]$^+$ 536, 538

Example 155 hu 1H NMR (400 MHz, CDCl$_3$): δ 12.54 (1H, s), 8.37 (1H, d), 8.08 (1H, s), 7.87 (1H, d), 7.24 (1H, m), 7.14 (2H, d), 6.93 (1H, m), 6.46 (1H, s), 6.40 (1H, d), 5.84 (1H, d), 4.28 (1H, m), 4.09 (1H, m), 3.82 (3H, s), 1.91 (8H, m). LCMS (electrospray): m/z [M+Na]$^+$ 538

Example 156

$^1$H NMR (400 MHz, CDCl$_3$): δ 12.53 (1H, s), 8.37 (1H, d), 8.06 (1H, s), 7.87 (1H, d), 7.24 (2H, m), 7.10 (2H, m), 6.46 (1H, s), 6.39 (1H, d), 5.84 (1H, d), 4.28 (1H, m), 4.11 (1H, m), 3.82 (3H, s), 1.90 (8H, m). LCMS (electrospray): m/z [M+Na]$^+$ 554, 556

Example 157

$^1$H NMR (400 MHz, CDCl$_3$): δ 12.59 (1H, s), 8.38 (1H, d), 8.08 (1H, d), 8.08 (1H, s), 7.39 (1H, t), 7.17 (1H, d), 6.99 (3H, m), 6.44 (1H, s), 6.38 (1H, d), 5.70 (1H, d), 4.29 (1H, s), 4.08 (1H, m), 3.82 (3H, s), 2.70 (2H, q), 1.90 (8H, m) 1.25 (3H, t). LCMS (electrospray): m/z [M+Na]$^+$ 530

Example 158

$^1$H NMR (400 MHz, CDCl$_3$): δ 12.59 (1H, s), 8.34 (1H, d), 8.08 (2H, m), 7.07 (1H, d), 6.88 (1H, d), 6.71 (1H, s), 6.64 (1H, d), 6.46 (1H, s), 6.39 (1H, d), 6.03 (2H, s), 5.78 (1H, d), 4.30 (1H, m), 4.08 (1H, m), 3.83 (3H, s), 1.93 (8H, m). LCMS (electrospray): m/z 546 [M+Na]$^+$

Example 159

$^1$H NMR (400 MHz, CDCl$_3$): δ 12.59 (1H, s), 8.37 (1H, d), 8.19 (1H, d), 8.07 (1H, s) 7.30 (1H, d), 7.02 (2H, m), 6.94 (1H, d), 6.46 (1H, s), 6.38 (1H, d), 5.74 (1H, d), 4.30 (1H, m), 4.08 (1H, m), 3.83 (3H, s), 2.94 (4H, m), 2.17 (2H, m) 1.93 (8H, m). LCMS (electrospray): m/z [M+Na]$^+$ 542

Example 160

Syn-5-Fluoro-N-[4-(2-hydroxy-4-methoxy-benzoylamino)-cyclohexyl]-2-m-tolyloxy-nicotinamide

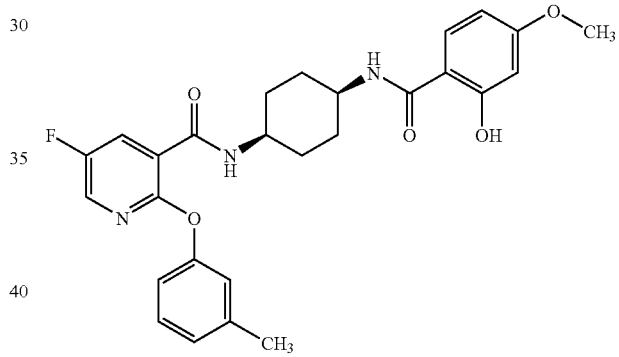

Caesium carbonate (116 mg, 0.36 mmol) was added to a solution of syn-2-chloro-5-fluoro-N-[4-(2-hydroxy-4-methoxy-benzoylamino)-cyclohexyl]-nicotin-amide (100 mg, 0.24 mmol, see Preparation 45) and 3-hydroxytoluene (28 mg, 0.26 mmol) in N,N-dimethylformamide (3 ml) and was stirred at 55° C. for 18 hours. A further portion of caesium carbonate (30 mg, 0.16 mmol) and 3-hydroxytoluene (10 mg, 0.9 mmol) were added and the mixture was heated to 65° C. for 3 hours. The reaction mixture was cooled to room temperature and partitioned between ethyl acetate and water. The ethyl acetate layer was washed with water and then a saturated aqueous solution of sodium chloride, dried over anhydrous magnesium sulphate and evaporated in-vacuo. The residue was purified by chromatography on silica gel using ethyl acetate in pentane (50:50) as eluant to give syn-5-fluoro-N-[4-(2-hydroxy-4-methoxy-benzoylamino)-cyclohexyl]-2-m-tolyloxy-nicotinamide (36 mg).

$^1$H NMR (400 MHz, CDCl$_3$): δ 12.56 (1H, s), 8.37 (1H, d), 8.16 (1H, d), 8.10 (1H, s), 7.36 (1H, m), 7.14 (1H, d), 6.97 (3H, d), 7.07 (2H, m), 6.48 (1H, s), 6.39 (1H, d), 5.70 (1H, d), 4.30 (1H, s), 4.06 (1H, m), 3.83 (3H, s), 2.40 (3H, s), 1.90 (8H, m). LCMS (electrospray): m/z [M−H]$^−$ 493

Example 161

Anti-2-(Benzo[1,3]dioxol-5-yloxy)-N-[4-(2-fluoro-6-hydroxy-benzoylamino)-cyclohexyl]-nicotinamide

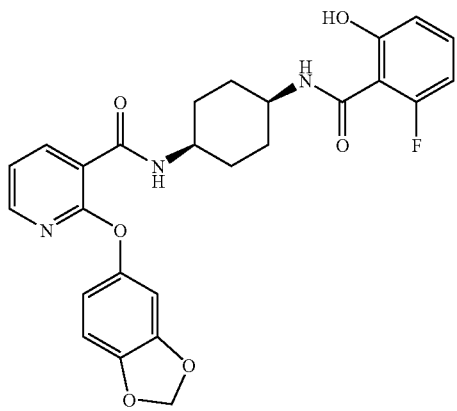

2-Fluoro-6-hydroxy-benzoic acid (119 mg, 0.77 mmol) was added to 1-hydroxybenzotriazole hydrate (155 mg 0.77 mmol) and 1-(3-dimethylaminopropyl-3-ethylcarbodiimide hydrochloride (220 mg, 0.77 mmol) in N,N-dimethylformamide (5 ml) and the mixture was stirred for 1.5 hours. Anti-N-(4-Amino-cyclohexyl)-2-(benzo[1,3]dioxol-5-yloxy)-nicotinamide hydrochloride (300 mg, 0.77 mmol, see Preparation 39) and 4-methylmorpholine (167 µl, 0.77 mmol) were added and the mixture was stirred for 18 hours and then partitioned between dichloromethane and 10% citric acid solution (10 ml). The organic layer was separated, passed through a hydrophobic frit and evaporated in-vacuo. The residue was triturated with methanol and the solid obtained isolated by filtration to give anti-2-(benzo[1,3]dioxol-5-yloxy)-N-[4-(2-fluoro-6-hydroxy-benzoylamino)-cyclohexyl]-nicotinamide (26 mg).

$^1$H NMR (400 MHz, CDCl$_3$): δ 13.36 (1H, s), 8.60 (1H, d), 8.21 (1H, d), 7.73 (1H, d), 7.27 (1H, m), 7.14 (1H, m), 6.93 (1H, m), 6.88 (1H, d), 6.79 (1H, d), 6.72 (1H, s), 6.60 (2H, m), 6.61 (2H, s), 4.02 (2H, m), 2.20 (4H, m), 1.46 (4H, m). LCMS (electrospray): m/z [M–H]$^-$ 492

Example 162

Exo-5-Fluoro-N-[8-(2-fluoro-6-hydroxy-benzoyl)-8-aza-bicyclo[3.2.1]oct-3-yl]-2-(4-fluoro-phenoxy)-nicotinamide

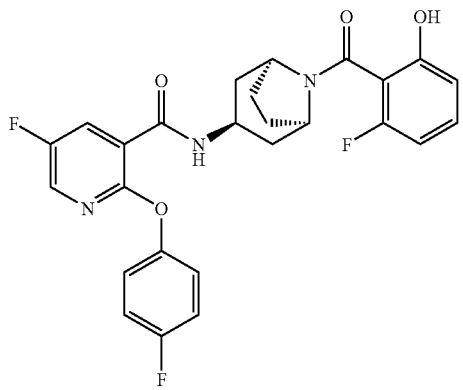

Exo-N-(8-Aza-bicyclo[3.2.1]oct-3-yl)-5-fluoro-2-(4-fluoro-phenoxy)-nicotinamide (155 mg, 0.43 mmol, see Preparation 35) was added to 1-(3-dimethylaminopropyl-3-ethylcarbodiimide hydrochloride (101 mg, 0.52 mmol), 2-fluoro-6-hydroxybenzoic acid (69 mg, 0.43 mmol) and 1-hydroxybenzotriazole hydrate (70 mg, 0.52 mmol) in dichloromethane (5 ml) containing 4-methylmorpholine (57 µl, 0.52 mmol) and the mixture was stirred at room temperature for 24 hours. Water was added and the mixture was concentrated in-vacuo. The residue was purified by chromatography on silica gel using methanol in dichloromethane (5:95) as eluant, to give exo-5-fluoro-N-[8-(2-fluoro-6-hydroxy-benzoyl)-8-aza-bicyclo[3.2.1]oct-3-yl]-2-(4-fluoro-phenoxy)-nicotinamide (85 mg).

$^1$H NMR (400 MHz, DMSO-d$^6$): δ 10.10 (1H, s), 8.19 (1H, d), 8.18 (1H, s), 7.92 (1H, d), 7.19 (5H, m), 6.86 (2H, m), 4.67 (1H, s), 4.33 (1H, m), 3.72 (1H, s), 1.79 (7H, m), 1.46 (1H, m). LCMS: m/z AP$^+$ 498 [M+H]$^+$

Example 163

Exo-5-Fluoro-2-(4-fluoro-phenoxy)-N-[8-(2-hydroxy-4-methoxy-benzoyl)-8-aza-bicyclo[3.2.1]oct-3-yl]-nicotinamide

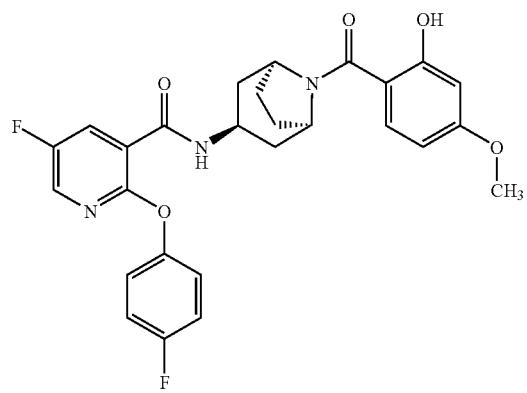

Exo-N-(8-aza-bicyclo[3.2.1]oct-3-yl)-5-fluoro-2-(4-fluoro-phenoxy)-nicotinamide (155 mg, 0.43 mmol, see Preparation 35) was added to 1-(3-dimethylaminopropyl-3-ethylcarbodiimide hydrochloride (101 mg, 0.52 mmol), 2-hydroxy-4-methoxybenzoic acid (73 mg, 0.43 mmol) and 1-hydroxybenzotriazole hydrate (70 mg, 0.52 mmol) in dichloromethane (5 ml) containing 4-methylmorpholine (57 µl, 0.52 mmol) and the mixture was stirred at room temperature for 24 hours. Water was added and the mixture was concentrated in-vacuo, the residue was purified by chromatography on silica gel using methanol in dichloromethane (5:95) as eluant, to give exo-5-Fluoro-2-(4-fluoro-phenoxy)-N-[8-(2-hydroxy-4-methoxy-benzoyl)-8-aza-bicyclo[3.2.1]oct-3-yl]-nicotinamide (165 mg).

¹H NMR (400 MHz, DMSO-d⁶): δ 10.13 (1H, s), 8.34 (1H, d), 8.19 (1H, s), 7.92 (1H, m), 7.19 (5H, m), 6.40 (2H, m), 4.36 (3H, m), 3.74 (3H, s), 1.79 (8H, m). LCMS: m/z AP⁺ 510 [M+H]⁺

Example 164

Exo-5-fluoro-2-(4-fluoro-phenoxy)-N-{8-[2-(4-hydroxy-phenyl)-acetyl]-8-aza-bicyclo[3.2.1]oct-3-yl}-nicotinamide

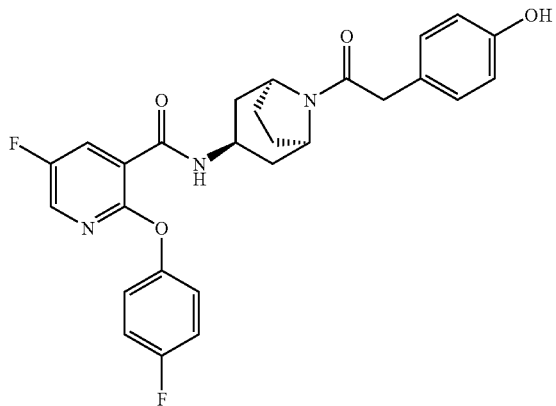

Exo-N-(8-aza-bicyclo[3.2.1]oct-3-yl)-5-fluoro-2-(4-fluoro-phenoxy)-nicotinamide (310 mg, 0.86 mmol, see Preparation 35) was added to 1-(3-dimethylaminopropyl-3-ethylcarbodiimide hydrochloride (185 mg, 0.95 mmol), 4-hydroxyphenylacetic acid (134 mg, 0.86 mmol) and 1-hydroxybenzotriazole hydrate (128 mg, 0.95 mmol) in dichloromethane (5 ml) containing 4-methylmorpholine (104 µl, 0.95 mmol) and the mixture was stirred at room temperature for 18 hours. The reaction mixture was diluted with water and the organic phase was concentrated in-vacuo and then purified by chromatography on silica gel using methanol in dichloromethane containing ammonium hydroxide solution as eluant (gradient from 1:99:0.1 to 5:95:0.5). The material obtained was triturated with methanol and isolated by filtration then dried in-vacuo to give exo-5-fluoro-2-(4-fluoro-phenoxy)-N-{8-[2-(4-hydroxy-phenyl)-acetyl]-8-aza-bicyclo[3.2.1]oct-3-yl}-nicotinamide (270 mg)

¹H NMR (400 MHz, DMSO-d⁶): δ 9.21 (1H, s), 8.31 (1H, d), 8.19 (1H, s), 7.94 (1H, d), 7.20 (4H, m), 7.00 (2H, d), 6.66 (2H, d), 4.46 (1H, m), 4.35 (2H, m), 3.56 (1H, d), 3.40 (1H, d), 1.79 (6H, m), 1.48 (2H, m). LCMS (electrospray): m/z [M+Na]⁺ 516

Example 165

Exo-3-{[5-Fluoro-2-(4-fluoro-phenoxy)-pyridine-3-carbonyl]-amino}-8-aza-bicyclo[3.2.1]octane-8-carboxylic acid 2-hydroxy-benzyl-amide

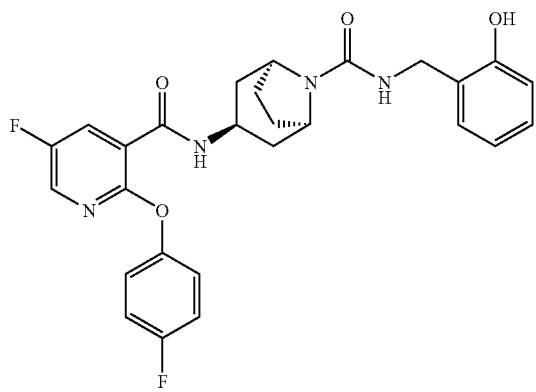

A solution of exo-3-{[5-fluoro-2-(4-fluoro-phenoxy)-pyridine-3-carbonyl]-amino}-8-aza-bicyclo[3.2.1]octane-8-carbonyl chloride was freshly prepared by adding exo-N-(8-aza-bicyclo[3.2.1]oct-3-yl)-5-fluoro-2-(4-fluoro-phenoxy)-nicotinamide (625 mg, 1.74 mmol, see Preparation 35) portionwise over 10 minutes to a solution of triphosgene (175 mg, 0.56 mmol) in dichloromethane (10 ml) and stirring for 18 hours at room temperature. Triethylamine (218 µl, 1.5 mmol) and 2-aminomethylphenol hydrochloride (96 mg, 0.6 mmol, see Tet. Lett. 2001, 41(49), 8665) were added to the above solution (3 ml, 0.52 mmol) and the mixture was stirred at room temperature for 18 hours. The reaction mixture was washed with a saturated solution of sodium chloride and evaporated in-vacuo. The residue was purified by chromatography on silica gel using methanol in dichloromethane as eluant (gradient from 0:100 to 5:95) the material isolated was triturated with diethylether and dried in-vacuo to give exo-3-{[5-fluoro-2-(4-fluoro-phenoxy)-pyridine-3-carbonyl]-amino}-8-aza-bicyclo[3.2.1]octane-8-carboxylic acid 2-hydroxy-benzylamide as an off white solid (22 mg).

¹H NMR (400 MHz, CDCl₃): δ 8.30 (1H, m), 8.01 (1H, s), 7.60 (1H, d), 7.10 (7H, m), 6.90 (1H, d), 6.80 (1H, m), 5.03 (1H, s), 4.54 (2H, m), 4.34 (1H, s), 4.21 (1H, s), 4.19 (2H, s), 1.86 (8H, m). LCMS (electrospray): m/z [M+Na]⁺ 531

Examples 166–167

The compounds of the following tabulated examples (Table 11) of the general formula

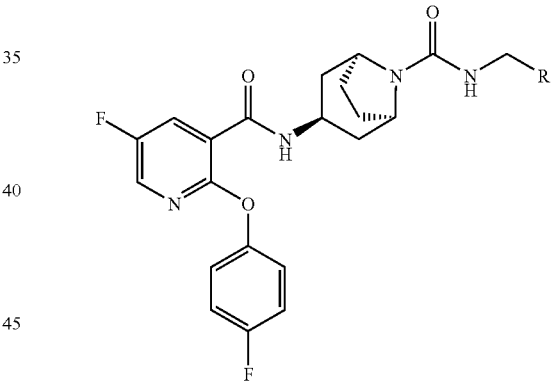

were prepared by a similar method to that of example 165 using the same carbamoyl chloride and the appropriate amine.

TABLE 12

| Example N° | R group |
|---|---|
| 166¹ | 3-hydroxyphenyl |
| 167² | 4-hydroxyphenyl |

¹For the amine, see reference Tet. Lett. 1995, 36(8), 1279
²For the amine, see reference DE 2552423

Example 166

$^1$H NMR (400 MHz, CDCl$_3$): δ 8.31 (1H, d) 8.02 (1H, s), 7.80 (1H, d), 7.13 (7H, m), 6.92 (1H, s), 6.80 (1H, m), 6.74 (1H, d), 4.41 (3H, m), 4.26 (2H, m), 2.10 (2H, m), 1.19 (4H, m), 1.88 (2H, m). LCMS (electrospray): m/z [M+Na]$^+$ 531

Example 167

$^1$H NMR (400 MHz, DMSO-d$_6$): δ 9.13 (1H, s), 8.32 (1H, d), 8.14 (1H, s), 7.93 (1H, m) 7.19 (4H, m), 7.03 (2H, d), 6.87 (1H, m), 6.67 (2H, m) 4.33 (1H, m), 4.24 (2H, s), 4.13 (2H, m), 1.86 (2H, m), 1.72 (4H, m), 1.60 (2H, m). LCMS (electrospray): m/z [M+Na]$^+$ 531

Example 168

Exo-3-{[5-Fluoro-2-(4-fluoro-phenoxy)-pyridine-3-carbonyl]-amino}-8-aza-bicyclo[3.2.1]octane-8-carboxylic acid 3-methyl-benzyl-amide

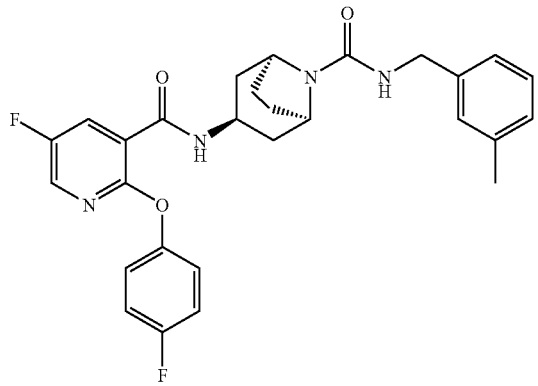

Syn-4-{[2-(benzo[1,3]dioxol-5-yloxy)-5-fluoro-pyridine-3-carbonyl]-amino}-cyclo-hexanecarboxylic acid (150 mg 0.37 mmol, see Preparation 58), 2-aminomethylphenol hydrochloride (65 mg, 0.41 mmol, see Tet. Lett. 2001, 41(49), 8665), O-(7-azabenzotriazol-1-yl)-N,N,N',N',-tetramethyluronium hexafluorophosphate (156 mg, 0.41 mmol) and 4-methylmorpholine (50 μl, 0.41 mmol) were mixed in N,N-dimethylformamide (4 ml) and were stirred at room temperature under a nitrogen atmosphere for 18 hours. The reaction mixture was partitioned between water (10 ml) and dichloromethane (10 ml). The dichloromethane layer was dried over magnesium sulphate and evaporated in-vacuo and the residue was purified by chromatography on silica gel using methanol in dichloromethane as eluant (gradient from 0:100 to 2:98). The material isolated was triturated with ethyl acetate in pentane (10:90) to give syn-2-(benzo[1,3]dioxol-5-yloxy)-5-fluoro-N-[4-(2-hydroxy-benzylcarbamoyl)-cyclohexyl]-nicotinamide as a white powder (61 mg)

$^1$H NMR (400 MHz, CD$_3$OD): δ 8.04 (1H, m), 8.01 (1H, m), 7.04 (2H, m), 6.79 (1H, d), 6.72 (3H, m), 6.61 (1H, d), 5.96 (2H, s), 4.27 (2H, s), 4.13 (1H, m), 2.33 (1H, m), 1.89 (2H, m), 1.71 (6H, m) LCMS (electrospray): m/z [M+Na]$^+$ 530

Example 169

Syn-2-(Benzo[1,3]dioxol-5-yloxy)-5-fluoro-N-[4-(3-hydroxy-benzylcarbamoyl)-cyclohexyl]-nicotinamide

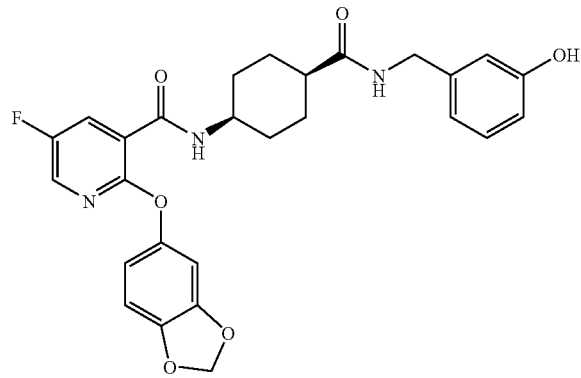

Syn-4-{[2-(benzo[1,3]dioxol-5-yloxy)-5-fluoro-pyridine-3-carbonyl]-amino}-cyclohexanecarboxylic acid (144 mg 0.36 mmol, see Preparation 58), 3-aminomethylphenol hydrochloride (225 mg 0.39 mmol, see reference Tet. Lett. 1995, 36(8), 1279), O-(7-azabenzotriazol-1-yl)-N,N,N',N',-tetramethyluronium hexafluorophosphate (149 mg, 0.39 mmol ) and 4-methylmorpholine (50 μl, 0.39 mmol) were mixed in N,N-dimethylformamide (4 ml) and were stirred at room temperature under a nitrogen atmosphere for 18 hours. The reaction mixture was partitioned between water (10 ml) and ethyl acetate (10 ml). The ethyl acetate layer was washed with a saturated solution of sodium chloride, dried over magnesium sulphate and evaporated in-vacuo. The residue was triturated with ethyl acetate in pentane (10:90) the solid formed was isolated by filtration and triturated with diethylether. This material was purified by chromatography on silica gel using methanol in dichloromethane as eluant (gradient from 2:98 to 3:97) to give syn-2-(benzo[1,3] dioxol-5-yloxy)-5-fluoro-N-[4-(3-hydroxy-benzylcarbamoyl)-cyclohexyl]-nicotinamide as a white foam (83 mg).

$^1$H NMR (400 MHz, CD$_3$OD): δ 8.08 (2H, m), 7.09 (1H, t), 6.80 (1H, d), 6.76 (1H, m), 6.66 (4H, m), 5.98 (2H, s), 4.27 (2H, s), 4.19 (1H, m), 2.38 (1H, m), 1.93 (2H, m), 1.75 (6H, m). LCMS (electrospray): m/z [M+H]$^+$ 508

Example 170

Syn-2-(Benzo[1,3]dioxol-5-yloxy)-5-fluoro-N-[4-(2-fluoro-4-hydroxy-benzylcarbamoyl)-cyclohexyl]-nicotinamide

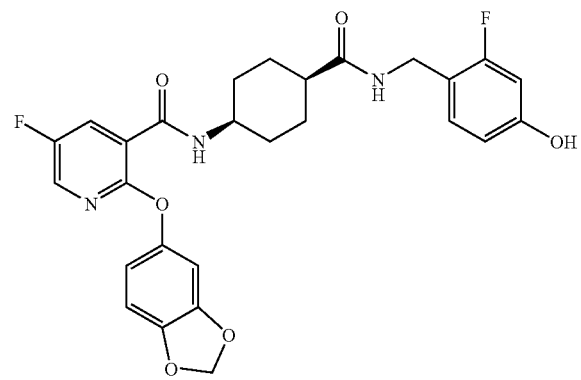

Syn-4-{[2-(Benzo[1,3]dioxol-5-yloxy)-5-fluoro-pyridine-3-carbonyl]-amino}-cyclo-hexanecarboxylic acid (200 mg 0.50 mmol, see Preparation 58), 4-aminomethyl-3-fluoro-phenol hydrochloride (97 mg, 0.55 mmol, see Preparation 49), O-(7-Azabenzotriazol-1-yl)-N,N,N',N',-tetramethyluronium hexafluoro-phosphate (189 mg, 0.55 mmol) and 4-methylmorpholine (60 µl, 0.55 mmol) were mixed in N,N-dimethylformamide (5 ml) and were stirred at room temperature under a nitrogen atmosphere for 18 hours. The reaction mixture was partitioned between water (10 ml) and dichloromethane (10 ml). The dichloromethane layer was dried over magnesium sulphate and evaporated in-vacuo. The residue was purified by chromatography on silica gel using methanol in dichloromethane as eluant (gradient from 0:100 to 2:98). The material isolated was triturated with ethyl acetate in pentane (10:90) syn-2-(benzo[1,3]dioxol-5-yloxy)-5-fluoro-N-[4-(2-fluoro-4-hydroxy-benzylcarbamoyl)-cyclohexyl]-nicotinamide as a white solid (83 mg)

$^1$H NMR (400 MHz, CD$_3$OD): δ 8.01 (2H, m), 7.04 (1H, m), 6.80 (1H, d), 6.74 (1H, m), 6.62 (1H, d), 6.48 (2H, m), 5.97 (2H, s), 4.23, (2H, s), 4.17 (1H, m), 2.13 (1H, m), 1.90 (2H, m), 1.72 (6H, m). LCMS (electrospray): m/z [M+Na]$^+$ 548

Example 171

Anti-5-Fluoro-2-(4-fluoro-phenoxy)-N-[4-(3-hydroxy-benzyl-carbamoyl)-cyclohexyl]-nicotinamide

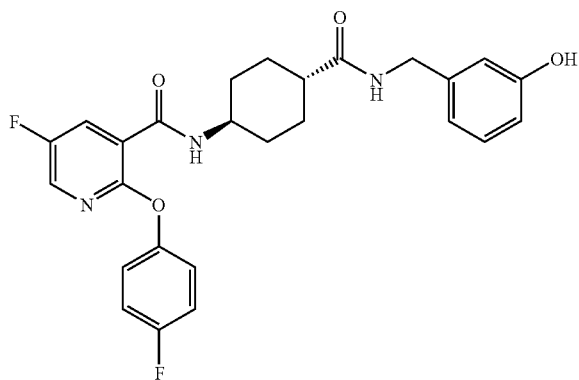

Anti-4-{[5-Fluoro-2-(4-fluoro-phenoxy)-pyridine-3-carbonyl]-amino}-cyclo-hexanecarboxylic acid (200 mg 0.53 mmol, see Preparation 52), 3-aminomethylphenol hydrochloride (334 mg 0.58 mmol, see reference Tet. Lett. 1995, 36(8), 1279), O-(7-azabenzotriazol-1-yl)-N,N,N',N',-tetramethyluronium hexafluorophosphate (222 mg, 0.58 mmol) and 4-methylmorpholine (70 µl, 0.58 mmol) were mixed in N,N-dimethylformamide (5 ml) and were stirred at room temperature under a nitrogen atmosphere for 18 hours. The reaction mixture was partitioned between water (10 ml) and dichloromethane (10 ml). The dichloromethane layer was dried over magnesium sulphate and evaporated in-vacuo. The residue was purified by chromatography on silica gel using methanol in dichloromethane as eluant (gradient from 0:100 to 2:98). The material isolated was dried in-vacuo to give anti-5-fluoro-2-(4-fluoro-phenoxy)-N-[4-(3-hydroxy-benzylcarbamoyl)-cyclohexyl]-nicotinamide as a white powder (127 mg).

$^1$H NMR (400 MHz, CD$_3$OD): δ 8.21 (1H, m), 8.07 (1H, d), 8.00 (1H, m), 7.13 (5H, m), 6.70 (3H, m), 4.29, (2H, d), 3.89 (1H, m), 2.26 (1H, m), 2.12 (2H, m), 1.95 (2H, m) 1.68 (2H, m), 1.39 (2H, m). LCMS (electrospray): m/z [M+Na]$^+$ 504

Example 172

Syn-2-(4-fluoro-phenoxy)-N-[4-(2-hydroxy-benzyl-carba-moyl)-cyclohexyl]-nicotinamide

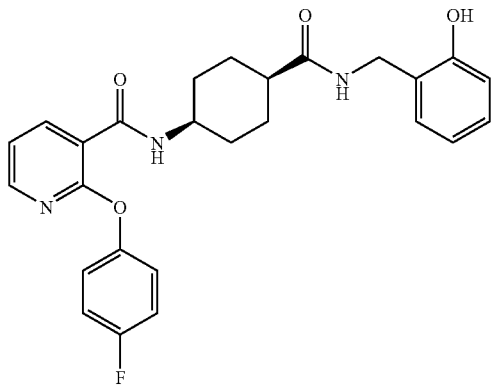

Syn-4-{[2-(4-fluoro-phenoxy)-pyridine-3-carbonyl]-amino}-cyclohexane-carboxylic acid (164 mg 0.46 mmol, see Preparation 55), 2-aminomethylphenol hydrochloride (80 mg 0.50 mmol, see reference Tet. Lett. 1995, 36(8), 1279), O-(7-azabenzotriazol-1-yl)-N,N,N',N',-tetramethyluronium hexafluorophosphate (149 mg, 0.50 mmol) and 4-methylmorpholine (60 µl, 0.50 mmol) were mixed in N,N-dimethylformamide (4 ml) and were stirred at room temperature under a nitrogen atmosphere for 18 hours. The reaction mixture was partitioned between water (10 ml) and ethyl acetate (10 ml). The ethyl acetate layer was washed with a saturated solution of sodium chloride, dried over magnesium sulphate and evaporated in-vacuo. The residue was triturated with diethylether, the solid formed was isolated by filtration and washed with diethylether. This material was purified by chromatography on silica gel using methanol in dichloromethane as eluant (2:98) to give syn-2-(4-fluoro-phenoxy)-N-[4-(2-hydroxy-benzylcarbamoyl)-cyclohexyl]-nicotinamide as a white foam (77 mg).

$^1$H NMR (400 MHz, CD$_3$OD): δ 8.26 (1H, d), 8.18 (1H, m), 7.21 (3H, m), 7.11 (4H, m), 6.78 (2H, m), 4.32 (2H, s), 4.20 (1H, m), 2.38 (1H, m), 1.92 (2H, m), 1.76 (6H, m). LCMS (thermospray): m/z [M+H]$^+$ 464

Example 173

Syn-N-[4-(2-Fluoro-4-hydroxy-benzylcarbamoyl)-cyclohexyl]-2-(4-fluoro-phenoxy)-nicotinamide

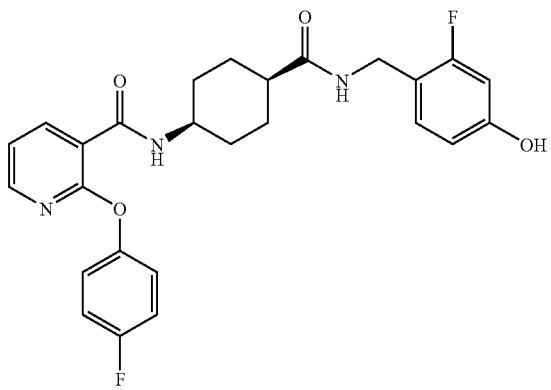

Syn-4-{[2-(benzo[1,3]dioxol-5-yloxy)-5-fluoro-pyridine-3-carbonyl]-amino}-cyclohexanecarboxylic acid (200 mg 0.56 mmol, see Preparation 55), 4-aminomethyl-3-fluoro-phenol hydrochloride (109 mg, 0.61 mmol, see Preparation 49), O-(7-azabenzotriazol-1-yl)-N,N,N',N',-tetramethyluronium hexafluorophosphate (189 mg, 0.61 mmol) and 4-methylmorpholine (70 μl, 0.61 mmol) were mixed in N,N-dimethylformamide (5 ml) and were stirred at room temperature under a nitrogen atmosphere for 18 hours. The reaction mixture was partitioned between water (10 ml) and dichloromethane (10 ml). The dichloromethane layer was dried over magnesium sulphate and evaporated in-vacuo. The residue was purified by chromatography on silica gel using methanol in dichloromethane as eluant (gradient from 0:100 to 2:98). The material isolated was triturated with diethylether in pentane (20:80) to give syn-N-[4-(2-fluoro-4-hydroxy-benzylcarbamoyl)-cyclohexyl]-2-(4-fluoro-phenoxy)-nicotinamide as a white powder (83 mg).

$^1$H NMR (400 MHz, CD$_3$OD): δ 8.40 (1H, d), 8.21 (1H, d), 8.14 (1H, d), 7.19 (3H, m), 7.09 (3H, m), 6.48 (2H, m), 4.22 (2H, s), 4.16 (1H, m), 2.31 (1H, m), 1.89 (2H, m), 1.70 (6H, m). LCMS (electrospray): m/z [M+Na]$^+$ 505

Example 174 syn-2-(3,4-Difluoro-phenoxy)-5-fluoro-N-[4-(2-hydroxy-5-methyl-benzoylamino)-cyclohexyl]-nicotinamide

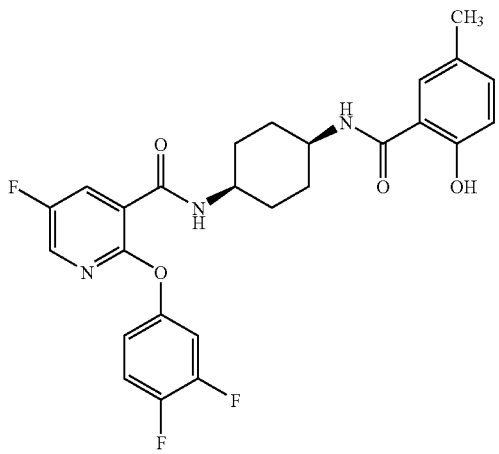

1-(3-Dimethylaminopropyl)-3-ethylcarbodiimide hydrochloride (9.45 g, 50 mmol) was added to a solution of the acid from preparation 60 (10.3 g, 38 mmol) and 1-hydroxybenzotriazole hydrate (5.65 g, 42 mmol) in 1-methyl-2-pyrrolidinone (150 ml) and the solution stired for 10 minutes. A solution of the amine from preparation 62 (11.8 g, 40 mmol) and Hünig's base (17.5 ml, 100 mmol) in 1-methyl-2-pyrrolidinone (50 ml) was then added and the reaction stirred at room temperature for 18 hours. The mixture was concentrated in vacuo, and the residue partitioned between ethyl acetate (1.25 L) and 1N hydrochloric acid (800 ml). The layers were separated, the organic phase washed with 2N hydrochloric acid (2-fold), water (2-fold) and brine, then dried over magnesium sulphate and evaporated in vacuo. The crude product was recrystallised from methanol, to afford the title compound as a white crystalline solid (15.6 g).

$^1$H NMR (400 MHz, CDCl$_3$): δ 1.56–1.66 (2H, m), 1.80–2.02 (6H, m), 2.26 (3H, s), 4.05 (1H, m), 4.25 (1H, m), 6.06 (1H, m), 6.90 (1H, d), 6.95 (1H, m), 6.99 (1H, s), 7.08 (1H, m), 7.19–7.30 (2H, m), 7.89 (1H, m), 8.05 (1H, s), 8.40 (1H, d), 11.98 (1H, s). LCMS (APCI): m/z [M+H]$^+$ 500

Example 175 syn-2-(3,4-Difluoro-phenoxy)-5-fluoro-N-[4-(2-hydroxy-4-isopropyl-benzoylamino)-cyclohexyl]-nicotinamide

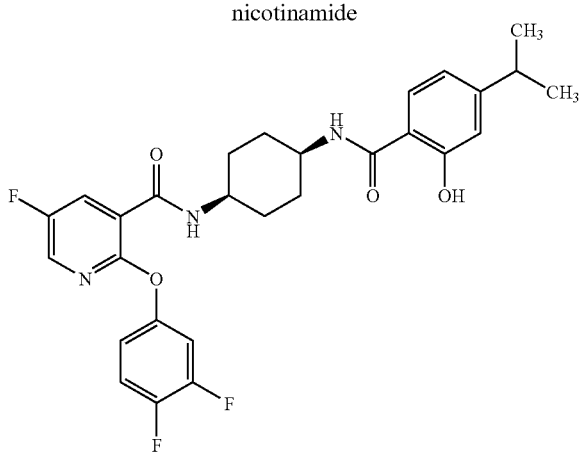

syn-N-(4-Amino-cyclohexyl)-2-(3,4-difluoro-phenoxy)-5-fluoro-nicotinamide (200 mg, 0.55 mmol, see preparation 64) was added to 1-(3-dimethylaminopropyl-3-ethylcarbodiimide hydrochloride (115 mg, 0.6 mmol), 1-hydroxybenzotriazole hydrate (81 mg, 0.6 mmol), 4-methylmorpholine (120 μl, 1.1 mmol) and 2-hydroxy-4-isopropyl-benzoic acid (109 mg, 0.6 mmol) in dichloromethane (10 ml) and the mixture was stirred at room temperature for 16 hours. Dichloromethane was added and the mixture was washed with saturated sodium hydrogen carbonate solution. The phases were separated and the organic phase was filtered through Whatman® phase separation tubes and concentrated in-vacuo. The residue was triturated with diethyl ether and dichloromethane to give syn-2-(3,4-difluoro-phenoxy)-5-fluoro-N-[4-(2-hydroxy-4-isopropyl-benzoylamino)-cyclohexyl]-nicotinamide as a white solid (145 mg).

$^1$H NMR (400 MHz, DMSO-d$_6$): δ 8.33 (m, 2H), 8.25 (d, 1H), 8.00 (m, 1H), 7.80 (d, 1H), 7.45 (m, 3H), 7.08 (m, 1H), 6.75 (m, 1H), 3.94 (m, 1H), 3.88 (m, 1H), 2.82 (m, 1H), 1.70 (m, 8H), 1.16 (d, 6H) LCMS (electrospray): m/z [M−H]$^−$ 526

Examples 176–194

The compounds of the following tabulated examples (Table 13) of the general formula:

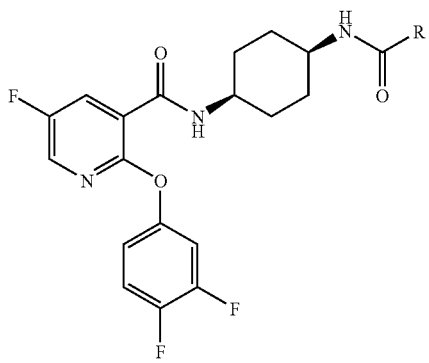

were prepared by a similar method to that of example 175 using the amine of preparation 64 and the appropriate carboxylic acid.

TABLE 13

| Example N° | R |
|---|---|
| 176 | 4-isopropyl-2-hydroxyphenyl |
| 177 | 4-ethyl-2-hydroxyphenyl |
| 178 | 2,6-dihydroxyphenyl |
| 179 | 3-fluoro-2-hydroxyphenyl |
| 180 | 3-methoxy-2-hydroxyphenyl |
| 181 | 4-ethoxy-2-hydroxyphenyl |
| 182 | 4-ethyl-2-hydroxyphenyl |

TABLE 13-continued

| Example N° | R |
|---|---|
| 183 | 5-(hydroxymethyl)-2-hydroxyphenyl |
| 184 | 3-ethyl-2-hydroxyphenyl |
| 185 | 3-isopropyl-2-hydroxyphenyl |
| 186[A] | 4-chloro-2-hydroxyphenyl |
| 187[A] | 4-methoxy-2-hydroxyphenyl |
| 188[A] | 3-methoxy-2-hydroxyphenyl |
| 189[A] | 4-fluoro-2-hydroxyphenyl |
| 190[A] | 2-hydroxyphenyl |
| 191[A] | 3-chloro-2-hydroxyphenyl |

TABLE 13-continued

| Example N° | R |
|---|---|
| 192[A] | 4,6-dichloro-2-hydroxyphenyl (Cl, Cl, OH substituents on benzene) |
| 193[AB] | 4,5-dichloro-2-hydroxyphenyl |
| 194[AC] | 4,5-dimethyl-2-hydroxyphenyl |

[A] Diisopropylethylamine was used as the base
[B] See reference Chem. And Pharm. Bull, 1996, 44(4), 734 for the starting carboxylic acid.
[C] See reference Synthesis 1984, (9), 758 for the starting carboxylic acid.

Example 176

$^1$H NMR (400 MHz, DMSO-$d_6$): δ 8.35 (m, 3H), 8.00 (m, 1H), 7.70 (s, 1H), 7.45 (m, 3H), 7.25 (d, 1H), 7.08 (m, 1H), 6.83 (d, 1H), 3.90 (m, 2H), 2.81 (m, 1H), 1.70 (m, 8H), 1.15 (d, 6H) LCMS (electrospray): m/z [M–H]⁻ 526

Example 177

$^1$H NMR (400 MHz, DMSO-$d_6$): δ 12.26 (s, 1H), 8.32 (m, 2H), 8.25 (d, 1H), 8.00 (m, 1H), 7.79 (d, 1H), 7.43 (m, 2H), 7.07 (m 1H), 6.72 (m, 2H), 3.90 (m, 2H), 2.55 (q, 2H), 1.73 (m, 8H), 1.14 (t, 3H) LCMS (electrospray): m/z [M–H]⁻ 512

Example 178

$^1$H NMR (400 MHz, DMSO-$d_6$): δ 12.55 (s, 2H), 8.88 (d, 1H), 8.41 (d, 1H), 8.22 (d, 1H), 8.22 (d, 1H), 7.45 (m, 1H), 7.18 (m, 1H), 7.16 (m, 1H), 7.04 (m, 1H), 6.35 (d, 2H), 3.94 (m, 2H), 1.70 (m, 8H) LCMS (electrospray): m/z [M–H]⁻ 500

Example 179

$^1$H NMR (400 MHz, DMSO-$d_6$): δ 9.95 (s, 1H), 8.29 (d, 1H), 8.22 (d, 1H), 7.99 (m, 2H), 7.41 (m, 2H), 7.22 (m, 1H), 7.06 (m, 1H), 6.68 (m, 2H), 3.88 (m, 2H), 1.66 (m, 8H) LCMS (electrospray): m/z [M–H]⁻ 502

Example 180

$^1$H NMR (400 MHz, DMSO-$d_6$): δ 1.60 (m, 2H), 1.73 (m, 6H), 3.75 (s, 3H), 3.95 (m, 2H), 6.51 (d,1H), 6.58 (d, 1H), 7.09 (m, 1H), 7.31 (m, 1H), 7.45 (m, 2H), 8.00 (m, 1H), 8.23 (m, 1H), 8.39 (d, 1H), 8.48 (d, 1H), 13.59 (s, 1H) LCMS (electrospray): m/z [M–H]⁻ 514

Example 181

$^1$H NMR (400 MHz, DMSO-$d_6$): δ 8.84 (d, 1H), 8.24 (m, 2H), 8.00 (d, 1H), 7.80 (d, 1H), 7.46 (m, 3H), 7.09 (m, 1H), 6.44 (d, 1H), 3.98 (m, 5H), 1.71 (m, 8H), 1.30 (t, 3H) LCMS (electrospray): m/z [M–H]⁻ 528

Example 182

$^1$H NMR (400 MHz, DMSO-$d_6$): δ 8.39 (m, 2H), 8.26 (s, 1H), 8.02 (d, 1H), 7.71 (s, 1H), 7.45 (m, 3H), 7.20 (m, 1H), 7.06 (m, 1H), 6.81 (d, 1H), 3.90 (m, 2H), 2.50 (q, 2H), 1.72 (m, 8H), 1.15 (t, 3H) LCMS (electrospray): m/z [M–H]⁻ 512

Example 183

$^1$H NMR (400 MHz, CD$_3$OD): δ 8.40 (m, 1H), 8.12 (s, 1H), m 8.03 (m, 1H), 7.79 (s, 1H), 7.30 (m, 3H), 6.86 (d, 1H), 4.52 (s, 2H), 4.13 (m, 1H), 4.05 (m, 1H), 1.83 (8H) LCMS (APCI): m/z [M–H]⁻ 514

Example 184

$^1$H NMR (400 MHz, CD$_3$OD): δ 8.11 (d, 1H), 8.07 (m, 1H), 7.48 (d, 1H), 7.30 (m, 3H), 7.04 (m, 1H), 6,78 (m, 1H), 4.15 (m, 1H), 3.98 (m, 1H), 2.63 (q, 2H), 1.88 (m, 8H), 1.09 (t, 3H) LCMS (APCI): m/z [M–H]⁻ 514

Example 185

$^1$H NMR (400 MHz, CD$_3$OD): δ 8.13 (s, 1H), 8.08 (d, 1H), 7.48 (d, 1H), 7.34 (d, 2H), 7.26 (m, 1H), 7.05 (m, 1H), 6.80 (m, 1H), 4.18 (m, 1H), 3.98 (m, 1H), 3.36 (m, 1H), 1.90 (m, 8H), 1.20 (d, 6H) LCMS (APCI): m/z [M+H]⁺ 528

Example 186

$^1$H NMR (400 MHz, DMSO-$d_6$): δ 12.58 (s, 1H), 8.40 (d, 1H), 8.33 (d, 1H), 8.23 (d, 1H), 8.00 (m, 1H), 7.92 (d, 1H), 7.43 (m, 2H), 7.07 (m, 1H), 6.98 (m, 2H), 3.90 (m, 2H), 1.72 (m, 8H) LCMS (electrospray): m/z [M–H]⁻ 518

Example 187

$^1$H NMR (400 MHz, DMSO-$d_6$): δ 12.60 (s, 1H), 8.45 (d, 1H), 8.39 (d, 1H), 8.23 (d, 1H), 7.99 (m, 1H), 7.41 (m, 3H), 7.06 (m, 1H), 6.99 (m, 1H), 6.84 (d, 1H), 3.96 (m, 1H), 3.87 (m, 1H), 3.72 (s, 3H), 1.72 (m, 8H) LCMS (electrospray): m/z [M+Na]⁺ 538

Example 188

$^1$H NMR (400 MHz, DMSO-d$_6$): δ 12.42 (s, 1H), 8.39 (d, 1H), 8.37 (d, 1H), 8.26 (d, 1H), 8.01 (m, 1H), 8.46 (m, 3H), 7.10 (d, 2H), 6.80 (m, 1H), 3.97 (m, 1H), 3.88 (m, 1H), 3.79 (s, 3H), 2.73 (m, 8H) LCMS (electrospray): m/z [M+Na]$^+$ 538

Example 189

$^1$H NMR (400 MHz, DMSO-d$_6$): δ 12.84 (s, 1H), 8.40 (d, 1H), 8.36 (d, 1H), 8.25 (s, 1H), 7.99 (m, 2H), 7.45 (m, 2H), 7.08 (d, 1H), 6.73 (m, 2H), 3.97 (m, 1H), 3.85 (m, 1H), 1.72 (m, 8H) LCMS (APCI): m/z [M+H]$^+$ 504

Example 190

$^1$H NMR (400 MHz, DMSO-d$_6$): δ 12.22 (s, 1H), 8.40 (d, 1H), 8.35 (d, 1H), 8.22 (d, 1H), 8.00 (m, 1H), 7.89 (d, 1H), 7.40 (m, 3H), 7.08 (m, 1H), 6.90 (m, 2H) 3.93 (m, 2H), 1.75 (m, 8H) LCMS (electrospray): m/z [M−H]$^-$ 484

Example 191

$^1$H NMR (400 MHz, DMSO-d$_6$): δ 13.55 (s, 1H), 8.63 (s, 1H), 8.31 (d, 1H), 8.23 (d, 1H), 8.00 (m, 1H), 7.89 (d, 1H), 7.59 (d, 1H), 7.41 (m, 2H), 7.08 (m, 1H), 6.88 (m, 1H), 3.98 (m, 1H), 3.84 (m, 1H), 1.74 (m, 8H) LCMS (electrospray): m/z [M+Na]$^+$ 542

Example 192

$^1$H NMR (400 MHz, CDCl$_3$): δ (rotamers) 12.68 (s, 1H), 8.36 (m, 1H), 8.05 (d, 1H), 7.86, 7.80 (2×d, 1H), 7.48 (d, 1H), 7.20 (m, 2H), 7.06 (m, 1H), 6.92 (d, 1H), 6.21, 6.10 (2×d, 1H), 4.22 (m, 1H), 4.10 (m, 1H), 1.93 (m, 6H), 1.62 (m, 2H) LCMS (electrospray): m/z [M−H]$^-$ 552

Example 193

$^1$H NMR (400 MHz, CDCl$_3$): δ 12.28 (s, 1H), 8.35 (m, 1H), 8.05 (d, 1H), 7.88 (d, 1H), 7.27 (m, 2H), 7.05 (m, 2H), 6.96 (d, 1H), 6.07 (d, 1H), 4.23 (m, 1H), 4.12 (m, 1H), 1.90 (m, 6H), 1.62 (m, 2H) LCMS (electrospray): m/z [M−H]$^-$ 552

Example 194

$^1$H NMR (400 MHz, DMSO-d$_6$): δ 12.04 (s, 1H), 8.36 (d, 1H), 8.26 (m, 2H), 8.00 (d, 1H), 7.62 (s, 1H), 7.45 (m, 2H), 7.07 (m, 1H), 6.68 (s, 1H), 3.96 (m, 1H), 3.85 (m, 1H), 2.18 (s, 3H), 2.14 (s, 3H), 1.71 (m, 8H) LCMS (electrospray): m/z [M−H]$^-$ 512

Example 195 syn-5-Fluoro-N-[4-(2-hydroxy-4-methyl-benzoylamino)-cyclohexyl]-2-(3-trifluoromethoxy-phenoxy)-nicotinamide

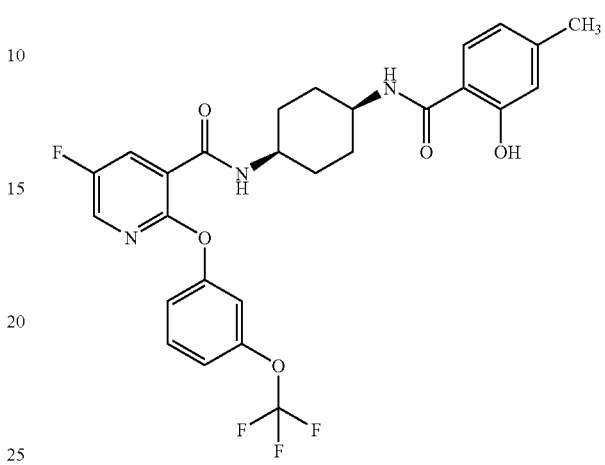

syn-2-Chloro-5-fluoro-N-[4-(2-hydroxy-4-methyl-benzoylamino)-cyclohexyl]-nicotinamide (150 mg, 0.37 mmol, see preparation 67) was mixed with caesium carbonate (602 mg, 1.85 mmol) and 3-trifluoromethoxyphenol (240 µl, 1.85 mmol) in N,N-dimethylformamide (5 ml) and the reaction mixture was heated at 65° C. under a nitrogen atmosphere for 16 hours. The reaction mixture was cooled to room temperature and was partitioned between ethyl acetate and water. The aqueous layer was adjusted to pH 4 by addition of citric acid and the layers were separated. The organic layer was washed with water and dried over magnesium sulphate and concentrated in-vacuo. The residue was purified by chromatography on silica gel using methanol in dichloromethane as eluant (gradient from 0:100 to 1:99). The material isolated was further purified by chromatography on silica gel using methanol in dichloromethane (0.5:99.5). The material obtained was re-suspended in diethyl ether and the solid formed was isolated by filtration to give syn-5-fluoro-N-[4-(2-hydroxy-4-methyl-benzoylamino)-cyclohexyl]-2-(3-trifluoromethoxy-phenoxy)-nicotinamide as a white solid (54 mg).

$^1$H NMR (400 MHz, DMSO-d$_6$): δ 1.70 (m, 8H), 2.26 (s, 3H), 3.90 (m, 2H), 6.70 (m, 2H), 7.24 (m, 3H), 7.52 (m, 1H), 7.77 (d, 1H), 8.01 (d, 1H), 8.28 (s, 1H), 8.34 (m, 2H), 12.32 (s, 1H) LCMS (electrospray): m/z [M−H]$^-$ 546

Examples 196–215

The compounds of the following tabulated examples (Table 14) of the general formula:

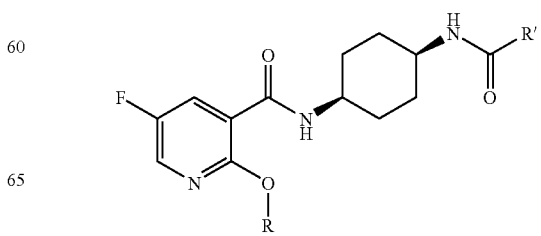

were prepared by a similar method to that of example 195 using the appropriate aryl chloride and phenol.

TABLE 14

| Example N° | R | R' |
|---|---|---|
| 196 | 4-(trifluoromethoxy)phenyl | 4-methyl-2-hydroxyphenyl |
| 197 | 3-methoxyphenyl | 5-methoxy-2-hydroxyphenyl |
| 198 | 4-methoxyphenyl | 5-methoxy-2-hydroxyphenyl |
| 199 | 3-(trifluoromethyl)phenyl | 4-methyl-2-hydroxyphenyl |
| 200 | 3-chloro-4-fluorophenyl | 4-methyl-2-hydroxyphenyl |
| 201 | 3-bromophenyl | 4-methyl-2-hydroxyphenyl |
| 202 | 3,4-dichlorophenyl | 5-methoxy-2-hydroxyphenyl |

TABLE 14-continued

| Example N° | R | R' |
|---|---|---|
| 203 | 4-fluoro-2-methylphenyl | 4-methyl-2-hydroxyphenyl |
| 204[A] | 3-cyclopropylphenyl | 4-methyl-2-hydroxyphenyl |
| 205[A] | 3-cyclobutoxyphenyl | 4-methyl-2-hydroxyphenyl |
| 206[A] | 3-cyclopropylphenyl | 2-methyl-6-hydroxyphenyl |
| 207[A] | 3-cyclobutoxyphenyl | 2-methyl-6-hydroxyphenyl |
| 208[A] | 3,4-difluorophenyl | 2-methyl-6-hydroxyphenyl |
| 209[AB] | 3-chloro-4-fluorophenyl | 2-methyl-6-hydroxyphenyl |

TABLE 14-continued

| Example N° | R | R' |
|---|---|---|
| 210[AB] | 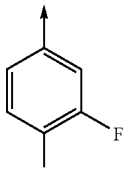 | 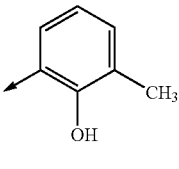 |
| 211[AB] | 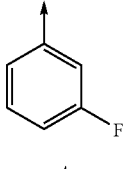 | 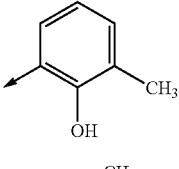 |
| 212[AB] | 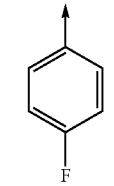 | 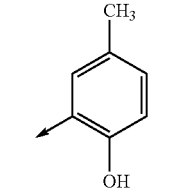 |
| 213[AB] | 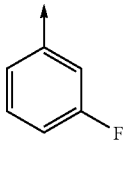 | 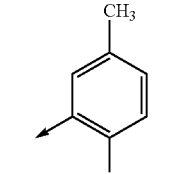 |
| 214[AB] | 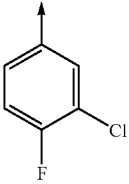 | 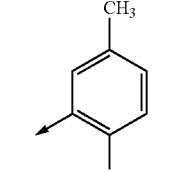 |
| 215[AB] | 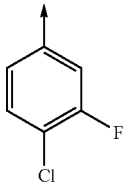 | 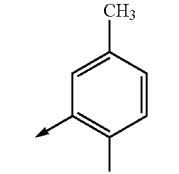 |

[A] Acetonitrile was used as solvent
[B] Purified by chromatography on silica gel using ethyl acetate in cyclohexane as eluant

Example 196

$^1$H NMR (400 MHz, DMSO-$d_6$): δ 12.31 (s, 1H), 8.35 (m, 2H), 8.25 (d, 1H), 8.00 (m, 1H), 7.78 (d, 1H), 7.40 (d, 2H), 7.31 (d, 2H), 6.69 (m, 2H), 3.90 (m, 2H), 2.26 (s, 3H), 1.70 (m, 8H) LCMS (electrospray): m/z [M−H]$^-$ 546

Example 197

$^1$H NMR (400 MHz, CDCl$_3$): δ 8.35 (m, 1H), 8.08 (m, 2H), 7.36 (m, 1H), 7.03 (d, 1H), 6.85 (d, 1H), 6.76 (m, 2H), 6.44 (s, 1H), 6.39 (d, 1H), 7.74 (d, 1H), 4.28 (m, 1H), 4.06 (m, 1H), 3.80 (2×s, 6H), 1.90 (m, 6H), 1.50 (m, 2H) LCMS (APCI): m/z [M−H]$^-$ 508

Example 198

$^1$H NMR (400 MHz, CDCl$_3$): δ 8.35 (d, 1H), 8.20 (d, 1H), 8.08 (d, 1H), 7.12 (d, 2H), 6.98 (m, 3H), 6.45 (s, 1H), 6.39 (d, 1H), 5.72 (d, 1H), 4.30 (m, 1H), 4.07 (m, 1H), 3.82 (2×s, 6H), 1.90 (m, 6H), 1.53 (m, 2H) LCMS (APCI): m/z [M−H]$^-$ 508

Example 199

$^1$H NMR (400 MHz, DMSO-$d_6$): δ 12.28 (s, 1H), 8.40 (d, 1H), 8.32 (d, 1H), 8.26 (s, 1H), 8.01 (m, 1H), 7.76 (d, 1H), 7.60 (m, 4H), 6.69 (m, 2H), 3.95 (m, 1H), 3.46 (m, 1H), 2.50 (s, 3H), 1.72 (m, 8H) LCMS (electrospray): m/z [M−H]$^-$ 530

Example 200

$^1$H NMR (400 MHz, DMSO-$d_6$): δ 12.30 (s, 1H), 8.33 (m, 2H), 8.23 (d, 1H), 8.00 (d, 1H), 7.77 (d, 1H), 7.53 (d, 1H), 7.46 (m, 1H), 7.24 (m, 1H), 6.70 (m, 2H), 3.97 (m, 1H), 3.86 (m, 1H), 2.28 (s, 3H), 1.74 (m, 8H) LCMS (electrospray): m/z [M−H]$^-$ 514

Example 201

$^1$H NMR (400 MHz, DMSO-$d_6$): δ 12.30 (s, 1H), 8.37 (m, 2H), 8.24 (d, 1H), 8.00 (d, 1H), 7.78 (d, 1H), 7.45 (s, 1H), 7.38 (m, 2H), 7.20 (d, 1H), 6.70 (m, 2H), 3.91 (m, 2H), 2.26 (s, 3H), 1.70 (m, 8H) LCMS (electrospray): m/z [M−H]$^-$ 542

Example 202

$^1$H NMR (400 MHz, CDCl$_3$): δ 7.32 (m, 5H), 7.13 (d, 1H), 7.04 (d, 1H), 6.44 (s, 1H), 6.39 (d, 1H), 6.14 (m, 1H), 4.42 (m, 1H), 4.29 (m, 1H), 3.79 (s, 3H), 1.90 (m, 8H) LCMS (APCI): m/z [M+H]$^+$ 548

Example 203

$^1$H NMR (400 MHz, CDCl$_3$): δ 8.38 (d, 1H), 8.10 (m, 1H), 8.00 (s, 1H), 7.02 (m, 4H), 6.79 (s, 1H), 6.62 (m, 1H), 5.92 (s, 1H), 4.26 (m, 1H), 4.08 (m, 1H), 2.38 (s, 3H), 2.20 (s, 3H), 2.02–1.80 (m, 6H), 1.59 (m, 2H).

Example 204

$^1$H NMR (400 MHz, CDCl$_3$): δ 12.00 (s, 1H), 8.35 (m, 1H), 8.13 (d, 1H), 8.08 (d, 1H), 7.35 (m, 1H), 7.20 (d, 1H), 7.00 (d, 1H), 6.95 (m, 2H), 6.86 (m, 2H), 5.91 (d, 1H), 4.28 (m, 1H), 4.07 (m, 1H), 2.31 (s, 3H), 1.90 (m, 6H), 1.52 (m, 3H), 0.97 (m, 2H), 0.68 (m, 2H) LCMS (electrospray): m/z [M+Na]$^+$ 526

Example 205

$^1$H NMR (400 MHz, CDCl$_3$): δ 12.00 (s, 1H), 8.18 (m, 1H), 8.09 (s, 1H), 7.33 (m, 1H), 7.20 (d, 1H), 6.95 (s, 1H), 6.87 (d, 1H), 6.72 (m, 2H), 6.61 (s, 1H), 5.92 (d, 1H), 4,59 (m, 1H), 4.27 (m, 1H), 4.05 (m, 1H), 2.34 (m, 6H), 1.80 (m, 11H) LCMS (electrospray): m/z [M+H]$^+$ 534

Example 206

$^1$H NMR (400 MHz, CDCl$_3$): δ 12.47 (s, 1H), 8.37 (m, 1H), 8.16 (d, 1H), 8.07 (s, 1H), 7.14 (m, 1H), 7.00 (d, 1H), 6.94 (m, 2H), 6.88 (s, 1H), 6.72 (m, 1H), 5.88 (d, 1H), 4.36 (m, 1H), 4.08 (m, 1H), 2.27 (s, 3H), 1.90 (m, 7H), 1,50 (m, 2H), 0.98 (m, 2H), 0.69 (m, 2H) LCMS (electrospray): m/z [M+H]$^+$ 504

Example 207

$^1$H NMR (400 MHz, CDCl$_3$): δ 12.49 (s, 1H), 8.38 (m, 1H), 8.16 (m, 2H), 7.34 (m, 1H), 6.99 (d, 1H), 6.73 (m, 3H), 6.63 (s, 1H), 5.90 (d, 1H), 4.60 (m, 1H), 4.29 (m, 1H), 4.08 (m, 1H), 2.39 (m, 2H), 2.26 (s, 3H), 2.15 (m, 2H), 1.80 (m, 11H) LCMS (electrospray): m/z [M+Na]$^+$ 556

Example 208

$^1$H NMR (400 MHz, CD$_3$OD): δ 8.11 (s, 1H), 8.06 (d, 1H), 7.49 (d, 1H), 7.30 (m, 3H), 7.05 (d, 1H), 6.75 (m, 1H), 4.16 (m, 1H), 3.99 (m, 1H), 2.20 (s, 3H), 1.86 (m, 8H) LCMS (APCl): m/z [M−H]$^-$ 498

Example 209

$^1$H NMR (400 MHz, CD$_3$OD): δ 8.13 (d, 1H), 8.08 (d, 1H), 7.49 (d, 1H), 7.42 (m, 1H), 7.27 (m, 3H), 6.75 (m, 1H), 4.17 (m, 1H), 3.99 (m, 1H), 2.19 (s, 3H), 1.85 (m, 8H) LCMS (electrospray): m/z [M+Na]$^+$ 538

Example 210

$^1$H NMR (400 MHz, CD$_3$OD): δ 8.15 (d, 1H), 8.06 (d, 1H), 7.50 (m, 2H), 7.22 (m, 2H), 7.06 (d, 1H), 6.75 (m, 1H), 4.16 (m, 1H), 3.99 (m, 1H), 2.20 (s, 3H), 1.85 (m, 8H) LCMS (electrospray): m/z [M+Na]$^+$ 538

Example 211

$^1$H NMR (400 MHz, CD$_3$OD): δ 8.15 (d, 1H), 8.07 (m, 1H), 7.48 (d, 1H), 7.42 (m, 1H), 7.25 (d, 1H), 7.01 M, 3H), 6.75 (m, 1H), 4.16 (m, 1H), 3.99 (m, 1H), 2.19 (s, 3H), 1.83 (m, 8H) LCMS (electrospray): m/z [M+Na]$^+$ 504

Example 212

$^1$H NMR (400 MHz, CDCl$_3$): δ 12.00 (s, 1H), 8.39 (m, 1H), 8.06 (m, 2H), 7.18 (m, 4H), 6.96 (s, 1H), 6.90 (m, 1H), 5.99 (d, 1H), 4.30 (m, 1H), 4.08 (m, 1H), 2.32 (s, 3H), 1.95 (m, 6H), 1.60 (m, 2H) LCMS (electrospray): m/z [M+Na]$^+$ 504

Example 213

$^1$H NMR (400 MHz, CDCl$_3$): δ 8.39 (m, 1H), 8.06 (d, 1H), 7.98 (d, 1H), 7.42 (m, 1H), 7.20 (d, 1H), 6.98 (m, 3H), 6.89 (d, 1H), 5.99 (d, 1H), 4.29 (m, 1H), 4.08 (m, 1H), 2.31 (s, 3H), 1.92 (m, 6H), 1.57 (m, 2H) LCMS (electrospray): m/z [M+Na]$^+$ 504

Example 214

$^1$H NMR (400 MHz, CDCl$_3$): δ 8.38 (m, 1H), 8.06 (d, 1H), 7.88 (d, 1H), 7.22 (m, 3H), 7.10 (m, 1H), 7.00 (s, 1H), 6.89 (d, 1H), 6.07 (d, 1H), 4.24 (m, 1H), 4.09 (m, 1H), 2.29 (s, 3H), 1.90 (m, 6H), 1.62 (m, 2H) LCMS (electrospray): m/z [M+Na]$^+$ 538

Example 215

$^1$H NMR (400 MHz, CDCl$_3$): δ 8.38 (m, 1H), 8.06 (d, 1H), 7.80 (m, 1H), 7.49 (m, 1H), 7.21 (d, 1H), 7.00 (m, 3H), 6.05 (d, 1H), 4.23 (m, 1H), 4.06 (m, 1H), 2.32 (s, 3H), 1.90 (m, 6H), 1.56 (m, 2H) LCMS (electrospray): m/z [M+Na]$^+$ 538

Example 216 syn-2-(3,4-Difluoro-phenoxy)-5-fluoro-N-[4-(2-hydroxy-4-methyl-benzoylamino)-cyclohexyl]-nicotinamide

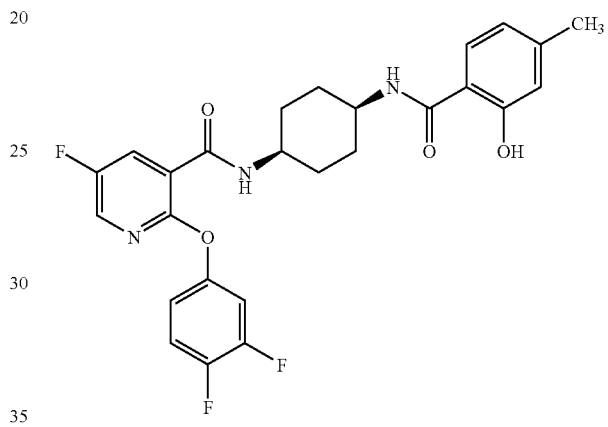

1-Hydroxybenzotriazole hydrate (6.06 g, 44.85 mmol) was added to 2-(3,4-difluoro-phenoxy)-5-fluoro-nicotinic acid (10.5 g, 39 mmol, see preparation 60) in 4-methylmorpholine (100 ml). 1-(3-Dimethylaminopropyl-3-ethylcarbodiimide hydrochloride (9.71 g, 50.7 mmol) was added portionwise and the mixture was stirred for 20 minutes at room temperature. Syn-N-(4-Amino-cyclohexyl)-2-hydroxy-4-methyl-benzamide hydrochloride (11.66 g, 40.9 mmol, see preparation 66) was dissolved in 4-methylmorpholine (100 ml) and diisopropylamine (12.6 g, 97.5 mmol) was added. The mixture was stirred at room temperature for 15 minutes and then was added to the mixture containing the carboxylic acid. The reaction mixture was stirred at room temperature for 17 hours and then was partitioned between ethyl acetate (1 l) and water (1.5 l). The phases were separated and the organic phase was washed with 10% citric acid solution (300 ml then 200 ml), saturated sodium hydrogen carbonate (3-fold 500 ml) and then was diluted with ethyl acetate (500 ml). The organic solution was washed with water (3-fold 500 ml) dried over magnesium sulphate and concentrated in-vacuo. The residue was triturated with methanol and the material obtained was isolated by filtration and was washed with methanol and diethyl ether. The material obtained was dried in-vacuo at 50° C. for 17 hours and was recrystalised from ethyl acetate/propan-2-ol. The material obtained was triturated with propan-2-ol and the residue was isolated by filtration and was washed with propan-2-ol and diethyl ether then dried in-vacuo at 50° C. for 17 hours to give syn-2-(3,4-difluoro-phenoxy)-5-fluoro-N-[4-(2-hydroxy-4-methyl-benzoylamino)-cyclohexyl]-nicotinamide as a white solid (15.3 g).

123

$^1$H NMR (400 MHz, DMSO-d$_6$): δ 12.25 (s, 1H), 8.33 (m, 2H), 8.23 (s, 1H), 7.99 (m, 1H), 7.75 (d, 1H), 7.42 (m, 2H), 7.08 (d, 1H), 6.68 (m, 2H), 3.97 (m, 1H), 3.86 (m, 1H), 2.26 (s, 3H), 1.72 (m, 8H) LCMS (APCl): m/z [M–H]$^-$ 498

Examples 217–218

The compounds of the following tabulated examples (Table 15) of the general formula:

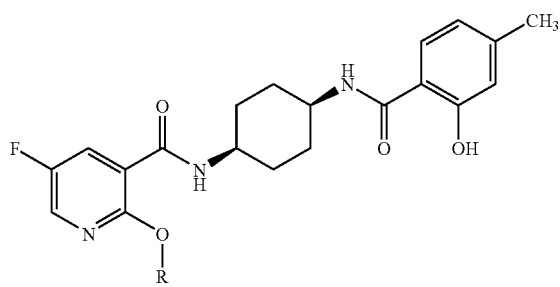

were prepared by a similar method to that of example 216 using syn-N-(4-Amino-cyclohexyl)-2-hydroxy-4-methyl-benzamide hydrochloride (see preparation 66) and the appropriate carboxylic acid.

TABLE 15

| Example N° | R Group |
|---|---|
| 217 | 3,5-difluorophenyl |
| 218 | 3,4-dichlorophenyl |

Example 217

$^1$H NMR (400 MHz, DMSO-d$_6$): δ 12.28 (s, 1H), 8.30 (m, 3H), 8.00 (m, 1H), 7.75 (d, 1H), 7.08 (m, 1H), 6.99 (m, 2H), 6.68 (m, 2H), 3.89 (m, 2H), 2.27 (s, 3H), 1.72 (m, 8H) LCMS (electrospray): m/z [M–H]$^-$ 498

Example 218

$^1$H NMR (400 MHz, DMSO-d$_6$): δ 12.28 (s, 1H), 8.31 (m, 2H), 8.27 (s, 1H), 8.00 (m, 1H), 7.75 (d, 1H), 7.67 (d, 1H), 7.57 (s, 1H), 7.22 (d, 1H), 6.68 (m, 2H), 3.90 (m, 2H), 2.26 (s, 3H), 1.73 (m, 8H) LCMS (electrospray): m/z [M–H]$^-$ 530

Preparations

Preparation 1 anti-(4-{[2-(Benzo[1,3]dioxol-5-yloxy)-pyridine-3-carbonyl]-amino}-cyclohexyl)-carbamic acid tert-butyl ester

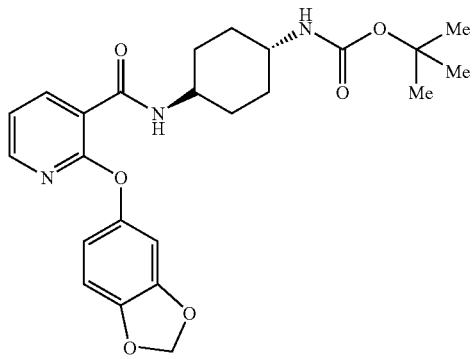

2-(4-Benzo[1,3]dioxol-5-yloxy)-nicotinic acid (5.0 g, 19.3 mmol, see reference WO 98/45268), anti-(4-amino-cyclohexyl)-carbamic acid tert-butyl ester (4.13 g, 19.3 mmol) (see Preparation 40), 1-hydroxybenzotriazole (3.91 g, 29 mmol), 1-(3-dimethylaminopropyl)-3-ethylcarbodiimide hydrochloride (4.81 g, 25.1 mmol) and N-methyl morpholine (3.18 ml, 29 mmol) were stirred in N,N-dimethylformamide (50 ml) at room temperature under an atmosphere of nitrogen for 18 hours. The reaction mixture was then partitioned between dichloromethane (200 ml) and a 2 N aqueous solution of sodium carbonate (150 ml), and the organic layer separated. The aqueous phase was extracted with dichloromethane (2-fold 200 ml) and the combined organic extracts were washed with a saturated aqueous solution of sodium chloride (200 ml). The combined organic extracts were then dried over anhydrous magnesium sulphate and the solvent removed in vacuo. The residue was triturated with diethylether (50 ml) giving anti-(4-{[2-(benzo[1,3]dioxol-5-yloxy)-pyridine-3-carbonyl]-amino}-cyclohexyl)-carbamic acid tert-butyl ester (6.5 g) as a white solid.

$^1$H NMR (400 MHz, DMSO-d$^6$): δ=8.06–8.12 (1H, m), 8.02–8.05 (1H, d), 7.94–7.98 (1H, d), 7.10–7.15 (1H, m), 6.82–6.87 (1H, d), 6.76–6.80 (1H, d), 6.50–6.70 (2H, m), 6.00 (2H, s), 3.50–370 (1H, m), 3.05–3.20 (1H, m), 1.70–1.90 (4H, m), 1.32 (9H, s), 1.10–1.30 (4H, m) ppm. LRMS (electrospray): m/z [M–H]$^+$ 454

Preparation 2 anti-N-(4-Amino-cyclohexyl)-2-(Benzo[1,3]dioxol-5-yloxy)-nicotinamide hydrochloride

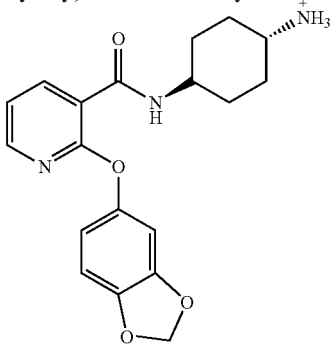

anti-(4-{[2-(Benzo[1,3]dioxol-5-yloxy)-pyridine-3-carbonyl]-amino}-cyclohexyl)-carbamic acid tert-butyl ester (5.2 g, 11.4 mmol) (see Preparation 1) was dissolved in dichloromethane (20 ml) and 4M HCl in dioxan (20 ml) added. The reaction mixture was stirred for 2 hours. The solvent was then removed in vacuo and the residue azeotroped with toluene to give anti-N-(4-amino-cyclohexyl)-2-(Benzo[1,3]dioxol-5-yloxy)-nicotinamide hydrochloride (5.02 g) as a colourless oil.

Preparation 3 anti-(4-{[2-(4-Fluorophenoxy)-pyridine-3-carbonyl]amino}-cyclohexyl)-carbamic acid tert-butyl ester

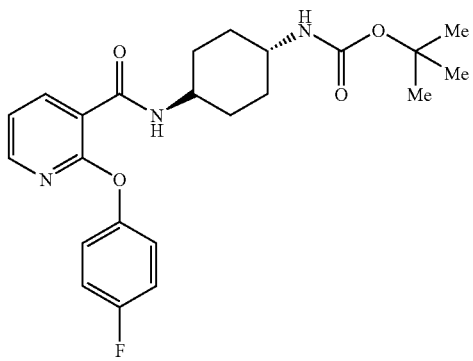

2-(4-Fluoro-phenoxy)-nicotinic acid (10.88 g, 0.046 mol) (see reference patent application WO 98/45268), 1-hydroxybenzotriazole (9.32 g, 0.069 mol) and 1-(3-dimethylaminopropyl)-3-ethylcarbodiimide hydrochloride (11.46 g, 0.06 mol) were stirred in N,N-dimethylformamide (150 ml) at room temperature and anti-(4-amino-cyclohexyl)-carbamic acid tert-butyl ester (10 g, 0.046 mol) (see Preparation 40) added followed by addition of N-methyl morpholine (7.59 ml, 0.069 mol). The reaction mixture was then stirred under an atmosphere of nitrogen at room temperature for 18 hours. The reaction mixture was then partitioned between ethyl acetate (400 ml) and water (400 ml), and the organic layer separated, washed with a saturated aqueous solution of sodium chloride (300 ml), dried over anhydrous sodium sulphate and the solvent removed in vacuo. The residue was triturated with diethylether (50 ml) giving anti-(4-{[2-(4-fluorophenoxy)-pyridine-3-carbonyl]amino}-cyclohexyl)-carbamic acid tert-butyl ester (14.52 g) as a white solid.

$^1$H NMR (400 MHz, DMSO-d$^6$/D$_2$O): δ=8.08–8.12 (1H, d), 7.94–7.98 (1H, d), 7.09–7.20 (5H, m), 3.58–3.63 (1H, m), 3.13–3.20 (1H, m), 1.79–1.83 (2H, m), 1.69–1.78 (2H, m), 1.30 (9H, s), 1.18–1.30 (4H, m) ppm. LRMS (electrospray): m/z [M−H]$^+$ 428

Preparation 4 anti-N-(4-Amino-cyclohexyl)-2-(4-fluoro-phenoxy)-nicotinamide hydrochloride

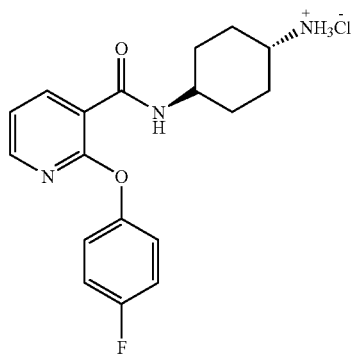

anti-(4-{[2-(4-Fluorophenoxy)-pyridine-3-carbonyl]amino}-cyclohexyl)-carbamic acid tert-butyl ester (14.81 g, 0.039 mol) (see Preparation 3) was dissolved in methanol (10 ml) and 4M HCl in dioxan (200 ml) added. The reaction mixture was stirred under an atmosphere of nitrogen at room temperature for 4 hours. The solvent was then removed in vacuo and the resultant white precipitate was triturated with ether (50 ml) giving anti-N-(4-amino-cyclohexyl)-2-(4-fluoro-phenoxy)-nicotinamide hydrochloride (14.00 g) as a white solid.

$^1$H NMR (400 MHz, DMSO-d$^6$): δ=8.20–8.26 (1H, d), 8.16–8.18 (1H, s), 8.04–8.15 (3H, brs), 7.98–8.02 (1H, d), 7.17–7.26 (4H, m), 3.42–3.57 (1H, m), 2.88–3.01 (1H, m), 1.88–2.03 (4H, m), 1.23–1.50 (4H, m) ppm. LRMS (thermospray): m/z [M+H]$^+$ 330

Preparation 5 anti-{4[(2-Chloro-5-fluoro-pyridine-3-carbonyl)amino]-cyclohexyl}-carbamic acid tert-butyl ester

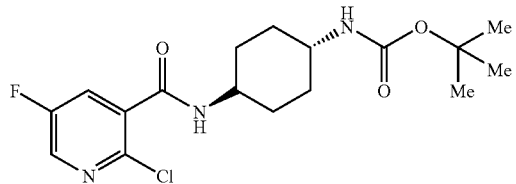

2-Chloro-5-fluoro nicotinic acid (3.95 g, 0.022 mol) (see Preparation 41), 1-hydroxybenzotriazole (4.56 g, 0.034 mol) and 1-(3-dimethylaminopropyl)-3-ethylcarbodiimide hydrochloride (5.61 g, 0.029 mol) were stirred in N,N-dimethylformamide (50 ml) at room temperature for 30 minutes. N-methyl morpholine (4.95 ml, 0.045 mol) was then added followed by anti-(4-amino-cyclohexyl)-carbamic acid tert-butyl ester (4.82 g, 0.022 mol) (see Preparation 43) and the reaction mixture stirred under an atmosphere of nitrogen at room temperature for 18 hours. The mixture was then partitioned between ethyl acetate (100 ml) and water (100 ml), the organic phase separated, washed with a saturated aqueous solution of sodium chloride (100 ml), dried over anhydrous magnesium sulphate and the solvent removed in vacuo. The residue was triturated with diethylether (3-fold 10 ml) giving anti-{4-[(2-chloro-5-fluoro-pyridine-3-carbonyl)-amino]-cyclohexyl}-carbamic acid tert-butyl ester (7.56 g) as a white solid.

$^1$H NMR (300 MHz, CDCl$_3$): δ=8.32–8.35 (1H, d), 7.82–7.88 (1H, m), 6.32–6.41 (1H, d), 4.38–4.51 (1H, m), 3.87–4.02 (1H, m), 2.03–2.21 (4H, m), 1.45 (9H, s), 1.26–1.41 (4H, m) ppm. LRMS (thermospray): m/z [M+H]$^+$ 389.

Preparation 6 anti-(4-{[5-Fluoro-2-(4-fluorophenoxy)-pyridine-3-carbonyl]amino}-cyclohexyl)-carbamic acid tert-butyl ester

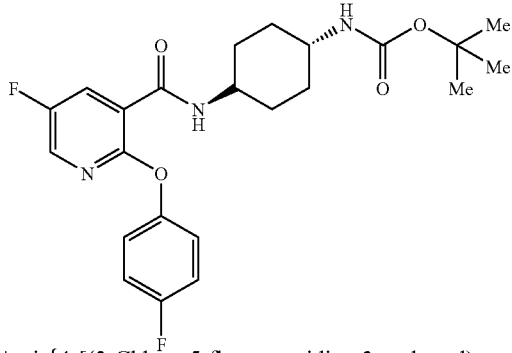

Anti-{4-[(2-Chloro-5-fluoro-pyridine-3-carbonyl) amino]-cyclohexyl}-carbamic acid tert-butyl ester (7.64 g, 0.02 mol) (see Preparation 5), 4-fluorophenol (2.30 g, 0.02 mol) and caesium carbonate (13.35 g, 0.04 mol) were stirred in N,N-dimethylformamide (50 ml) at 60° C. under an atmosphere of nitrogen for 18 hours. The mixture was then partitioned between ethyl acetate (100 ml) and water (100 ml), the organic layer separated, washed with a saturated aqueous solution of sodium chloride (100 ml), dried over anhydrous magnesium sulphate and the solvent removed in vacuo. The residue was purified by flash column chromatography on silica gel eluting with a solvent gradient of 100% dichloromethane changing to 98:2, by volume, dichloromethane:methanol giving anti-(4-{[5-fluoro-2-(4-fluorophenoxy)-pyridine-3-carbonyl]amino}-cyclo hexyl)-carbamic acid tert-butyl ester (4.93 g) as a white solid.

$^1$H NMR (300 MHz, CDCl$_3$): δ=8.31–8.37 (1H, m), 8.02–8.05 (1H, d), 7.65–7.72 (1H, d), 7.10–7.20 (4H, m), 4.38–4.48 (1H, m), 3.88–4.02 (1H, m), 2.01–2.20 (4H, m), 1.43 (9H, s), 1.23–1.40 (4H, m) ppm. LRMS (thermospray): m/z [M+NH$_4$]$^+$ 465

Preparation 7 anti-N-(4-Amino-cyclohexyl)-5-fluoro-2-(4-fluoro-phenoxy)-nicotinamide hydrochloride

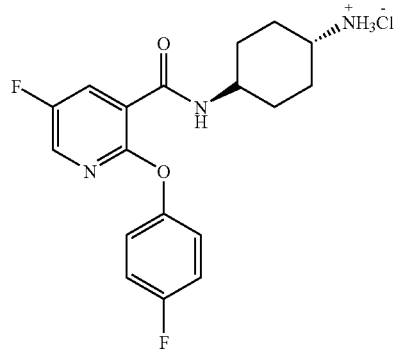

Anti-(4-{[5-Fluoro-2-(4-fluorophenoxy)-pyridine-3-carbonyl]amino}-cyclohexyl)-carbamic acid tert-butyl ester (4.93 g, 0.011 mol) (see Preaparation 6) was dissolved in dichloromethane (50 ml) and hydrogen chloride gas bubbled through the solution at 0° C. until the solution became saturated (30 minutes). The reaction mixture was then stirred under an atmosphere of nitrogen at room temperature for a further 2 hours and the solvent then removed in vacuo. The resultant white precipitate was triturated with ether (3-fold 10 ml) giving anti-N-(4-amino-cyclohexyl)-5-fluoro-2-(4-fluoro-phenoxy)-nicotinamide hydrochloride (3.64 g) as a white solid.

$^1$H NMR (300 MHz, DMSO-d$^6$): δ=8.32–8.38 (1H, d), 8.18–8.22 (1H, m), 7.92–8.08 (4H, m), 7.16–7.28 (4H, m), 3.60–3.77 (1H, m), 2.95–3.07 (1H, m), 1.83–2.03 (4H, m), 1.23–1.52 (4H, m) ppm. LRMS (thermospray): m/z [M+H]$^+$ 348

Preparation 8 anti-[(4-{[5-Fluoro-2-(4-fluoro-phenoxy)-pyridine-3-carbonyl]amino}-cyclohexylcarbamoyl)-methyl]-carbamic acid tert-butyl ester

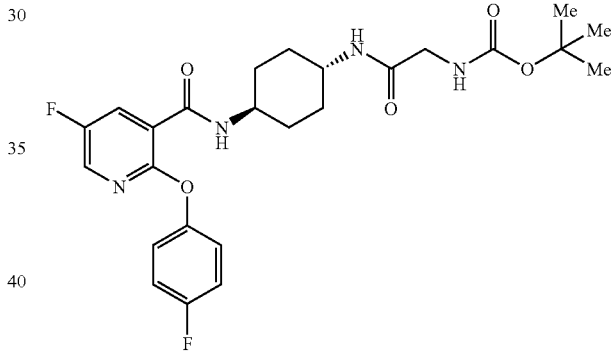

Anti-N-(4-Amino-cyclohexyl)-5-fluoro-2-(4-fluoro-phenoxy)-nicotinamide hydrochloride (1.13 g, 2.94 mmol) (see Preparation 7), 1-hydroxybenzotriazole (597 mg, 4.42 mmol), 1-(3-dimethylaminopropyl)-3-ethylcarbodiimide hydrochloride (734 mg, 3.83 mmol), N-methyl morpholine (0.65 ml, 5.89 mol) and tert-butoxycarbonylamino-acetic acid (516 mg, 2.94 mmol) were stirred in N,N-dimethylformamide (10 ml) at room temperature for 18 hours. The reaction mixture was then partitioned between ethyl acetate (50 ml) and water (50 ml), the organic layer separated, washed with a saturated aqeous solution of sodium chloride (50 ml), dried over anhydrous magnesium sulphate and the solvent removed in vacuo giving anti-[(4-{[5-fluoro-2-(4-fluoro-phenoxy)-pyridine-3-carbonyl]amino}-cyclohexyl-carbamoyl)-methyl]-carbamic acid tert-butyl ester (1.48 g) as a white solid.

$^1$H NMR (300 MHz, CDCl$_3$): δ=8.30–8.40 (1H, m), 8.00–8.04 (1H, d), 7.67–7.77 (1H, d), 7.08–7.21 (4H, m), 6.00–6.11 (1H, m), 5.09–5.21 (1H, brs), 3.92–4.06 (1H, m), 3.75–3.84 (3H, m), 2.00–2.25 (4H, m), 1.28–1.60 (13H, m) ppm. LRMS (thermospray): m/z [M+H]$^+$ 505, [M+H-Boc]$^+$ 405.

Preparation 9 anti-N-[4-(2-Amino-acetylamino)-cyclohexyl]-5-fluoro-2-(4-fluoro-phenoxy)-nicotinamide hydrochloride

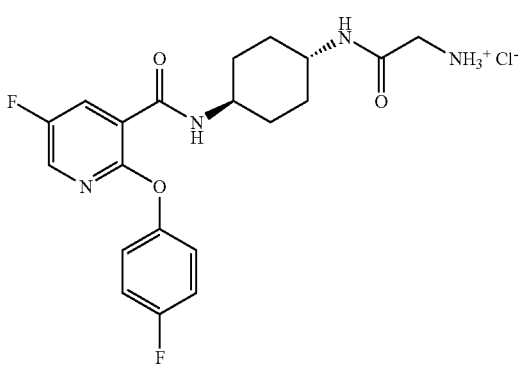

anti-[(4-{[5-Fluoro-2-(4-fluoro-phenoxy)-pyridine-3-carbonyl]amino}-cyclohexyl carbamoyl)-methyl]-carbamic acid tert-butyl ester (1.47 g, 2.91 mmol) (see Preparation 8) was dissolved in dichloromethane (20 ml) and hydrogen chloride gas bubbled into the solution at 0° C. until the solution became saturated (30 minutes). The reaction was then stirred under an atmosphere of nitrogen at room temperature for a further 18 hours, and the solvent then removed in vacuo. The resultant white precipitate was triturated with ether (3-fold 10 ml) giving anti-N-[4-(2-amino-acetylamino)-cyclohexyl]-5-fluoro-2-(4-fluoro-phenoxy)-nicotinamide hydrochloride (1.24 g) as a white solid.

$^1$H NMR (300 MHz, DMSO-d$^6$): δ=8.34–8.43 (2H, m), 8.19–8.21 (1H, d), 8.10–8.18 (3H, brs), 7.92–7.99 (1H, dd), 7.18–7.32 (4H, m), 3.66–3.82 (1H, m), 3.42–3.60 (3H, m, partially masked by solvent), 1.78–1.99 (4H, m), 1.22–1.50 (4H, m) ppm. LRMS (thermospray): m/z [M+H]$^+$ 405.

Preparation 10 anti-(4-{[5-Fluoro-2-(3,4-difluorophenoxy)-pyridine-3-carbonyl]amino}-cyclohexyl)-carbamic acid tert-butyl ester

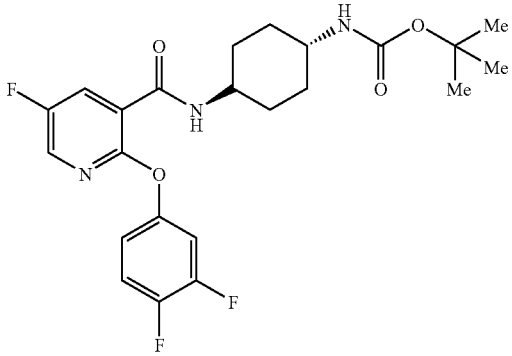

Anti-{4-[(2-Chloro-5-fluoro-pyridine-3-carbonyl)amino]-cyclohexyl}-carbamic acid tert-butyl ester (675 mg, 1.81 mmol) (see Preparation 5), 3,4-difluorophenol (236 mg, 1.81 mmol) and caesium carbonate (1.18 g, 3.63 mmol) were stirred in N,N-dimethylformamide (10 ml) at 60° C. under an atmosphere of nitrogen for 18 hours. The mixture was then partitioned between ethyl acetate (20 ml) and water (20 ml), the organic layer separated, washed with a saturated aqueous solution of sodium chloride (20 ml), dried over anhydrous magnesium sulphate and the solvent removed in vacuo. The residue was triturated with diethylether (3-fold 5 ml) giving anti-(4-{[5-fluoro-2-(3,4-difluorophenoxy)-pyridine-3-carbonyl]amino}-cyclohexyl)-carbamic acid tert-butyl ester (490 mg) as a white solid.

$^1$H NMR (300 MHz, CDCl$_3$): δ=8.31–8.38 (1H, m), 8.03–8.06 (1H, d), 7.68–7.77 (1H, d), 7.17–7.28 (1H, m, partially masked by solvent), 7.00–7.08 (1H, m), 6.86–6.93 (1H, m), 4.34–4.45 (1H, m), 3.86–4.04 (1H, m), 2.01–2.20 (4H, m), 1.45 (9H, s), 1.24–1.40 (4H, m) ppm. LRMS (thermospray): m/z [M+NH$_4$]$^+$ 483

Preparation 11 anti-N-(4-Amino-cyclohexyl)-5-fluoro-2-(3,4-difluoro-phenoxy)-nicotinamide hydrochloride

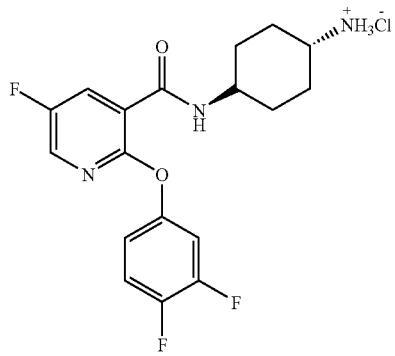

Anti-(4-{[5-Fluoro-2-(3,4-difluorophenoxy)-pyridine-3-carbonyl]amino}-cyclo hexyl)-carbamic acid tert-butyl ester (480 mg, 1.03 mmol) (see Preparation 10) was dissolved in dichloromethane (10 ml) and hydrogen chloride gas bubbled into the solution at 0° C. until the solution became saturated (30 minutes). The reaction mixture was then stirred under an atmosphere of nitrogen at room temperature for 18 hours and the solvent then removed in vacuo. The resultant white precipitate was triturated with ether (3-fold 5 ml) giving anti-N-(4-amino-cyclohexyl)-5-fluoro-2-(3,4-difluoro-phenoxy)-nicotinamide hydrochloride (360 g) as a white solid.

$^1$H NMR (300 MHz, DMSO-d$^6$): δ=8.36–8.41 (1H, d), 8.21–8.26 (1H, d), 7.93–8.11 (4H, m), 7.35–7.60 (2H, m), 7.01–7.13 (1H, m), 3.60–3.83 (1H, m), 2.88–3.12 (1H, m), 1.85–2.10 (4H, m), 1.25–1.58 (4H, m) ppm. LRMS (thermospray): m/z [M+H]$^+$ 366

Preparation 12 anti-(4-{5-Fluoro-2-(3-chloro-4-fluorophenoxy)-pyridine-3-carbonyl]amino}-cyclohexyl)-carbamic acid tert-butyl ester

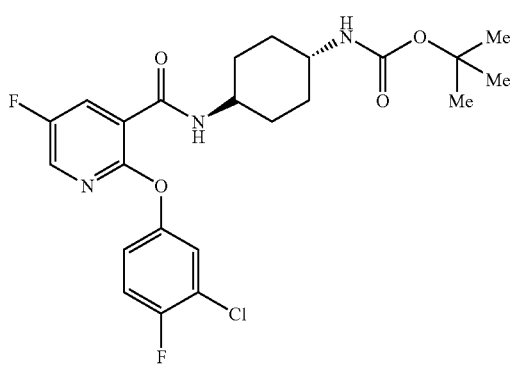

Anti-{4-[(2-Chloro-5-fluoro-pyridine-3-carbonyl)amino]-cyclohexyl}-carbamic acid tert-butyl ester (675 mg, 1.81 mmol) (see Preparation 5), 3-chloro-4-fluorophenol (266 mg, 1.81 mmol) and caesium carbonate (1.18 g, 3.63 mmol) were stirred in N,N-dimethylformamide (10 ml) at 60° C. under an atmosphere of nitrogen for 18 hours. The reaction mixture was then partitioned between ethyl acetate (20 ml) and water (20 ml), and the organic layer separated, washed with a saturated aqueous solution of sodium chloride (20 ml), dried over anhydrous magnesium sulphate and the solvent removed in vacuo. The residue was triturated with diethylether (3-fold 5 ml) giving anti-(4-{[5-fluoro-2-(3-chloro-4-fluorophenoxy)-pyridine-3-carbonyl]amino}-cyclohexyl)-carbamic acid tert-butyl ester (540 mg) as a white solid.

$^1$H NMR (300 MHz, CDCl$_3$): δ=8.31–8.38 (1H, m), 8.03–8.06 (1H, d), 7.50–7.58 (1H, d), 7.18–7.30 (1H, m, partially masked by solvent), 7.02–7.10 (1H, m), 4.36–4.45 (1H, m), 3.80–4.05 (1H, m), 2.01–2.20 (4H, m), 1.44 (9H, s), 1.28–1.41 (4H, m) ppm 1.28–1.41 (4H, m) ppm. LRMS (thermospray): m/z [M+NH$_4$]$^+$ 499, 501.

Preparation 13 anti-N-(4-Amino-cyclohexyl)-5-fluoro-2-(3-chloro-4-fluoro-phenoxy)-nicotinamide hydrochloride

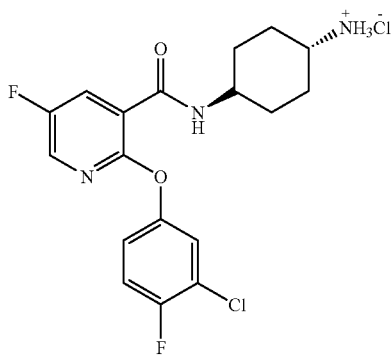

anti-(4-{[5-Fluoro-2-(3-chloro-4-fluorophenoxy)-pyridine-3-carbonyl]amino}-cyclo hexyl)-carbamic acid tert-butyl ester (530 mg, 1.10 mmol) (see Preparation 12) was dissolved in dichloromethane (10 ml) and hydrogen chloride gas bubbled into the solution at 0° C. until the solution became saturated (30 minutes). The reaction mixture was stirred under an atmosphere of nitrogen at room temperature for 18 hours, and the solvent then removed in vacuo. The resultant white precipitate was triturated with ether (3-fold 5 ml) giving anti-N-(4-amino-cyclohexyl)-5-fluoro-2-(3-chloro-4-fluoro-phenoxy)-nicotinamide hydrochloride (390 g) as a white solid.

$^1$H NMR (300 MHz, DMSO-d$^6$): δ=8.32–8.40 (1H, d), 8.22–8.26 (1H, d), 7.93–8.11 (3H, brs), 7.90–8.02 (1H, m), 7.40–7.52 (2H, m), 7.16–7.24 (1H, m), 3.60–3.81 (1H, m), 2.90–3.08 (1H, m), 1.85–2.00 (4H, m), 1.23–1.60 (4H, m) ppm. LRMS (thermospray): m/z [M+H]$^+$ 382.

Preparation 14

4-(tert-Butyl-dimethyl-silanyloxy)-benzaldehyde

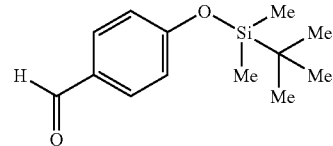

4-Hydroxybenzaldehyde (5.14 g, 42.1 mmol) was added to a suspension of tert-butyl-dimethyl-silyl chloride (6.7 g, 44.4 mmol) and imidazole (3.03 g, 44.5 mmol) in dichloromethane (100 ml) under an atmosphere of nitrogen at room temperature. The reaction mixture was stirred at room temperature for 18 hours, and then washed sequentially with 1 M hydrochloric acid (2-fold 50 ml) followed by a saturated aqueous solution of sodium hydrogen carbonate (50 ml). The organic phase was separated, dried over anhydrous magnesium sulphate and the solvent removed in vacuo. The residual yellow oil was passed through a plug of silica gel eluting with 1:1, by volume, dichloromethane:pentane giving 4-(tert-butyl-dimethyl-silanyloxy)-benzaldehyde (7.5 g) as a golden yellow oil.

$^1$H NMR (400 MHz, CDCl$_3$): δ=9.88 (1H, s), 7.74–7.81 (2H, d), 6.87–6.95 (2H, d), 1.00 (9H, s), 0.25 (6H, s) ppm.

Preparation 15

3-(tert-Butyl-dimethyl-silanyloxy)-benzaldehyde

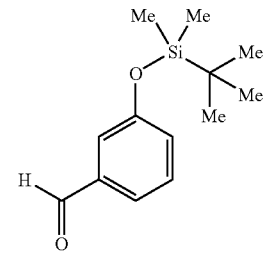

3-Hydroxybenzaldehyde (5.14 g, 42.1 mmol) was added to a suspension of tert-butyl-dimethyl-silyl chloride (6.7 g, 44.4 mmol) and imidazole (3.03 g, 44.5 mmol) in dichloromethane (100 ml) under an atmosphere of nitrogen at room temperature. The reaction mixture was stirred at room temperature for 18 hours, and the mixture washed sequentially with 1 M hydrochloric acid (2-fold 50 ml) followed by a saturated aqueous solution of sodium hydrogen carbonate (50 ml). The organic phase was separated, dried over anhydrous magnesium sulphate and the solvent removed in vacuo. The residual yellow oil was passed through a plug of silica gel eluting with 1:1, by volume, dichloromethane: pentane giving 3-(tert-butyl-dimethyl-silanyloxy)-benzaldehyde (9.2 g) as a golden yellow oil.

$^1$H NMR (400 MHz, CDCl$_3$): δ=9.98 (1H, s), 7.42–7.46 (1H, m), 7.35–7.41 (1H, t), 7.28–7.34 (1H, m), 7.05–7.11 (1H, m), 0.98 (9H, s), 0.22 (6H, s) ppm.

Preparation 16

2-(tert-Butyl-dimethyl-silanyloxy)-benzaldehyde

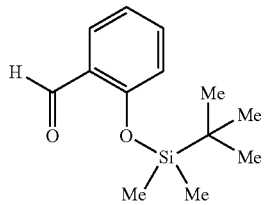

2-Hydroxybenzaldehyde (5.14 g, 42.1 mmol) was added to a suspension of tert-butyl-dimethyl-silyl chloride (6.7 g, 44.4 mmol) and imidazole (3.03 g, 44.5 mmol) in dichloromethane (100 ml) under an atmosphere of nitrogen at room temperature. The reaction mixture was stirred at room temperature for 18 hours, and then washed sequentially with 1 M hydrochloric acid (2-fold 50 ml) followed by a saturated aqueous solution of sodium hydrogen carbonate (50 ml). The organic phase was separated, dried over anhydrous magnesium sulphate and the solvent removed in vacuo. The residual yellow oil was passed through a plug of silica gel eluting with 1:1, by volume, dichloromethane:pentane giving 2-(tert-butyl-dimethyl-silanyloxy)-benzaldehyde (8.6 g) as a golden yellow oil.

$^1$H NMR (400 MHz, CDCl$_3$): δ=10.48 (1H, s), 7.78–7.83 (1H, d), 7.42–7.47 (1H, t), 6.96–7.04 (1H, t), 6.86–6.91 (1H, d), 1.01 (9H, s), 0.29 (6H, s) ppm.

Preparation 17 anti-N-{4-[4-(tert-Butyl-dimethyl-silanyloxy)-benzylamino]-cyclohexyl}-5-fluoro-2-(4-fluoro-phenoxy)-nicotinamide

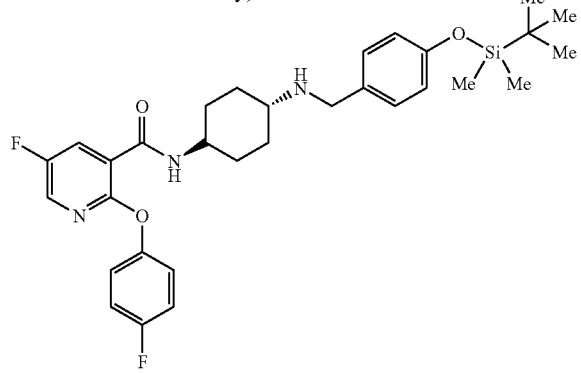

Anti-N-(4-Amino-cyclohexyl)-5-fluoro-2-(4-fluoro-phenoxy)-nicotinamide hydrochloride (500 mg, 2.15 mmol) (see Preparation 7) was dissolved in dichloromethane (15 ml) and diisopropylethylamine (0.44 ml, 2.54 mmol) added. The reaction mixture was stirred for 1 hour and 4-(tert-butyl-dimethyl-silanyloxy)-benzaldehyde (750 mg, 3.173 mmol) (see Preparation 14), sodium triacetoxyborohydride (673 mg, 3.173 mmol) and acetic acid (0.3 ml, 5.08 mmol) then added sequentially. The reaction mixture was stirred under an atmosphere of nitrogen at room temperature for 18 hours. The reaction mixture was then washed with a saturated aqueous solution of sodium hydrogen carbonate (15 ml) and the organic phase dried over anhydrous magnesium sulphate. The solvent was removed in vacuo and the residue was purified by flash column chromatography on silica gel, eluting with a solvent gradient of 100:2, changing to 100:4, by volume, dichloromethane:methanol giving anti-N-{4-[4-(tert-butyl-dimethyl-silanyloxy)-benzylamino]-cyclohexyl}-5-fluoro-2-(4-fluoro-phenoxy)-nicotinamide (270 mg) as an off-white solid.

$^1$H NMR (400 MHz, CDCl$_3$): δ=8.28–8.34 (1H, m), 7.97–7.99 (1H, d), 7.61–7.65 (1H, d), 7.16–7.19 (2H, d), 7.03–7.15 (4H, m), 6.72–6.78 (2H, d), 3.90–4.03 (1H, m), 3.71 (2H, s), 2.46–2.57 (1H, m), 2.07–2.18 (2H, d), 1.97–2.06 (2H, d), 1.17–1.29 (4H, m), 0.95 (9H, s), 0.17 (6H, s) ppm. LRMS (thermospray): m/z [M+H]$^+$ 568.

Preparation 18 anti-N-{4-[3-(tert-Butyl-dimethyl-silanyloxy)-benzylamino]-cyclohexyl}-5-fluoro-2-(4-fluoro-phenoxy)-nicotinamide

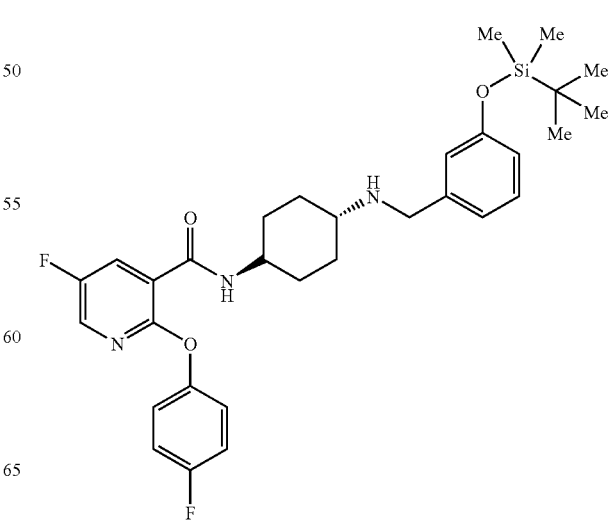

Anti-N-(4-Amino-cyclohexyl)-5-fluoro-2-(4-fluoro-phenoxy)-nicotinamide hydrochloride (500 mg, 2.14 mmol) (see Preparation 7) was dissolved in dichloromethane (10 ml) and diisopropyl ethylamine (0.56 ml, 3.21 mmol) added. The reaction mixture was stirred at room temperature for 1 hour and 3-(tert-butyl-dimethyl-silanyloxy)-benzaldehyde (766 mg, 3.21 mmol) (see Preparation 15), sodium triacetoxyborohydride (681 mg, 3.21 mmol) and acetic acid (0.19 ml, 3.21 mmol) were added sequentially. The reaction mixture was stirred under an atmosphere nitrogen at room temperature for a further 18 hours. The reaction mixture was then washed with a saturated aqueous solution of sodium hydrogen carbonate (15 ml), the organic phase separated and dried over anhydrous magnesium sulphate. The solvent was removed in vacuo and the residue was purified by flash column chromatography on silica gel, eluting with 100:2, by volume, dichloromethane:methanol giving anti-N-{4-[3-(tert-butyl-dimethyl-silanyloxy) -benzylamino]-cyclohexyl}-5-fluoro-2-(4-fluoro-phenoxy)-nicotinamide (937 mg) as an off-white solid.

$^1$H NMR (400 MHz, CDCl$_3$): δ=8.32–8.36 (1H, m), 8.00–8.03 (1H, d), 7.65–7.70 (1H, d), 7.10–7.20 (5H, m), 6.86–6.94 (1H, d), 6.81 (1H, s), 6.68–6.74 (1H, d), 3.94–4.02 (1H, m), 3.78 (2H, s), 2.47–2.55 (1H, m), 2.07–2.15 (2H, m), 1.96–2.05 (2H, m), 1.20–1.42 (4H, m), 0.98 (9H, s), 0.19 (6H, s) ppm. LRMS (thermospray): m/z [M+H]$^+$ 568.

Preparation 19 anti-Acetic acid 2-{[acetyl-(4-{[5-fluoro-2-(4-fluoro-phenoxy)-pyridine-3-carbonyl]-amino}-cyclohexyl)-amino]-methyl}-phenyl ester

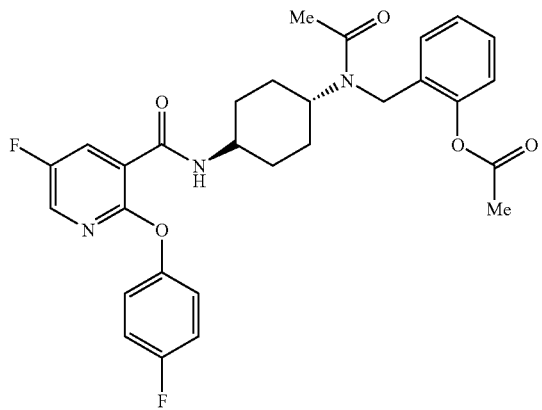

Anti-5-Fluoro-2-(4-fluoro-phenoxy)-N-[4-(2-hydroxy-benzylamino)-cyclohexyl]-nicotinamide (350 mg, 0.772 mmol) (see Preparation 26) and diisopropyl ethylamine (0.38 ml, 2.16 mmol) were dissolved in dichloromethane (10 ml) and acetyl chloride (0.14 ml, 1.85 mmol) added. The reaction mixture was stirred under an atmosphere of nitrogen at room temperature for 18 hours. The reaction mixture was then washed sequentially with a saturated aqueous solution of sodium hydrogen carbonate (10 ml), a 10% solution of citric acid in water (10 ml) and water (10 ml) before drying the organic phase over anhydrous magnesium sulphate giving anti-acetic acid 2-{[acetyl-(4-{[5-fluoro-2-(4-fluoro-phenoxy)-pyridine-3-carbonyl]-amino}-cyclohexyl)-amino]-methyl}-phenyl ester (277 mg) as a cream foam.

$^1$H NMR (400 MHz, CDCl$_3$): δ=8.27–8.42 (1H, m), 7.99–8.14 (1H, m), 7.58–7.75 (1H, m), 7.00–7.42 (7H, m), 4.43–4.67 (1H, m), 4.37 (2H, s), 3.81–3.98 (1H, m), 2.00–2.50 (10H, m), 1.74–1.86 (2H, m), 1.24–1.60 (4H, m) ppm. LRMS (thermospray): m/z [M+H]$^+$ 538, [M+Na]$^+$ 560 LRMS (electrospray) [M−H−OAc]$^+$ 568.

Preparation 20

{4-[(2-Chloro-5-fluoro-pyridine-3-carbonyl)amino]-cyclohexyl}-carbamic acid tert-butyl ester

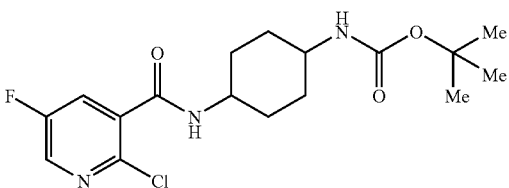

2-Chloro-5-fluoro nicotinic acid (3.00 g, 0.017 mol) (see Preparation 41), was dissolved in dichloromethane (100 ml) and N,N-dimethylformamide (1 drop) was added, followed by oxalyl chloride (3.0 ml, 0.034 mol). The reaction mixture was held at room temperature for 4 hours, after which time the solvent was removed in vacuo. The residue was suspended in dichloromethane (100 ml) and triethylamine (5 ml) added followed by addition of (4-amino-cyclohexyl)-carbamic acid tert-butyl ester (5.40 g, 0.026 mol) (Preparation 42a). The reaction mixture was then held under an atmosphere of nitrogen at room temperature for a further 18 hours. The reaction mixture was then washed with water (100 ml) and the organic phase dried over anhydrous magnesium sulphate. The solvent was removed in vacuo, and the residue triturated with ethyl acetate/pentane (1:1, by volume, 10 ml) giving {4-[(2-chloro-5-fluoro-pyridine-3-carbonyl) amino]-cyclohexyl}-carbamic acid tert-butyl ester (2.5 g, 80:20 syn:anti) as a white solid.

$^1$H NMR (300 MHz, CDCl$_3$): δ=8.32–8.38 (1H, d), 7.95–8.00 (0.8H, m), 7.81–7.88 (0.2H, d), 6.58–6.75 0.8H, m), 6.29–6.37 (0.2H, m), 4.38–4.62 (1H, m), 4.12–4.25 (0.8H, m), 3.95–4.03 (0.2H, m), 3.58–3.73 (0.8H, m), 3.38–3.56 (0.2H, m), 2.03–2.2 (0.8H, m), 1.66–1.95 (6.4H, m), 3.87–4.02 (1H, m), 1.58 (9H, s), 1.23–1.44 (0.8H, m, partially masked by solvent) ppm.

Preparation 21 syn-(4-{[5-Fluoro-2-(4-fluorophenoxy)-pyridine-3-carbonyl]amino}-cyclohexyl)-carbamic acid tert-butyl ester

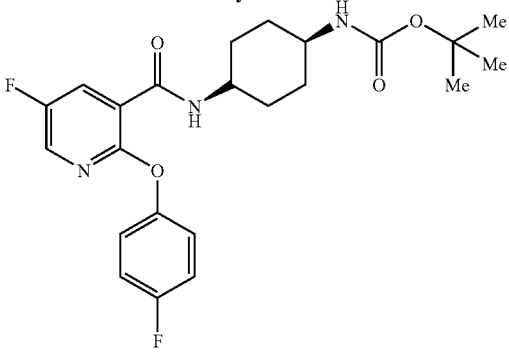

{4-[(2-Chloro-5-fluoro-pyridine-3-carbonyl)amino]-cyclohexyl}-carbamic acid tert-butyl ester (2.4 g, 6.46 mmol) (80:20 syn/anti mixture) (see Preparation 20), 4-fluorophenol (800 mg, 7.11 mmol) and caesium carbonate (4.2 g, 12.02 mmol) were stirred in N,N-dimethylformamide (40 ml) at 50° C. under an atmosphere of nitrogen for 18 hours. The reaction mixture was then partitioned between ethyl acetate (100 ml) and water (100 ml), and the organic layer separated, washed with a saturated aqueous solution of sodium chloride (100 ml), dried over anhydrous magnesium sulphate and the solvent removed in vacuo. The residue was purified by flash column chromatography on silica gel eluting with a solvent gradient of 100% dichloromethane changing to 98:2, by volume, dichloromethane:methanol giving syn-(4-{[5-fluoro-2-(4-fluorophenoxy)-pyridine-3-carbonyl]amino}-cyclohexyl)-carbamic acid tert-butyl ester (2.4 g) as a white solid.

$^1$H NMR (300 MHz, CDCl$_3$): δ=8.32–8.39 (1H, m), 8.01–8.04 (1H, d), 7.90–7.99 (1H, d), 7.10–7.22 (4H, m), 4.25–4.47 (1H, m), 4.15–4.23 (1H, m), 3.56–3.68 (1H, m), 1.63–1.91 (6H, m), 1.38–1.60 (11H, m, partially masked by solvent) ppm. LRMS (thermospray): m/z [M+H]$^+$ 448.

Preparation 22 syn-N-(4-Amino-cyclohexyl)-5-fluoro-2-(4-fluoro-phenoxy)-nicotinamide hydrochloride

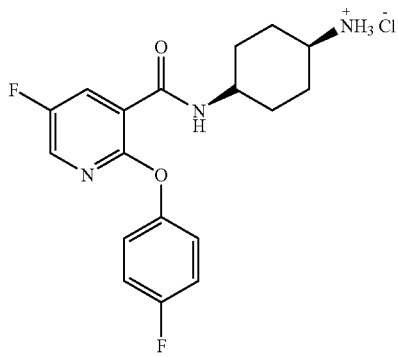

Syn-(4-{[5-Fluoro-2-(4-fluorophenoxy)-pyridine-3-carbonyl]amino}-cyclohexyl)-carbamic acid tert-butyl ester (2.4 g, 5.4 mmol) (see Preparation 21) was dissolved in 4 M HCl in dioxan (100 ml) and stirred under an atmosphere of nitrogen at room temperature for 4 hours. The solvent was removed in vacuo and the resultant white precipitate triturated with dichloromethane (20 ml), ethyl acetate (20 ml) and diethylether (20 ml) giving syn-N-(4-amino-cyclohexyl)-5-fluoro-2-(4-fluoro-phenoxy)-nicotinamide hydrochloride (1.7 g) as a white solid.

$^1$H NMR (400 MHz, CD$_3$OD): δ=8.01–8.10 (2H, m), 7.08–7.23 (4H, m), 4.10–4.18 (1H, m), 3.18–3.33 (1H, m, partially masked by solvent), 1.78–2.00 (6H, m), 1.61–1.77 (2H, m) ppm. LRMS (thermospray): m/z [M+H]$^+$ 348.

Preparation 23 syn-[(4-{[5-Fluoro-2-(4-fluoro-phenoxy)-pyridine-3-carbonyl]amino}-cyclohexylcarbamoyl)-methyl]-carbamic acid tert-butyl ester

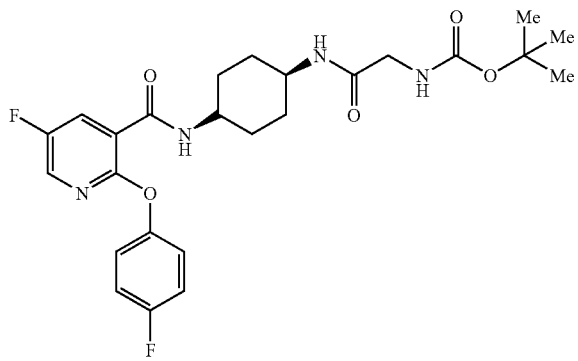

Syn-N-(4-Amino-cyclohexyl)-5-fluoro-2-(4-fluoro-phenoxy)-nicotinamide hydrochloride (200 mg, 0.521 mmol) (see Preparation 22), 1-hydroxybenzotriazole (106 mg, 0.782 mmol), 1-(3-dimethylaminopropyl)-3-ethylcarbodiimide hydrochloride (130 mg, 0.677 mmol), N-methyl morpholine (0.12 ml, 1.04 mmol) and tert-butoxycarbonylamino-acetic acid (100 mg, 0.573 mmol) were stirred in N,N-dimethylformamide (5 ml) at room temperature for 18 hours. The reaction mixture was then partitioned between ethyl acetate (10 ml) and water (10 ml) and the organic layer separated, washed with a saturated aqueous solution of sodium chloride (10 ml), dried over anhydrous magnesium sulphate and the solvent removed in vacuo. The residue was then triturated with diethylether (5 ml) giving syn-[(4-{[5-fluoro-2-(4-fluoro-phenoxy)-pyridine-3-carbonyl]amino}-cyclohexylcarbamoyl)-methyl]-carbamic acid tert-butyl ester (182 mg) as a white solid.

$^1$H NMR (400 MHz, CDCl$_3$): δ=8.32–8.38 (1H, dd), 8.02–8.04 (1H, d), 7.89–7.97 (1H, d), 7.10–7.19 (4H, m), 6.08–6.23 (1H, brs), 5.03–5.17 (1H, brs), 4.13–4.21 (1H, m), 3.89–3.98 (1H, m), 3.64–3.71 (2H, d), 1.74–1.91 (4H, m), 1.62–1.73 (2H, m), 1.47–1.60 (2H, m), 1.36 (9H, s) ppm. LRMS (electrospray): m/z [M+Na]$^+$ 527.

Preparation 24 syn-N-[4-(2-Amino-acetylamino)-cyclohexyl]-5-fluoro-2-(4-fluoro-phenoxy)-nicotinamide hydrochloride

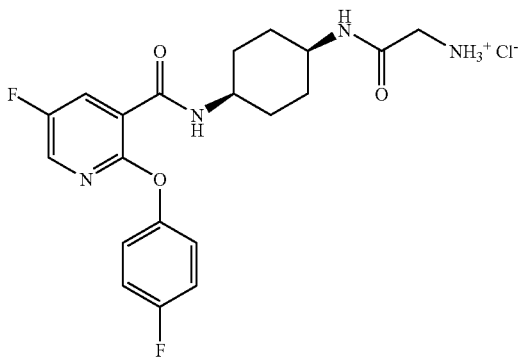

Syn-[(4-{[5-Fluoro-2-(4-fluoro-phenoxy)-pyridine-3-carbonyl]amino}-cyclohexyl carbamoyl)-methyl]-carbamic acid tert-butyl ester (1.47 g, 2.91 mmol) (see preparation 23) was dissolved in dichloromethane (20 ml) and hydrogen chloride gas bubbled into the solution at 0° C. until the solution became saturated (15 minutes). The reaction mixture was then stirred under an atmosphere of nitrogen at room temperature for a further 45 minutes, and the solvent then removed in vacuo. The resultant white precipitate was triturated with ether (3-fold 10 ml) giving syn-N-[4-(2-amino-acetylamino)-cyclohexyl]-5-fluoro-2-(4-fluoro-phenoxy)-nicotinamide hydrochloride (2.07 g) as a white solid.

LRMS (thermospray): m/z [M+H]+ 405.

Preparation 25 syn-5-Fluoro-2(4-fluoro-phenoxy)-N-{(4-[(imidazole-1-carbonyl)-amino]-cyclohexyl}-nicotinamide

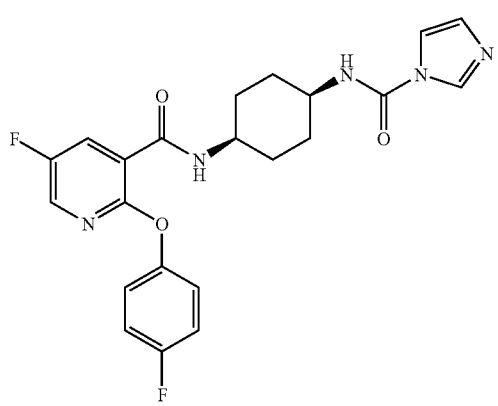

A solution of syn-N-(4-amino-cyclohexyl)-5-fluoro-2-(4-fluoro-phenoxy)-nicotinamide (220 mg, 0.52 mmol) (see Preparation 22) in dichloromethane (5 ml) was added dropwise to a suspension of carbonyldiimidazole (253 mg, 1.563 mmol) and triethylamine (0.08 ml, 0.521 mmol) in dichloromethane (5 ml) over a 35 minute period. The reaction mixture was then washed sequentially with water (10 ml) followed by a saturated aqueous solution of sodium chloride (10 ml). The organic phase was separated and dried over anhydrous magnesium sulphate. The solvent was then removed in vacuo, and the residue purified by flash column chromatography on silica gel eluting with a solvent gradient of 100% dichloromethane changing to 99:1 then 98:2, by volume, dichloromethane:methanol giving syn-5-fluoro-2 (4-fluoro-phenoxy)-N-{4-[(imidazole-1-carbonyl)-amino]-cyclohexyl}-nicotinamide (147 mg) as a white foam.

$^1$H NMR (400 MHz, CD$_3$OD): δ=8.32–8.39 (1H, m), 7.95–8.06 (3H, m) 7.19 (1H, s), 7.08–7.17 (4H, m), 7.05 (1H, s), 4.18–4.26 (1H, m), 3.92–4.02 (1H, m), 1.78–2.02 (6H, m), 1.57–1.77 (2H, m) ppm. LRMS (thermospray): m/z [M+H]+ 442, [M+Na]+ 464

Preparation 26 anti-5-Fluoro-2-(4-fluoro-phenoxy)-N-[4-(2-hydroxy-benzylamino)-cyclohexyl]-nicotinamide

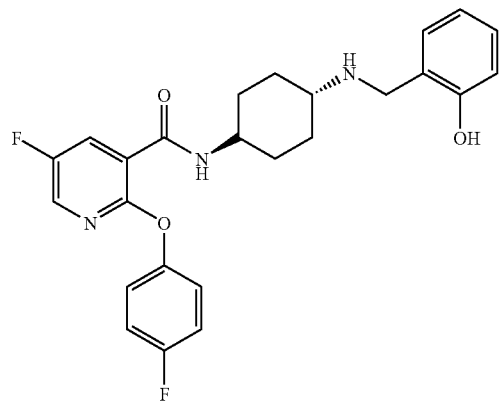

2-(tert-Butyl-dimethyl-silanyloxy)-benzaldehyde (769 mg, 3.21 mmol) (see Preparation 16) and anti-N-(4-Amino-cyclohexyl)-5-fluoro-2-(4-fluoro-phenoxy)-nicotinamide hydrochloride (900 mg, 2.14 mmol) (see Preparation 7) were dissolved in dichloromethane (10 ml) and diisopropylethylamine (0.56 ml, 3.21 mmol) added. The reaction mixture was stirred at room temperature for 30 minutes and acetic acid (0.19 ml, 3.21 mmol) added followed by addition of sodium triacetoxyborohydride (0.681 g, 3.21 mmol). The reaction mixture was then held at room temperature for 18 hours. The mixture was then quenched with water (10 ml), the organic phase separated and dried over anhydrous magnesium sulphate. The solvent was then removed in vacuo and the residue purified by flash column chromatography on silica gel eluting with 100:2, by volume, dichloromethane:methanol giving anti-5-fluoro-2-(4-fluoro-phenoxy)-N-[4-(2-hydroxy-benzylamino)-cyclohexyl]-nicotinamide (800 mg) as a white solid (acetate salt).

$^1$H NMR (400 MHz, CDCl$_3$): δ=8.32–8.38 (1H, m), 8.01–8.04 (1H, d), 7.64–772 (1H, d), 7.05–7.21 (5H, m), 6.95–6.99 (1H, d), 6.81–6.84 (1H, d), 6.73–6.80 (1H, t), 3.92–4.04 (3H, m), 2.50–2.62 (1H, m), 2.02–2.20 (7H, s+m), 1.20–1.40 (4H, m) ppm. LRMS (electrospray): m/z [M+H]+ 454

Preparation 27

4-[(2-Chloro-5-fluoro-pyridine-3-carbonyl)-amino]-piperldine-1-carboxylic acid tert-butyl ester

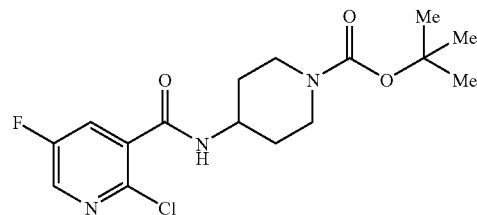

2-Chloro-5-fluoro nicotinic acid (5.00 g, 28.48 mmol) (see Preparation 41), was dissolved in dichloromethane (200 ml) and N,N-dimethylformamide (1 drop) was added, followed by addition of oxalyl chloride (7.45 ml, 85.44 mmol). The reaction mixture was held at room temperature for 18 hours, after which the solvent was removed in vacuo. The residue was th en suspended in dichloromethane (150 ml) and triethylamine (11.91 ml, 85.44 mmol) added followed by addition of 4-amino-piperidine-1-carboxylic acid tert-butyl ester (6.85 g, 34.18 mmol). The reaction mixture was then stirred under an atmosphere of nitrogen at room temperature for 64 hours before being washed sequentially with water (2-fold 100 ml), a saturated aqueous solution of sodium chloride (100 ml) and a 10% solution of citric acid in water (50 ml). The organic phase was separated, dried over anhydrous magnesium sulphate and the solvent was removed in vacuo giving 4-[(2-chloro-5-fluoro-pyridine-3-carbonyl)-amino]-piperidine-1-carboxylic acid tert-butyl ester (8.7 g) as an off-white solid.

$^1$H NMR (400 MHz, CDCl$_3$): δ=8.28–8.30 (1H, d), 7.78–7.83 (1H, m), 6.46–6.52 (1H, m), 4.04–4.13 (1H, m), 3.96–4.03 (1H, m), 2.83–2.98 (2H, t), 1.97–2.03 (2H, d), 1.38–1.50 (11H, m) ppm. LRMS (thermospray): m/z [M+Na]$^+$ 380 LRMS (electrospray):m/z [M–H]$^+$ 356.

Preparation 28

4-{[5-Fluoro-2-(4-fluorophenoxy)-pyridine-3-carbonyl]-amino}-piperidine-1-carboxylic acid tert-butyl ester

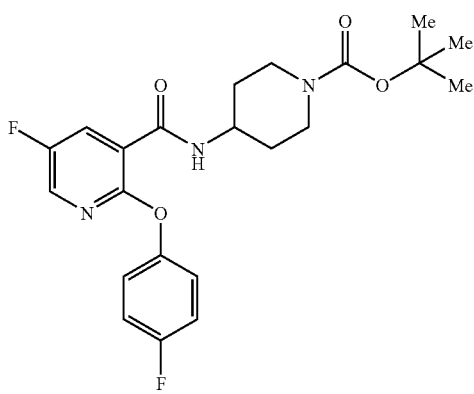

4-[(2-Chloro-5-fluoro-pyridine-3-carbonyl)-amino]-piperidine-1-carboxylic acid tert-butyl ester (4.0 g, 11.18 mmol) (see Preparation 27), 4-fluorophenol (1.378 g, 12.3 mmol) and caesium carbonate (7.29 g, 33.54 mmol) were stirred in N,N-dimethylformamide (40 ml) at 55° C. under an atmosphere of nitrogen for 18 hours. The reaction mixture was then partitioned between ethyl acetate (50 ml) and water (30 ml) and the organic layer separated. The organic layer was then washed with a saturated aqueous solution of sodium chloride (40 ml), dried over anhydrous magnesium sulphate and the solvent removed in vacuo. The residue was purified by flash column chromatography on silica gel eluting with dichloromethane. The product was finally triturated with diethylether (25 ml) giving 4-{[5-fluoro-2-(4-fluorophenoxy)-pyridine-3-carbonyl]-amino}-piperidine-1-carboxylic acid tert-butyl ester (2.59 g) as a white solid.

$^1$H NMR (400 MHz, CDCl$_3$): δ=8.30–8.33 (1H, m), 7.78–8.00 (1H, d), 7.73–7.80 (1H, d), 7.02–7.13 (4H, m), 4.07–4.20 (1H, m), 3.90–4.04 (1H, m), 2.87–3.03 (2H, d), 1.37–1.45 (11H, m) ppm. LRMS (thermospray): m/z [M+Na]$^+$ 456, [M–H]$^{3O}$ 432.

Preparation 29

5-Fluoro-2-(4-fluoro-phenoxy)-N-piperidin-4-yl-nicotinamide hydrochloride

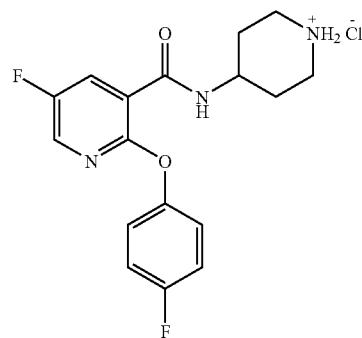

4-{[5-Fluoro-2-(4-fluorophenoxy)-pyridine-3-carbonyl]-amino}-piperidine-1-carboxylic acid tert-butyl ester (2.58 g, 5.95 mmol) (see Preparation 28) was dissolved in dichloromethane (15 ml) and hydrogen chloride gas bubbled through the solution at 0° C. for 10 minutes. The reaction mixture was then held under an atmosphere of nitrogen at room temperature for a further 45 minutes and the solvent tremoved in vacuo. The resultant white precipitate was triturated with diethylether (2-fold 10 ml) giving 5-fluoro-2-(4-fluoro-phenoxy)-N-piperidin-4-yl-nicotinamide hydrochloride (2.14 g) as a white solid.

$^1$H NMR (400 MHz, CD$_3$OD): δ=8.04–8.07 (1H, d), 7.96–8.01 (1H, m), 7.10–7.21 (4H, m), 4.13–4.22 (1H, m), 3.39–3.44 (2H, d), 3.11–3.20 (2H, t), 2.18–2.26 (2H, d), 1.77–1.90 (2H, m) ppm. LRMS (thermospray): m/z [M+H]$^+$ 334.

Preparation 30 endo-3-[(2-Chloro-5-fluoro-pyridine-3-carbonyl)-amino]-8-aza-bicyclo[3.2.1]octane-8-carboxylic acid tert-butyl ester

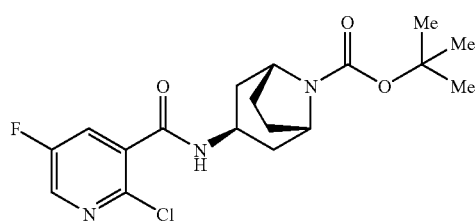

2-Chloro-5-fluoro nicotinic acid (1.75 g, 10 mmol) (see Preparation 44) was dissolved in dichloromethane (250 ml) and N,N-dimethylformamide (0.4 ml) added followed by addition of oxalyl chloride (4.4 ml, 50 mmol). The reaction mixture was then held at room temperature for 18 hours after which time the solvent was removed in vacuo. The residue was azeotroped with toluene, then suspended in dichloromethane (200 ml) and 3-amino-8-aza-bicyclo[3.2.1]oc-tane-8-carboxylic acid tert-butyl ester (2.26 g, 10 mmol) (see reference Patent application WO 00/38680) added followed by addition of triethylamine (2.82 ml, 20 mmol). The reaction mixture was then was held under an atmosphere of nitrogen at room temperature for 3 hours before being washed with a saturated aqueous solution of sodium chloride (3-fold 100 ml) aqnd the organic layer separated. The solvent was then removed in vacuo and the residue purified by flash column chromatography on silica gel eluting with a solvent gradient of 100:0 changing to 90:10, by volume, dichloromethane:methanol giving endo-3-[(2-chloro-5-fluoro-pyridine-3-carbonyl)-amino]-8-aza-bicyclo[3.2.1]octane-8-carboxylic acid tert-butyl ester (1.12 g) as a white foam.

$^1$H NMR (400 MHz, CDCl$_3$): δ=8.31–8.34 (1H, d), 7.97–8.02 (1H, dd), 7.18–7.23 (1H, m, partially masked by solvent), 4.34–4.39 (1H, m), 4.15–4.32 (2H, brs), 2.19–2.38 (2H, brs), 2.07–2.13 (2H, m), 1.82–1.90 (2H, m), 1.71–1.79 (2H, d), 1.45 (9H, s) ppm. LRMS (electrospray): m/z [M+Na]$^+$ 406, [M–H]$^+$ 382.

Preparation 31 endo-3-{[(5-Fluoro-2-(4-fluoro-phenoxy)-pyridine-3-carbony]-amino}-8-aza-bicyclo[3.2.1]octane-8-carboxylic acid tert-butyl ester

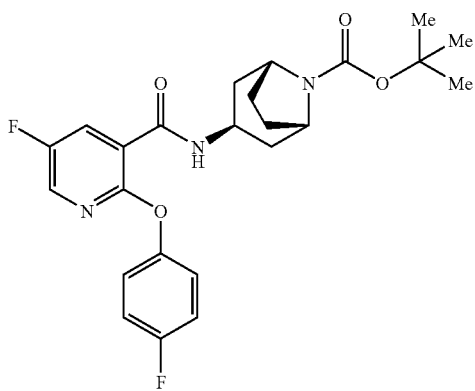

Endo-3-[(2-Chloro-5-fluoro-pyridine-3-carbonyl)-amino]-8-aza-bicyclo[3.2.1]octane-8-carboxylic acid tert-butyl ester (119 mg, 0.31 mmol) (see Preparation 30), 4-fluorophenol (39 mg, 0.34 mmol) and caesium carbonate (202 mg, 0.62 mmol) were stirred in N,N-dimethylformamide (2 ml) at 60° C. under an atmosphere of nitrogen for 18 hours. The reaction mixture was then partitioned between ethyl acetate (10 ml) and water (10 ml), and the organic layer separated. The organic layer was then washed with a saturated aqueous solution of sodium chloride (3-fold 10 ml) and concentrated in vacuo to give a residue which was purified by flash column chromatography on silica gel eluting with a solvent gradient of 10:90 changing to 50:50, by volume, ethyl acetate:pentane. The product was finally triturated with pentane (5 ml) giving endo-3-{[(5-fluoro-2-(4-fluoro-phenoxy)-pyridine-3-carbonyl]-amino}-8-aza-bicyclo[3.2.1]octane-8-carboxylic acid tert-butyl ester (100 mg) as a white solid.

$^1$H NMR (400 MHz, CDCl$_3$): δ=8.51–8.56 (1H, d), 8.32–8.36 (1H, dd), 7.98–8.00 (1H, d), 7.01–7.15 (4H, m), 4.37–4.43 (1H, m), 4.11–4.30 (2H, brs), 2.14–2.36 (2H, brs), 1.91–1.98 (2H, m), 1.70–1.84 (4H, m), 1.43 (9H, s) ppm. LRMS (electrospray): m/z [M+Na]$^+$ 482, [M–H]$^+$ 458.

Preparation 32 endo-N-(8-Aza-bicyclo[3.2.1]oct-3-yl)-5-fluoro-2-(4-fluoro-phenoxy)-nicotinamide

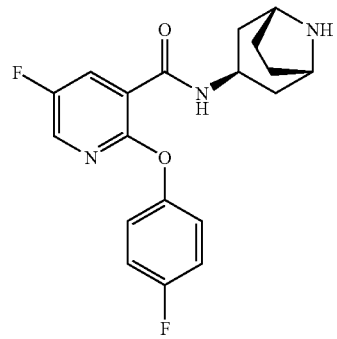

Endo-3-{[(5-Fluoro-2-(4-fluoro-phenoxy)-pyridine-3-carbonyl]-amino}-8-aza-bicyclo[3.2.1]octane-8-carboxylic acid tert-butyl ester (1.92 g, 4.2 mmol) (see Preparation 31) was dissolved in 2.2 M acetyl chloride in methanol (20 ml) and the reaction stirred at room temperature under an atmosphere of nitrogen for 1 hour. The reaction mixture was then heated at 50° C. for 3 hours before removal of the solvent in vacuo. The residue was then partitioned between dichloromethane (50 ml) and water (50 ml), the pH of the aqueous phase adjusted to pH>8 by addition of sodium hydrogen carbonate and the organic layer separated. The aqueous phase was then further extracted with ethyl acetate (50 ml) followed by 10% methanol in dichloromethane (5-fold 50 ml). The combined organic extracts were then concentrated under reduced pressure. The residue was azeotroped with toluene giving endo-N-(8-aza-bicyclo[3.2.1]oct-3-yl)-5-fluoro-2-(4-fluoro-phenoxy)-nicotinamide (1.40 g) as a white solid.

$^1$H NMR (400 MHz, DMSO-d$^6$): δ=8.34–8.39 (1H, d), 8.16–8.18 (1H, d), 7.97–8.01 (1H, dd), 7.18–7.23 (4H, d), 3.99–4.06 (1H, m), 3.33–3.40 (2H, brs, partially masked by solvent), 1.85–1.99 (4H, m), 1.64–1.72 (2H, d), 1.49–1.57 (2H, m) ppm. LRMS (thermospray):m/z [M+H]$^+$ 360.

Preparation 33 exo-N-(8-Benzyl-8-aza-bicyclo[3.2.1]oct-3-yl-2-chloro-5-fluoro-nicotinamide

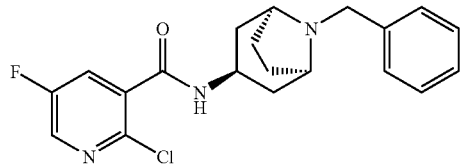

2-Chloro-5-fluoro nicotinic acid (8.78 g, 50 mmol) (see Preparation 41), was dissolved in dichloromethane (1 l) and N,N-dimethylformamide (0.4 ml) added, followed by addition of oxalyl chloride (22.3 ml, 250 mmol). The reaction mixture was then held at room temperature for 18 hours after which time the solvent was removed in vacuo. The residue was azeotroped with toluene, then suspended in dichloromethane (300 ml) and exo-8-benzyl-8-aza-bicyclo[3.2.1]oct-3-ylamine reference Patent application WO 00/38680) (10.82 g, 50 mmol) added followed by addition of triethylamine (14 ml, 100 mmol) in dichloromethane (100 ml). The reaction mixture was then held under an atmosphere of nitrogen at room temperature for 5 hours and then washed with a saturated aqueous solution of sodium chloride (3-fold 300 ml). The organic phase was separated, concentrated in vacuo and the residue purified by flash column chromatography on silica gel eluting with a solvent gradient of 100:0 changing to 90:10, by volume, dichloromethane:methanol giving exo-N-(8-benzyl-8-aza-bicyclo[3.2.1]oct-3-yl-2-chloro-5-fluoro-nicotinamide (17 g) as a white solid.

¹H NMR (400 MHz, CDCl₃): δ=8.30–8.32 (1H, d), 7.81–7.85 (1H, dd), 7.20–7.38(5H, m, partially masked by solvent), 6.28–6.31 (1H, d), 4.30–4.42 (1H, m), 3.55 (2H, s), 3.22–3.30 (2H, brs), 2.02–2.13 (2H, m), 1.91–1.99 (2H, m), 1.72–1.80 (2H, quart), 1.60–1.70 (2H, t) ppm. LRMS (electrospray):m/z [M+H]⁺ 374, [M–H]⁺ 372.

Preparation 34 exo-N-(8-Benzyl-8-aza-bicyclo[3.2.1]oct-3-yl-5-fluoro-2-(4-fluoro-phenoxy)-nicotinamide

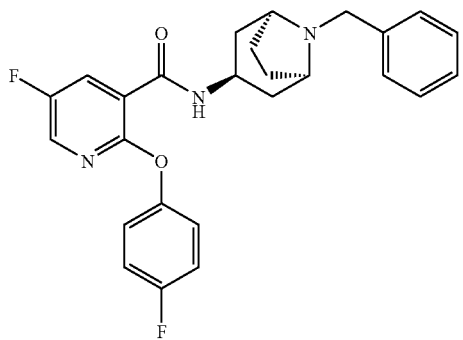

Exo-N-(8-Benzyl-8-aza-bicyclo[3.2.1]oct-3-yl-2-chloro-5-fluoro-nicotinamide (7.9 g, 21 mmol) (see Preparation 33), 4-fluorophenol (2.6 g, 23 mmol) and caesium carbonate (13.8 g, 42 mmol) were stirred in N,N-dimethylformamide (200 ml) at 70° C. under an atmosphere of nitrogen for 20 hours. The reaction mixture was then partitioned between ethyl acetate (300 ml) and water (300 ml) and the organic layer separated. The organic phase was then washed with a saturated aqueous solution of sodium chloride (3-fold 200 ml), concentrated in vacuo and the residue purified by flash column chromatography on silica gel eluting with a solvent gradient of 20:80 changing to 100:0, by volume, ethyl acetate:pentane. The product was triturated with pentane (30 ml) giving exo-N-(8-benzyl-8-aza-bicyclo[3.2.1]oct-3-yl-5-fluoro-2-(4-fluoro-phenoxy)-nicotinamide (6.3 g) as a white solid.

¹H NMR (400 MHz, CDCl₃): δ=8.26–8.30 (1H, dd), 7.96–7.98 (1H, d), 7.58–7.64 (1H, d), 7.17–7.33 (5H, m), 7.04–7.16 (4H, m), 4.30–4.42 (1H, m), 3.48 (2H, s), 3.20–3.25 (2H, brs), 2.03–2.11 (2H, m), 1.88–1.96 (2H, m), 1.72–1.80 (2H, quartet), 1.55–1.62 (2H, m, partially masked by solvent) ppm. LRMS (electrospray): m/z [M+H]⁺ 450, [M–H]⁺ 448.

Preparation 35 exo-N-(8-Aza-bicyclo[3.2.1]oct-3-yl)-5-fluoro-2-(4-fluoro-Phenoxy)-nicotinamide

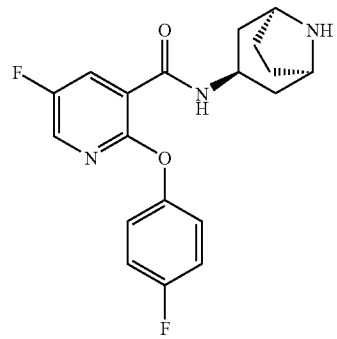

10% Palladium on carbon (0.5 g) and ammonium formate (7.5 g, 115 mmol) were added to a solution of exo-N-(8-benzyl-8-aza-bicyclo[3.2.1]oct-3-yl-5-fluoro-2-(4-fluoro-phenoxy)-nicotinamide (5.15 g, 11.5 mmol) (see Preparation 34) in ethanol (35 ml) under an atmosphere of nitrogen and the reaction mixture heated at reflux for 25 minutes. The reaction mixture was then cooled, filtered through a short column of arbocel (washing with ethanol) and the filtrate concentrated under reduced pressure. The residue was purified by flash column chromatography on silica gel eluting with 90:10:1, by volume, dichloromethane:methanol:ammonia giving exo-N-(8-aza-bicyclo[3.2.1]oct-3-yl)-5-fluoro-2-(4-fluoro-phenoxy)-nicotinamide (3.4 g) as a white foam.

¹H NMR (400 MHz, CDCl₃): δ=8.26–8.31 (1H, dd), 7.97–7.99 (1H, d), 7.56–7.70 (1H, d), 7.00–7.14 (4H, m), 4.33–4.43 (1H, m), 3.52–3.60 (2H, brs),1.97–2.06 (2H, m), 1.73–1.88 (4H, m), 1.41–1.50 (2H, t) ppm. LRMS (thermospray): m/z [M+H]⁺ 360.

Preparation 36 exo-[2-(3-{[5-Fluoro-2-(4-fluoro-phenoxy)-pyridine-3-carbonyl]-amino}-8-azo-bicyclo[3.2.1]-oct-8-yl)-2-oxo-ethyl]-carbamic acid-tert-butyl ester

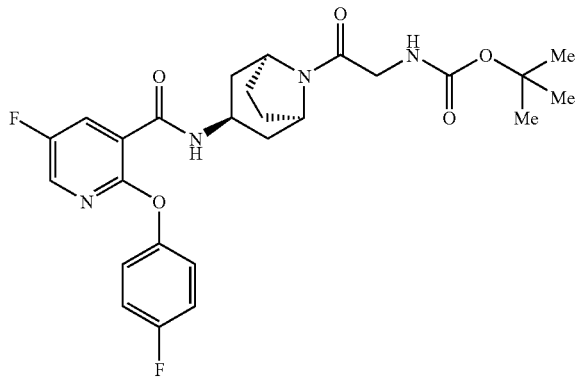

N-tert-Butoxycarbonyl-glycine (284 mg, 1.6 mmol), 1-hydroxybenzotriazole (257 mg, 1.9 mmol) and 1-(3-dimethylaminopropyl)-3-ethylcarbodiimide hydrochloride (375 mg, 1.9 mmol) were stirred in dichloromethane (10 ml) at room temperature and exo-N-(8-aza-bicyclo[3.2.1]oct-3-yl)-5-fluoro-2-(4-fluooro-phenoxy)-nicotinamide (570 mg, 1.6 mmol) (see Preparation 35) added followed by addition of N-methyl morpholine (0.21 ml, 1.9 mmol). The reaction mixture was then stirred under an atmosphere of nitrogen at room temperature for 4 hours before being washed with water (10 ml). The organic phase was separated, concentrated in vacuo and the residue purified by flash column chromatography on silica gel eluting with 100:0 changing to 98:2, by volume, dichloromethane:methanol giving exo-[2-(3-{[5-fluoro-2-(4-fluoro-phenoxy)-pyridine-3-carbonyl]-amino}-8-azo-bicyclo[3.2.1]-oct-8-yl)-2-oxo-ethyl]-carbamic acid-tert-butyl ester (760 mg) as an oil.

$^1$H NMR (400 MHz, CDCl$_3$): δ=8.28–8.34 (1H, m), 8.0–8.02 (1H, m), 7.59–7.65 (1H, d), 7.05–7.16 (4H, m), 5.37–5.43 (1H, brs), 4.72–4.78 (1H, brs), 4.57–4.70 (1H, m), 4.15–4.20 (1H, brs), 3.89–3.94 (2H, brs), 2.16–2.23 (1H, m), 1.94–2.15 (2H, m), 1.82–1.92 (1H, m), 1.58–1.68 (1H, t), 1.40–1.56 (10H, m), 0.90–0.96 (2H, d) ppm. LRMS (electrospray): m/z [M+Na]$^+$ 539, [M–H]$^+$ 515.

Preparation 37 exo-N-[8-(2-Amino-acetyl)-8-aza-bicyclo[3.2.1]oct-3-yl)-5-fluoro-2-(4-fluoro-phenoxy)-nicotinamide hydrochloride

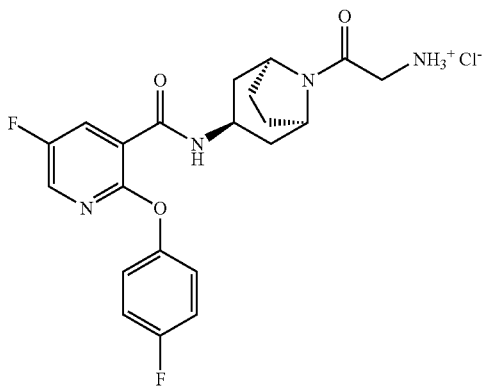

Exo-[2-(3-{[5-Fluoro-2-(4-fluoro-phenoxy)-pyridine-3-carbonyl]-amino}-8-azo-bicyclo[3.2.1]-oct-8-yl)-2-oxo-ethyl]-carbamic acid-tert-butyl ester (760 g, 1.5 mmol) (see Preparation 36) was dissolved in 2 M acetyl chloride in methanol (10 ml). The reaction mixture was stirred 50° C. under an atmosphere of nitrogen for 3 hours and the solvent then removed in vacuo. The residue was azeotroped with methanol (5 ml) and dried in vacuo giving exo-N-[8-(2-amino-acetyl)-8-aza-bicyclo[3.2.1]oct-3-yl)-5-fluoro-2-(4-fluoro-phenoxy)-nicotinamide hydrochloride (600 mg) as a white solid.

$^1$H NMR (400 MHz, DMSO-d$^6$): δ=8.29–8.33 (1H, d), 8.13–8.23 (3H, m), 7.92–7.96 (1H, dd), 7.16–7.25 (4H, m), 4.50–4.58 (1H, brs), 4.28–4.41 (1H, m), 4.21–4.27 (1H, m), 3.80–3.90 (1H, m), 3.60–3.72 (1H, m), 1.70–2.06 (6H, m), 1.49–1.64 (2H, m) ppm. LRMS (thermospray): m/z [M+H]$^+$ 417.

Preparation 38 anti-(4-{[2-(Benzo[1,3]dioxol-5-vioxy)-5-fluoro-pyridine-3-carbonyl]-amino}-cyclohexyl)-carbamic acid tert-butyl ester

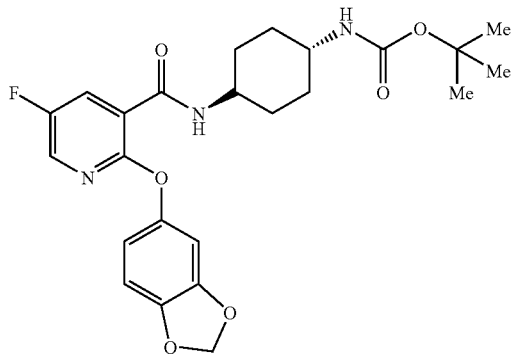

2-(4-Benzo[1,3]dioxol-5-yloxy)-5-fluoro-nicotinic acid (5.0 g, 18.04 mmol) (see reference patent application WO 98/45268), 1-hydroxybenzotriazole (3.66 g, 27.06 mmol), 1-(3-dimethylaminopropyl)-3-ethylcarbodiimide hydrochloride (4.50 g, 23.45 mmol) were stirred in N,N-dimethylformamide (40 ml) at room temperature under an atmosphere of nitrogen for 45 minutes. anti-(4-Amino-cyclohexyl)-carbamic acid tert-butyl ester (3.87 g, 18.04 mmol) (see Preparation 40) was then added followed by addition of N-methyl morpholine (4 ml, 36.08 mmol) and the reaction mixture stirred for a further 16 hours. The solvent was then removed in vacuo, the residue dissolved in ethyl acetate and the solution washed sequentially with water and a saturated aqueous solution of sodium chloride. The organic layer was separated, dried over anhydrous sodium sulphate and the solvent removed in vacuo. The residue was then triturated with diethyl ether and dried in vacuo to give anti-(4-{[2-(benzo[1,3]dioxol-5-yloxy)-5-fluoro-pyridine-3-carbonyl]-amino}-cyclohexyl)-carbamic acid tert-butyl ester (6.695 g) as a white solid.

$^1$H NMR (400 MHz, DMSO-d$^6$): δ=8.15 (1H, m), 7.88 (1H, m), 6.85 (1H, d), 6.78 (1H, d), 6.64 (1H, d), 6.58 (2H, m), 5.99 (2H, s), 3.62 (1H, m), 3.15 (1H, m), 1.70–1.90 (4H, m), 1.32 (9H, s), 1.10–1.30 (4H, m) ppm. LRMS (thermospray): m/z [M+Na]$^+$ 496

Preparation 39 anti-N-(4-Amino-cyclohexyl)-2-(Benzo[1,3]dioxol-5-vloxy)-5-fluoro-nicotinamide hydrochloride

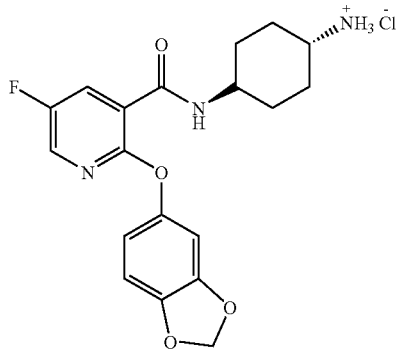

Anti-(4-{[2-(Benzo[1,3]dioxol-5-yloxy)-5-fluoro-pyridine-3-carbonyl]-amino}-cyclohexyl)-carbamic acid tert-butyl ester (6.7 g, 14.15 mmol) (see Preparation 38) was treated with 4M HCl in dioxan (40 ml) and the reaction mixture stirred for 90 minutes. The solvent was then reduced in vacuo and a solid precipitated. The precipitate was suspended in diethyl ether, filtered and then dried in vacuo to give anti-N-(4-amino-cyclohexyl)-2-(Benzo[1,3]dioxol-5-yloxy)-5-fluoro-nicotinamide hydrochloride (6.13 g) as a white solid.

$^1$H NMR (400 MHz, DMSO-d$^6$): δ=8.24 (1H, d), 8.20 (1H, d), 7.86–7.99 (4H, m), 6.86 (1H, d), 6.80(1H, d), 6.58 (1H, m), 5.99 (2H, s), 3.60–3.70 (1H, m), 2.90–2.95 (1H, m), 1.85–1.98 (4H, m), 1.25–1.45 (4H, m) ppm.

Preparation 40 anti-(4-Amino-cyclohexyl)-carbamic acid tert-butyl ester

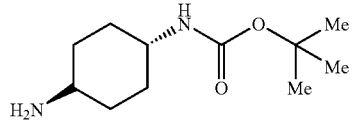

Anti 1,4-Diamino cyclohexane (18.27 g, 0.16 mol) was dissolved in dichloromethane (80 ml) and the solution cooled at 0° C. under an atmosphere of nitrogen. The reaction mixture was maintained at 0° C. and a solution of di-tert-butyl dicarbonate (6.98 g, 0.032 mol) in dichloromethane (70 ml) added dropwise over a period of 5 hours. The reaction mixture was stirred at room temperature for a further 16 hours and then washed with water (200 ml). The organic layer was separated, extracted with a 10% aqueous solution of citric acid (200 ml) and the organic phase disgarded. The pH of the aqueous phase was then increased to pH>8 by the addition of 0.88 ammonia and extracted with dichloromethane (3-fold 150 ml). The organic extracts were combined, dried over anhydrous magnesium sulphate and the solvent removed in vacuo to give anti (4-amino-cyclohexyl)-carbamic acid tert-butyl ester (4.83 g) as a solid.

$^1$H NMR (400 MHz, CDCl3): δ=4.35 (brs, 1H), 4.55 (brs, 1H), 3.40 (br S, 1H), 2.60–2.65 (m, 1H), 1.80–2.00 (m, 4H), 1.10–1.50 (m, ~14H) ppm. LRMS (electrospray): m/z [M+H]$^+$ 215.

Preparation 41

2-Chloro-5-fluoro nicotinic acid

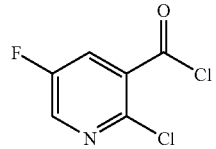

Ethyl-2-chloro-5-fluoro-nicotinoate (50.4 g, 0.247 mol) (see reference *J. Med. Chem.*, 1993, 36(18), 2676–88) was dissolved in tetrahydrofuran (350 ml) and a 2 M aqueous solution of lithium hydroxide (247 ml, 0.495 mol) added. The reaction mixture was stirred at room temperature for 3 days. The pH of the solution was reduced to pH1 by addition of 6 N hydrochloric acid and then extracted with dichloromethane (3 fold). The combined extracts were dried over anhydrous magnesium sulphate and the solvent removed in vacuo to give a solid which was triturated with diethyl ether and then dried in vacuo to give 2-chloro-5-fluoro nicotinic acid (40.56 g) as a white solid. $^1$H NMR (400 MHz, DMSO-d$^6$): δ=8.20 (1H, s), 8.62 (1H, s) ppm. LRMS (electrospray): m/z [M+H]$^+$ 174.

Preparation 42a

80:20 syn:anti(4-Amino-cyclohexyl)-carbamic acid tert-butyl ester

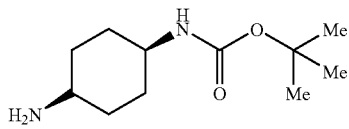

80:20 syn:anti 1,4-Diamino cyclohexane (20 g, 0.175 mol) was dissolved in dichloromethane (160 ml) and the solution cooled at 0° C. under an atmosphere of nitrogen. The reaction mixture was maintained at 0° C. and a solution of di-tert-butyl dicarbonate (7.65 g, 0.035 mol) in dichloromethane (40 ml) added dropwise over a period of 5 hours. The reaction mixture was stirred at room temperature for a further 16 hours and then washed with water (200 ml). The organic layer was separated, extracted with a 10% aqueous solution of citric acid (200 ml) and the organic phase disgarded. The pH of the aqueous phase was then increased to pH>8 by the addition of 0.88 ammonia and extracted with dichloromethane (2-fold 150 ml). The organic extracts were combined, dried over anhydrous magnesium sulphate and the solvent removed in vacuo. The residue was then triturated with pentane to give 80:20 syn:anti (4-amino-cyclohexyl)-carbamic acid tert-butyl ester (5.143 g) as a solid.

$^1$H NMR (400 MHz, CDCl3): δ=4.60 (brs, 0.8H), 4.36 (brs, 0.2H), 3.63 (br S, 0.8H), 3.39 (brs, 0.2H), 3.80–3.86 (m, 0.8H), 2.60–2.65 (m, 0.2H), 1.96–2.00 (m, 0.2H), 1.80–1.86 (m, 0.2H), 1.10–2.75 (m, ~17H) ppm. LRMS (electrospray): m/z [M+H]$^+$ 215.

Preparation 42b

Syn-(4-Amino-cyclohexyl)-carbamic acid tert-butyl ester

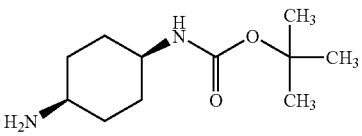

5% Palladium on charcoal (5 g) was mixed with toluene (10 ml) and was added to (4-azido-cyclohexyl)-carbamic acid tert-butyl ester (170 g, 0.71 mol, see WO 99/54284) in methanol (400 ml). The mixture was hydrogenated (80 atmospheres) at room temperature for 18 hours and then filtered. The solvent was evaporated in-vacuo and the residue was triturated with ethyl acetate (50 ml) and then with hexane (200 ml). The solid obtained was isolated by filtration, dissolved in ethyl acetate (600 ml) and filtered through Celite®). The filtrate was concentrated in-vacuo to give a slush that was diluted with hexane (300 ml). The solid obtained was isolated by filtration and was washed with ethyl acetate in hexane (20:80). The mother liquors were combined and evaporated in-vacuo, the residue was purified by chromatography on silica gel using ethyl acetate and then methanol as eluant. The material obtained was crystallised from ethyl acetate and hexane and combined with the first crop to give syn-(4-amino-cyclohexyl)-carbamic acid tert-butyl ester as a white solid (76 g).

Mp 88–90° C.

Preparation 43

Syn-{4-[(2-Chloro-5-fluoro-pyridine-3-carbonyl)-amino]-cyclohexyl}-carbamic acid tert-butyl ester

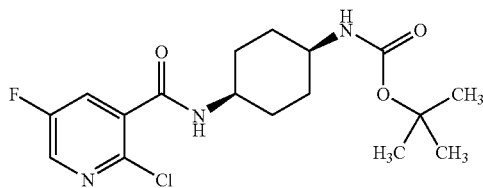

2-Chloro-5-fluoro nicotinic acid (1 g, 5.7 mmol, see Preparation 41), 1-(3-dimethylaminopropyl-3-ethylcarbodiimide hydrochloride (1.2 g, 6.27 mmol) and 1-hydroxybenzotriazole hydrate (0.847 g, 6.27 mmol) were added to (4-amino-cyclohexyl)-carbamic acid tert-butyl ester (1.28 g, 5.98 mmol, see Preparation 42b) in N,N-dimethylformamide (20 ml) containing triethylamine (2.38 ml, 17 mmol). The mixture was stirred for 18 hours and then partitioned between ethyl acetate and water. The organic solution was washed with water and then with saturated solution of sodium chloride, dried over magnesium sulphate and evaporated in-vacuo. The residue was purified by chromatography on silica gel using cyclohexane in ethyl acetate (40:60) to give syn-{4-[(2-chloro-5-fluoro-pyridine-3-carbonyl)-amino]-cyclohexyl}-carbamic acid tert-butyl ester (1.01 g).

$^1$H NMR (400 MHz, CDCl$_3$): δ 8.33 (1H, d), 7.80 (1H, m), 6.67 (1H, s), 4.54 (1H, m), 4.16 (1H, m), 3.64 (1H, s), 1.86 (6H, m), 1.76 (2H, m), 1.27 (9H, s). LCMS (electrospray): m/z [M+Na]$^+$ 394, 396

Preparation 44

Syn-N-(4-amino-cyclohexyl)-2-chloro-5-fluoro-nicotinamide hydrochloride

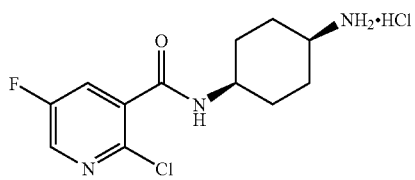

Hydrogen chloride (4M in 1,4-dioxane, 20 ml) was added to syn-{4-[(2-chloro-5-fluoro-pyridine-3-carbonyl)-amino]-cyclohexyl}-carbamic acid tert-butyl ester (1.01 g, 2.72 mmol, see Preparation 43) in 1,4-dioxane (10 ml) and was stirred for 1 hour. The solvent was evaporated in-vacuo and the residue triturated with diethylether. The resulting material was dried in-vacuo to give syn-N-(4-amino-cyclohexyl)-2-chloro-5-fluoro-nicotinamide hydrochloride as an off white solid (1.11 g).

$^1$H NMR (400 MHz, CD$_3$OD): δ 8.41 (1H, d), 7.79 (1H, m), 4.07 (1H, m), 3.25 (1H, m), 1.88 (8H, m). LCMS (electrospray): m/z [M+H]$^+$ 372, 274

Preparation 45

Syn-2-Chloro-5-fluoro-N-[4-(2-hydroxy-4-methoxy-benzoylamino)-cyclohexyl]-nicotinamide

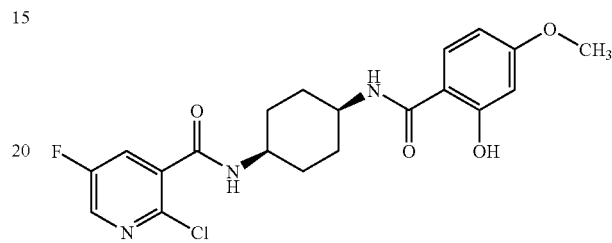

1-(3-Dimethylaminopropyl-3-ethylcarbodiimide hydrochloride (3.27 g, 17 mmol) was added to syn-N-(4-amino-cyclohexyl)-2-chloro-5-fluoro-nicotinamide hydrochloride (3.5 g, 11.3 mmol, see Preparation 44), 1-hydroxybenzotriazole hydrate (1.69 g, 12.5 mmol) and 2-hydroxy-4-methoxybenzoic acid (1.91 g, 11.31 mmol) in N,N-dimethylformamide (50 ml) containing triethylamine (8 ml, 57 mmol). The mixture was stirred 18 hours and then was evaporated in-vacuo. The residue was partitioned between ethyl acetate and water and the organic phase was dried and evaporated in-vacuo. The residue was purified by chromatography on silica gel using ethyl acetate in pentane (30:70) then changing the eluant for the column to ammonium hydroxide and methanol in dichloromethane (1:10:90). The material obtained was triturated with methanol in dichloromethane (5:95) to give syn-2-chloro-5-fluoro-N-[4-(2-hydroxy-4-methoxy-benzoylamino)-cyclohexyl]-nicotinamide as a white solid (940 mg).

$^1$H NMR (400 MHz, DMSO-d$_6$): δ 12.78 (1H, s), 8.53 (2H, s), 8.23 (1H, d), 7.94 (1H, m), 7.84 (1H, d), 6.43 (1H, d), 6.38 (1H, s), 3.88 (2H, m), 3.74 (3H, s), 1.73 (8H, m). LCMS (electrospray): m/z [M+H]$^+$ 444, 446

Preparation 46

Syn-(4-(4-{[2-(4-Fluoro-phenoxy)-pyridine-3-carbonyl]-amino}-cyclohexyl)-carbamic acid tert-butyl ester

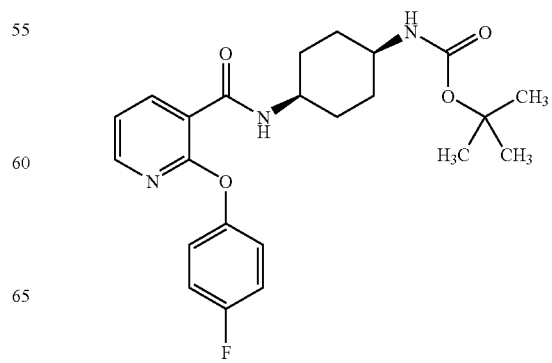

O-(7-Azabenzotriazol-1-yl)-N,N,N',N',-tetramethyluronium hexafluorophosphate (2.24 g, 5.89 mmol) was added to 2-(4-fluoro-phenoxy)-nicotinic acid (0.916 g, 3.93 mmol), Hünig's base (1.37 ml, 7.86 mmol) and to syn-(4-amino-cyclohexyl)-carbamic acid tert-butyl ester (1.01 g, 4.71 mmol, see Preparation 42-B) in N,N-dimethylformamide (26.2 ml) and was stirred for 18 hours. The reaction mixture was partitioned between water (100 ml) and a mixture of diethylether (200 ml) and ethyl acetate (50 ml). The aqueous layer was separated and extracted with ethyl acetate (50 ml) and the combined organic layers were washed with a saturated solution of sodium chloride, dried over magnesium sulphate and evaporated in-vacuo. The residue was purified by chromatography on silica gel using ethyl acetate in cyclohexane as eluant (gradient from 25:73 to 50:50) to give syn-(4-{[2-(4-fluoro-phenoxy)-pyridine-3-carbonyl]-amino}-cyclohexyl)-carbamic acid tert-butyl ester as white solid (1.07 g).

$^1$H NMR (400 MHz, CDCl$_3$): δ 8.60 (1H, d), 8.20 (1H, d), 1.91 (1H, d), 1.17 (5H, m), 4.40 (1H, m), 4.19 (1H, s), 3.61 (1H, s), 1.77 (8H, m), 1.42 (9H, s). LCMS (electrospray): m/z [M+Na]$^+$ 452

Preparation 47

Syn-N-(4-Amino-cyclohexyl)-2-(4-fluoro-phenoxy)-nicotinamide hydrochloride

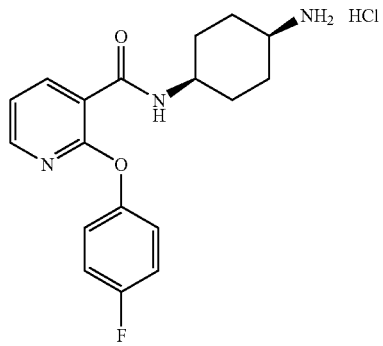

Syn-(4-{[2-(4-fluoro-phenoxy)-pyridine-3-carbonyl]-amino}-cyclohexyl)-carbamic acid tert-butyl ester (989 mg, 2.3 mmol, see Preparation 46) was suspended in a solution of hydrogen chloride in 1,4-dioxane (4M, 20 ml) and was stirred for 3.5 hours at room temperature after which the solvent was evaporated in-vacuo to give syn-N-(4-amino-cyclohexyl)-2-(4-fluoro-phenoxy)-nicotinamide hydrochloride as a white solid (1.04 g).

$^1$H NMR (400 MHz, CD$_3$OD): δ 8.29 (1H, d), 8.19 (1H, d), 7.22 (5H, m), 4.19 (1H, m), 3.28 (1H, m), 2.94 (6H, m), 1.73 (2H, m). LCMS (electrospray): m/z [M+H]$^+$ 330

Preparation 48

Syn-2-(4-Fluoro-phenoxy)-N-{4-[(imidazole-1-carbonyl)-amino]-cyclohexyl}-nicotinamide

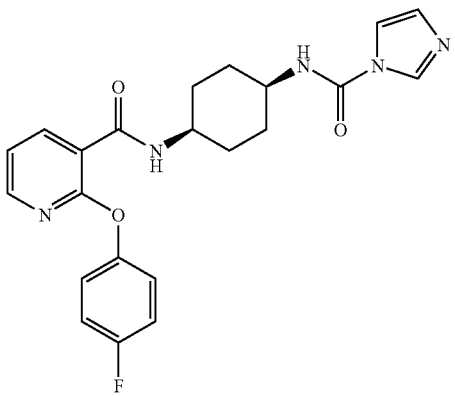

A solution of syn-N-(4-amino-cyclohexyl)-2-(4-fluoro-phenoxy)-nicotinamide hydrochloride (300 mg, 0.82 mmol) (see Preparation 47) and triethylamine (110 μl, 0.82 mmol) in dichloromethane (10 ml) was added over 1 hour to a solution of 1,1'-carbonyldiimidazole (399 mg, 2.46 mmol) in dichloromethane (5 ml) under a nitrogen atmosphere. The mixture was stirred for 18 hours and then diluted with water (10 ml). The organic solution was washed with saturated solution of sodium chloride (10 ml) dried over magnesium sulphate and evaporated in-vacuo. The residue was purified by chromatography on silica gel using methanol in dichloromethane (5:95) to give syn-2-(4-Fluoro-phenoxy)-N-{4-[(imidazole-1-carbonyl)-amino]-cyclohexyl}-nicotinamide as a white foam (269 mg).

$^1$H NMR (400 MHz, CDCl$_3$): δ 8.61 (1H, d), 8.39 (1H, m), 8.21 (1H, d), 7.99 (1H, d), 7.13 (7H, m), 5.78 (1H, m), 4.23 (1H, m), 4.00 (1H, m), 1.88 (8H, m) LCMS (electrospray): m/z [M+H]$^+$ 426

Preparation 49

4-Aminomethyl-3-fluorophenol hydrochloride

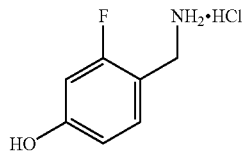

A mixture of 2-fluoro-4-hydroxy-benzonitrile (6 g, 43.8 mmol), palladium hydroxide (600 mg), ethanol (60 ml) and 2N hydrochloric acid (6 ml) was hydrogenated (60 psi) for 18 hours. The mixture was filtered through Arbocel® and the filter cake was washed with methanol and the filtrates were evaporated in-vacuo. The residue was triturated with diethylether to give 4-aminomethyl-3-fluoro phenol hydrochloride (4.71 g).

$^1$H NMR (400 MHz, DMSO-d$_6$): δ 10.26 (1H, s), 8.30 (1H, s), 7.39 (1H, m), 6.63 (2H, m), 3.94 (2H, d).

Preparation 50

Anti-4-[(2-Chloro-5-fluoro-pyridine-3-carbonyl)-amino]-cyclohexanecarboxylic acid methyl ester

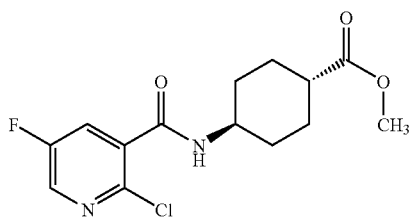

2-Chloro-5-fluoro nicotinic acid (3 g, 17 mmol, see Preparation 41), 1-(3-dimethylaminopropyl-3-ethylcarbodiimide hydrochloride (4.26 g, 22 mmol) and 1-hydroxybenzotriazole hydrate (3.46 g, 26 mmol) were stirred in N,N-dimethylformamide (20 ml) for 30 minutes. Anti-4-amino-cyclohexanecarboxylic acid methyl ester hydrochloride (3.31 g, 17 mmol, see Reference J. Med. Chem. 1977, 20(2), 279) and 4-methyl morpholine (3.76 ml, 34 mmol) were added and the mixture was stirred at room temperature for 18 hours. The mixture was partitioned between water and ethyl acetate and the organic solution was washed with a saturated solution of sodium chloride, dried over magnesium sulphate and evaporated in-vacuo. The residue was purified by chromatography on silica gel using methanol in dichloromethane as eluant (gradient from 0:100 to 3:97) the material isolated was dried in-vacuo to give anti-4-[(2-chloro-5-fluoro-pyridine-3-carbonyl)-amino]-cyclohexanecarboxylic acid methyl ester as a solid (4.23 g).

$^1$H NMR (300 MHz, CDCl$_3$): δ 8.32 (1H, d), 7.83 (1H, m), 6.44 (1H, d), 3.96 (1H, m), 3.69 (3H, s), 2.16 (5H, m), 1.63 (2H, m), 1.33 (2H, m). LCMS (electrospray): m/z [M–H]$^-$ 313

Preparation 51

Anti-4-{[5-Fluoro-2-(4-fluoro-phenoxy)-pyridine-3-carbonyl]-amino}-cyclohexanecarboxylic acid methyl ester

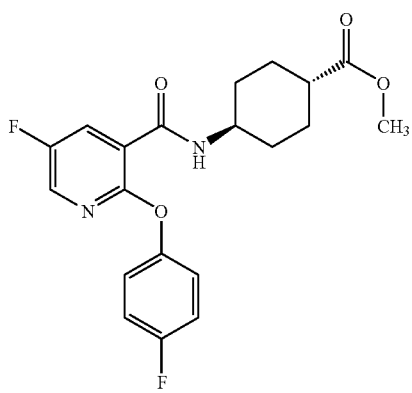

Anti-4-[(2-Chloro-5-fluoro-pyridine-3-carbonyl)-amino]-cyclohexanecarboxylic acid methyl ester (4.22 g, 13 mmol, see Preparation 50) was added to a mixture of 4-fluorophenol (1.5 g, 13 mmol) and caesium carbonate (8.71 g, 27 mmol) in N,N-dimethylformamide (30 ml) and was stirred under a nitrogen atmosphere at 60° C. for 18 hours. The mixture was partitioned between water and ethyl acetate and the organic solution was washed with a saturated solution of sodium chloride, dried over magnesium sulphate and evaporated in-vacuo. The residue was purified by chromatography on silica gel using methanol in dichloromethane as eluant (gradient from 0:100 to 2:98) the material isolated was dried in-vacuo to give anti-4-{[5-fluoro-2-(4-fluoro-phenoxy)-pyridine-3-carbonyl]-amino}-cyclohexanecarboxylic acid methyl ester as a solid (3.71 g).

$^1$H NMR (300 MHz, CDCl$_3$): δ 8.36 (1H, m), 8.02 (1H, d), 7.72 (1H, d), 7.14 (4H, m), 4.00 (1H, m), 3.70 (3H, s), 2.22 (3H, m), 1.67 (2H, m), 1.30 (2H, m). LCMS (thermospray): m/z [M]$^+$ 390

Preparation 52

Anti-4-{[5-Fluoro-2-(4-fluoro-phenoxy)-pyridine-3-carbonyl]-amino}-cyclohexanecarboxylic acid

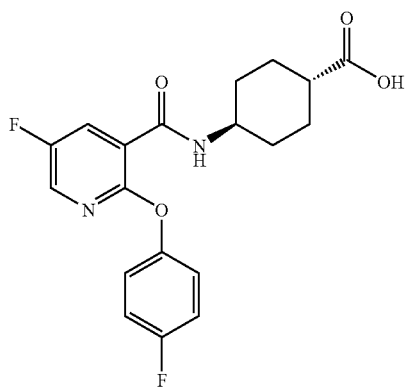

Anti-4-{[5-Fluoro-2-(4-fluoro-phenoxy)-pyridine-3-carbonyl]-amino}-cyclohexane-carboxylic acid methyl ester (3.7 g, 9.48 mmol, see Preparation 52) was dissolved in a mixture of tetrahydrofuran (40 ml) and 1M lithium hydroxide solution (19 ml, 19 mmol) and was stirred under a nitrogen atmosphere for 18 hours. 2N Hydrochloric acid (10 ml) was added and the mixture was extracted with dichloromethane (3 fold). The combined organic solutions were washed with saturated solution of sodium chloride dried over magnesium sulphate and evaporated in-vacuo. The residue was triturated with diethylether and the solid obtained was dried in-vacuo to give anti-4-{[5-fluoro-2-(4-fluoro-phenoxy)-pyridine-3-carbonyl]-amino}-cyclohexanecarboxylic acid (2.45g).

$^1$H NMR (300 MHz, CDCl$_3$): δ 12.0 (1H, s), 8.29 (1H, d), 8.20 (1H, d), 7.95 (1H, d), 7.21 (4H, m), 3.70 (1H, m), 2.17 (1H, m), 1.91 (4H, m), 1.34 (4H, m). LCMS (thermospray): m/z [M]$^+$ 376

Preparation 53

Syn-4-[(2-Chloro-pyridine-3-carbonyl)-amino]-cyclohexanecarboxylic acid benzyl ester

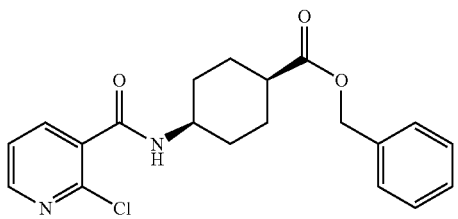

2-Chloronicotinic acid (2 g, 12.69 mmol) was suspended in dichloromethane (320 ml) under a nitrogen atmosphere, oxalyl chloride (3.32 ml, 38 mmol) was added and then one drop of N,N-dimethylformamide was added and the mixture was stirred for 3 hours. The solvent was evaporated in-vacuo and the residue was dissolved in dichloromethane (110 ml). A solution of syn-4-amino-cyclohexanecarboxylic acid benzyl ester tosylate (6.18 g, 15.23 mmol, see preparation 62) and triethylamine (5.31 ml, 38 mmol) in dichloromethane (50 ml) was added and the mixture was stirred under a nitrogen atmosphere for 18 hours. The reaction mixture was washed with water (2-fold 100 ml), then saturated solution of sodium chloride (100 ml), dried over magnesium sulphate and evaporated in-vacuo. The residue was dissolved in dichloromethane (50 ml), washed with citric acid solution (50 ml), dried with saturated solution of sodium chloride and evaporated in-vacuo to give syn-4-[(2-chloro-pyridine-3-carbonyl)-amino]-cyclohexanecarboxylic acid benzyl ester as an orange solid (4.80 g).

$^1$H NMR (400 MHz, CDCl$_3$): δ 8.43 (1H, m), 8.06 (1H, m), 7.31 (6H, m), 6.44 (1H, m), 5.11 (2H, s), 4.16 (1H, m), 2.37 (1H, m), 1.94 (2H, m), 1.73 (6H, m). LCMS (electrospray): m/z [M+Na]$^+$ 395, 397

Preparation 54

Syn-4-{[2-(4-Fluoro-phenoxy)-pyridine-3-carbonyl]-amino}-cyclohexanecarboxylic acid benzyl ester

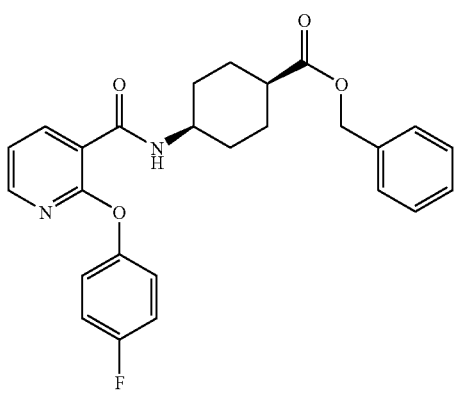

Syn-4-[(2-chloro-pyridine-3-carbonyl)-amino]-cyclohexanecarboxylic acid benzyl ester (2 g, 5.36 mmol, see Preparation 53) was added to a mixture of 4-fluorophenol (661 mg, 5.90 mmol) and caesium carbonate (3.495 g, 10.72 mmol) in N,N-dimethylformamide (20 ml) and was stirred under a nitrogen atmosphere at 55° C. for 18 hours. The mixture was partitioned between water (20 ml) and ethyl acetate (30 ml) the organic solution was washed with a saturated solution of sodium chloride (20 ml), dried over magnesium sulphate and evaporated in-vacuo. The residue was purified by chromatography on silica gel using methanol in dichloromethane as eluant (gradient from 0:100 to 1:99) to give syn-4-{[2-(4-fluoro-phenoxy)-pyridine-3-carbonyl]-amino}-cyclohexanecarboxylic acid benzyl ester as white solid (1.078 g).

$^1$H NMR (400 MHz, CDCl$_3$): δ 8.78 (1H, d), 8.17 (1H, d), 7.91 (1H, d), 7.28 (5H, m), 7.10 (5H, m), 5.04 (2H, s), 4.20 (1H, m), 2.52 (1H, m), 1.80 (8H, m). LCMS (electrospray): m/z [M+Na]$^+$ 449

Preparation 55

Syn-4-{[2-(4-fluoro-phenoxy)-pyridine-3-carbonyl]-amino}-cyclohexanecarboxylic acid

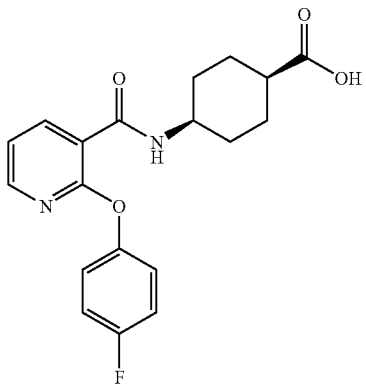

10% Palladium on carbon (250 mg) was added to syn-4-[(2-chloro-pyridine-3-carbonyl)-amino]-cyclohexanecarboxylic acid benzyl ester (1.07 g, 5.36 mmol, see Preparation 54) in methanol (25 ml). The mixture was hydrogenated at 60 psi for 30 minutes and then was filtered through Arbocel®. The filter cake was washed with methanol and the combined filtrates were evaporated in-vacuo. The residue was purified by chromatography on silica gel using methanol in dichloromethane (gradient from 0:100 to 1:99) to give syn-4-[(2-chloro-pyridine-3-carbonyl)-amino]-cyclohexanecarboxylic acid as a white powder (363 mg).

$^1$H NMR (400 MHz, CD$_3$OD): δ 8.39 (1H, d), 8.24 (1H, d), 8.17 (1H, d), 7.16 (5H, m), 4.10 (1H, m), 2.48 (1H, m), 1.89 (2H, m), 1.77 (6H, m) LCMS (thermospray): m/z [M]$^+$ 359

Preparation 56

Syn4-[(2-Chloro-5-fluoro-pyridine-3-carbonyl)-amino]-cyclohexanecarboxylic acid benzyl ester

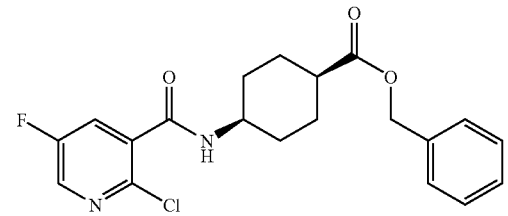

2-Chloro-5-fluoronicotinic acid (1 g, 5.7 mmol, see Preparation 41) was suspended in dichloromethane (80 ml) under a nitrogen atmosphere, oxalyl chloride (1.49 ml, 17.1 mmol) was added and then one drop of N,N-dimethylformamide was added and the mixture stirred for 1.25 hours. The solvent was evaporated in-vacuo and the residue was dissolved in dichloromethane (60 ml). A suspension of 4-amino-cyclohexanecarboxylic acid benzyl ester tosylate (2.77 g, 6.84 mmol, see preparation 62) and triethylamine (2.38 ml, 17.1 mmol) in dichloromethane (20 ml) was added and the mixture was stirred under a nitrogen atmosphere for 18 hours. The mixture was washed with water (2-fold 75 ml) a saturated solution of sodium chloride (100 ml), dried over magnesium sulphate and evaporated in-vacuo. The residue was purified by chromatography on silica gel using methanol in dichloromethane as eluant (gradient from 0:100 to 1:99) to give syn-4-[(2-chloro-5-fluoro-pyridine-3-carbonyl)-amino]-cyclohexanecarboxylic acid benzyl ester as an orange solid (2.18 g).

$^1$H NMR (400 MHz, CD$_3$OD): δ 8.30 (1H, d), 7.87 (1H, m), 7.33 (5H, m), 6.64 (1H, s), 5.12 (2H, s), 4.14 (1H, m), 2.55 (1H, m), 1.93 (2H, m), 1.79 (4H, m), 1.68 (2H, m). LCMS (thermospray): m/z [M+NH$_4$]$^+$ 408

Preparation 57

Syn-4-{[2-(Benzo[1,3]dioxol-5-yloxy)-5-fluoro-pyridine-3-carbonyl]-amino}-cyclohexanecarboxylic acid benzyl ester

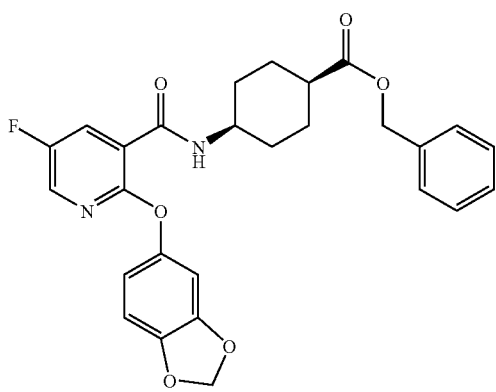

Caesium carbonate (3.38 g, 10.38 mmol) and 3,4-methylenedioxyphenol (78 mg, 5.71 mmol) were added to a solution of syn-4-[(2-chloro-5-fluoro-pyridine-3-carbonyl)-amino]-cyclohexanecarboxylic acid benzyl ester (2.03 g, 5.19 mmol, see Preparation 56) in N,N-dimethylformamide (20 ml) and the mixture was stirred under a nitrogen atmosphere for 18 hours at 55° C. The mixture was partitioned between water (30 ml) and ethyl acetate (30 ml) the organic solution was washed with a saturated solution of sodium chloride (30 ml), dried over magnesium sulphate and evaporated in-vacuo. The residue was purified by chromatography on silica gel using dichloromethane as eluant to give syn-4-{[2-(4-fluoro-phenoxy)-pyridine-3-carbonyl]-amino}-cyclohexane-carboxylic acid benzyl ester as an orange solid (2.07 g).

$^1$H NMR (400 MHz, CDCl$_3$): δ 8.34 (1H, m), 8.06 (1H, m), 8.00 (1H, m), 7.31 (5H, m), 6.80 (1H, d), 6.65 (1H, m), 6.59 (1H, m), 6.00 (2H, s), 5.09 (2H, s), 4.19 (1H, m), 2.34 (1H, m),1.80 (8H, m). LCMS (electrospray): m/z [M+Na]$^+$ 515

Preparation 58

Syn-4-{[2-(Benzo[1,3]dioxol-5-yloxy)-5-fluoro-pyridine-3-carbonyl]-amino}-cyclohexanecarboxylic acid

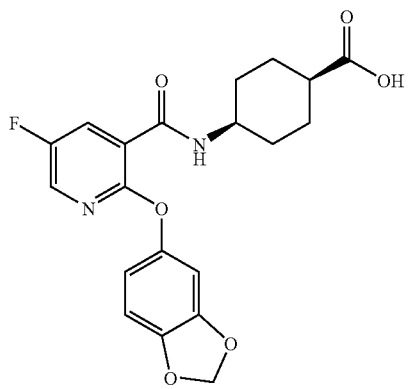

10% Palladium on carbon (50 mg) was added to syn-4-{[2-(4-fluoro-phenoxy)-pyridine-3-carbonyl]-amino}-cyclohexanecarboxylic acid benzyl ester (200 mg, 0.406 mmol, see Preparation 57) in methanol (5 ml). The mixture was hydrogenated at 60 psi for 2 hours and then was filtered through Arbocel®. The filter cake was washed with methanol and the combined filtrates were evaporated in-vacuo. The residue was purified by chromatography on silica gel using methanol in dichloromethane (2:98) to give syn-4-{[2-(benzo[1,3]dioxol-5-yloxy)-5-fluoro-pyridine-3-carbonyl]-amino}-cyclohexanecarboxylic acid as a white solid (50 mg).

$^1$H NMR (400 MHz, CDCl$_3$): δ 8.30 (1H, m), 8.01 (2H, m), 6.79 (1H, d), 6.66 (1H, d), 6.57 (1H, m), 5.97 (2H, s), 4.18 (1H, m), 2.53 (1H, m), 1.79 (8H, m). LCMS (electrospray): m/z [M+Na]$^+$ 425

Preparation 59

Syn-4-Amino-cyclohexanecarboxylic acid benzyl ester tosylate

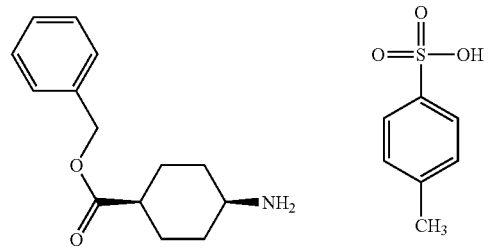

4-Amino-cyclohexanecarboxylic acid (10 g, 69.9 mmol) was dissolved in 1N hydrochloric acid (70 ml, 70 mmol) and the mixture was evaporated in-vacuo. The residue was dried by toluene azeotrope (2-fold 50 ml). Benzyl alcohol (36 ml, 0.25 mol), toluene (220 ml) and p-toluenesulphonic acid hydrate (15.9 g, 83.6 mmol) were added and the mixture was heated at reflux for 24 hours using a Dean and Starke trap. The reaction mixture was cooled to room temperature and diethyl ether (100 ml) was added. The solid formed was isolated by filtration and washed with diethyl ether and then dried in-vacuo at 40° C. to give the title compound (27.3 g).

LCMS (electrospray): m/z [M+Na]+ 283

Preparation 60

2-(3,4-Difluoro-phenoxy)-5-fluoro-nicotinic acid

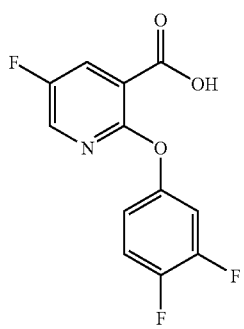

A solution of 3,4-difluorophenol (29.25 g, 225 mmol) in dioxan (300 ml) was dried over magnesium sulphate, then filtered. Ethyl-2-chloro-5-fluoro-nicotinoate (J. Med. Chem., 1993, 36(18), 2676–88) (30.6 g, 150 mmol) and freshly dried cesium carbonate (73.2 g, 225 mmol) were added and the reaction stirred under reflux for 18 hours. The cooled mixture was concentrated in vacuo, the residue partitioned between water (1500 ml) and ether (1500 ml), and the layers separated. The aqueous phase was further extracted with ether and the combined organic solutions were washed with saturated sodium bicarbonate solution, water, then brine, dried over magnesium sulphate and evaporated in vacuo to give a brown oil (48.3 g). A mixture of this intermediate ester and 1N lithium hydroxide solution (450 ml), in tetrahydrofuran (450 ml), was stirred vigorously at room temperature for 18 hours. The tetrahydrofuran was removed in vacuo and the residual aqueous solution was acidified to pH 5 using 2N hydrochloric acid (ca. 150 ml). The solution was washed with ether (2-fold) and then further acidified by the addition of more 2N hydrochloric acid (150 ml). The resulting precipitate was filtered off and dried to afford the title compound as a white solid (25.92 g).

1H NMR (400 MHz, CD$_3$OD): δ 6.94 (1H, m), 7.10 (1H, m), 7.25 (1H, dd), 8.14 (2H, m).

Preparation 61 syn-[4-(2-Hydroxy-5-methyl-benzoylamino)-cyclohexyl]-carbamic acid tert-butyl ester

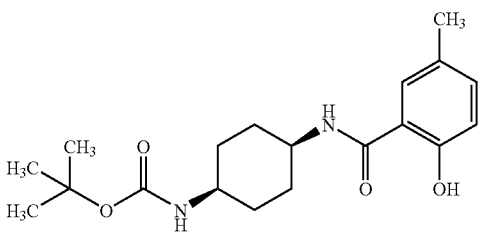

Hünig's base (8.72 g, 67.5 mmol) followed by 1-hydroxybenzotriazole hydrate (6.99 g, 51.75 mmol) were added to a solution of the amine from preparation 42B (9.64 g, 45 mmol) in dichloromethane (110 ml), and the suspension stirred for 5 minutes. 1-(3-Dimethylaminopropyl)-3-ethylcarbodiimide hydrochloride (11.22 g, 58.5 mmol) followed by 5-methyl salicylic acid (6.33 g, 41.6 mmol) were then added portionwise, and the reaction stirred at room temperature for 48 hours. The mixture was diluted with dichloromethane (200 ml), and washed with water (250 ml). The aqueous layer was acidified to pH 3 using 2M hydrochloric acid and re-partitioned with the organic layer. This organic phase was separated, washed with water, dried over magnesium sulphate and evaporated in vacuo. The residual orange oil was triturated with ethyl acetate and then ether, the resulting solid filtered off, washed with ether and dried under vacuum to afford the title compound as a white crystalline solid, (9.95 g).

$^1$H NMR (400 MHz, DMSOd$_6$): δ 1.38 (9H, s), 1.55 (4H, m), 1.67 (4H, m), 2.22 (3H, s), 3.40 (1H, m), 3.82 (1H, m), 6.66 (1H, m), 6.75 (1H, s), 7.15 (1H, d), 7.69 (1H, s), 8.38 (1H, d), 12.08 (1H, s). LCMS (electrospray): m/z [M+Na]+ 371

Preparation 62 syn-N-(4-Amino-cyclohexyl)-2-hydroxy-5-methyl-benzamide hydrochloride

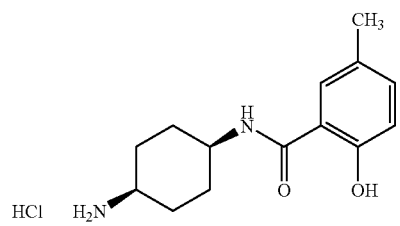

A solution of the protected amine from preparation 61 (9.8 g, 28.1 mmol) in dry dichloromethane (600 ml) was cooled to 4° C., and purged with nitrogen. This solution was saturated with hydrogen chloride gas, and then stirred for a further 3 hours. The mixture was concentrated in vacuo, and the residue azeotroped with dichloromethane. The product was triturated with ether, and the resulting solid filtered off, and dried to afford the title compound (7.6 g).

$^1$H NMR (400 MHz, DMSOd$_6$): δ 1.55–1.92 (8H, m), 2.10 (3H, s), 3.10 (1H, m), 3.90 (1H, m), 6.80 (1H, d), 7.15

(1H, d), 7.73 (1H, s), 8.00 (3H, s), 8.35 (1H, s), 11.35 (1H, s). LCMS (electrospray): m/z [M+H]+ 249

Preparation 63 syn-(4-{[2-(3,4-Difluoro-phenoxy)-5-fluoro-pyridine-3-carbonyl]-amino}-cyclohexyl)-carbamic acid tert-butyl ester

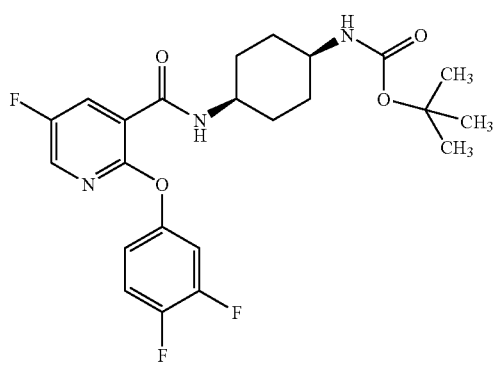

Syn-{4-[(2-Chloro-5-fluoro-pyridine-3-carbonyl)-amino]-cyclohexyl}-carbamic acid tert-butyl ester (500 mg, 1.35 mmol, see preparation 43) was mixed with 3,4-difluorophenol (280 mg, 2 mmol) and caesium carbonate (2.2 g, 6.7 mmol) in N-methylpyrrolidinone (10 ml) and was heated to 80° C. for 16 hours. The reaction mixture was cooled to room temperature and the solvent was concentrated in-vacuo. The residue was dissolved in 1N sodium hydroxide solution and the solution was extracted with ethyl acetate (4-fold 25 ml). The combined organic solutions were washed with 10% citric acid solution (2-fold 20 ml) and brine (20 ml), then dried over magnesium sulphate and concentrated in-vacuo. The residue was purified by chromatography on silica gel using ethyl acetate in pentane as eluant (50:50) to give syn-(4-{[2-(3,4-difluoro-phenoxy)-5-fluoro-pyridine-3-carbonyl]-amino}-cyclohexyl)-carbamic acid tert-butyl ester as a white solid (340 mg).

LCMS (electrospray): m/z [M+H]+ 466

Preparation 64 syn-N-(4-Amino-cyclohexyl)-2-(3,4-difluoro-phenoxy)-5-fluoro-nicotinamide

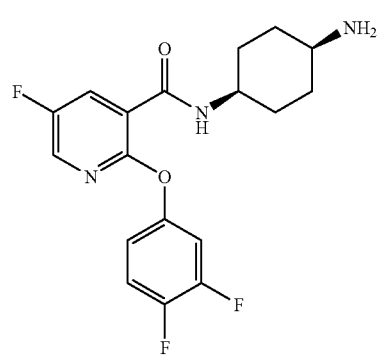

Syn-(4-{[2-(3,4-Difluoro-phenoxy)-5-fluoro-pyridine-3-carbonyl]-amino}-cyclo-hexyl)-carbamic acid tert-butyl ester (11.25 g, 24.2 mmol, see preparation 63) was dissolved in dichloromethane (200 ml) at 0° C. Hydrogen chloride gas was bubbled into the solution with stirring for 45 minutes and the mixture was stirred at 0° C. for a further 20 minutes. The reaction mixture was concentrated in-vacuo and the residue was dissolved in 1N sodium hydroxide solution. The aqueous solution was extracted with dichloromethane. The phases were separated and the organic solution was dried over magnesium sulphate and concentrated in-vacuo to give syn-N-(4-amino-cyclohexyl)-2-(3,4-difluoro-phenoxy)-5-fluoro-nicotinamide (7.36 g).

LCMS (electrospray): m/z [M+H]+ 366

Preparation 65 syn-[4-(2-Hydroxy-4-methyl-benzoylamino)-cyclohexyl]-carbamic acid tert-butyl ester

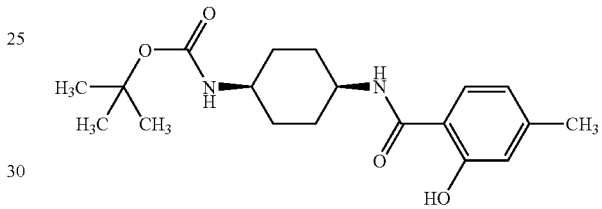

4-Methylsalycilic acid (3.5 g, 23 mmol) was added to a mixture of the syn-(4-amino-cyclohexyl)-carbamic acid tert-butyl ester (5.35 g, 25 mmol, see preparation 42-b) 1-hydroxybenzotriazole hydrate (3.88 g, 28.8 mmol) 1-(3-dimethylaminopropyl-3-ethylcarbodiimide hydrochloride (6.23 g, 32.5 mmol) and diisopropylethylamine (4.84 g, 37.5 mmol) in dichloromethane (65 ml). The mixture was stirred at room temperature for 72 hours and was diluted with dichloromethane (100 ml). Water (150 ml) was added and the aqueous layer was acidified to pH 3 by addition of 2M hydrochloric acid. The phases were separated and the organic phase was washed with water (2-fold 100 ml) and dried over magnesium sulphate. The organic solution was concentrated in-vacuo and the residue was triturated with hot ethyl acetate to give syn-[4-(2-hydroxy-4-methyl-benzoylamino)-cyclohexyl]-carbamic acid tert-butyl ester (5.2 g).

LCMS (electrospray): m/z [M+Na]+ 371

Preparation 66 syn-N-(4-Amino-cyclohexyl)-2-hydroxy-4-methyl-benzamide hydrochloride

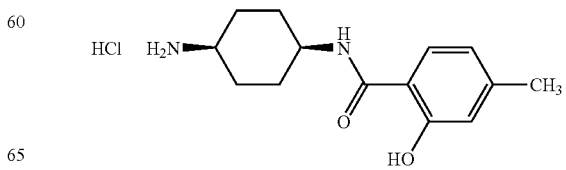

Syn-[4-(2-Hydroxy-4-methyl-benzoylamino)-cyclohexyl]-carbamic acid tert-butyl ester (5.1 g, 14.6 mmol, see Preparation 65) was suspended in dichloromethane (400 ml) and was cooled to 0° C. The mixture was purged under nitrogen and hydrogen chloride gas was bubbled into the mixture for 10 minutes to give a saturated solution. The reaction mixture was stirred at 4° C. for 3 hours and then concentrated in-vacuo. The residue was co-evaporated with dichloromethane (2 fold) and triturated with diethyl ether. The material obtained was isolated by filtration and was washed with diethyl ether to give syn-N-(4-amino-cyclohexyl)-2-hydroxy-4-methyl-benzamide hydrochloride as a white solid (4.21 g).

LCMS (electrospray): m/z [M+H]$^+$ 249

Preparation 67 syn-2-Chloro-5-fluoro-N-[4-(2-hydroxy-4-methyl-benzoylamino)-cyclohexyl]-nicotinamide

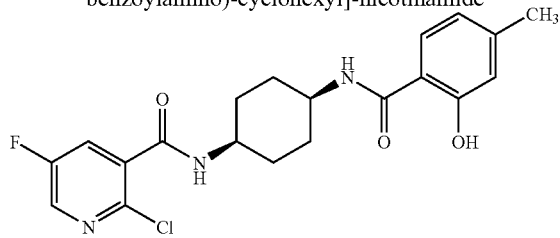

1-(3-Dimethylaminopropyl-3-ethylcarbodiimide hydrochloride (1.68 g, 5.85 mmol) was added to syn-N-(4-amino-cyclohexyl)-2-hydroxy-4-methyl-benzamide hydrochloride (2 g, 7.02 mmol)(see preparation 66), 2-chloro-5-fluoronicotinic acid (1.03 g, 5.85 mmol, see preparation 41), 1-hydroxybenzotriazole hydrate (0.95 g, 7.02 mmol) and diisopropylethylamine (4.6 ml, 26.3 mmol) in dichloromethane (50 ml) and the mixture was stirred at room temperature under a nitrogen atmosphere for 16 hours. Additional 1-(3-dimethylaminopropyl-3-ethylcarbodiimide hydrochloride (0.56 g, 2.9 mmol) was added and the mixture was stirred for a further 2 hours. The reaction mixture was partitioned between 1N hydrochloric acid and dichloromethane. The phases were separated and the aqueous layer was extracted with dichloromethane (2 fold). The combined organic solutions were dried over magnesium sulphate and concentrated in-vacuo. The material obtained was recrystalised from isopropyl acetate to give syn-2-chloro-5-fluoro-N-[4-(2-hydroxy-4-methyl-benzoylamino)-cyclohexyl]-nicotinamide as a white solid (1.3 g).

LCMS (electrospray): m/z [M+H]$^+$ 406

Preparation 68 syn-2-Chloro-5-fluoro-N-[4-(2-hydroxy-5-methyl-benzoylamino)-cyclohexyl]-nicotinamide

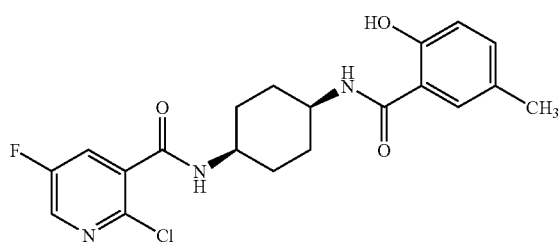

1-(3-Dimethylaminopropyl-3-ethylcarbodiimide hydrochloride (245 mg, 3.9 mmol) was added to a mixture of syn-N-(4-amino-cylcohexyl)-2-hydroxy-5-methyl-benzamide hydrochloride (1 g, 3.5 mmol, see preparation 62), 1-hydroxybenzotriazole hydrate (492 mg, 3.7 mmol), 2-chloro-5-fluoronicotinic acid (0.65 g, 3.7 mmol, see preparation 41), and triethylamine (0.96 ml, 8.75 mmol) in N,N-dimethylformamide (20 ml) and the mixture was stirred at room temperature for 16 hours. The reaction mixture was concentrated in-vacuo and the residue was partitioned between ethyl acetate and water. The layers were separated and the organic layer was dried over magnesium sulphate and concentrated in-vacuo to give syn-2-chloro-5-fluoro-N-[4-(2-hydroxy-5-methyl-benzoylamino)-cyclohexyl]-nicotinamide (1 g).

LCMS (electrospray): m/z [M+H]$^+$ 406

Preparation 69 syn-[4-(2-Hydroxy-3-methyl-benzoylamino)-cyclohexy]-carbamic acid tert-butyl ester

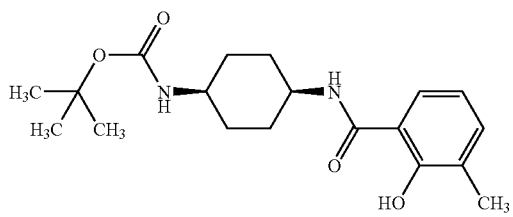

3-Methylsalycilic acid (2.74 g, 18 mmol) was added to a mixture of the syn-(4-amino-cyclohexyl)-carbamic acid tert-butyl ester (4.28 g, 20 mmol, see preparation 42-b) 1-hydroxybenzotriazole hydrate (3.19 g, 24 mmol) 1-(3-dimethylaminopropyl-3-ethylcarbodiimide hydrochloride (4.97 g, 26 mmol) and diisopropylethylamine (3.87 g, 30 mmol) in dichloromethane (45 ml). The mixture was stirred at room temperature for 40 hours and was partitioned between dichloromethane and water (75 ml). The aqueous layer was extracted with dichloromethane and the combined organic phases dried over magnesium sulphate and concentrated in-vacuo. The material obtained was isolated by filtration to give syn-[4-(2-hydroxy-3-methyl-benzoylamino)-cyclohexyl]-carbamic acid tert-butyl ester (1.14 g)

LCMS (electrospray): m/z [M+H]$^+$ 349

Preparation 70 syn-N-(4-Amino-cyclohexyl)-2-hydroxy-3-methyl-benzamide hydrochloride

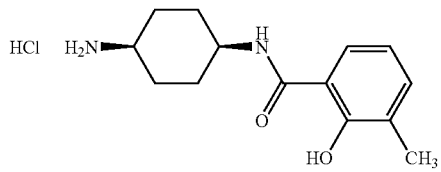

syn-[4-(2-Hydroxy-3-methyl-benzoylamino)-cyclohexyl]-carbamic acid tert-butyl ester (1.14 g, 3.3 mmol, see preparation 69) was suspended in dichloromethane (17 ml) and was cooled to 0° C. Hydrogen chloride gas was bubbled into the mixture for 20 minutes and the mixture was warmed to room temperature and was stirred for 16 hours. Hydrogen chloride was bubbled into the mixture for a further 15 minutes and the mixture was stirred at room temperature for 15 minutes. Methanol was added to the reaction mixture and the solvent was concentrated in-vacuo to give syn-N-(4-amino-cyclohexyl)-2-hydroxy-3-methyl-benzamide hydrochloride (0.96 g).

LCMS (electrospray): m/z [M+H]$^+$ 249

Preparation 71 syn-2-Chloro-5-fluoro-N-[4-(2-hydroxy-3-methyl-benzoylamino)-cyclohexyl]-nicotinamide

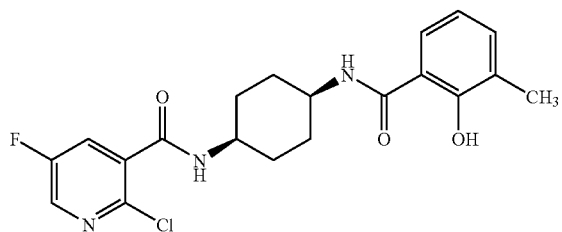

1-(3-Dimethylaminopropyl-3-ethylcarbodiimide hydrochloride (0.81 g, 4.24 mmol) was added to a mixture of syn-N-(4-amino-cyclohexyl)-2-hydroxy-3-methyl-benzamide hydrochloride (0.96 g, 3.4 mmol, see preparation 70), 1-hydroxybenzotriazole hydrate (459 mg, 3.4 mmol), 2-chloro-5-fluoronicotinic acid (497 mg, 2.8 mmol, see preparation 41), and diisopropylamine (2.2 ml, 12.7 mmol) in dichloromethane (20 ml) and the mixture was stirred at room temperature for 16 hours. The reaction mixture was concentrated in-vacuo and the residue was partitioned between dichloromethane and water. The layers were separated and the organic layer was washed with 10% citric acid solution, dried over magnesium sulphate and concentrated in-vacuo to give syn-2-chloro-5-fluoro-N-[4-(2-hydroxy-3-methyl-benzoylamino)-cyclohexyl]-nicotin-amide (0.71 g).

LCMS (electrospray): m/z [M+H]$^+$ 406

Preparation 72

2-(3,4-Dichloro-phenoxy)-5-fluoro-nicotinic acid ethyl ester

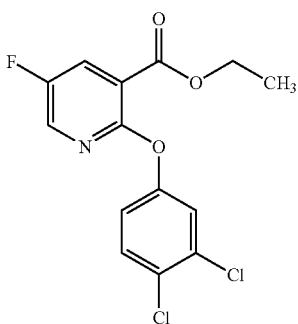

Ethyl 2-chloro-5-fluoronicotinate (5.09 g, 25 mmol, see reference J. Med. Chem., 1993, 36(18) 267–88) and 3,4-dichlorophenol (6.11 g, 37.5 mmol) were dissolved in 1,4-dioxane and the solution was purged with argon. Anhydrous caesium carbonate (12.21 g, 37.5 mmol) was added and the mixture was heated under reflux for 17 hours. The reaction mixture was partitioned between water (300 ml) and ethyl acetate (300 ml). The aqueous layer was acidified to pH 3 by addition of 2M hydrochloric acid and the phases were separated. The aqueous layer was extracted with ethyl acetate (2-fold 100 ml) and the combined organic solutions were dried over magnesium sulphate and concentrated in-vacuo to give a red oil. The material isolated was redissolved in ethyl acetate and was washed with 5% potassium carbonate solution (2-fold 200 ml), 0.5 M sodium hydroxide solution (2-fold 200 ml) and saturated sodium hydrogen carbonate solution (100 ml). The organic phase was dried over magnesium sulphate and concentrated in-vacuo. The residue was purified by chromatography on silica gel using ethyl acetate in pentane as eluant (4:96) to give 2-(3,4-dichloro-phenoxy)-5-fluoro-nicotinic acid ethyl ester as a colourless oil that crystallised on standing (4.95 g).

LCMS (electrospray): m/z [M+Na]$^+$ 352

Preparation 73

2-(3,4-Dichloro-phenoxy)-5-fluoro-nicotinic acid

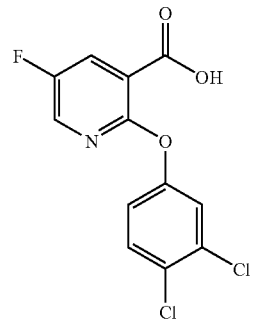

2-(3,4-Dichloro-phenoxy)-5-fluoro-nicotinic acid ethyl ester (4.9 g, 14.8 mmol, see preparation 72) was dissolved in tetrahydrofuran (50 ml). Water (27 ml) and lithium hydroxide (1.56 g, 37.1 mmol) were added and the mixture was stirred vigorously for 7 hours. The reaction mixture was acidified to pH5 by addition of 2 M hydrochloric acid and the mixture was partitioned between ethyl acetate (200 ml) and water (200 ml). The aqueous layer was acidified to pH 3 by addition of 2 M hydrochloric acid and the phases were separated. The aqueous phase was extracted with ethyl acetate (2-fold 50 ml) and the combined organic solutions were dried over magnesium sulphate and concentrated in-vacuo to give 2-(3,4-dichloro-phenoxy)-5-fluoro-nicotinic acid as a white solid (4.4 g).

LCMS (electrospray): m/z [M+Na]$^+$ 348

Preparation 74

2-(3,5-Difluoro-phenoxy)-5-fluoro-nicotinic acid ethyl ester

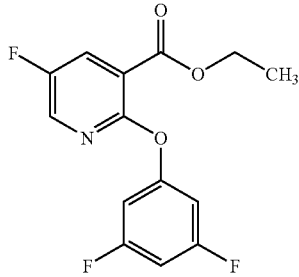

The title compound was prepared from ethyl 2-chloro-5-fluoronicotinate and 3,5-difluorophenol in 23% yield following the procedure described in preparation 72.

LCMS (electrospray): m/z [M+Na]$^+$ 371

Preparation 75

2-(3,5-Difluoro-phenoxy)-5-fluoro-nicotinic acid

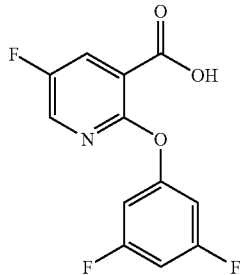

2-(3,4-Dichloro-phenoxy)-5-fluoro-nicotinic acid ethyl ester (0.68 g, 2.25 mmol, see Preparation 74) was dissolved in tetrahydrofuran (8 ml). Water (4.5 ml) and lithium hydroxide (239 mg, 5.7 mmol) were added and the mixture was stirred vigorously for 7 hours. The reaction mixture was acidified to pH 5 by addition of 2 M hydrochloric acid and the mixture was partitioned between ethyl acetate (50 ml) and water (50 ml). The aqueous layer was acidified to pH 3 by addition of 2 M hydrochloric acid and the phases were separated. The aqueous phase was extracted with ethyl acetate (2-fold 25 ml) and the combined organic solutions were dried over magnesium sulphate and concentrated in-vacuo to give 2-(3,5-difluoro-phenoxy)-5-fluoro-nicotinic acid as a white solid (0.57 g).

LCMS (electrospray): m/z [M−H]$^-$ 268

Preparation 76

Acetic acid 3-cyclobutoxy-phenyl ester

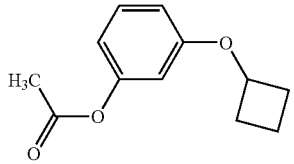

Acetic acid 3-hydroxy-phenyl ester (1 ml, 9 mmol) was mixed with cyclobutanol (0.58 g, 8 mmol), triphenylphosphine (2.1 g, 8 mmol) and diisopropyl azodicarboxylate (1.57 ml, 8 mmol) in tetrahydrofuran (20 ml) at 0° C. under a nitrogen atmosphere. The mixture was warmed to room temperature and stirred for 16 hours. The reaction mixture was concentrated in-vacuo the residue was purified by chromatography on silica gel using ethyl acetate in pentane as eluant (gradient from 0:100 to 15:85) to give acetic acid 3-cyclobutoxy-phenyl ester (340 mg).

LCMS (electrospray): m/z [M+H]$^+$ 207

Preparation 77

3-Cyclobutoxy-phenol

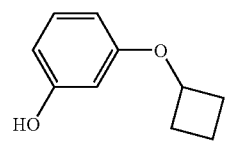

Acetic acid 3-cyclobutoxy-phenyl ester (340 mg, 1.65 mmol) was dissolved in methanol (6 ml) and 1 M sodium hydroxide solution (2 ml, 2 mmol) was added. The reaction mixture was stirred at room temperature for 24 hours and then was acidified with 2 M hydrochloric acid. The reaction mixture was extracted with ethyl acetate and the organic solution was dried over magnesium sulphate and concentrated in-vacuo to give 3-cyclobutoxy-phenol (300 mg).

LCMS (electrospray): m/z [M+H]$^+$ 165

In Vitro Activity of the Nicotinamide Derivatives

The PDE4 inhibitory activity of the nicotinamide derivatives of the formula (1) is determined by the ability of compounds to inhibit the hydrolysis of cAMP to AMP by PDE4 (see also reference 1). Tritium labelled cAMP is incubated with PDE4. Following incubation, the radiolabelled AMP produced is able to bind ytrium silicate SPA beads. These SPA beads subsequently produce light that can be quantified by scintillation counting. The addition of a PDE4 inhibitor prevents the formation of AMP from cAMP and counts are diminished. The IC$_{50}$ of a PDE4 inhibitor can be defined as the concentration of a compound that leads to a 50% reduction in counts compared to the PDE4 only (no inhibitor) control wells.

The anti-inflammatory properties of the nicotinamide derivatives of the formula (1) are demonstrated by their ability to inhibit TNFα release from human peripheral blood mononuclear cells (see also reference 2). Venous blood is collected from healthy volunteers and the mononuclear cells purified by centrifugation through Histopaque (Ficoll) cush ions. TNFα production from these cells is stimulated by addition of lipopolysaccharide. After 18 hours incubation in the presence of LPS, the cell supernatant is removed and the concentration of TNFα in the supernatant determined by ELISA. Addition of PDE4 inhibitors reduces the amount of TNFα produced. An $IC_{50}$ is determined which is equal to the concentration of compound that gives 50% inhibition of TNFα production as compared to the LPS stimulated control wells.

All the examples were tested in the assay described above and found to have an $IC_{50}$ (TNFα screen) of less than 300 nM. And for most of the tested compounds, they were found to have an $IC_{50}$ (TNFα screen) of even less than 100 nM.

For illustrating purpose, the following table indicates the exact $IC_{50}$ (TNFα screen) of some representative examples of the present invention:

| Example N° | $IC_{50}$ (nM) | Example N° | $IC_{50}$ (nM) |
|---|---|---|---|
| 6 | 23.5 | 8 | 22 |
| 14 | 13 | 16 | 0.28 |
| 17 | 8.5 | 20 | 113 |
| 22 | 156 | 23 | 7.8 |
| 25 | 8.5 | 26 | 5.4 |
| 27 | 39.5 | 28 | 217 |
| 30 | 2.6 | 41 | 4.9 |
| 44 | 91 | 47 | 0.28 |
| 48 | 1.66 | 51 | 2.09 |
| 54 | 2.8 | 56 | 1.9 |
| 57 | 13 | 58 | 3.5 |
| 66 | 18.3 | 69 | 49 |
| 72 | 1.1 | 76 | 49 |
| 79 | 25.5 | 80 | 7.4 |
| 81 | 30 | 85 | 28 |
| 88 | 114 | 91 | 37 |
| 92 | 185 | 93 | 5 |
| 95 | 3.2 | 97 | 30 |
| 100 | 56 | 106 | 3.6 |
| 110 | 14 | 116 | 25 |
| 123 | 21 | 129 | 30 |
| 135 | 74 | 137 | 16 |
| 152 | 0.2 | 12 | 1 |
| 155 | 0.09 | 156 | 0.14 |
| 157 | 2 | 159 | 4.6 |
| 172 | 4.3 | 173 | 2.1 |
| 174 | 0.014 | 178 | 0.15 |
| 183 | 0.07 | 186 | 0.2 |
| 187 | 0.006 | 190 | 0.06 |
| 193 | 9 | 194 | 0.07 |
| 195 | 0.4 | 197 | 1.8 |
| 199 | 0.7 | 200 | 0.05 |
| 201 | 0.3 | 203 | 7 |
| 204 | 0.3 | 205 | 0.55 |
| 208 | 0.09 | 210 | 13 |
| 213 | 0.2 | 217 | 0.3 |

REFERENCES

1. Thompson J W, Teraski W L, Epstein P M, Strada S J., "Assay of nucleotidephosphodiesterase and resolution of multiple molecular forms of the isoenzyme", *Advances in cyclic nucleotides research*, edited by Brooker G, Greengard P. Robinson G A. Raven Press, New York 1979, 10, p. 69–92.
2. Yoshimura T, Kurita C, Nagao T, Usami E, Nakao T, Watanabe S, Kobayashi J, Yamazaki F, Tanaka H, Nagai H., "Effects of cAMP-phosphodiesterase isozyme inhibitor on cytokine production by lipopolysaccharide-stimulated human peripheral blood mononuclear cells", *Gen. Pharmacol.*, 1997, 29(4), p. 63

The invention claimed is:
1. 2-(3,4-Difluoro-phenoxy)-5-fluoro-N-[4-(2-hydroxy-5-hydroxymethyl-benzoylamino)-cyclohexyl]-nicotinamide of the formula

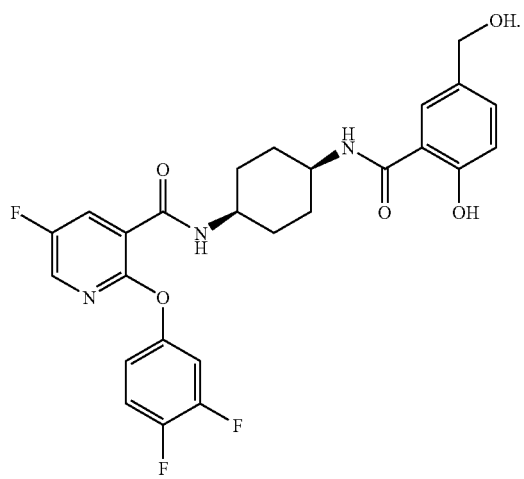

or a pharmaceutically acceptable salt, tautomer or isomer thereof.

2. A pharmaceutical composition comprising a compound of claim 1 or a pharmaceutically acceptable salt thereof and a pharmaceutically acceptable excipient and/or additive.

3. A method of treating asthma in a mammal, said method comprising administering to said mammal a therapeutically effective amount of a compound of claim 1 or a pharmaceutically acceptable salt thereof.

4. A method of claim 3 wherein said asthma is atopic asthma; non-atopic asthma; allergic asthma; bronchial asthma; essential asthma; extrinsic asthma caused by environmental factors; essential asthma of unknown or inapparent cause; bronchitic asthma; emphysematous asthma; exercise-induced asthma; occupational asthma; infective asthma caused by bacterial, fungal, protozoal or viral infection; non-allergic asthma; incipient asthma; or wheezy infant syndrome.

5. A method of treating chronic or acute bronchoconstriction; chronic bronchitis; small airways obstruction; emphysema; chronic obstructive pulmonary disease; or adult respiratory distress syndrome in a mammal, said method comprising administering to said mammal a therapeutically effective amount of a compound of claim 1 or a pharmaceutically acceptable salt thereof.

6. A method of claim 5 wherein said chronic obstructive pulmonary disease is characterized by irreversible, progressive airways obstruction.

7. A method of treating bronchitis; acute bronchitis; chronic bronchitis; acute laryngotracheal bronchitis; arachidic bronchitis; catarrhal bronchitis; croupus bronchitis; dry bronchitis; infectious asthmatic bronchitis; productive bronchitis; staphylococcus bronchitis; streptococcal bronchitis; or vesicular bronchitis in a mammal, said method comprising administering to said mammal a therapeutically effective amount of a compound of claim 1 or a pharmaceutically acceptable salt thereof.

8. A method of treating bronchiectasis; cylindric bronchiectasis; sacculated bronchiectasis; fusiform brochiectasis; capillary bronchiectasis; cystic bronchiectasis; dry bronchiectasis or follicular bronchiectasis in a mammal, said method comprising administering to said mammal a therapeutically effective amount of a compound of claim 1 or a pharmaceutically acceptable salt thereof.

9. A method of treating seasonal allergic rhinitis; perennial allergic rhinitis; sinusitis; purulent sinusitis; nonpurulent sinusitis; acute sinusitis; chronic sinusitis; ethmoid sinusitis; frontal sinusitis; or sphenoid sinusitis in a mammal, said method comprising administering to said mammal a therapeutically effective amount of a compound of claim 1 or a pharmaceutically acceptable salt thereof.

10. A method of any one of claims 3–9 wherein said compound or pharmaceutically acceptable salt thereof is administered together with a pharmaceutically acceptable excipient and/or additive.

* * * * *